(12) United States Patent
Kuyler et al.

(10) Patent No.: US 12,727,895 B2
(45) Date of Patent: Sep. 8, 2026

(54) CONTOUR GUIDE FOR SMALL BONE SURFACE MODIFICATION

(71) Applicant: Treace Medical Concepts, Inc., Ponte Vedra, FL (US)

(72) Inventors: Adriaan Kuyler, Ponte Vedra, FL (US); W. Bret Smith, Durango, CO (US); Madeline Lindemann, Palm Coast, FL (US); Sean F. Scanlan, Jacksonville, FL (US); Jason May, St. John's, FL (US); Robert D. Santrock, Morgantown, WV (US); Mark Erik Easley, Durham, NC (US); Paul Dayton, Ankeny, IA (US); Jody McAleer, Jefferson City, MO (US); William T. DeCarbo, Pittsburgh, PA (US); Daniel J. Hatch, Greeley, CO (US); Steve Norton, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 18/437,073

(22) Filed: Feb. 8, 2024

(65) Prior Publication Data

US 2024/0260977 A1 Aug. 8, 2024

Related U.S. Application Data

(60) Provisional application No. 63/583,746, filed on Sep. 19, 2023, provisional application No. 63/519,036, (Continued)

(51) Int. Cl.
*A61B 17/17* (2006.01)
*A61B 17/064* (2006.01)
(Continued)

(52) U.S. Cl.
CPC ...... *A61B 17/1775* (2016.11); *A61B 17/0642* (2013.01); *A61B 17/10* (2013.01);
(Continued)

(58) Field of Classification Search
CPC ..... A61B 17/17; A61B 17/1775; A61B 17/90; A61B 17/16; A61B 17/1615;
(Continued)

(56) References Cited

U.S. PATENT DOCUMENTS 4,263,903 A 4/1981 Griggs
4,454,875 A 6/1984 Pratt et al.
(Continued)

FOREIGN PATENT DOCUMENTS

AU 2006252612 B2 4/2012
CA 2715491 C 4/2014
(Continued)

OTHER PUBLICATIONS

Acumed, "Acu-Loc Wrist Plating System," Brochure and Surgical Technique, effective date Apr. 2012, reported publication date Sep. 23, 2013, 19 pages.
(Continued)

*Primary Examiner* — Marcela I. Shirsat
(74) *Attorney, Agent, or Firm* — Fredrikson & Byron, P.A.

(57) ABSTRACT

A method of modifying a bone surface for receiving an implant includes: positioning a contour guide at a first bone and a second bone and across a separation between the first bone and the second bone; using the contour guide to modify a surface region of at least one of the first bone and the second bone to form a modified surface region at one or both of the first bone and the second bone; and positioning an implant in contact at least with the modified surface region.

16 Claims, 48 Drawing Sheets

Related U.S. Application Data filed on Aug. 11, 2023, provisional application No. 63/444,226, filed on Feb. 8, 2023.

(51) Int. Cl.

| | |
|---|---|
| ***A61B 17/068*** | (2006.01) |
| ***A61B 17/10*** | (2006.01) |
| ***A61B 17/16*** | (2006.01) |
| ***A61B 17/56*** | (2006.01) |
| ***A61B 17/90*** | (2006.01) |
| ***A61F 2/30*** | (2006.01) |
| ***A61F 2/42*** | (2006.01) |
| ***A61F 2/46*** | (2006.01) |

(52) U.S. Cl.

CPC ............ *A61B 17/90* (2021.08); *A61F 2/4225* (2013.01); *A61F 2/4606* (2013.01); *A61B 2017/0641* (2013.01); *A61B 17/0644* (2013.01); *A61B 2017/0645* (2013.01); *A61B 17/068* (2013.01); *A61B 17/0682* (2013.01); *A61B 17/1615* (2013.01); *A61B 17/1682* (2013.01); *A61B 17/1728* (2013.01); *A61B 17/1732* (2013.01); *A61B 17/1739* (2013.01); *A61B 2017/564* (2013.01); *A61B 2017/565* (2013.01); *A61F 2002/30622* (2013.01); *A61F 2002/4228* (2013.01); *A61F 2002/4233* (2013.01); *A61F 2002/4238* (2013.01); *A61F 2/4241* (2013.01); *A61F 2/4603* (2013.01); *A61F 2002/4625* (2013.01); *A61F 2002/4629* (2013.01)

(58) Field of Classification Search

CPC ............ A61B 17/1655; A61B 17/1682; A61B 17/1728; A61B 17/1732; A61B 17/1739; A61B 17/068; A61B 17/076; A61B 17/08; A61B 17/064; A61B 17/0644; A61B 17/0642; A61F 2/42; A61F 2/4225; A61F 2/4606; A61F 2/4241; A61F 2/46; A61F 2/4603; A61F 2002/30622; A61F 2002/4625; A61F 2002/4629; A61F 2002/4228; A61F 2002/4233; A61F 2002/4238; A61F 2002/4243; A61F 2002/4251

USPC ........................................................... 606/75

See application file for complete search history.

(56) References Cited

U.S. PATENT DOCUMENTS

| | | | |
|---|---|---|---|
| D281,814 | S | 12/1985 | Pratt et al. |
| 4,592,346 | A | 6/1986 | Jurgutis |
| D286,442 | S | 10/1986 | Korthoff et al. |
| 4,793,335 | A | 12/1988 | Frey et al. |
| 4,848,328 | A | 7/1989 | Laboureau et al. |
| 4,852,558 | A | 8/1989 | Outerbridge |
| 4,959,065 | A | 9/1990 | Arnett et al. |
| 4,994,063 | A | 2/1991 | Garner |
| 5,015,247 | A | 5/1991 | Michelson |
| 5,053,038 | A | 10/1991 | Sheehan |
| 5,304,180 | A | 4/1994 | Slocum |
| 5,529,075 | A | 6/1996 | Clark |
| 5,665,089 | A | 9/1997 | Dall et al. |
| 5,667,510 | A | 9/1997 | Combs |
| 5,690,639 | A | 11/1997 | Lederer et al. |
| 5,702,396 | A | 12/1997 | Hoenig et al. |
| 5,709,686 | A | 1/1998 | Talos et al. |
| 5,709,687 | A | 1/1998 | Pennig |
| 5,785,712 | A | 7/1998 | Runciman et al. |
| 5,807,403 | A | 9/1998 | Beyar et al. |
| 5,868,749 | A | 2/1999 | Reed |
| 5,919,193 | A | 7/1999 | Slavitt |
| 6,120,503 | A | 9/2000 | Michelson |
| 6,183,475 | B1 | 2/2001 | Lester et al. |
| 6,336,928 | B1 | 1/2002 | Guerin et al. |
| 6,391,031 | B1 | 5/2002 | Toomey |
| 6,413,260 | B1 | 7/2002 | Berrevoets et al. |
| 6,447,524 | B1 | 9/2002 | Knodel et al. |
| 6,540,746 | B1 | 4/2003 | Bhler et al. |
| 6,638,297 | B1 | 10/2003 | Huitema |
| 6,689,136 | B2 | 2/2004 | Stoffella |
| 6,706,046 | B2 | 3/2004 | Orbay et al. |
| 6,780,115 | B2 | 8/2004 | Schmieding et al. |
| 6,783,531 | B2 | 8/2004 | Allen |
| 6,786,909 | B1 | 9/2004 | Dransfeld et al. |
| 6,966,911 | B2 | 11/2005 | Groiso |
| 7,037,309 | B2 | 5/2006 | Weil et al. |
| 7,041,106 | B1 | 5/2006 | Carver et al. |
| 7,175,667 | B2 | 2/2007 | Saunders et al. |
| 7,182,766 | B1 | 2/2007 | Mogul |
| 7,229,445 | B2 | 6/2007 | Hayeck et al. |
| 7,344,538 | B2 | 3/2008 | Myerson et al. |
| D586,915 | S | 2/2009 | Grim |
| 7,537,596 | B2 | 5/2009 | Jensen |
| 7,552,853 | B2 | 6/2009 | Mas et al. |
| 7,578,825 | B2 | 8/2009 | Huebner |
| 7,625,381 | B2 | 12/2009 | Michelson |
| 7,651,017 | B2 | 1/2010 | Ortiz et al. |
| 7,678,121 | B1 | 3/2010 | Knodel |
| 7,695,473 | B2 | 4/2010 | Ralph et al. |
| 7,722,653 | B2 | 5/2010 | Young et al. |
| 7,727,264 | B2 | 6/2010 | Orbay et al. |
| 7,785,355 | B2 | 8/2010 | Mohr et al. |
| 7,931,680 | B2 | 4/2011 | Myerson et al. |
| 8,021,367 | B2 | 9/2011 | Bourke et al. |
| 8,021,389 | B2 | 9/2011 | Molz, IV |
| 8,069,858 | B2 | 12/2011 | Gall |
| 8,100,983 | B2 | 1/2012 | Schulte |
| 8,133,283 | B2 | 3/2012 | Wilson |
| 8,162,996 | B2 | 4/2012 | Schelling |
| 8,167,918 | B2 | 5/2012 | Strnad et al. |
| 8,172,884 | B2 | 5/2012 | Bouman |
| 8,172,886 | B2 | 5/2012 | Castaneda et al. |
| 8,177,819 | B2 | 5/2012 | Huebner et al. |
| 8,177,820 | B2 | 5/2012 | Anapliotis et al. |
| 8,177,822 | B2 | 5/2012 | Medoff |
| 8,216,257 | B2 | 7/2012 | Huitema et al. |
| 8,231,662 | B2 | 7/2012 | Huebner |
| 8,235,994 | B2 | 8/2012 | Hollawell |
| 8,235,995 | B2 | 8/2012 | Focht et al. |
| 8,236,034 | B2 | 8/2012 | Binder et al. |
| 8,241,338 | B2 | 8/2012 | Castaneda et al. |
| 8,246,661 | B2 | 8/2012 | Beutter et al. |
| 8,257,403 | B2 | 9/2012 | Den Hartog et al. |
| 8,257,405 | B2 | 9/2012 | Haidukewych et al. |
| 8,262,712 | B2 | 9/2012 | Coillard-Lavirotte et al. |
| D675,734 | S | 2/2013 | Cheney et al. |
| 8,382,807 | B2 | 2/2013 | Austin et al. |
| 8,398,687 | B2 | 3/2013 | Vasta et al. |
| 8,403,966 | B2 | 3/2013 | Ralph et al. |
| 8,425,554 | B2 | 4/2013 | Denove et al. |
| 8,444,679 | B2 | 5/2013 | Ralph et al. |
| 8,496,690 | B2 | 7/2013 | Sixto et al. |
| 8,512,339 | B2 | 8/2013 | Medoff et al. |
| 8,529,608 | B2 | 9/2013 | Terrill et al. |
| 8,529,611 | B2 | 9/2013 | Champagne et al. |
| D691,720 | S | 10/2013 | Cheney et al. |
| 8,545,540 | B2 | 10/2013 | Castaneda et al. |
| 8,585,721 | B2 | 11/2013 | Kirsch |
| 8,652,142 | B2 | 2/2014 | Geissler |
| D701,307 | S | 3/2014 | Protopsaltis et al. |
| 8,679,123 | B2 | 3/2014 | Kinmon et al. |
| 8,685,024 | B2 | 4/2014 | Roman |
| 8,702,762 | B2 | 4/2014 | Jacene et al. |
| D705,930 | S | 5/2014 | Cheney |
| 8,715,325 | B2 | 5/2014 | Weiner et al. |
| 8,715,326 | B2 | 5/2014 | Champagne et al. |
| 8,721,646 | B2 | 5/2014 | Fox |
| 8,734,492 | B2 | 5/2014 | Mohr et al. |
| D706,927 | S | 6/2014 | Cheney et al. |

(56) References Cited

U.S. PATENT DOCUMENTS

D707,357 S 6/2014 Cheney et al.
8,757,465 B2 6/2014 Woodard, Jr. et al.
8,764,807 B2 7/2014 Michel et al.
8,764,842 B2 7/2014 Graham
8,784,457 B2 7/2014 Graham
8,784,498 B2 7/2014 Scheland
8,801,786 B2 8/2014 Bernard et al.
8,808,294 B2 8/2014 Fox et al.
8,808,334 B2 8/2014 Strnad et al.
8,828,063 B2 9/2014 Blitz et al.
8,834,532 B2 9/2014 Velikov et al.
8,834,537 B2 9/2014 Castaneda et al.
8,852,249 B2 10/2014 Ahrens et al.
8,888,824 B2 11/2014 Austin et al.
8,888,826 B2 11/2014 Kinmon et al.
8,940,026 B2 1/2015 Hilse et al.
8,940,029 B2 1/2015 Leung et al.
8,998,999 B2 4/2015 Lewis et al.
9,011,540 B1 4/2015 Castro
9,017,329 B2 4/2015 Tyber et al.
9,039,414 B2 5/2015 Bulloch et al.
9,056,014 B2 6/2015 Mccormick et al.
9,072,564 B2 7/2015 Reed et al.
9,138,244 B2 9/2015 Mebarak et al.
9,138,274 B1 9/2015 Biesinger et al.
9,149,313 B2 10/2015 Strnad et al.
9,220,501 B2 12/2015 Bedard et al.
9,220,515 B2 12/2015 Castaneda et al.
9,226,756 B2 1/2016 Teisen et al.
9,271,769 B2 3/2016 Batsch et al.
9,282,977 B2 3/2016 Penzimer et al.
9,314,245 B2 4/2016 Hester et al.
9,370,356 B2 6/2016 Euteneuer et al.
9,381,015 B2 7/2016 Johnson et al.
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,452,057 B2 9/2016 Dacosta et al.
9,474,561 B2 10/2016 Shemwell et al.
9,486,212 B2 11/2016 Miller et al.
9,492,215 B2 11/2016 Augoyard et al.
9,504,582 B2 11/2016 Sander et al.
D777,329 S 1/2017 Montoya et al.
9,545,274 B2 1/2017 Mccormick
9,554,914 B2 1/2017 Taylor et al.
9,597,130 B2 3/2017 Pappalardo et al.
9,603,643 B2 3/2017 Reed et al.
9,622,805 B2 4/2017 Santrock et al.
9,642,656 B2 5/2017 Kotuljac et al.
9,668,793 B2 6/2017 Gaudin
9,675,344 B2 6/2017 Combrowski et al.
9,675,391 B2 6/2017 Roman et al.
9,681,869 B2 6/2017 Wiedrich et al.
9,687,250 B2 6/2017 Dayton et al.
9,687,256 B2 6/2017 Granberry et al.
9,717,543 B2 8/2017 Brown et al.
9,724,139 B2 8/2017 Mccormick et al.
9,743,926 B2 8/2017 Fox
9,750,553 B1 9/2017 Forrester et al.
9,757,168 B2 9/2017 Seavey et al.
9,775,630 B2 10/2017 Leavitt et al.
9,775,656 B2 10/2017 Cheney et al.
9,808,296 B2 11/2017 Mccormick
D804,666 S 12/2017 Guo et al.
9,839,458 B2 12/2017 Bouduban et al.
9,867,642 B2 1/2018 Simon
9,888,931 B2 2/2018 Bake
9,901,338 B2 2/2018 Anderson
9,936,994 B2 4/2018 Smith et al.
9,955,968 B2 5/2018 Euteneuer
9,962,202 B2 5/2018 Anderson
D822,206 S 7/2018 Shelton, IV et al.
10,045,777 B2 8/2018 Rogers et al.
10,064,618 B2 9/2018 Allen
10,080,597 B2 9/2018 Shemwell et al.
10,085,743 B2 10/2018 Roedl et al.
10,105,134 B2 10/2018 Biedermann et al.
10,111,690 B2 10/2018 Anderson et al.
10,117,647 B2 11/2018 Cheney
10,123,831 B2 11/2018 Gephart
10,159,499 B2 12/2018 Dacosta et al.
10,172,613 B1 1/2019 Wade
10,206,678 B2 2/2019 Shelton, IV et al.
10,226,287 B2 3/2019 Langford et al.
10,238,437 B2 3/2019 Simon
10,245,038 B2 4/2019 Hopkins et al.
10,278,697 B2 5/2019 Shelton, IV et al.
10,292,713 B2 5/2019 Fallin et al.
10,292,743 B2 5/2019 Taylor et al.
10,292,745 B2 5/2019 Palmer et al.
10,307,156 B1 6/2019 Blair et al.
10,342,590 B2 7/2019 Bays et al.
10,368,860 B2 8/2019 Nering et al.
10,376,367 B2 8/2019 Fallin et al.
10,383,671 B2 8/2019 Prandi et al.
10,420,547 B2 9/2019 Weiner et al.
10,426,465 B1 10/2019 Wade
10,456,130 B2 10/2019 Cheney et al.
10,470,766 B2 11/2019 Wixey et al.
10,470,779 B2 11/2019 Fallin et al.
10,470,807 B2 11/2019 Barry et al.
10,492,841 B2 12/2019 Hartdegen et al.
10,507,021 B2 12/2019 Miller et al.
10,517,595 B2 12/2019 Hunter et al.
10,543,030 B2 1/2020 Seavey et al.
10,555,757 B2 2/2020 Dayton
10,575,862 B2 3/2020 Bays et al.
10,588,628 B2 3/2020 Vasta
10,603,046 B2 3/2020 Dayton et al.
10,610,222 B2 4/2020 Wahl
10,610,241 B2 4/2020 Wagner et al.
D883,482 S 5/2020 Majors et al.
10,646,263 B2 5/2020 Lamm et al.
10,653,462 B2 5/2020 Chen et al.
D886,299 S 6/2020 Cundiff et al.
10,682,168 B2 6/2020 Kay et al.
10,709,901 B2 7/2020 Kostrzewski et al.
10,736,641 B2 8/2020 Fallin et al.
D895,113 S 9/2020 Blair et al.
10,758,237 B2 9/2020 Williams
10,772,632 B2 9/2020 Kostrzewski
10,779,816 B2 9/2020 Goldstein et al.
10,786,292 B2 9/2020 Singh et al.
10,799,276 B2 10/2020 Dacosta et al.
10,813,770 B2 10/2020 Cavanagh et al.
10,835,247 B2 11/2020 Shelton, IV et al.
10,842,487 B2 11/2020 Ritz et al.
10,849,631 B2 12/2020 Hatch et al.
10,849,663 B2 12/2020 Dayton et al.
10,856,925 B1 12/2020 Pontell
10,874,389 B2 12/2020 Biedermann et al.
10,881,436 B2 1/2021 Muller et al.
10,888,319 B2 1/2021 Vasta
10,932,833 B2 3/2021 Gephart
11,000,327 B2 5/2021 Schlotterback et al.
11,006,949 B2 5/2021 Daniel
11,020,110 B1 6/2021 Blair et al.
11,020,148 B2 6/2021 Hollis et al.
11,051,804 B2 7/2021 Gaston et al.
11,058,467 B2 7/2021 Lueth et al.
11,058,546 B2 7/2021 Hollis et al.
11,090,043 B2 8/2021 Biedermann et al.
11,116,499 B1 9/2021 Blair et al.
11,141,204 B2 10/2021 Davison et al.
11,147,590 B2 10/2021 Dayton et al.
11,160,590 B2 11/2021 Davison et al.
11,202,666 B2 12/2021 Taylor et al.
11,213,327 B2 1/2022 Gault et al.
11,246,588 B2 2/2022 Maclure et al.
11,272,943 B2 3/2022 Stamp et al.
11,278,332 B2 3/2022 Davison et al.
11,284,886 B2 3/2022 Hartdegen et al.

(56) References Cited

U.S. PATENT DOCUMENTS 11,304,705 B2 4/2022 Fallin et al.
11,304,735 B2 4/2022 Sayger et al.
11,311,289 B1 4/2022 Ritz et al.
11,382,619 B2 7/2022 Wahl
11,439,415 B2 9/2022 Cundiff et al.
11,457,915 B2 10/2022 Wahl
11,478,254 B2 10/2022 Fallin et al.
11,529,178 B2 12/2022 Hansson et al.
11,547,425 B1 1/2023 Lebrija et al.
11,596,443 B2 3/2023 Treace et al.
11,607,250 B2 3/2023 Treace et al.
11,622,797 B2 4/2023 Decarbo et al.
11,771,443 B2 10/2023 Bays et al.
11,779,359 B2 10/2023 Sayger et al.
11,957,390 B2 4/2024 Sidebotham et al.
2003/0060827 A1 3/2003 CoughIn
2004/0116930 A1 6/2004 O'Driscoll et al.
2005/0033430 A1 2/2005 Powers et al.
2005/0192578 A1 9/2005 Horst
2006/0116679 A1 6/2006 Lutz et al.
2006/0149264 A1 7/2006 Castaneda et al.
2006/0235397 A1 10/2006 Sanders et al.
2006/0241607 A1 10/2006 Myerson et al.
2006/0241608 A1 10/2006 Myerson et al.
2006/0276795 A1 12/2006 Orbay et al.
2007/0088360 A1 4/2007 Orbay et al.
2007/0093839 A1 4/2007 Beckendorf et al.
2007/0123884 A1 5/2007 Abdou
2007/0191848 A1 8/2007 Wack et al.
2008/0015591 A1 1/2008 Castaneda et al.
2009/0118768 A1 5/2009 Sixto, Jr. et al.
2009/0210010 A1 8/2009 Strnad et al.
2009/0210013 A1 8/2009 Kay et al.
2009/0222047 A1 9/2009 Graham
2009/0254090 A1 10/2009 Lizee
2009/0281543 A1 11/2009 Orbay et al.
2010/0004691 A1 1/2010 Amato et al.
2010/0023010 A1 1/2010 Nelson et al.
2010/0125300 A1 5/2010 Blitz et al.
2010/0133316 A1 6/2010 Lizee et al.
2011/0008745 A1 1/2011 Mcquillan et al.
2011/0022099 A1 1/2011 Ashman
2011/0087295 A1 4/2011 Kubiak et al.
2011/0093017 A1 4/2011 Prasad et al.
2011/0137351 A1 6/2011 Huebner et al.
2011/0166607 A1 7/2011 Castaneda et al.
2011/0264149 A1 10/2011 Pappalardo et al.
2012/0022535 A1* 1/2012 Mayer .................. A61F 2/4611
606/1
2012/0065689 A1 3/2012 Prasad et al.
2012/0265204 A1 10/2012 Schmierer et al.
2013/0090695 A1 4/2013 Bernstein et al.
2013/0172942 A1 7/2013 Wright et al.
2013/0226248 A1 8/2013 Hatch et al.
2013/0238032 A1 9/2013 Schilter
2013/0261670 A1 10/2013 Laeng et al.
2014/0012887 A1 1/2014 Tamano
2014/0039549 A1 2/2014 Belsky et al.
2014/0052193 A1 2/2014 Prandi et al.
2014/0081341 A1 3/2014 Lin et al.
2014/0107650 A1 4/2014 Dacosta et al.
2014/0107798 A1 4/2014 Jeng et al.
2014/0172021 A1 6/2014 Castaneda et al.
2014/0180343 A1 6/2014 Gaudin
2014/0214093 A1 7/2014 Courtney et al.
2014/0257291 A1 9/2014 Houff
2014/0276881 A1 9/2014 Taylor
2014/0277176 A1 9/2014 Buchanan et al.
2015/0032168 A1 1/2015 Orsak et al.
2015/0039033 A1 2/2015 Biedermann
2015/0045839 A1 2/2015 Dacosta et al.
2015/0250514 A1 9/2015 Terrill et al.
2015/0282819 A1 10/2015 Austin et al.
2015/0313592 A1 11/2015 Coillard-Lavirotte et al.
2015/0313652 A1 11/2015 Burckhardt et al.
2015/0335366 A1 11/2015 Dacosta et al.
2015/0359580 A1 12/2015 Dacosta et al.
2016/0030098 A1 2/2016 Dacosta et al.
2016/0192970 A1 7/2016 Dayton et al.
2016/0235454 A1 8/2016 Treace et al.
2016/0256204 A1 9/2016 Patel et al.
2016/0338697 A1 11/2016 Biedermann et al.
2017/0007305 A1 1/2017 Hollis et al.
2017/0056083 A1 3/2017 Fallin et al.
2017/0181779 A1 6/2017 Leither et al.
2017/0196604 A1 7/2017 Hartdegen et al.
2017/0209193 A1 7/2017 Hartdegen et al.
2017/0252036 A1 9/2017 Palmer et al.
2018/0168617 A1 6/2018 Shelton, IV et al.
2018/0344371 A1 12/2018 Monk et al.
2019/0046183 A1 2/2019 Hartdegen et al.
2019/0150921 A1 5/2019 Fonte et al.
2019/0192140 A1 6/2019 Ducharme et al.
2019/0231404 A1 8/2019 Taylor et al.
2019/0357950 A1 11/2019 Bernstein et al.
2020/0000464 A1 1/2020 Gaston et al.
2020/0000465 A1 1/2020 Maclure et al.
2020/0008799 A1 1/2020 Isch et al.
2020/0038076 A1 2/2020 Amis et al.
2020/0046345 A1 2/2020 Zink et al.
2020/0197005 A1 6/2020 Daniel
2020/0229813 A1 7/2020 Seykora et al.
2020/0360063 A1 11/2020 Tellman
2021/0052289 A1* 2/2021 Stamp .................... A61B 17/17
2021/0077192 A1* 3/2021 Perler .................... G16H 30/40
2021/0113223 A1 4/2021 Schaumann et al.
2021/0128145 A1 5/2021 Taylor et al.
2021/0236180 A1 8/2021 Decarbo et al.
2021/0298748 A1 9/2021 Campbell et al.
2021/0386422 A1 12/2021 Maclure et al.
2022/0117599 A1 4/2022 Fein et al.
2022/0211387 A1 7/2022 Perler et al.
2022/0257267 A1 8/2022 Decarbo et al.
2022/0273348 A1 9/2022 Schaefer et al.
2022/0338934 A1 10/2022 Perler et al.
2022/0370082 A1 11/2022 Kuyler et al.
2022/0370211 A1 11/2022 Campbell et al.
2023/0000506 A1 1/2023 Schaumann et al.
2023/0013727 A1 1/2023 Korman et al.
2023/0255623 A1 8/2023 Ritz et al.
2023/0263536 A1 8/2023 Kuyler et al.
2023/0310013 A1 10/2023 Perler et al.
2023/0371966 A1 11/2023 Spitler

FOREIGN PATENT DOCUMENTS

CN 2701408 Y 5/2005
CN 101836888 A 9/2010
CN 201912210 U 8/2011
CN 102755186 A 10/2012
CN 103892954 A 7/2014
DE 4110123 A1 10/1992
EP 2389884 B1 7/2013
EP 2441406 B1 9/2013
ES 2379929 T3 5/2012
FR 3023468 A1 1/2016
GB 2252911 A 8/1992
IL 184773 A 7/2006
IN 200607174 P1 8/2007
JP 07313522 A 12/1995
KR 101081268 B1 11/2011
WO 2004024009 A1 3/2004
WO 2006065512 A1 6/2006
WO 2007006430 A1 1/2007
WO 2007106962 A1 9/2007
WO 2008029142 A2 3/2008
WO 2008029143 A2 3/2008
WO 2008149308 A1 12/2008
WO 2009091770 A1 7/2009
WO 2013186205 A1 12/2013
WO 2014152535 A1 9/2014
WO 2015094410 A1 6/2015
WO 2016003477 A1 1/2016
WO 2020026174 A1 2/2020

(56) References Cited

FOREIGN PATENT DOCUMENTS

| | | | |
|---|---|---|---|
| WO | 2021034799 | A1 | 2/2021 |
| WO | 2021178132 | A1 | 9/2021 |
| WO | 2021236838 | A1 | 11/2021 |

OTHER PUBLICATIONS

Acumed, "Hand Fracture System," Brochure, effective date Sep. 2014, reported publication date Jan. 29, 2016, 6 pages.
Acumed, "Hub Cap Fusion Plates," Retrieved from <http://www.acumed.net/products/hand-wrist/carpal/hub-cap- fusion-plates>, 2016, 8 pages.
Arthrex, "Double Compression Plates," Retrieved from <https://www.arthrex.com/foot-ankle/double-compression-plates>, 2016, 3 pages.
Arthrex, "Plantar Lapidus Plate," 2015, 6 pages.
Arthrex, "Proximal Metatarsal Osteotomy using Plates," Retrieved from <http://www.arthrex.com/foot-ankle/proximal-metatarsal-osteotomy-using-plates>, 2016, 2 pages.
Chang et al., "Lapidus Arthrodesis: A Different Perspective," Journal of the American Podiatric Medical Association, vol. 84, No. 6, Jun. 1994, pp. 281-288.
Couzens et al., "Stainless Steel Versus Titanium Volar Multi-Axial Locking Plates for Fixation of Distal Radius Fractures: A Randomised Clinical Trial," BMC Musculoskeletal Disorders, vol. 15, No. 74, Mar. 2014, 7 pages.
Horton et al., "Deformity Correction and Arthrodesis of the Midfoot with a Medial Plate," Foot & Ankle, vol. 14, No. 9, Nov./Dec. 1993, pp. 493-499.
International Searching Authority, "International Preliminary Report on Patentability", From Application No. PCT/US2024/015047, Dated Aug. 12, 2025, 9 pages.
International Searching Authority, "International Preliminary Report on Patentability", From Application No. PCT/US2024/015049, Aug. 12, 2025, 10 pages.
International Searching Authority, "International Preliminary Report on Patentability", From Application No. PCT/US2024/015054, mailed Aug. 12, 2025, 9 pages.
Diaconu et el., "Locking Plates for Fixation of Extra-Articular Fractures of the First Metacarpal Base: A Series of 15 Cases" Chirurgie de la Main, vol. 30, No. 1, pp. 26-30, Abstract only.
Merete GMBH, "MetaFix OpenWedge," Retrieved from <http://www.merete-medical.com/de/produkte/fuss/hallux-valgus/metafixr-openwedge.html>, 2016, 4 pages (Google Translation).
Osteomed, "ExtremiLock Ankle Plating System," Brochure, published prior to Nov. 20, 2014, 6 pages.
Osteomed, "ExtremiLock Foot Plating System," Brochure, published prior to Nov. 20, 2014, 6 pages.
Osteomed, "Hand Plating System," Brochure, published prior to Nov. 20, 2014, 8 pages.
Plaass et al, "Anterior Double Plating for Rigid Fixation of Isolated Tibiotalar Arthrodesis," Foot and Ankle International, vol. 30, No. 7, Jul. 2009, pp. 631-639.
Plaass et al., "Placement of Plantar Plates for Lapidus Arthrodesis: Anatomical Considerations," Foot and Ankle International, vol. 37, No. 4, Apr. 2016, pp. 427-432.
Rochet et al., "Proximal Ulna Comminuted Fractures: Fixation Using a Double-Plating Technique," Revue de Chirurgie Orthopdique et Traumatologique, vol. 96, No. 7, Nov. 2010, pp. 800-807.
Smith & Nephew, Inc, "D-Rad Smart Pack," Single-Use Volar Distal Radius Plating System, Brochure, Jun. 2014, 8 pages.
Smith & Nephew, Inc, "Evos Mini," Plating System, Brochure, May 2015, 12 pages.
Smith & Nephew, Inc, "Medial Column Fusion for Midfoot Deformity Correction," VLP Foot Variable Angle Locked Plating System, Surgical Technique, 2013, 20 pages.
Smith & Nephew, Inc, "Proximal Humerus Locking Plate," Peri-Loc Upper Extremity Locked Plating System, Surgical Technique, Sep. 2006, 36 pages.
Stryker, "Anchorage Plating System," Operative Technique, Rev. 2, Aug. 2015, 32 pages.
Stryker, "VariAx Foot Locked Plating System," Jun. 2008, 25 pages.
Synthes, "LCP Periprosthetic System," 2009, 8 pages.
Tornier, "CalcLock Extreme," Retrieved from <http://www.tornier-us.com/lower/foot/footra011/>, 2014, 2 pages.
Tornier, "CoverLoc Volar Plate," Retrieved from <http://www.tornier-us.com/upper/hand/writra003/>, 2016, 2 pages.
Tornier, "DFX Distal Fibula and DTX Distal Tibia Plates," Retrieved from <http://www.tornier-us.com/lower/ankle/anktra003/>, 2016, 2 pages.
Tornier, "Hand and Wrist," Retrieved from <http://www.tornier-us.com/upper/hand/>, 2016, 1 page.
Vilex, "The Vilex Plate System," Brochure, 2011, 4 pages.
Wright Medical Group N.V., "DARCO Modular Rearfoot System (MRS) LPS Lapidus Plating System," Brochure, Aug. 2016, 1 page.
Wright Medical Group N.V., "Foot & Ankle," Retrieved from <http://www.wright.com/physicians/foot-ankle>, 2016, 4 pages.
Zimmer, Inc. "Foot and Ankle Solutions," Retrieved from <http://www.zimmer.com/medical-professionals/products/ foot-and-ankle.html>, 2014, 3 pages.
International Searching Authority, "International Search Report and Written Opinion", From Application No. PCT/US2024/015047, mailed Jul. 2, 2024, 13 pages.
International Searching Authority, "International Search Report and Written Opinion", From Application No. PCT/US2024/015049, mailed Jun. 28, 2024, 14 pages.
International Searching Authority, "International Search Report and Written Opinion", From Application No. PCT/US2024/015054, mailed Jun. 28, 2024, 13 pages.

* cited by examiner 4050
4006
4000
4008
4004
3000
4010

CONTOUR GUIDE FOR SMALL BONE SURFACE MODIFICATION

RELATED APPLICATIONS

This disclosure claims priority to each of U.S. provisional patent application No. 63/444,226, filed on Feb. 8, 2023; U.S. provisional patent application No. 63/519,036, filed on Aug. 11, 2023; and U.S. provisional patent application No. 63/583,746, filed on Sep. 19, 2023. The contents of each of U.S. provisional patent application No. 63/444,226, U.S. provisional patent application No. 63/519,036, and U.S. provisional patent application No. 63/583,746 are hereby incorporated by reference in their entirety.

TECHNICAL FIELD

Embodiments of this disclosure generally relate to devices, systems, and techniques for small bone anatomy in the foot.

BACKGROUND

Bones within the human body, such as bones in the foot, may be anatomically misaligned. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion.

Surgical intervention may be used to correct a bunion deformity. A variety of different surgical procedures exist to correct bunion deformities and may involve removing the abnormal bony enlargement on the first metatarsal and/or realigning the first metatarsal relative to the adjacent metatarsal. In some procedures, an implant can be used to fixate a position of the metatarsal after realignment. The implant can be applied between the metatarsal and opposed cuneiform, across the tarsometatarsal joint. Such an implant can hold the metatarsal in a realigned position while bone grows to form a fused connection between the metatarsal and opposed cuneiform.

SUMMARY

In general, this disclosure is directed to devices, systems, and techniques for creating one or more bone surface modifications at one or more bones. Embodiments are disclosed herein relating to, for example, bone surface modification(s) as applied to small bone anatomy in the foot, though other embodiments within the scope of this disclosure can be applied to bones at other anatomical locations, such as applied to small bone anatomy in the hand and/or other bone anatomy elsewhere.

Embodiments disclosed herein for creating one or more bone surface modifications to one or more bones can be useful, for instance, in creating a suitable, modified bone surface at one or more bone portions and at which an implant can then be positioned. In one example, a contour guide can be configured to guide one or more bone surface modifications at one or more bone surface regions that are to contact an implant that is subsequently placed thereat. In this way, use of the contour guide can act to modify one or more bone surfaces so as to create a more suitable, modified bone surface for receiving the implant. Embodiments disclosed herein can also include help to guide placement of the implant at the modified bone surface, for instance, using an implant guide sleeve. In some examples, the implant can sleeve can be positioned relative to the contour guide (e.g., the contour guide slot) and/or the modified bone surface so that the implant guide sleeve is configured to help accurately guide placement of the implant at the modified bone surface.

Certain embodiments disclosed herein include devices, systems, and surgical techniques for modifying a bone surface that is to receive an implant and then guiding placement of that implant at the modified bone surface. Such embodiments can include modifying a surface at one or more bones, such as two opposed, separated bones. In the case of two opposed bones, the two bones can be separated, for instance, by a joint, an osteotomy location, or a bone fracture that is being fused together. In some implementations, the one or more bone surfaces can be modified after the one or more bone portions having the one or more bone surfaces have been moved to a corrected bone position following a realignment procedure. Certain contour guide features and implant guided placement techniques disclosed herein can be useful to help to facilitate more stable, efficient, and accurate implant placement and, as a result, when the implant is configured to fuse such bone portions more stable, efficient, and accurate bone fixation and resulting fusion. As one example, features relating to contour guide and implant guided placement techniques are disclosed herein that can help to increase the stability of implant placement relative to one or more target bones by modifying implant placement surface(s) at the one or more target bones to provide a more stable implant receiving surface at the one or more target bones while also helping to decrease the time it takes to suitably place the implant at one or more target bones.

A contour guide can be configured to receive thereat one or more bone surface modification instruments. The at least one bone surface modification instrument received at the contour guide can be configured to remove at least a portion of the surface at one or more bones. For example, the bone surface modification instrument received at the contour guide can be configured to break up bone at, or otherwise modify (e.g., smooth out the bone surface) the surface of the one or more bones to thereby create the modified surface region, for instance, that has a modified surface geometry in at least two dimensions. In one specific example, the bone surface modification instrument received at the contour guide can be configured to modify the surface of the one or more bones to thereby create the modified surface region that is more planar in two dimensions than that surface was prior to being modified using bone surface modification instrument received at the contour guide.

During a surgical procedure, an orthopedic implant can be applied to opposed bones across a separation between the bones, such as a joint separating different bones or a fracture or osteotomy separating a single bone into different bone portions. The implant can fixate the position of the bones relative to each other for healing during which bone growth closes the separation between the bones, fusing the bones together. Example implants that can be used during an orthopedic procedure include a bone plate that is secured to underlying bones using two or more screws and/or a bone staple having at least two legs that are inserted into underlying bones.

In practice, for instance in the case of small bone anatomy in the foot, it can be challenging for a clinician to align and stably place an implant at a target bone surface given the relatively small size of such bones and they generally curved nature of the exterior surface of such bones. Prior to placing the implant at the target bone surface, a contour guide can be aligned relative to the target bone surface that is to receive the implant. The contour guide can be placed relative to the target bone surface such that a guide slot of the contour guide can be aligned with the target bone surface that is to receive the implant. The bone surface modification instrument can be placed at the guide slot and, thus, the bone surface modification instrument can be guided by the contour guide for placement at the aligned target bone surface such that the bone surface modification is created at the target bone surface using the bone surface modification instrument relative to the contour guide. This can facilitate an accurate modification to the target bone surface in a way that modifies the target bone surface to be better suited for receiving the implant (e.g., more planar to more receive a planar bone facing surface of the implant). With the target bone surface modified, the implant can then be placed at the modified target bone surface, for instance, using an implant guide sleeve that is placed relative to the contour guide and/or relative to the modified target bone surface.

One embodiment includes a method of modifying a bone surface for receiving an implant. This method embodiment includes: positioning a contour guide at a first bone and a second bone and across a separation between the first bone and the second bone; using the contour guide to modify a surface region of at least one of the first bone and the second bone to form a modified surface region at one or both of the first bone and the second bone; and positioning an implant in contact at least with the modified surface region.

In a further embodiment of this method, using the contour guide to modify the surface region of at least one of the first bone and the second bone includes using the contour guide to modify a first surface region at the first bone to form a modified first surface region along the first bone and a second surface region at the second bone to form a modified second surface region along the second bone. And positioning the implant in contact at least with the modified surface region can include placing the implant in contact with each of the modified first surface region and the modified second surface region. For example, the implant can have an implant length. The modified first surface region and the modified second surface region can define a modified bone surface length along the first bone and the second bone, and the modified bone surface length can be equal to or greater than the implant length. As one specific such example, the implant can be a staple, the first bone can be a metatarsal, the second bone can be a cuneiform, and the separation between the first bone and the second bone can be a joint space between the metatarsal and the cuneiform. And positioning the implant in contact at least with the modified surface region includes placing a first leg of the staple through the modified first surface region at the metatarsal and placing a second leg of the staple through the modified second surface region at the cuneiform. In various example, the implant can be placed in contact with each of the modified first surface region and the modified second surface region and with the implant bridging the separation between the first bone and the second bone.

In a further embodiment of this method, using the contour guide to modify the surface region of at least one of the first bone and the second bone to form the modified surface region at one or both of the first bone and the second bone incudes positioning a bone surface modification instrument at the contour guide and in contact with the surface region of at least one of the first bone and the second bone. For example, the bone surface modification instrument, placed at the contour guide and in contact with the surface region of at least one of the first bone and the second bone, can be configured to break up bone at the surface region of at least one of the first bone and the second bone. For instance, the bone surface modification instrument, positioned at the contour guide and in contact with the surface region of at least one of the first bone and the second bone, can include at least one of a burr and a saw.

In a further embodiment of this method, the contour guide includes a contour guide body having a top side and a bottom side. The bottom side includes a guide slot that defines a guide slot cross-sectional area that is greater than a cross-sectional area of the implant. Positioning the contour guide includes positioning the bottom side of the contour guide at the first bone and the second bone and across the separation between the first bone and the second bone. For example, positioning the bottom side of the contour guide at the first bone and the second bone and across the separation between the first bone and the second bone can include positioning the guide slot over the first bone and the second bone and across the separation between the first bone and the second bone. In some such embodiments, the contour guide body can include a guide aperture, and using the contour guide to modify the surface region of at least one of the first bone and the second bone to form the modified surface region at one or both of the first bone and the second bone includes placing a bone surface modification instrument at least partially in the guide aperture, at least partially in the guide slot, and in contact with the surface region of at least one of the first bone and the second bone. For instance, the guide aperture can be aligned with the guide slot, and, when the contour guide is positioned at the first bone and the second bone and across the separation between the first bone and the second bone, the bone surface modification instrument can first inserted through the guide aperture, then inserted through the guide slot, and then placed in contact with the surface region of at least one of the first bone and the second bone to modify the surface region of at least one of the first bone and the second bone.

In a further embodiment of this method, the method can additionally include positioning an implant guide sleeve at the first bone and the second bone and across the separation between the first bone and the second bone. The contour guide can be positioned at the first bone and the second bone and across the separation between the first bone and the second bone using the implant guide sleeve. In one example, this method embodiment can further include, prior to positioning the contour guide at the first bone and the second bone and across the separation between the first bone and the second bone using the implant guide sleeve, fixating the implant guide sleeve at the first bone and the second bone. In another additional or alternative example, using the contour guide to modify the surface region of at least one of the first bone and the second bone to form the modified surface region at one or both of the first bone and the second bone can include using the contour guide to modify the surface region while the contour guide is positioned at least partially within the implant guide sleeve. In another additional or alternative example, after positioning the contour guide using the implant guide sleeve and after using the contour guide to modify the surface region of at least one of the first bone and the second bone to form the modified surface region at one or both of the first bone and the second bone, an inserter, operatively connected to the implant, can be advanced relative to the implant guide sleeve to place the implant in contact at least with the modified surface region.

Another embodiment includes a system. This system embodiment includes a contour guide and an implant guide sleeve. The contour guide includes a contour guide body having a top side and a bottom side. The bottom side is configured to interface with a first bone, a second bone, and a separation between the first bone and the second bone. The bottom side includes a guide slot that defines a guide slot cross-sectional area. The guide slot cross-sectional area is configured to receive a bone surface modification instrument to modify a surface region of at least one of the first bone and the second bone to form a modified surface region at one or both of the first bone and the second bone. The implant guide sleeve defines an interior cross-sectional area that is greater than the guide slot cross-sectional area. The interior area of the implant guide sleeve is configured to receive and guide placement of the bottom side of the contour guide body to interface with the first bone, the second bone, and the separation between the first bone and the second bone.

In a further embodiment of this system, the contour guide body can further include at least one guide aperture that extends through at least a portion of the contour guide body from the top side. The at least one guide aperture can be axially aligned with the guide slot, and the at least one guide aperture can be configured to at least partially receive the bone surface modification instrument. In one example, the at least one guide aperture includes a first guide aperture and a second guide aperture that is spaced apart from the first guide aperture. The first guide aperture can extend through at least a portion of the contour guide body from the top side at a first skewed orientation, and the second guide aperture can extend through at least a portion of the contour guide body from the top side at a second skewed orientation that is different than the first skewed orientation. Each of the first guide aperture and the second guide aperture can be configured to receive the bone surface modification instrument.

In a further embodiment of this system, the interior area of the implant guide sleeve can further be configured to both: (i) guide creation of a first implant hole at the modified surface region at first bone and a second implant hole at the modified surface region at the second bone, and (ii) guide placement of a first leg of an implant at the first implant hole at the modified surface region at the first bone and a second leg of the implant at the second implant hole at the modified surface region at the second bone.

Another embodiment includes a method of placing an implant at one or more bone portions. This method embodiment includes placing a trialing member at the one or more bone portions, the trialing member simulating a configuration of the implant at the one or more bone portions; determining a relative fit of the trialing member at the one or more bone portions; after placing the trialing member at the one or more bone portions, creating one or more implant receiving apertures at a location at the one or more bone portions where the trialing member was placed; and placing the implant at the one or more created implant receiving apertures.

In a further embodiment of this method, the implant is a staple, wherein the trialing member simulates at least one dimension of the staple. For example, trialing member can include a trialing bridge that defines a trialing arch, and the trialing arch can correspond to an arch defined by a bridge of the staple. For instance, determining a relative fit of the trialing member at the one or more bone portions can include determining a fit of the trialing arch at the one or more bone portions.

The details of one or more examples are set forth in the accompanying drawings and the description below. Other features, objects, and advantages will be apparent from the description and drawings, and from the claims.

BRIEF DESCRIPTION OF DRAWINGS

FIG. 5A is a perspective view of this embodiment of the staple, and FIG. 5B is a side elevational view of a longitudinal cross-section of the staple shown at FIG. 5A.

FIG. 9A shows disassembled components of this inserter, FIG. 9B shows assembled components of this inserter, and FIG. 9C shows this inserter operatively connected to a staple with a load force removed such that the staple is in its biased, compression state.

FIG. 11A is a perspective view of the implant guide sleeve positioned at a first bone, a second bone, and across a separation between the first bone and the second bone. FIG. 11B is a perspective view of the implant guide sleeve secured to the first bone and the second bone.

FIG. 11C is a perspective view of the implant guide sleeve used for guiding creation of implant holes. FIG. 11D is a perspective view of the implant guide sleeve used for aligning an inserter, operatively connected to the staple, with the implant guide sleeve. FIG. 11E is a perspective view of the implant guide sleeve used for advancing the inserter, relative to the implant guide sleeve, to position the staple at the first bone and the second bone. FIG. 11F is a perspective view of the inserter with the staple positioned in contact with the first bone and the second bone after the implant guide sleeve has been used to help guide positioning of the staple at the first and second bones and the implant guide sleeve is removed.

FIG. 12A is a top plan view of the implant guide sleeve positioned at a first bone, a second bone, and across a separation between the first bone and the second bone. FIG. 12B is a top plan view of the implant guide sleeve secured to the first bone and the second bone and used for guiding creation of implant holes. FIG. 12C is a top plan view of the implant guide sleeve used for aligning an inserter, operatively connected to the staple, with the implant guide sleeve and used for advancing the inserter, relative to the implant guide sleeve, to position the staple at the first bone and the second bone. FIG. 12D is a bottom plan view of the implant guide sleeve in isolation.

FIG. 12E is a top plan view of the implant guide sleeve at a first size configuration. FIG. 12F is a top plan view of the implant guide sleeve at a second size configuration, and FIG. 12G is a perspective view of the implant guide sleeve at the second size configuration. FIGS. 12H-12I illustrate the implant guide sleeve embodiment of FIGS. 12E-12G but with a modified guide sleeve profile, for instance, to help minimize incision size needed in using the implant guide sleeve. FIG. 12H is a bottom plan view of a bone facing side of the implant guide sleeve at the second size configuration, and FIG. 12I is a perspective view of the bone facing side of the implant guide sleeve at the second size configuration.

FIG. 15A is a perspective view of the contour guide along with an optional accompanying implant guide sleeve, FIG. 15B is an elevational view of the contour guide placed at the implant guide sleeve to modify a surface of one or more bone portions, and FIG. 15C is a perspective view of the contour guide placed at a different implant guide sleeve embodiment.

FIG. 16A is a perspective view of the trialing member at the drill guide, FIG. 16B is an elevational view of the trialing member placed at one or more bone portions, and FIG. 16C is a plan view of the trialing member at the drill guide.

FIG. 16D is a perspective view and FIG. 16E is a top plan view of the exemplary trialing member at the drill guide with one or more pin apertures included.

FIG. 17A is a perspective view of the trialing member at the drill guide, and FIG. 17B is an elevational view of the trialing member placed at one or more bone portions.

FIG. 17C is a perspective view and FIG. 17D is a top pan view of the trialing member at the drill guide with one or more pin apertures included.

FIG. 19A is a side elevational view of the pinning and drilling instrument embodiment in a pinning configuration. FIG. 19B is a side elevational view of the pinning and drilling instrument embodiment in a drilling configuration.

FIG. 20A is a side elevational view of the pinning and drilling instrument embodiment in a pinning configuration. FIG. 20B is a side elevational view of the pinning and drilling instrument embodiment in a drilling configuration.

FIG. 22A is a side elevational view of exemplary pinning and drilling instruments being advanced toward an exemplary drill guide that is placed at bone portions of a foot. FIG. 22B is a side elevational view of the pinning and drilling instruments each inserted a first distance into the respective bone portion such that a pin portion of the respective pinning and drilling instrument is inserted into the respective bone portion. FIG. 22C is a side elevational view of the pinning and drilling instruments each inserted a second, further distance into the respective bone portion such that a drill portion of the respective pinning and drilling instrument is inserted into the respective bone portion.

Like reference characters are used in the following description and in the drawings to indicate like elements.

DETAILED DESCRIPTION

Figure 1B:
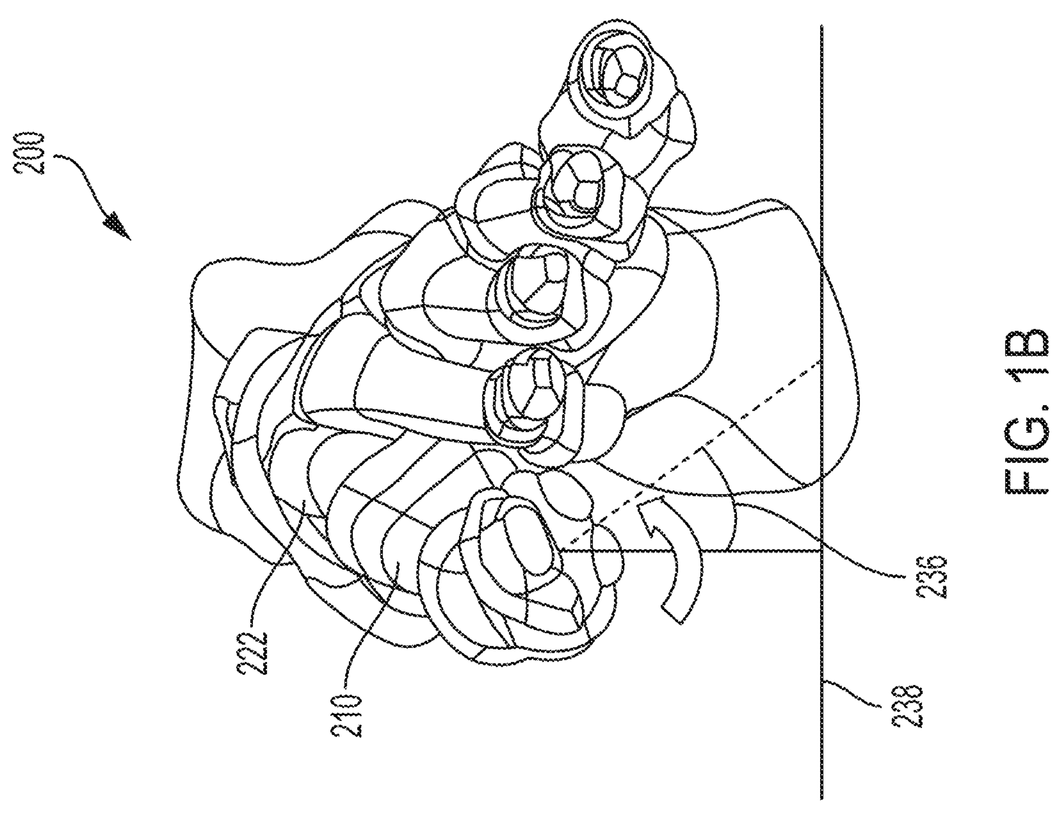
FIGS. 1A and 1B are front views of a foot showing a normal first metatarsal position and an example frontal plane rotational misalignment position, respectively.

This disclosure generally relates to devices, systems (e.g., kits), and techniques for fixating one or more bones using one or more guide sleeves to position one or more implants, including devices, systems, and techniques for fixating repositioned bones in the foot using one or more guide sleeves to position one or more implants. In some examples, a guide sleeve can be used to align and advance an implant at one or more bones, for instance, to fixate a repositioned bone, or bones, during a surgical procedure, such as a metatarsal realignment and fusion procedure. In exemplary applications, the devices, systems, and techniques can be used during a surgical procedure performed on one or more bones, such as a bone alignment, osteotomy, fusion procedure, fracture repair, and/or other procedures where one or more bones are to be set in a desired position. Such a procedure can be performed, for example, on bones (e.g., adjacent bones separated by a joint or different portions of a single bone) in the foot or hand, where bones are relatively small compared to bones in other parts of the human anatomy. In one example, a procedure utilizing devices and/or techniques of the disclosure can be performed to correct an alignment between a metatarsal (e.g. a first metatarsal) and a cuneiform (e.g., a medial cuneiform), such as a bunion correction. An example of such a procedure is a lapidus procedure. In another example, the devices, systems, and/or techniques can be utilized when modifying a position of one portion of a bone relative to another portion of the same bone. An example of such a procedure is an osteotomy procedure (e.g., metatarsal osteotomy procedure) in which the bone is cut into at least two different bones and one portion (e.g., a distal portion) is realigned relative to another bone portion (e.g., a proximal portion) of the same bone.

Preparation, fixation, and/or fusion of two opposed bone portions, such as a metatarsal and cuneiform, may be performed according to the disclosure for a variety of clinical reasons and indications. Preparation and fusion of a metatarsal and cuneiform at the tarsometatarsal ("TMT") joint may be performed to treat hallux valgus and/or other bone and/or joint conditions.

Hallux valgus, also referred to as hallux abducto valgus, is a complex progressive condition that is characterized by lateral deviation (valgus, abduction) of the hallux and medial deviation of the first metatarsophalangeal joint. Hallux valgus typically results in a progressive increase in the hallux abductus angle, the angle between the long axes of the first metatarsal and proximal phalanx in the transverse plane. An increase in the hallux abductus angle may tend to laterally displace the plantar aponeurosis and tendons of the intrinsic and extrinsic muscles that cross over the first metatarsophalangeal joint from the metatarsal to the hallux. Consequently, the sesamoid bones may also be displaced (e.g., laterally relative to the first metatarsophalangeal joint), resulting in subluxation of the joints between the sesamoid bones and the head of the first metatarsal. This can increase the pressure between the medial sesamoid and the crista of the first metatarsal head.

While techniques and devices are generally described herein in connection with the first metatarsal and medial cuneiform of the foot, the techniques and devices may be used on other adjacent bones (e.g., separated from each other by a joint) and/or adjacent bone portions (e.g., portions of the same bone separated from each other by a fracture or osteotomy). In various examples, the devices, systems, and/or techniques of the disclosure may be utilized on comparatively small bones in the foot such as a metatarsal (e.g., first, second, third, fourth, or fifth metatarsal), a cuneiform (e.g., medial, intermediate, lateral), a cuboid, a phalanx (e.g., proximal, intermediate, distal), and/or combinations thereof. The bones may be separated from each other by a tarsometatarsal ("TMT") joint, a metatarsophalangeal ("MTP") joint, or other joint. Accordingly, reference to a first metatarsal and medial cuneiform herein may be replaced with other bone pairs as described herein. Further, where an implant according to the disclosure is intended to be used on a different bone or combination of bones other than the first metatarsal and medial cuneiform, the configuration of the implant (e.g., size, shape) may be adjusted to accommodate the specific bone or combination of bones being fixated while following the implant, such as staple, configuration teachings outlined herein.

To further understand example devices, systems, and techniques of the disclosure, the anatomy of the foot will first be described with respect to FIGS. 1-3 along with example misalignments that may occur and be corrected and fixated according to the present disclosure. A bone misalignment may be caused by hallux valgus (bunion), a natural growth deformity, and/or other condition.

Figure 1A:
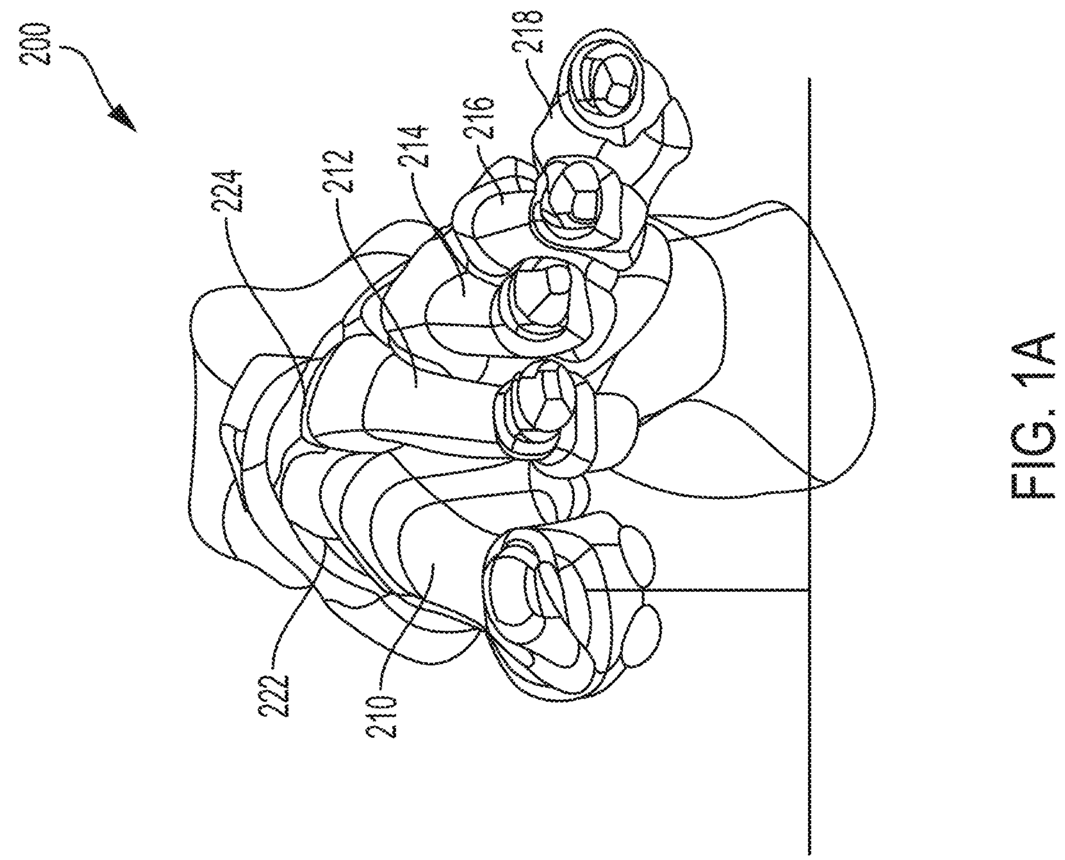
Figure 2B:
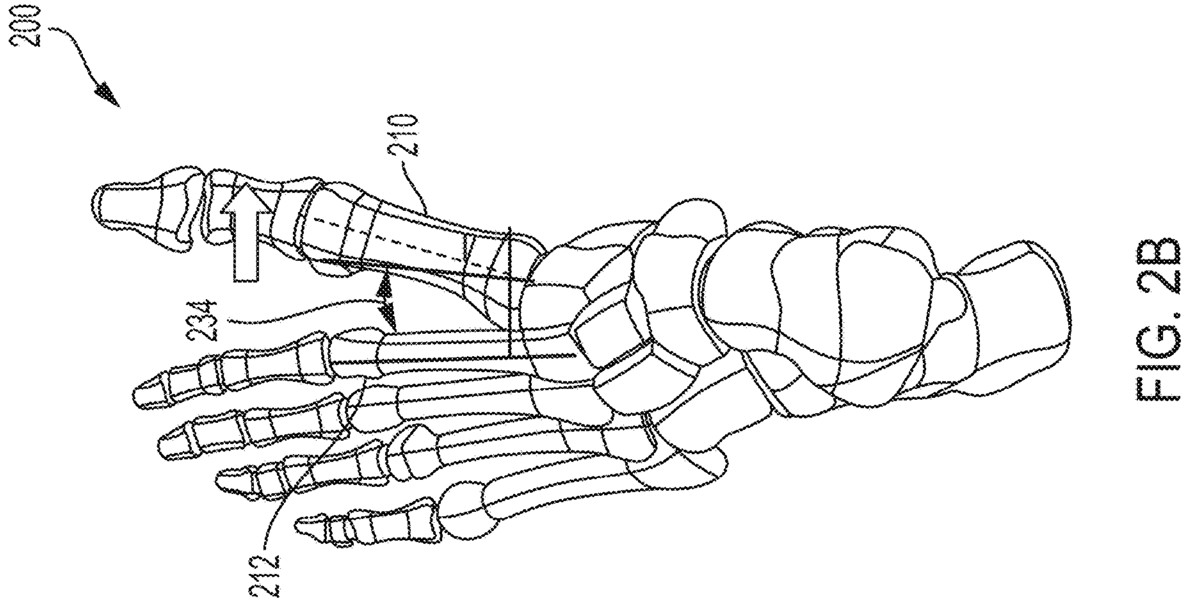
FIGS. 2A and 2B are top views of a foot showing a normal first metatarsal position and an example transverse plane misalignment position, respectively.
Figure 2A:
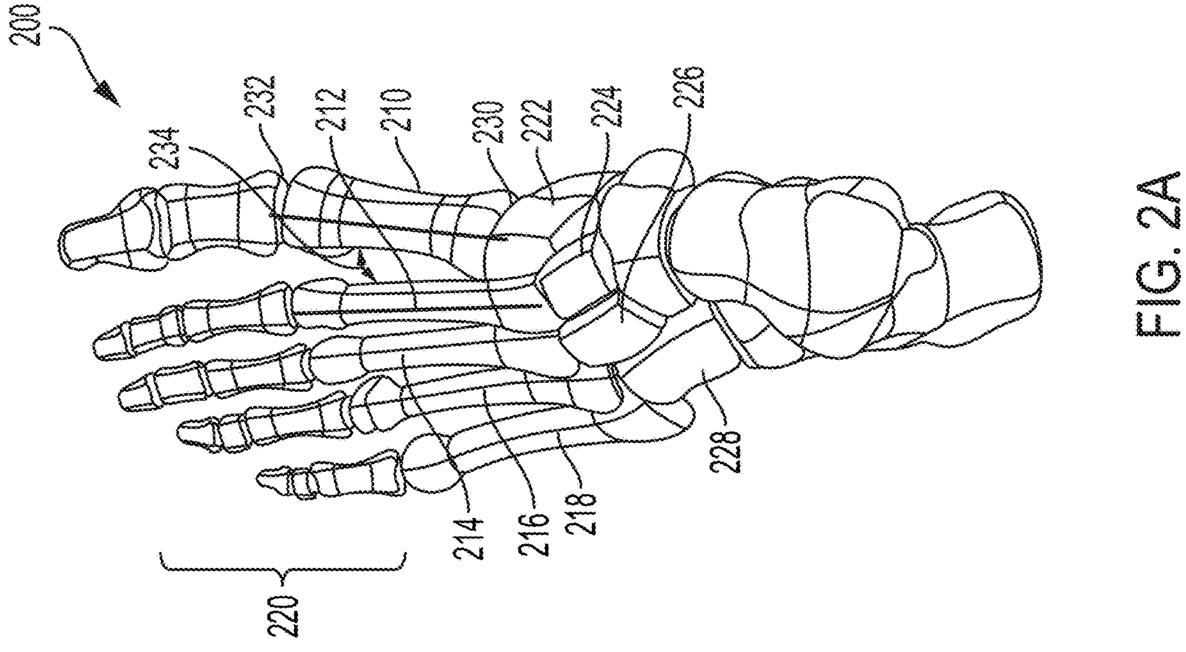
Figures 3A, 3B:
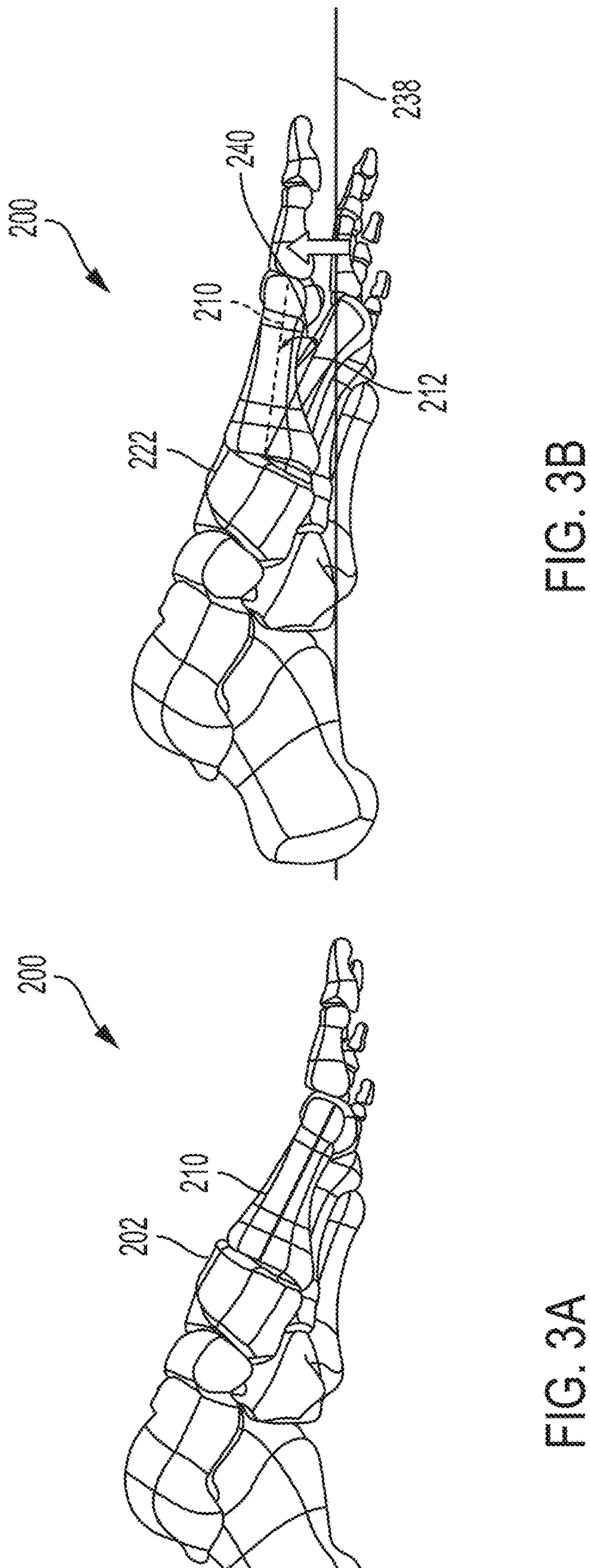
FIGS. 3A and 3B are side views of a foot showing a normal first metatarsal position and an example sagittal plane misalignment position, respectively.

FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected. Further, a bone condition treated according to the disclosure may not present any of the example misalignments described with respect to FIGS. 1B, 2B, and 3B, and it should be appreciated that the disclosure is not limited in this respect.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal 214 is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal

210 with a typical rotational position in the sagittal plane. FIG. 3B shows first metatarsal 210 with a sagittal plane rotational deformity characterized by a rotational angle 240 relative to ground, as indicated by line 238.

Surgical techniques and instruments according to the disclosure can be useful during a procedure to correct a misalignment of one or more bones, such as the metatarsal and opposed cuneiform, and/or to promote fusion of the metatarsal and cuneiform across the TMT joint. In some applications, a realignment procedure involves surgically accessing the TMT joint (e.g., from a medial side of the foot and/or a dorsal side of the foot). The clinician can insert a bone preparation instrument through an incision to prepare the end face of one or both bones.

Before or after preparing one or both ends of first metatarsal 210 and medial cuneiform 222, the clinician can realign the metatarsal relative to the cuneiform. The clinician can pivot the distal end of first metatarsal 210 laterally toward second metatarsal 212 to close an intermetatarsal angle between the first and second metatarsal. Additionally or alternatively, the clinician can rotate first metatarsal 210 in the frontal plane to correct a frontal plane rotation of the metatarsal and/or move the first metatarsal 210 in the sagittal plane to correct a sagittal plane position of the metatarsal. Realignment of first metatarsal 210 can be performed freehand by the clinician or with the aid of a bone positioning device to facilitate the realignment. After desired realignment in one or more planes, the clinician can fixate the moved position of first metatarsal 210 by applying one or more implants (e.g., one or more staples, plates, pins, screws, rods). The present disclosure provides exemplary embodiments of a staple as one type of implant that can be used to fixate one or more bones for fusion, though other embodiments within the scope of this disclosure can use the teachings outlined herein applied to other types of implants, such as a plate, for fixating one or more bones for fusion.

Figure 4:
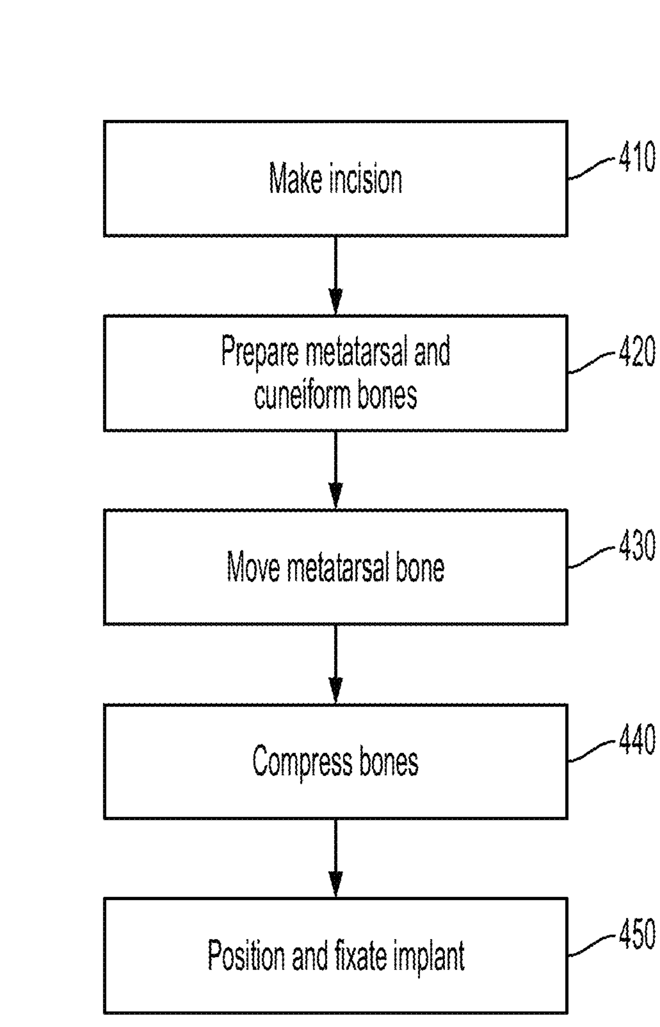
FIG. 4 is a flow diagram of an example surgical technique for positioning and fixating an implant.

FIG. 4 is a flow diagram of an example method 400 that can include, among other steps, positioning an implant to fixate bones for fusion. As will be described, in one example, the method 400 can be used to prepare, realign, and fixate a tarsometatarsal joint. One or more portions of the method 400 relating to positioning and fixating an implant to fixate bones for fusion (step 450) will be described further with reference to FIGS. 5-14. Additional details on example surgical techniques, including example instrumentation that can be used during the techniques, can be found in U.S. Pat. No. 9,622,805, issued Apr. 18, 2017 and entitled "BONE POSITIONING AND PREPARING GUIDE SYSTEMS AND METHODS" and US patent Publication No. 2020/0015856, published Jan. 16, 2020 and entitled "COMPRESSOR-DISTRACTOR FOR ANGULARLY REALIGNING BONE PORTIONS," the entire contents of each of which are incorporated herein by reference.

At step 410, the method 400 includes making an incision. The incision can be made through the skin, such as on a dorsal side of the foot, a medial side of the foot, or on a dorsal-medial side of the foot. The incision can be made to provide surgical access to the TMT joint 230 which separates first metatarsal 210 from opposed medial cuneiform 222. To surgically access the joint, the patient may be placed in a supine position on the operating room table and general anesthesia or monitored anesthesia care administered. Hemostasis can be obtained by applying thigh tourniquet or mid-calf tourniquet. In some examples, imaging of the foot can be used to assist the clinician in ascertaining the location of TMT joint 230 about which incision can be centered when subsequently cutting through skin.

At step 420, the method 400 includes preparing first metatarsal 210 and/or medial cuneiform 222. With the TMT joint 230 exposed via the incision, an end face (e.g., proximal end face) of first metatarsal 210 and/or an end face (e.g., distal end face) of medial cuneiform 222 can be prepared. It is to be noted that one or both of the end faces of the metatarsal and the cuneiform can be prepared before and/or after the metatarsal is moved relative to the cuneiform in one or more planes. Accordingly, unless otherwise specified, the order of bone preparation and/or movement is not limited.

In general, the clinician can prepare the end of each bone forming TMT joint 230 so as to promote fusion of the bone ends across the TMT joint following realignment. Bone preparation may involve using a tissue removing instrument to apply a force to the end face of the bone so as to create a bleeding bone face to promote subsequent fusion. Example tissue removing instruments that can be used include, but are not limited to, a saw, a rotary bur, a rongeur, a reamer, an osteotome, a curette, and the like. The tissue removing instrument can be applied to the end face of the bone being prepared to remove cartilage and/or bone. For example, the tissue removing instrument may be applied to the end face to remove cartilage (e.g., all cartilage) down to subchondral bone. Additionally or alternatively, the tissue removing instrument may be applied to cut, fenestrate, morselize, and/or otherwise reshape the end face of the bone and/or form a bleeding bone face to promote fusion. In instances where a cutting operation is performed to remove an end portion of a bone, the cutting may be performed freehand or with the aid of a cutting guide having a guide surface positionable over the portion of bone to be cut. When using a bone preparation guide, a cutting instrument can be inserted against a guide surface (e.g., between a slot define between two guide surfaces) of the bone preparation guide to guide the cutting instrument for bone removal.

At step 430, the method 400 includes moving first metatarsal 210. As noted, first metatarsal 210 can be moved before and/or after first metatarsal 210 and/or medial cuneiform 222 are prepared. Moving first metatarsal 210 at step 430 can include moving first metatarsal 210 in at least one plane. For example, first metatarsal 210 can be moved in at least transverse plane to close IMA 234 between first metatarsal 210 and adjacent second metatarsal 212 and/or a frontal plane (e.g., to reposition the sesamoid bones substantially centered under the metatarsal). In some examples, first metatarsal 210 can be moved in multiple planes, such as the transverse plane and/or frontal plane and/or sagittal plane (e.g., each of the transverse, frontal, and sagittal planes). The clinician may or may not utilize a bone positioning device to facilitate movement of the bone portion. The moved position of first metatarsal 210 can result is realignment of first metatarsal 210 relative to one of more other adjacent bones.

At step 440, the method 400 may include compressing one or more bones. In some embodiments, the step 440 can be omitted depending on the realigned position of the first metatarsal 210. When step 440 is included, the prepared end faces of the bone portions of first metatarsal 210 and medial cuneiform 222 can be compressed together prior to fixating one or more plates at these bones. The clinician may compress the end faces together with hand pressure and/or using a compressing instrument physically attached to both the first bone portion and the second bone portion. Accordingly, discussion of applying an implant to a first bone portion and a second bone portion, with the implant bridging a space between the bone portions, refers to the implant bridging a separation (e.g., joint, osteotomy, fracture)

between the two bone portions but does not require a gap between the bone portions, as the end faces of the bone portions may be in contact with each other and compressed together.

At step 450, the method 400 includes positioning an implant (e.g., an embodiment of a staple disclosed herein) over a portion of first metatarsal 210 and over a portion of medial cuneiform 222 and across TMT joint 230 separating first metatarsal 210 from medial cuneiform 222. For example, positioning an implant at step 450 can include positioning an embodiment of a staple (e.g., compression staple) using an implant guide sleeve. Positioning an implant, such as a staple, can include using an implant guide sleeve to position at least one leg of the staple over first metatarsal 210 and position at least another leg of the staple over medial cuneiform 222 with a bridge, which connects the legs of the staple, extending across the TMT joint 230. Further, in some examples, positioning an implant, such as a staple, can include using an implant guide sleeve to position one leg of the staple over first metatarsal 210 and then into contact with first metatarsal 210 in a first implant hole at first metatarsal 210 and to position another leg of the staple over medial cuneiform 222 and then into contact with medial cuneiform 222 in a second implant hole at medial cuneiform 222. As described further herein, the implant guide sleeve can also be used to help create the implant hole(s) at the respective bones (e.g., the same implant guide sleeve used to create the implant hole at the respective bones and to guide positioning of the implant).

FIGS. 5A-8 illustrate various embodiments of a staple as one exemplary type of implant that can be positioned using the implant guide sleeve and used to fixate bones for fusion.

Figure 5A:
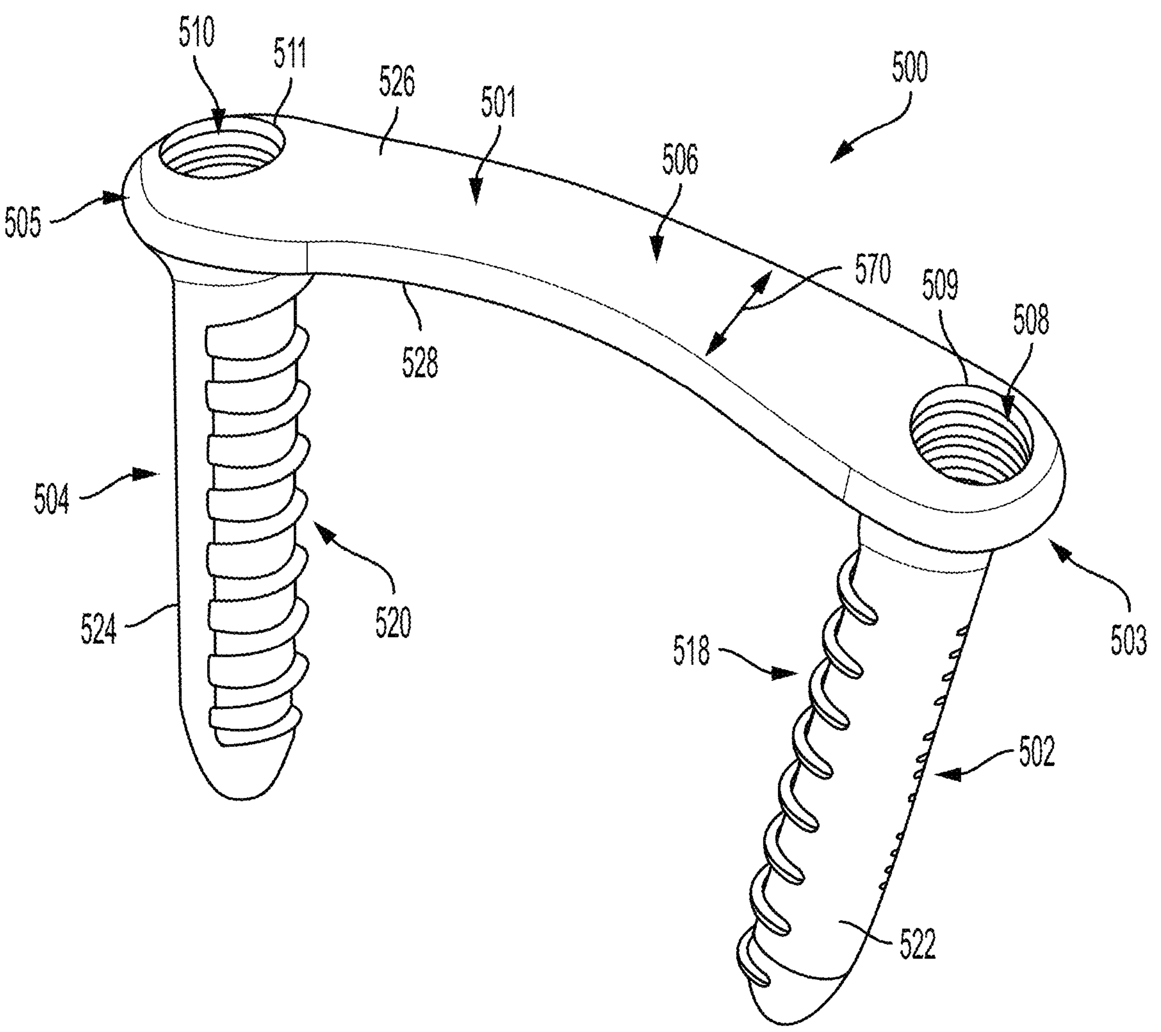
FIGS. 5A and 5B illustrate an orthopedic implant in the form of a staple.
Figure 5B:
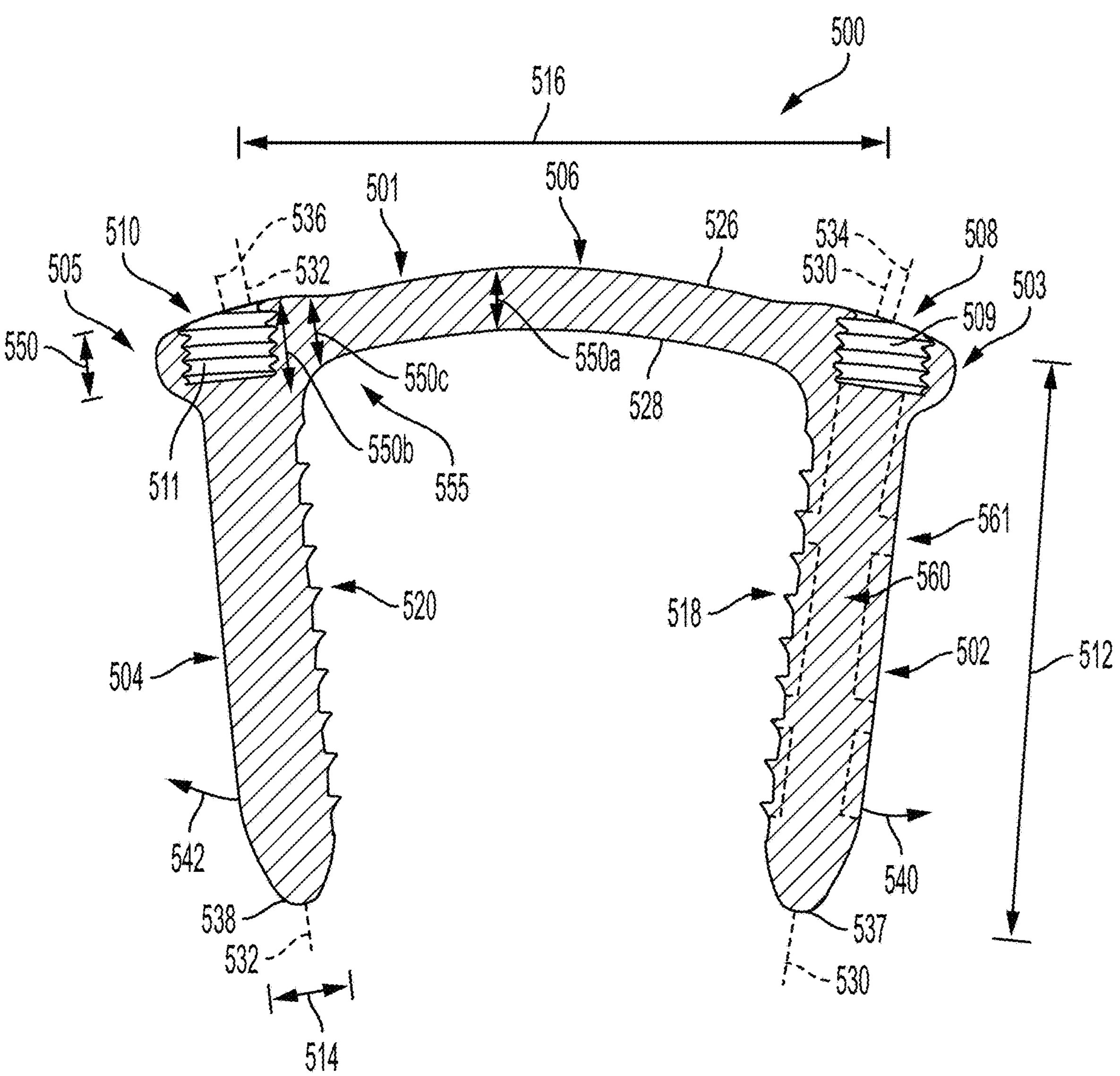

FIGS. 5A and 5B illustrate an embodiment of a staple 500. FIG. 5A is a perspective view of the staple 500, and FIG. 5B is a side elevational view of a longitudinal cross-section of the staple 500. As described elsewhere herein, the staple 500 can be configured to apply a compression force at the bones and across the space (e.g., joint) between the bones for use in fixating and fusing bones.

The staple 500 can include a staple body 501 having a first leg 502, a second leg 504, and a bridge 506. For the illustrated embodiment, the staple 500 includes the first leg 502 at a first side 503 of the staple 500 and the second leg 504 at a second side 505 of the staple 500. In this example, the first side 503 is opposite the second side 505. The bridge 506 can connect the first leg 502 and the second leg 504.

The legs 502, 504 of the staple 500 can be configured for positioning in bones, such as one or more relatively small bones of the foot. For example, a length 512 of each of the legs 502, 504 can range from 8 mm to 25 mm, which can provide sufficient length to robustly anchor within a bone of the foot, such as a metatarsal (e.g., first metatarsal) and/or cuneiform (e.g., medial cuneiform). A width 514 of each of the legs can range from 2 mm to 3 mm, which likewise can provide sufficient length to robustly anchor within a bone of the foot. A bridge length 516 of the bridge 506 can range from 12 mm to 20 mm, which can be sufficient to allow for positioning the bridge across a space (e.g. joint) between bones in the foot while maintaining the legs 502, 504 at such bones separated by the space. A staple according to the disclosure can be configured with dimensions other than the foregoing examples, and the disclosure is not limited in this respect.

As an example shown at FIG. 5B, the bridge length 516 can be as measured from a central longitudinal axis of one leg closest to one side of the bridge 506 to a central longitudinal axis of another leg closest to an opposite side of the bridge 506. The bridge 506 can also define a bridge width 570. In some examples, the bridge width 570 of the staple 500 is constant over the entire width of the staple. In other examples, the bridge width 570 of the staple 500 varies over the width of the staple. For example, the bridge width 570 can be substantially constant over a central region along the bridge length 516, and the bridge width 570 can increase moving along the bridge length 516 from the central region toward each of the first leg 502 and the second leg 504 (e.g., such that the greatest bridge width 570 is at or adjacent the first and second legs 502, 504). As one specific such example, the bridge width 570 can define a generally hourglass profile with the narrow, center of the hourglass at a central region along the bridge length 516 and the increasing width end portions of the hourglass at opposite ends of the bridge length 516.

The first leg 502 can include a first set of teeth 518 at a perimeter 522 of the first leg 502, and the second leg 504 can include a second set of teeth 520 at a perimeter 524 of the second leg 504. The teeth 518, 520 can extend out from the respective leg 502, 504 and be configured to provide an anchoring mechanism for maintaining the respective leg 502, 504 within the respective bone at which the respective leg 502, 504 is placed. As illustrated here, the first set of teeth 518 can extend partially around the perimeter 522 of the first leg 502, and the second set of teeth 520 can extend partially around the perimeter 524 of the second leg 504. For example, the first set of teeth 518 can extend around a portion of the perimeter 522 of the first leg 502 facing the bridge 506, and the second set of teeth 520 can extend around a portion of the perimeter 525 of the second leg 504 facing the bridge 506. As one specific such example, the first set of teeth 518 can extend around approximately one hundred and eighty degrees of the perimeter 522 of the first leg 502 nearest the bridge 506, and the second set of teeth 520 can extend around approximately one hundred and eighty degrees of the perimeter 524 of the second leg 504 nearest the bridge 506.

The staple 500 can further include a first handling coupling 508 and a second handling coupling 510 defined by the staple body 501. For the illustrated embodiment, the staple 500 includes the first handling coupling 508 at the first side 503 of the staple 500 and the second handling coupling 510 at the second side 505 of the staple 500. The first handling coupling 508 can include a first handling coupling receptacle 509 extending from a top surface 526 of the staple body 501 of the staple 500 toward (e.g., to) a bottom surface 528 of the staple body 501 of the staple 500. As one such specific example, the first handling coupling receptacle 509 can extend from the top surface 526 down a portion, but less than all of, of the length 512 of the first leg 502. The second handling coupling 510 can include a second handling coupling receptacle 511 extending from the top surface 526 of the staple body 501 of the staple 500 toward (e.g., to) the bottom surface 528 of the staple body 501 of the staple 500. As one such specific example, the second handling coupling receptacle 511 can extend from the top surface 526 down a portion, but less than all of, of the length 512 of the second leg 504. As such, the first handling coupling 508 and first handling coupling receptacle 509 as well as the second handling coupling 510 and second handling coupling receptacle 511 can be accessible from the top surface 526 of the staple 500 which can be useful in helping to facilitate generally flush placement of the bottom surface 528 of the staple 500 against one or more bones (e.g., against each of two bones separated by a space, such as a joint).

The first handling coupling receptacle 509 of the first handling coupling 508 can be configured to couple to a first coupling shaft of an inserter, such as at a location between the top surface 526 and the bottom surface 528. The second handling coupling receptacle 511 of the second handling coupling 510 can be configured to couple to a second coupling shaft of an inserter, such as at a location between the top surface 526 and the bottom surface 528. As such, the first and second handling coupling receptacles 509, 511 can be configured to operatively couple to the respective first and second coupling shafts of the inserter such that the first and second coupling shafts of the inserter are inserted into the respective first and second handling coupling receptacles 509, 511 from the top surface 526 and maintained within the respective first and second handling coupling receptacles 509, 511 so as to not extend out from the bottom surface 528. The illustrated embodiment of the first and second handling coupling receptacles 509, 511 includes threads extending along a length of the first and second handling coupling receptacles 509, 511 between the top and bottom surfaces 526, 528, and these threads can be configured to connect to complementary threads at the respective first and second coupling shafts of the inserter. Though in other embodiments the first and second handling coupling receptacles 509, 511 and first and second coupling shafts of the inserter can include others means to facilitate an operative connection therebetween the respective components.

Depending on the application in which the staple 500 is used, the staple 500 can be configured to receive one or more solid or liquid substances after insertion of the staple into bone. As one such example, one or both of the first and second handling coupling receptacles 509, 511 can be configured to receive a filler material therein to substantially plug the first and/or second handling coupling receptacles 509, 511 at the top surface 526. This filler material can be placed in the first and/or second handling coupling receptacles 509, 511 after removing the respective first and/or second coupling shaft from the respective first and/or second handling coupling receptacles 509, 511. For instance, a biologically compatible wax or other biologically compatible filler material can be placed into the first and/or second handling coupling receptacles 509, 511 to plug the first and/or second handling coupling receptacles 509, 511 at or near the top surface 526 so as to help impede passage of biologic substances into the first and/or second handling coupling receptacles 509, 511.

As another such example, one or both of the legs 502, 504 can be configured to receive and convey a substance therethrough. For instance, a cannula 560 can be defined within one or both of the legs 502, 504, and the cannula 560 can extend along at least a portion (e.g., all) of the length 512 of the leg 502 and/or 504. When included, the cannula 560 can have an inlet, for instance at the respective handling coupling 508, 510, and the cannula 560 can have one or more outlets 561 at a location along the respective leg 502, 504 spaced apart from the respective handling coupling 508, 510. For the illustrated embodiment, the outlets 561 can be included at the respective leg 502 and/or 504 between teeth 518, 520. A medication, structural support substance, or other biologically compatible substance can be introduced into the cannula 560 at the inlet (e.g., at the respective handling coupling 508, 510) and this substance can be delivered to one or more bones, at which the staple 500 is placed, via the one or more outlets 561.

Additionally or alternatively, the staple 500 can be configured with a cannulation extending through the length of leg 502 and/or 504 for receiving corresponding wires inserted into bone to help facilitate positioning and placement of the staple into underlying bone. For example, in lieu of using an inserter having wire receiving openings to guide positioning of an implant as will be described, wires inserted into underlying bones can be aligned with cannulations extending through at least two legs of the staple. The cannulations can be aligned with the wires positioned in the bones and the staple guided along the wires.

The first leg 502 can define, and length 512 of the leg can extend along, a first leg central longitudinal axis 530, and the second leg 504 can define, and the length 512 of the leg can extend along, a second leg central longitudinal axis 532. Likewise the first handling coupling receptacle 509 can define, and extend a length from the top surface 526 toward (e.g., to) the bottom surface 528 along, a first handling coupling receptacle central longitudinal axis 534, and the second handling coupling receptacle 511 can define, and extend a length from the top surface 526 toward (e.g., to) the bottom surface 528 along, a second handling coupling receptacle central longitudinal axis 536.

As shown for the illustrated embodiment of the staple 500 at FIG. 5B, the first leg central longitudinal axis 530 can be offset from the first handling coupling receptacle central longitudinal axis 534, and the second leg central longitudinal axis 532 can be offset from the second handling coupling receptacle central longitudinal axis 536. In particular, in this illustrated embodiment of the staple 500, the first leg central longitudinal axis 530 can be closer to the bridge 506 than the first handling coupling receptacle central longitudinal axis 534, and the second leg central longitudinal axis 532 can be closer to the bridge 506 than the second handling coupling receptacle central longitudinal axis 536. This offset arrangement can be helpful to increase a cross-sectional area at an intersection of the bridge 506 and the first leg 502 and/or the second leg 504 and, thereby, help to increase the ability of the staple body 501 of the staple 500 to accommodate a load force, applied at the staple 500, in a manner that results in elastic deformation of the staple 500 as the staple 500 moves between a natural, undeformed state and a deformed insertion state upon application/removal of a load force.

The staple 500 can have a thickness 550 that can differ at different regions of the staple 500. For example, the staple 500 can have a bridge thickness 550*a* at the bridge 506, a leg thickness 550*b* at the first leg 502 and the second leg 504, and a thickness transition region 555 where the bridge 506 transitions to the respective first leg 502 and the second leg 504. As shown for the illustrated embodiment, the leg thickness 550*b* can be greater than the bridge thickness 550*a* (e.g., at a central location of the bridge along the bridge length 516), and the thickness transition region 555 can have a thickness transition region thickness 550*c* that is greater than the bridge thickness 550*a* and less than the leg thickness 550*b*. In particular, the thickness transition region 555 can include an increase in thickness of the staple 500 moving in a direction from the bridge 506 toward the respective leg 502, 504. In one example, the first handling coupling 508 and the first handling coupling receptacle 509 can be located at the thickness transition region 555 adjacent the first leg 502, and the second handling coupling 510 and the second handling coupling receptacle 511 can be located at the thickness transition region 555 adjacent the second leg 504. Such location of the first handling coupling 508 and the first handling coupling receptacle 509 as well as the second handling coupling 510 and the second handling coupling receptacle 511 at the increased thickness portion of the staple 500 can help to increase the strength of the staple 500 for receiving a load force.

As noted, the staple 500 can be configured to have a natural, undeformed state, an example of such state is shown at FIGS. 5A and 5B, and to transition to a deformed insertion state upon application of a load force at the staple 500. For example, the staple 500 can have the biased compression-inducing state where the first leg 502 and the second leg 504 are angled toward one another, which can help to apply a compression force to urge bones together when the staple 500 is positioned at and across such bones. Upon application of a load force to the staple 500, the staple 500 can be configured to transition from a undeformed state in which the legs of the staple are at their natural or resting positions to a deformed insertion state at which the first and second legs 502, 504 (e.g., end portion 537 of first leg 502 and end portion 538 of second leg 504) are spaced further apart (e.g., and oriented generally parallel to one another) as compared to the natural state. In particular, the staple 500 can be configured such that upon application of the load force at the staple 500, the first leg 502 is configured to move in a direction 540 (e.g., away from the bridge 506) and the second leg 504 is configured to move in a direction 542 (e.g., away from the bridge 506) from the undeformed state to the deformed insertion state. Conversely, upon reduction or removal of the applied load force at the staple 500, the staple 500 can be configured such that the first leg 502 is configured to move in a direction opposite the direction 540 (e.g., toward the bridge 506) from the deformed insertion state back toward the undeformed state and the second leg 504 is configured to move in a direction opposite the direction 542 (e.g., toward the bridge 506) from the deformed insertion state back toward the deformed state.

In use, the staple 500 can provide compression across the end faces of the bones into which the staple is inserted. Compression can occur when the legs of the staple are inserted into the bones (e.g., into pre-drilled implant openings in the bones) at a spacing and/or angle greater than the natural, undeformed configuration of the legs. The staple legs can be deformed to be inserted into the bones and, when the force applied to deform the legs is released, the staple legs can elastically bias toward their unbiased (natural or undeformed) shape. However, the spacing and/or angulation of the legs inserted into the bones can prevent the legs from fully returning to their undeformed state. As a result, the staple can apply a compressive force between the end faces of the bones into which the staple legs are inserted (e.g., with the force directed in the direction of convergence of the staple legs). The compressive force may help promote bone healing and fusion between the bones into which the staple is inserted.

Figure 6:
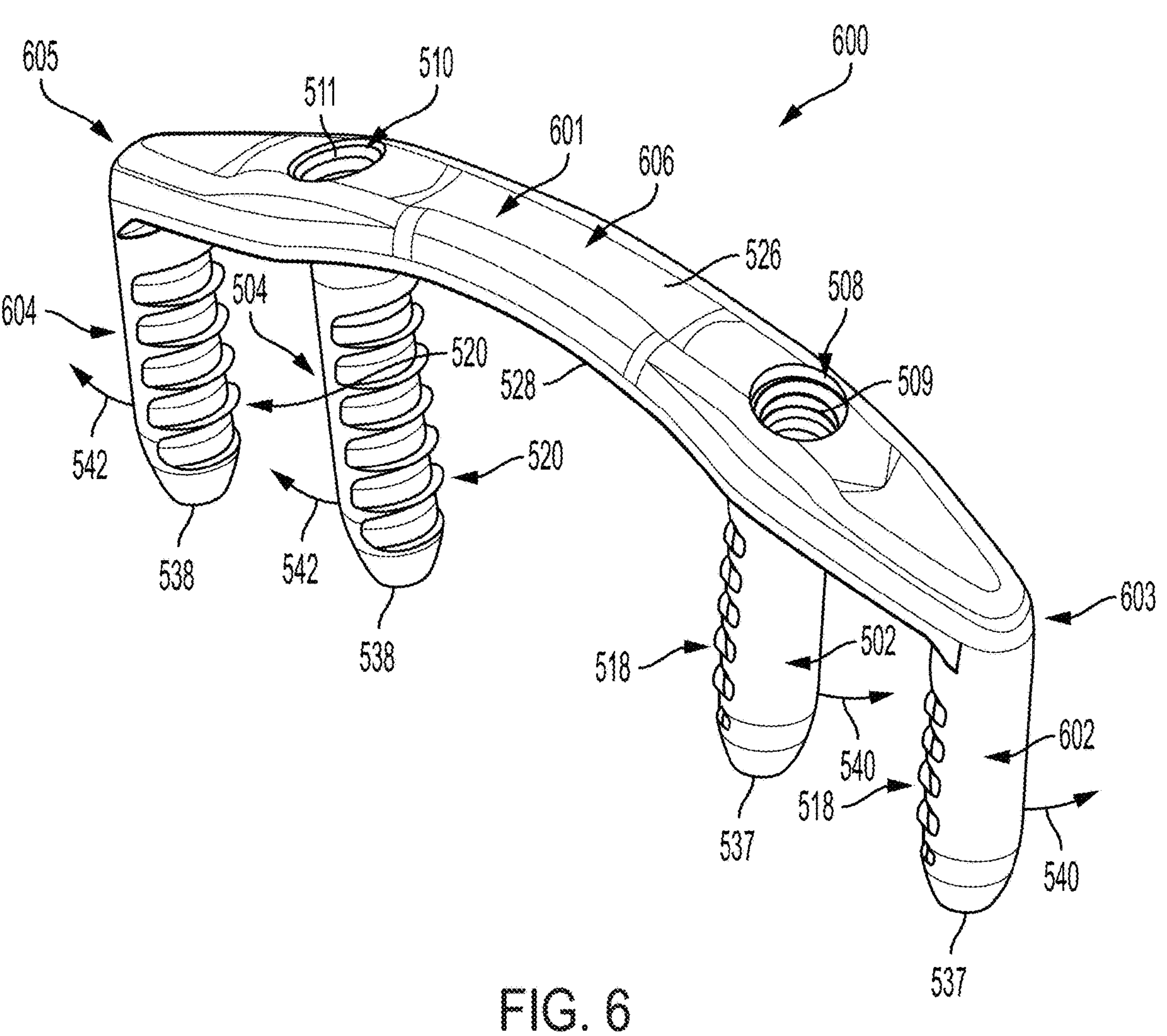
FIG. 6 is a perspective view of another example configuration of a staple.

FIG. 6 is a perspective view of another embodiment of a staple 600. The staple 600 can be similar to, or the same as, the staple 500 described previously except as noted here. For example, the staple 600 can include one or more (e.g., each) of the features disclosed herein with respect to the staple 500 except as otherwise noted here.

For example, the staple 600 can include a body 601 and, in addition to the first leg 502 and the second leg 504 at the body 601, a third leg 602 and a fourth leg 604 at the body 601. For the illustrated embodiment, the staple 600 includes the first leg 502 and the third leg 602 at a first side 603 of a bridge 606, and thus of the staple 600, and the second leg 504 and the fourth leg 604 at a second side 605 of the bridge 606, and thus of the staple 600. Here the first side 603 is opposite the second side 605. The arrangement of the legs 502, 504, 602, 604 of the staple 600 can thus be a four-leg, in-line arrangement. In some examples, each of the legs 502, 504, 602, 604 can each have an equal length 512, and in the biased compression-inducing state of the staple 600 shown at FIG. 6, the bridge 606 can arch upward away from end portions 537, 538 of legs 502, 504, 602, 604 such that the end portions 537, 538 of legs 602, 604 are at a different elevation than the end portions 537, 538 of legs 502, 504. This arrangement can result in starting insertion of the legs 602, 604 into one or more bones before starting insertion of the legs 502, 504 into one or more bones (e.g., because the legs 602, 604 can contact the one or more bones first and the legs 502, 504 contact the one or more bones later after the legs 602, 604 of the staple 600 has begun inserting into the one or more bones).

The bridge 606 can connect the first and third legs 502, 602 to the second and fourth legs 504, 604. The bridge length 516 of the bridge 606 can range from 28 mm to 34 mm, which can be sufficient to allow for positioning the bridge across a space (e.g. joint) between bones in the foot while maintaining the legs 502, 602 at one bone and the legs 504, 604 at another bone with the bridge 606 placed across the spaced between such bones. As an example, the bridge length 516 for the bridge 606 can be measured from a central longitudinal axis of the outermost leg 602 at the first side 603 to a central longitudinal axis of the outermost leg 604 at the second side 605.

The staple 600 can have the first handling coupling 508, second handling coupling 510, first handling coupling receptacle 509, and second handling coupling receptacle 511 and one or more (e.g., all) of the features associated therewith as disclosed with respect to the staple 500. Furthermore, the staple 600 can have the material and teeth 518, 520 as well as be configured to transition between the biased compression-inducing state and the deformed insertion state as disclosed with respect to the staple 500.

Figure 7:
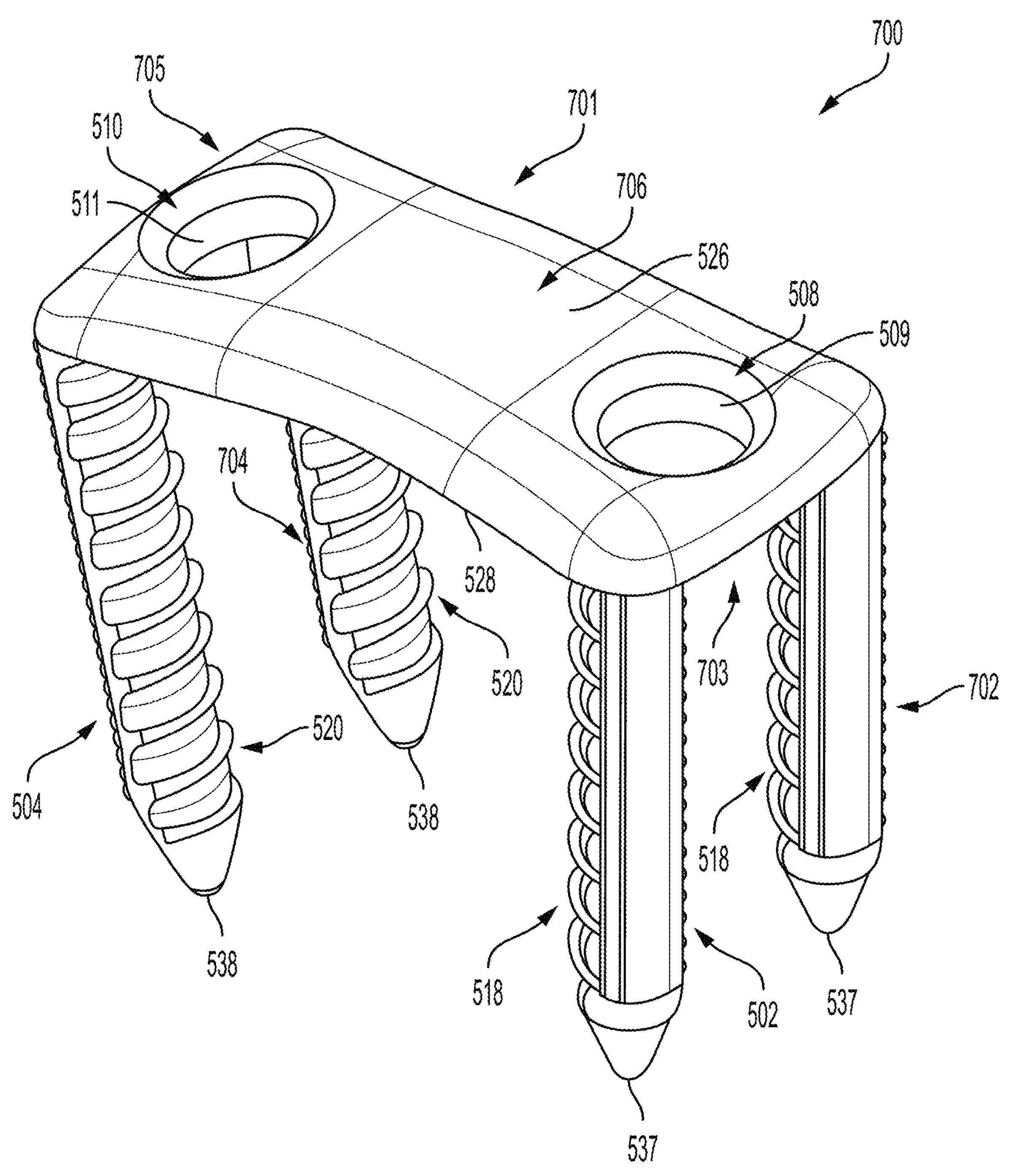
FIG. 7 is a perspective view of another example configuration of a staple.

FIG. 7 is a perspective view of yet another embodiment of a staple 700. The staple 700 can be similar to, or the same as, the staple 500 described previously except as noted here. For example, the staple 700 can include one or more (e.g., each) of the features disclosed herein with respect to the staple 500 except as otherwise noted here.

For example, the staple 700 can include a body 701 and, in addition to the first leg 502 and the second leg 504 at the body 701, a third leg 702 and a fourth leg 704 at the body 701. For the illustrated embodiment, the staple 700 includes the first leg 502 and the third leg 702 at a first side 703 of a bridge 706, and thus of the staple 700, and the second leg 504 and the fourth leg 704 at a second side 705 of the bridge 706, and thus of the staple 700. Here the first side 703 is opposite the second side 705. The arrangement of the legs 502, 504, 702, 704 of the staple 700 can thus be a two-by-two leg arrangement, with the legs 502, 504 generally aligned across the bridge 706 and the legs 702, 704 generally aligned across the bridge 706. In some examples, each of the legs 502, 504, 702, 704 can each have an equal length 512, and in the biased compression-inducing state of the staple 700 shown at FIG. 7, the bridge 706 can arch upward away from end portions 537, 538 of legs 502, 504, 702, 704.

The bridge 706 can connect the first and third legs 502, 702 to the second and fourth legs 504, 704. The bridge length 516 of the bridge 706 can range from 15 mm to 20 mm, which can be sufficient to allow for positioning the bridge across a space (e.g. joint) between bones in the foot while maintaining the legs 502, 702 at one bone and legs 504, 704 another bone separated from the one bone by the space. As an example, the bridge length 516 can be as measured from a central longitudinal axis of leg 502 at side 703 of the bridge 706 to a central longitudinal axis of leg 504 at opposite side 705 of the bridge 706 or from a central longitudinal axis of leg 702 at side 703 of the bridge 706 to a central longitudinal axis of leg 704 at opposite side 705 of the bridge 706.

The staple 700 can have the first handling coupling 508, second handling coupling 510, first handling coupling receptacle 509, and second handling coupling receptacle 511 and one or more (e.g., all) of the features associated therewith as disclosed with respect to the staple 500. Furthermore, the staple 700 can have the material and teeth 518, 520 as well as be configured to transition between the biased compression-inducing state and the deformed insertion state as disclosed with respect to the staple 500.

Figure 8:
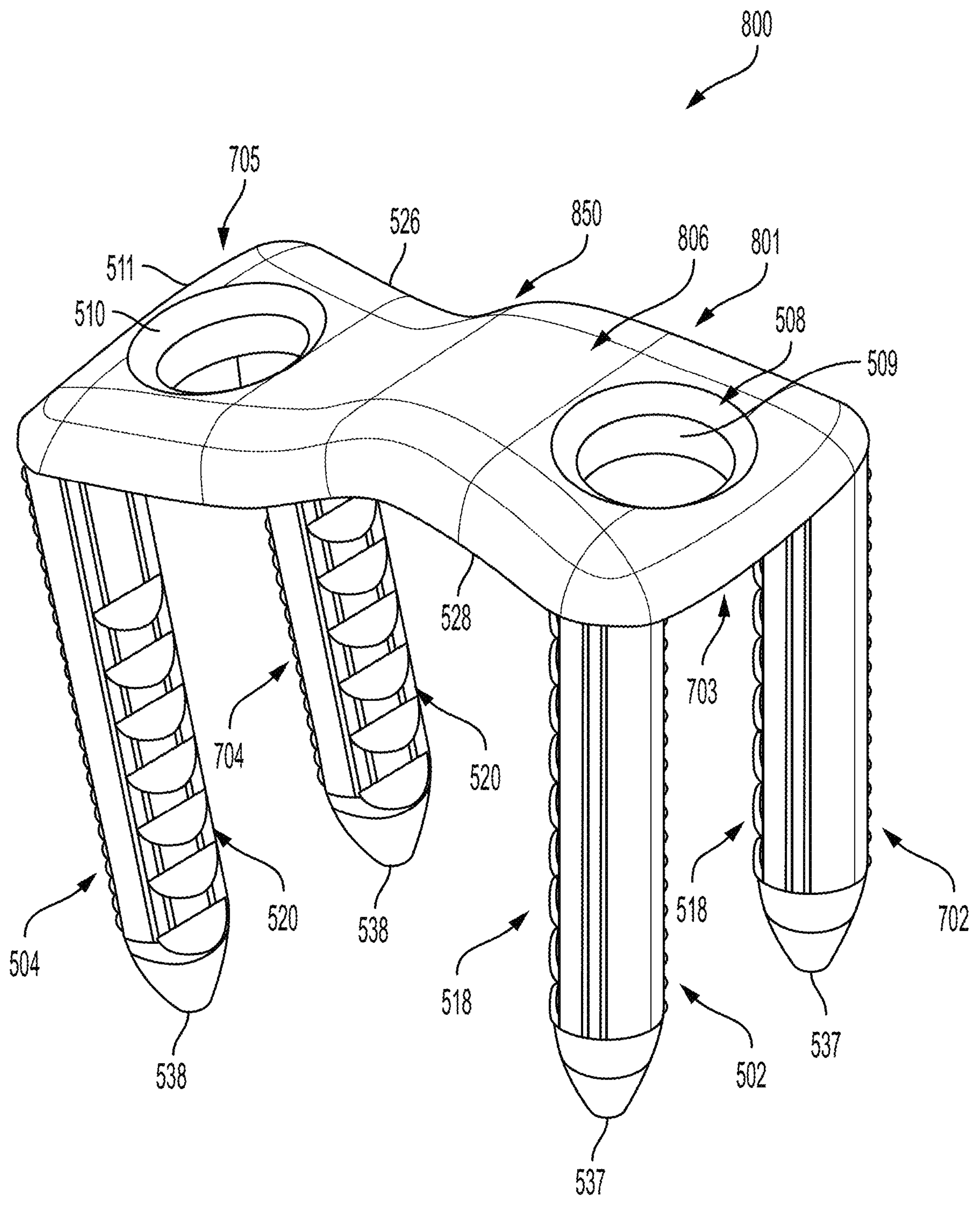
FIG. 8 is a perspective view of another example configuration of a staple.

FIG. 8 is a perspective view of an additional embodiment of a staple 800. The staple 800 can be similar to, or the same as, the staple 500 described previously except as noted here. For example, the staple 800 can include one or more (e.g., each) of the features disclosed herein with respect to the staple 500 except as otherwise noted here.

For example, the staple 800 can include a body 801 and, in addition to the first leg 502 and the second leg 504 at the body 801, and the third leg 702 and the fourth leg 704 at the body 801. For the illustrated embodiment, the staple 800 includes the first leg 502 and the third leg 702 at the first side 703 of a bridge 806, and thus of the staple 800, and the second leg 504 and the fourth leg 704 at the second side 705 of the bridge 806, and thus of the staple 800. Here the first side 703 is opposite the second side 705. The arrangement of the legs 502, 504, 702, 704 of the staple 700 can thus be a two-by-two leg arrangement, with the legs 502, 504 generally aligned across the bridge 706 and the legs 702, 704 generally aligned across the bridge 706. In some examples, each of the legs 502, 504, 702, 704 can each have an equal length 512, and in the biased compression-inducing state of the staple 700 shown at FIG. 7, the bridge 806 can arch upward away from end portions 537, 538 of legs 502, 504, 702, 704.

The bridge 806 can connect the first and third legs 502, 702 to the second and fourth legs 504, 704. The bridge length 516 of the bridge 806 can range from 15 mm to 20 mm, which can be sufficient to allow for positioning the bridge across a space (e.g. joint) between bones in the foot while maintaining the legs 502, 702 at one bone and legs 504, 704 another bone separated from the one bone by the space. As an example, the bridge length 516 can be as measured from a central longitudinal axis of leg 502 at side 703 of the bridge 806 to a central longitudinal axis of leg 504 at opposite side 705 of the bridge 806 or from a central longitudinal axis of leg 702 at side 703 of the bridge 806 to a central longitudinal axis of leg 704 at opposite side 705 of the bridge 806.

The staple 800 can further include an elevation transition region 850 at the bridge 806. The elevation transition region 850 can define an elevation change along a length of the bridge 806. For example, as a result of the presence of the elevation transition region 850 at the bridge 806, the side 703 can be at a different elevation than the side 705. For the illustrated embodiment of the staple 800, the side 703 is at a higher elevation than the side 705. The presence of the elevation transition region 850 at the bridge 806 can be useful in facilitating a stable positioning and fixation of the staple 800 at bone surfaces of differing elevations. For example, elevation transition region 850 can be placed at an elevation offset between a metatarsal and opposed cuneiform across the tarsometatarsal joint.

The staple 800 can have the first handling coupling 508, second handling coupling 510, first handling coupling receptacle 509, and second handling coupling receptacle 511 and one or more (e.g., all) of the features associated therewith as disclosed with respect to the staple 500. Furthermore, the staple 700 can have the material and teeth 518, 520 as well as be configured to transition between the biased compression-inducing state and the deformed insertion state as disclosed with respect to the staple 500.

A staple according to the present disclosure (e.g., staple 500, 600, 700, 800) can be fabricated from a variety of different materials. The staple may be fabricated from a biocompatible metal (e.g., titanium, stainless steel, nickel titanium alloy (nitinol)). In one example, the staple is fabricated from titanium (e.g., the staple is formed of a metal consisting of or consisting essential of titanium). The metal forming the staple may be substantially or entirely devoid of nickel. Titanium can be useful in that the metal can resist high energy forces without breakage and can avoid nickel sensitivity issues that may be exhibited by some patients. When so configured, the entire body of the staple (e.g., bridge, legs) can be formed of titanium. During insertion, the legs of the titanium staple may be elastically deformed, allowing the legs to return to toward their original, undeformed position. Other materials, including combinations of different materials, may be used in other configurations of a staple according to the disclosure.

Figure 9A:
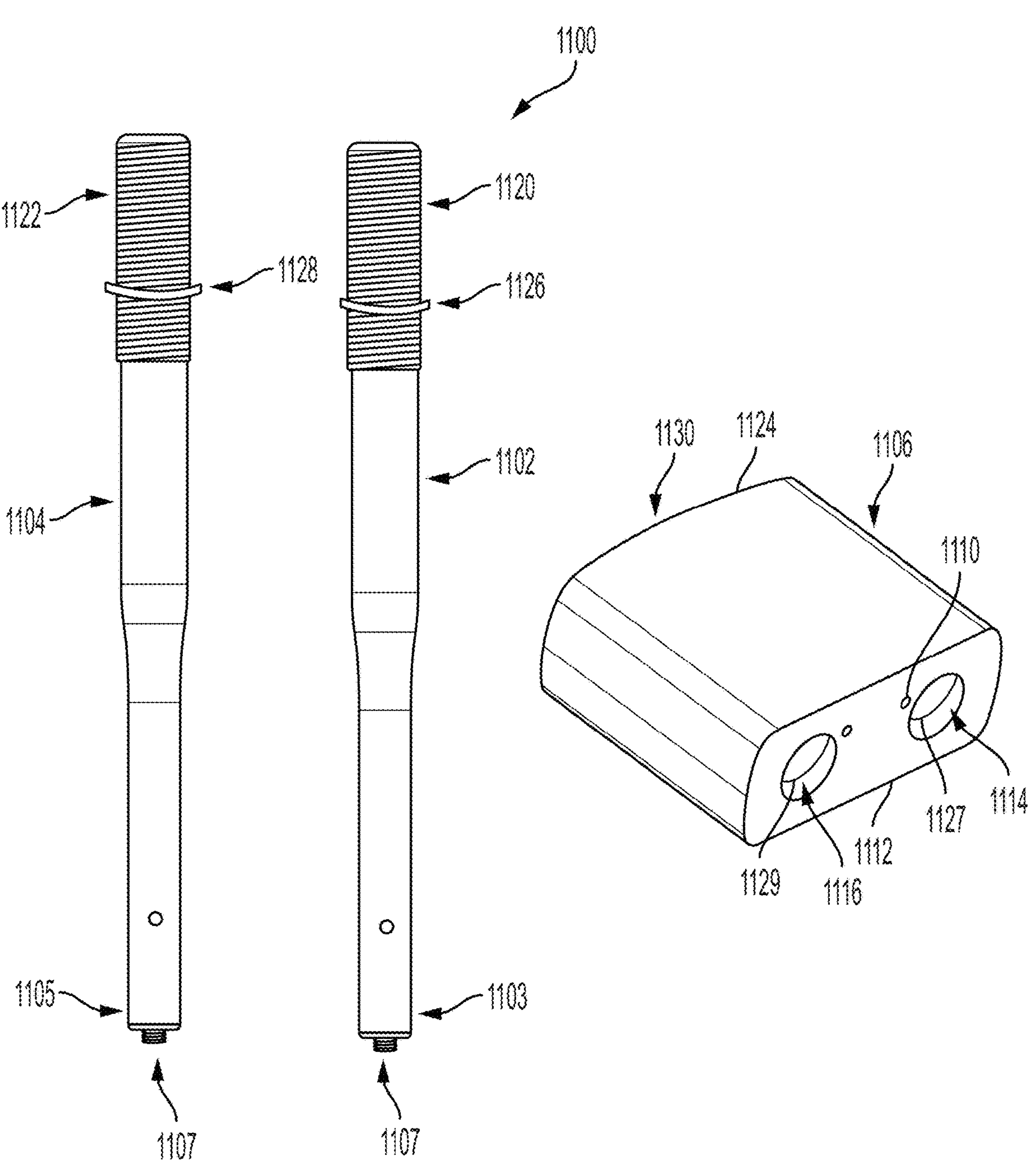
FIGS. 9A-9C illustrate an embodiment of an inserter.
Figures 9B, 9C:
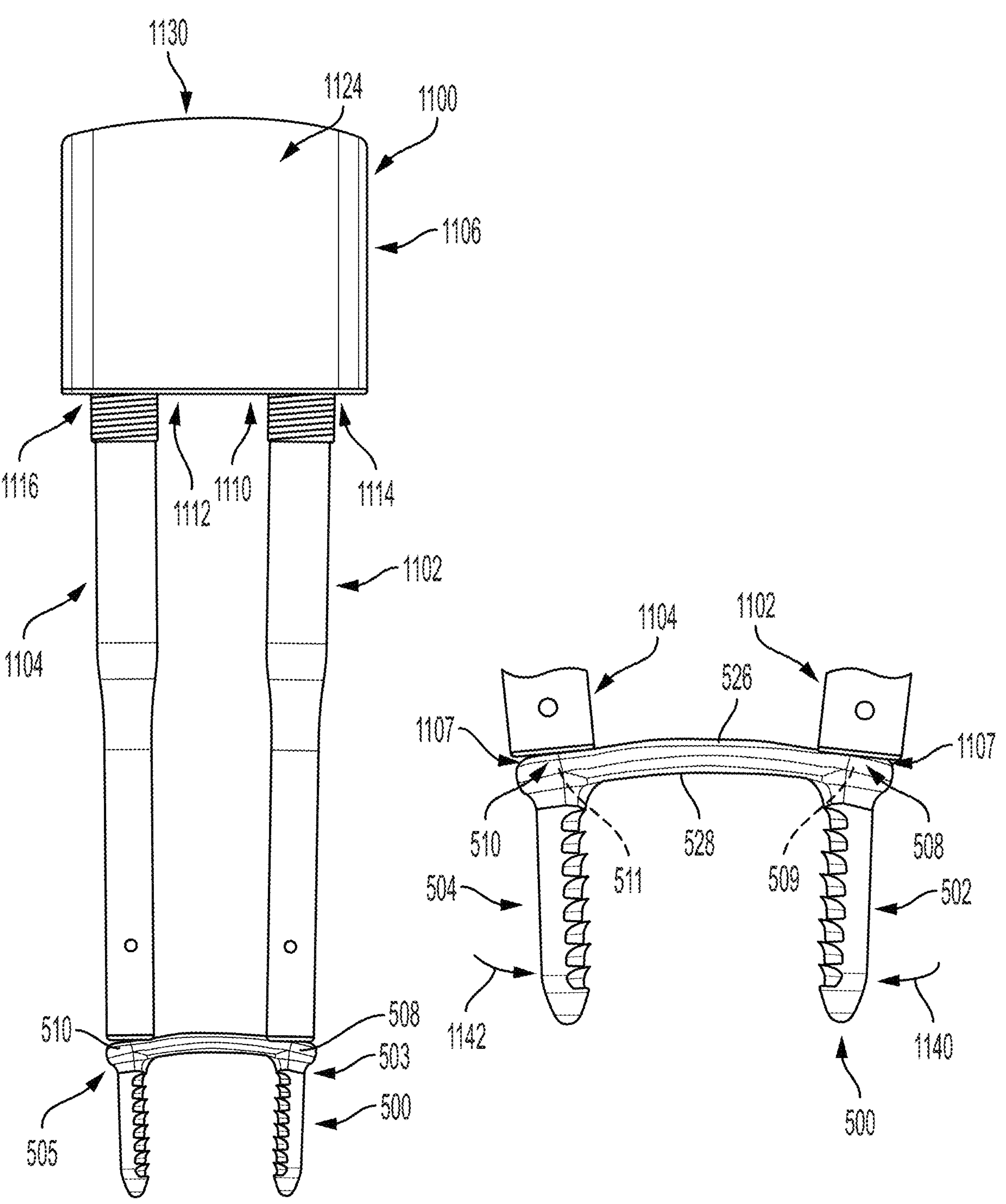

FIGS. 9A-9C illustrate an embodiment of an inserter 1100. FIG. 9A shows disassembled components of the inserter 1100, FIG. 9B shows assembled components of the inserter 1100, and FIG. 9C shows the inserter 1100 operatively connected to staple 500 with a load force removed such that the staple 500 is in its biased, compression state.

The inserter 1100 can include a first coupling shaft 1102, a second coupling shaft 1104, and a connector 1106. The first and second coupling shafts 1102, 1104 can be configured to operatively connect to an implant, such as a staple. The illustrated embodiment of the inserter 1100 shows the first and second coupling shafts 1102, 1104 each configured to operatively couple to the staple 500 (or another staple configuration, such as any of those as described elsewhere herein). The connector 1106 can be configured to join the first coupling shaft 1102 and the second coupling shaft 1104, for instance as shown at the example of FIG. 9B.

In particular, the first coupling shaft 1102 can be configured to operatively couple to the staple 500 at the first handling coupling 508, and the second coupling shaft 1104 can be configured to operatively couple to the second handling coupling 510. For example, the first coupling shaft 1102 can have a distal end portion 1103 and the second coupling shaft 1104 can have a distal end portion 1105, and each of such distal end portions 1103, 1105 can include an implant coupling member 1107. The coupling member 1107 at the distal end portion 1103 of the first coupling shaft 1102 can be configured to operatively connect to a complementary coupling member at the first handling coupling 508, and the coupling member 1107 at the distal end portion 1105 of the second coupling shaft 1104 can be configured to operatively connect to a complementary coupling member at the second handling coupling 510. In this way, the inserter 1100 can include the first coupling shaft 1102 connected to a first side of the implant, such as the first side 503 of the staple 500, and the second coupling shaft 1104 connected to a second side of the implant, such as the second side 505 of the staple 500.

As one such specific example, each of the first and second handling couplings 508, 510 can include threading as a type of complementary coupling member thereat. The coupling member 1107 at the distal end portions 1103, 1105 of the respective first and second coupling shafts 1102, 1104 can include threading that is configured to operatively couple to the complementary threading at the respective first and second handling couplings 508, 510. Thus, in this particular example, operatively coupling the inserter 1100 to an implant, such as the staple 500, can include threadingly inserting the first coupling shaft 1102 into the first handling coupling 508 (e.g., from the top surface 526 of the staple 500) and threadingly inserting the second coupling shaft 1104 into the second handling coupling 510 (e.g., from the top surface 526 of the staple 500). Other types of mechanical connections than threading can be used.

As best seen at FIG. 9C, each of the first coupling shaft 1102 and the second coupling shaft 1104 can be configured to couple to the respective first and second handling coupling receptacles 509, 511 at a location between the top surface 526 of the staple 500 and the bottom surface 528 of the staple 500. For example, the first coupling shaft 1102 can operatively couple to the first handling coupling 508 from the top surface 526 and in a direction toward the bottom surface 528 but without the first coupling shaft 1102 extending out from the bottom surface 528. Likewise, the second coupling shaft 1104 can operatively couple to the second handling coupling 510 from the top surface 526 and in a direction toward the bottom surface 528 but without the second coupling shaft 1104 extending out from the bottom surface 528. As one such example, the coupling member 1107 at the first coupling shaft 1102 can extend within the first handling coupling receptacle 509 such that a distal end of the coupling member 1107 at the first coupling shaft 1102 is contained within the staple 500 (e.g., within the first handling coupling receptacle 509). Similarly, the coupling member 1107 at the second coupling shaft 1104 can extend within the second handling coupling receptacle 511 such that a distal end of the coupling member 1107 at the second coupling shaft 1104 is contained within the staple 500 (e.g., within the second handling coupling receptacle 511).

In a further embodiment, to help provide added stability when applying a load force at the implant (e.g., staple 500), the first and/or second coupling shaft 1102, 1104 can include a shaft stabilizing arm. When so included, the shaft stabilizing arm can be included at the respective distal end portion 1103, 1105 of the respective coupling shaft 1102, 1104 and extend in a direction parallel to a central longitudinal axis of the respective coupling shaft 1102, 110. Where the implant is a staple, the shaft coupling arm can be configured to contact the bridge of the staple (e.g., at a top and/or side surface of the bridge but not a bottom surface of the bridge) when the coupling member 1107 of the respective shaft 1102, 1104 is at the respective handling coupling at the staple. The inclusion of such shaft stabilizing arm can be useful to help provide additional stability during the application of a load force at the implant (e.g., staple) and placement of the implant (e.g., staple) at the target anatomy.

In some examples, such as the embodiment illustrated at FIGS. 9A-9C, the inserter 1100 can further include a first wire receiving opening 1110, a second wire receiving opening 1112, a first receptacle 1114, and a second receptacle 1116. The first wire receiving opening 1110 can be configured to receive a first wire, and the second wire receiving opening 1112 can be configured to receive a second wire. The first receptacle 1114 can be configured to receive and hold the first coupling shaft 1102, for instance a proximal end portion 1120 of the first coupling shaft 1102, and the second receptacle 1116 can be configured to receive and hold the second coupling shaft 1104, for instance a proximal end portion 1122 of the second coupling shaft 1104. For the illustrated embodiment, each of the first wire receiving opening 1110, the second wire receiving opening 1112, the first receptacle 1114, and the second receptacle 1116 is included at the connector 1106.

As noted, the connector 1106 can be configured to join the first coupling shaft 1102 and the second coupling shaft 1104, for instance as shown at the example of FIG. 9B. As one example, the connector 1106 can be configured to join the first and second coupling shafts 1102, 1104 by receiving the first coupling shaft 1102 at the first receptacle 1114 at the connector 1106 and receiving the second coupling shaft 1104 at the second receptacle 1116 at the connector 1106. As such, with the receptacles 1114, 1116 at the connector 1106 receiving and holding the respective coupling shaft 1102, 1104, the connector 1106 can removably join the coupling shafts 1102, 1104. The receptacles 1114, 1116 at the connector 1106 are illustrated here at a bottom surface of the connector 1106, and in other embodiments the receptacles 1114, 1116 can be at other locations at the connector 1106, such as receptacle 1114 extending along one side surface of the connector 1106 and the receptacle 1116 extending along another (e.g., opposite) side surface of the connector 1106.

To help facilitate a more robust joining of the coupling shafts 1102, 1104 via the connector 1106, the first coupling shaft 1102 can include a first retention feature 1126 and the second coupling shaft 1104 can include a second retention feature 1128. For example, the first retention feature 1126 can be located at or near the proximal end portion 1120 of the first coupling shaft 1102, and the second retention feature 1128 can be located at or near the proximal end portion 1122 of the second coupling shaft 1104. The first retention feature 1126 can be configured to help hold the first coupling shaft 1102 in the first receptacle 1114 and the second retention feature 1128 can be configured to help hold the second coupling shaft 1104 in the second receptacle 1116. In one such further example, the connector 1106 can include a first retention mating feature 1127 at the first receptacle 1114 and a second retention mating feature 1129 at the second receptacle 1116. The first retention mating feature 1127 can be complementary to the first retention feature 1126 and configured to receive and hold the first retention feature 1126, and the second retention mating feature 1129 can be complementary to the second retention feature 1128 and configured to receive and hold the second retention feature 1128. The first retention feature 1126 and the first retention mating feature 1127 as well as the second retention feature 1128 and the second retention mating feature 1129 can take any of a variety of suitable forms of complementary connector pairs, such as, for one suitable, non-limiting example, complementary structures that create an interference fit. As one such specific example, the first retention feature 1126 and the first retention mating feature 1127 as well as the second retention feature 1128 and the second retention mating feature 1129 can be complementary connector pairs that provide a retention force in a direction generally parallel to a longitudinal axis of the coupling shafts 1102, 1104 and configured to release this retention force upon movement of at least one of the complementary connectors of the pair (e.g., movement of one of the coupling shaft 1102 and the receptacle 1114 and movement of one of the coupling shaft 1104 and the receptacle 1116) in a direction generally transverse to longitudinal axis of the coupling shafts 1102, 1104.

As one specific such example, the connector 1106 as shown for the illustrated embodiment of the inserter 1100 can include a cap 1124. For the illustrated embodiment of the inserter 1100, the cap 1124 can be configured to be positioned over the proximal end portion 1120 (e.g., opposite the implant, such as the staple 500) of the first coupling shaft 1102 and over the proximal end portion 1122 (e.g., opposite the implant, such as the staple 500) of the second coupling shaft 1104. For instance, the cap 1124 can be configured to join the first and second coupling shafts 1102, 1104 by placing the first receptacle 1114 at the cap 1124 over the proximal end portion 1120 of the first coupling shaft 1102 and the second receptacle 1116 at the cap 1124 over the proximal end portion 1122 of the second coupling shaft 1104, and then moving the cap 1124 as so positioned relative to the first and second coupling shafts 1102, 1104 (e.g., in a direction toward one or more bones) such that the proximal end portions 1120, 1122 are received and held at the respective receptacles 1114, 1116. Likewise, in certain embodiments of the cap 1124 that include wire receiving openings, the cap 1124 can similarly be configured to receive and hold first and second wires, positioned at one or more bones, at respective first and second wire receiving openings 1110, 1112 as the cap 1124 is moved relative to such wires (e.g., in a direction toward one or more bones).

The cap 1124 can further include a surface contour 1130. The surface contour 1130 can be adapted to fit at a hand of a user. For the illustrated example, the surface contour 1130 can have a highest elevation at a location between the receptacles 1114, 1116 and a lowest elevation outside of the receptacles 1114, 1116 such that the surface contour 1130 angles downward toward the implant, such as the staple 500, when moving along the surface contour 1130 away from the highest elevation between the receptacles 1114, 1116. Accordingly, when positioning the implant, such as the staple 500, in contact with the first bone and the second bone, a user's hand can tamp at the surface contour 1130 of the cap 1124 to apply insertion force at the implant, such as the staple 500.

The inserter 1100 can be configured to place the implant, such as the staple 500, in one or more bones (e.g., using an implant guide sleeve to guide advancement of the inserter 1100 and thereby guide positional placement of the staple 500 into one or more bones). For example, the inserter 1100 can be operatively connected to the staple 500 via the first and second coupling shafts 1102, 1104, and the connector 1106 (e.g., cap 1124) can be joined to the first and second coupling shafts 1102, 1104, such as shown at the example of FIG. 9B. When the connector 1106 is joined to the first coupling shaft 1102 and the second coupling shaft 1104, such as shown at the example of FIG. 9B, the connector 1106 can be configured to bias the first coupling shaft 1102 and the second coupling shaft 1104 toward each other to apply a load force to the staple 500. When the first coupling shaft 1102 and the second coupling shaft 1104 are so biased toward each other to apply the load force to the staple 500, the first leg 502 and the second leg 504 can be oriented generally parallel to one another, such as shown at the example of FIG. 9B. This application of the load force to the staple 500 can cause the legs 502, 504 to move away from each other to the generally parallel orientation which can be a configuration useful for inserting the staple 500 in and/or across the bones. Then, after the staple 500 has been inserted as desired at and across the bones, the connector 1106 can be removed from at least one of the first coupling shaft 1102 and the second coupling shaft 1104 to cause, as shown at the example of FIG. 9C, the first leg 502 and the second leg 504 to move toward one another. Specifically, removing the connector 1106 can cause the first leg 502 to move in a direction 1140 toward the second leg 504 and cause the second leg 504 to move in a direction 1142 toward the first leg 502.

Figure 10:
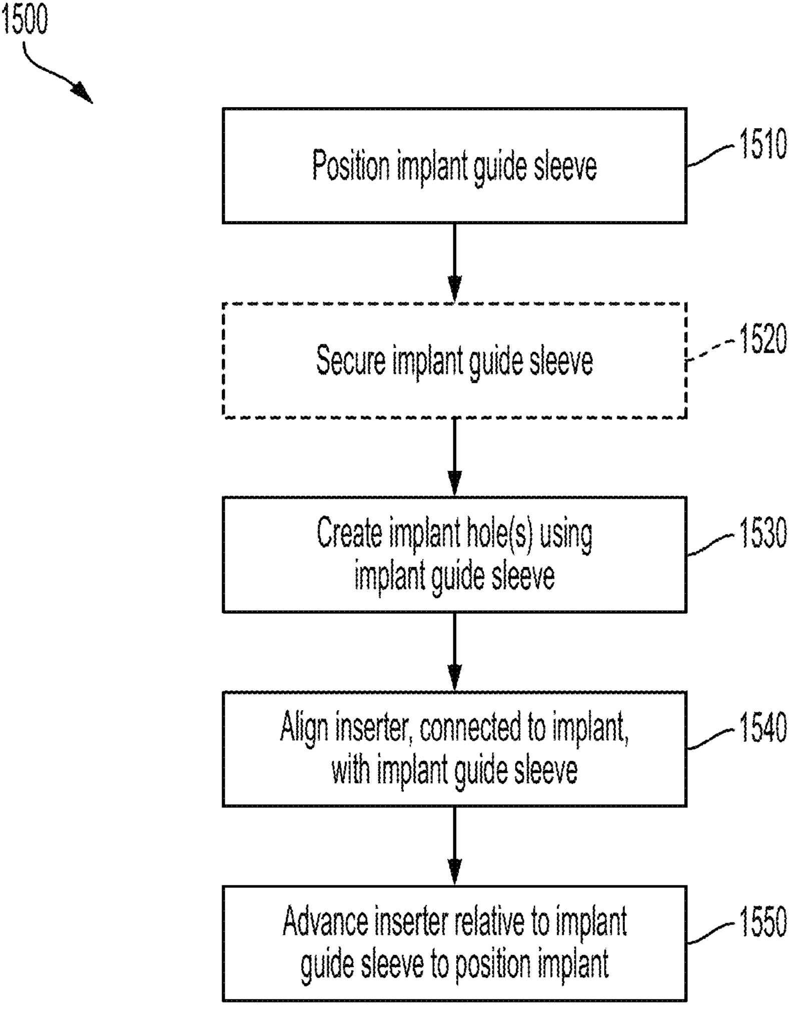
FIG. 10 is a flow diagram of an example surgical technique for positioning an implant, such as a staple, to fixate bones for fusion.

FIG. 10 is a flow diagram of an embodiment of a method 1500. The method 1500 can be used as, for example, a surgical technique for positioning an implant, such as a staple, to fixate bones for fusion. After describing the method 1500, FIGS. 11A-14 will be referenced and described to further detail various means that can be used to carry out at least some of the steps of the method 1500.

Referring to FIG. 10, at step 1510, the method 1500 can include positioning an implant guide sleeve. For example, step 1510 can include positioning an implant guide sleeve at a first bone and a second bone and across a separation between the first bone and the second bone. As one example, the first bone can be a metatarsal (e.g., a first metatarsal), the second bone can be a cuneiform (e.g., a medial cuneiform), and the separation between the first bone and the second bone can be a tarsometatarsal joint space separating the metatarsal from the cuneiform.

At step 1520, the method 1500 can include a step of securing the implant guide sleeve to one or more bones. Step 1520 can be optional in carrying out method 1500 depending on the particular application and the need for enhanced stabilization that can be provided by securing the implant guide sleeve to one or more bones. As one example, the implant guide sleeve can be secured by fixating the implant guide sleeve to the first bone (e.g., a metatarsal, such as the first metatarsal) at which the implant guide sleeve is positioned and fixating the implant guide sleeve to the second bone (e.g., a cuneiform, such as the medial cuneiform) at which the implant guide sleeve is positioned. The implant guide sleeve can be so fixated using one or more pins, wires, and/or other appropriate mechanical fixation means. As such, a first pin can be inserted through the implant guide sleeve and into the first bone to fixate the implant guide sleeve at the first bone, and a second pin can be inserted through the implant guide sleeve and into the second bone to fixate the implant guide sleeve at the second bone.

At step 1530, the method 1500 can include creating one or more implant holes in one or more bones. The one or more implant holes can be created in one or more bones at step 1530 using the implant guide sleeve positioned at step 1510. For example, the implant guide sleeve can be used to guide creation of a first implant hole in the first bone at which the implant guide sleeve is positioned and to guide creation of a second implant hole in the second bone at which the implant guide sleeve is positioned. As one such particular example, the implant guide sleeve (e.g., an interior area defined by the implant guide sleeve) can be used to guide placement of a drill at the first bone for creating the first implant hole and to guide placement of a drill at the second bone for creating the second implant hole. As another such particular example, the implant guide sleeve (e.g., an interior area defined by the implant guide sleeve) can be used to receive and position a drill guide so that the drill guide as so positioned relative to the implant guide sleeve can be used to drill the first and second implant holes at the respective first and second bones. In this example, the drill guide can be aligned with the implant guide sleeve and then the drill guide can be placed at the implant guide sleeve.

At step 1540, the method 1500 can include aligning an inserter with the implant guide sleeve. The inserter can be operatively connected to an implant, such as a staple. As one example, aligning the inserter, operatively connected to the implant, with the implant guide sleeve at step 1540 can include aligning the inserter and the implant on a common axis with an interior area of the implant guide sleeve such that the inserter and implant can be moved along the common axis into the interior area of the implant guide sleeve. For instance, the common axis can extend in a plantar-dorsal direction and perpendicular to a longitudinal axis of the first and/or second bones.

At step 1550, the method 1500 can include advancing the inserter, relative to the implant guide sleeve, to position the implant at one or more target bones. For example, step 1550 can include advancing the inserter, relative to the implant guide sleeve, to position the implant in contact with the first bone and the second bone with the implant bridging between the first bone and the second bone. This could include advancing the inserter, relative to the implant guide sleeve, to position the first leg of the staple in the first implant hole created at step 1530 and to position the second leg of the staple in the second implant hole created at step 1530. Thus, in various embodiments, the same implant guide sleeve can be used to create the implant holes in the first and second bones and also to then align and advance the inserter and implant coupled to the inserter, relative to the implant guide sleeve, to position the implant at those implant holes. In examples where the implant is a staple, once the staple is positioned, using the implant guide sleeve, at the first and second bones with the staple bridging the first and second bones, the staple can be transitioned from a deformed insertion state a compression-inducing state, as described elsewhere herein, to apply a compressive force between the first and second bones.

FIGS. 11A-11F illustrate one embodiment of an implant guide sleeve 2000. The implant guide sleeve 2000 can be used, as one example, to help carry out one or more of the steps of the method 1500 described previously. Thus, in one exemplary application, the implant guide sleeve 2000 can be used in a surgical technique for positioning an implant, such as a staple, to fixate bones for fusion, and one or more aspects described and/or illustrated with respect to the implant guide sleeve 2000 can be applied in the method 1500.

Figure 11A:
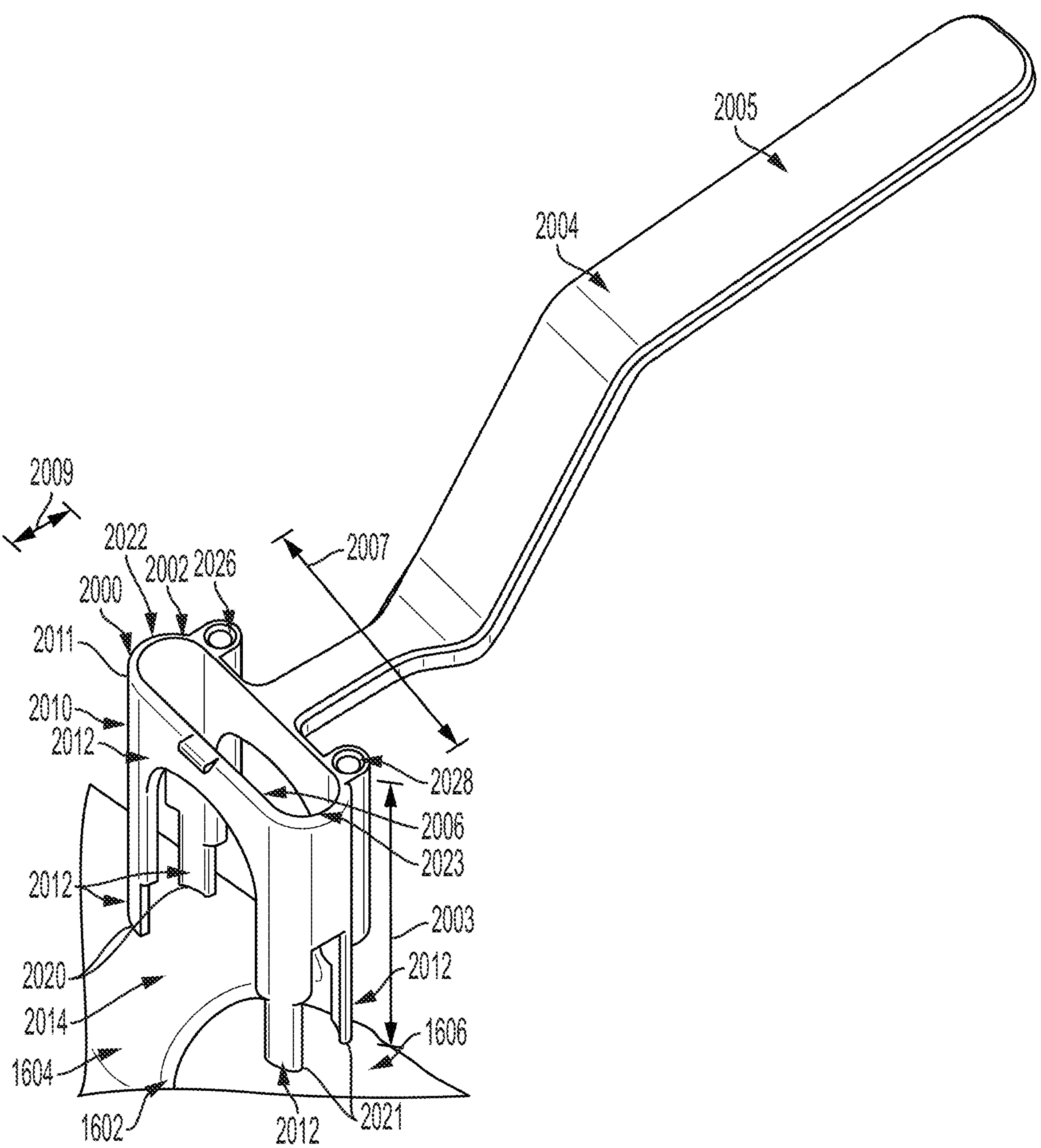
FIGS. 11A-11F illustrate one embodiment of an implant guide sleeve that can be used for an embodiment of a surgical technique for positioning a staple to fixate bones for fusion.

FIG. 11A is a perspective view of the implant guide sleeve 2000 positioned at a first bone 1604 (e.g., a metatarsal, such as a first metatarsal), a second bone 1606 (e.g., a cuneiform, such as a medial cuneiform), and across a separation 1602 (e.g., a joint space, such as a TMT joint space) between the first bone 1604 and the second bone 1606. In the illustrated example, the first bone 1604 is a metatarsal, more specifically a first metatarsal, the second bone 1606 is a cuneiform, more specifically a medial cuneiform, and the separation 1602 is a joint space, more specifically a tarsometatarsal (TMT) joint space, between the first and second bones 1604, 1606. Though as described elsewhere herein, embodiments disclosed herein can be applied similarly to other bones in the foot or hand or other (e.g., small) bones more generally.

The implant guide sleeve 2000 can be configured to be placed at one or more bones, such as the first and second bones 1604, 1606, to guide creation of implant holes at such one or more bones and/or to guide placement of an implant, such as a staple, at the one or more bones. For example, the implant guide sleeve 2000 can be configured to be placed at the first and second bones 1604, 1606 and configured to (i) guide creation of a first implant hole at the first bone 1604 and to guide creation of a second implant hole at the second bone 1606, and (ii) then guide placement of an implant at those previously created first and second implant holes. With the implant guide sleeve 2000 configured to sequentially guide implant hole creation followed by implant placement using the same implant guide sleeve 2000 (e.g., the same implant guide sleeve 2000 maintained at the same general orientation relative to the bones 1604, 1606 for both the implant hole creation and the implant placement), the implant guide sleeve 2000 can be useful in facilitating more accurate and efficient implant procedures. This can be especially useful in applications involving relatively small bones of the foot or hand where the location of previously created implant holes in such small bones can otherwise be difficult to discern when attempting to position the implant at these relatively small implant holes.

The implant guide sleeve 2000 can include a guide sleeve body 2002 and a handle 2004. The body 2002 can have a height 2003 that extends in a direction away from bones 1604, 1606 when the body 2002 is placed at the bones 1604, 1606. The height 2003 can range from one to twelve inches, such as ranging from one to six inches, so as to be sufficiently tall to provide the guiding functions described herein but yet not too tall to impede workflow in the region of the bones 1604, 1606. The body 2002 can have a length 2007 that extends in a direction generally parallel to the longitudinal axis of at least one of bones 1604, 1606, and the length 2007 can range from one to twelve inches, such as ranging from one to six inches. The length 2007 can be configured so as to accommodate therein a corresponding length of one or more tools or devices used in creating implant holes in the bones 1604, 1606 (e.g., drill) and positioning an implant at the bones 1604, 1606 (e.g., inserter and staple). And the body 2002 can have a width 2009 that extends in a direction generally perpendicular to the longitudinal axis of at least one of bones 1604, 1606, and the width 2009 can range from one-tenth of an inch to six inches, such as ranging from one-tenth of an inch to one inch. The width 2009 can be configured so as to accommodate therein a corresponding width of one or more tools or devices used in creating implant holes in the bones 1604, 1606 (e.g., drill) and positioning an implant at the bones 1604, 1606 (e.g., inserter and staple). The handle 2004 can extend outward from the body 2002. The handle 2004 can be configured to be gripped with a hand of a user to move and place the body 2002. As illustrated, the implant guide sleeve 2000 can be configured such that when the body 2002 is positioned at the first and second bones 1604, 1606, the handle 2004 can extend away from the bones 1604, 1606. As also illustrated, the handle 2004 can extend away from the body 2002 in more than one plane to increase the ergonomic and ease of use of the implant guide sleeve 2000. In particular, the handle 2004 can have a distal end portion 2005 that extends along a plane that is generally perpendicular to the longitudinal axis of at least one of the first bone 1604 and the second bone 1606. This orientation of the distal end portion 2005 of the handle 2004 can help to increase the precision of the locational accuracy of the placement of the body 2002 relative to the first and second bones 1604, 1606.

The illustrated embodiment of the implant guide sleeve 2000 can define an interior area 2006 that can be configured to guide implant hole creation and/or implant placement. As one example, the interior area 2006 can be an internal volume defined by the body 2002. In this example, the interior area 2006 can be defined as the area equal to the length 2007 multiplied by the width 2009 multiplied by the height 2003. The interior area 2006 can be defined by the body 2002 and configured to receive therein one or more tools for creating implant holes at the bones 1604, 1606 and/or to receive therein one or more implants being placed at the bones 1604, 1606. For the illustrated example, the interior area 2006 can be configured to both receive therein a drill to create a first implant hole at the first bone 1604 and to create a second implant hole at the second bone 1606 while the drill is within the interior area 2006. Also for the illustrated example, the interior area 2006 can be configured to receive therein an inserter and implant that is operatively coupled to the inserter.

The implant guide sleeve 2000, for instance at the body 2002, can include one or more walls 2010. The one or more walls 2010 can define, at least in part, the interior area 2006 as bounded between the one or more walls 2010. The walls 2010 making up the illustrated embodiment of the body 2002 include a top wall 2011, which can extend continuously around a perimeter of the body 2002 at a top portion (e.g., portion opposite bones 1604, 1606) of the body 2002, and a sidewall 2012 that extends continuously a distance downward from the top wall 2011 in the direction of the height 2003 toward the bones 1604, 1606. In this configuration, the body 2002 includes the top wall 2011 and the sidewall 2012 each extending continuously around the perimeter of the body 2002 at both the top portion of the body 2002 as well as extending continuously around the perimeter of the body 2002 as the body 2002 extends downward from the top wall 2011. As shown for the illustrated embodiment, this region that includes the continuous top wall 2011 and the continuous sidewall 2012 can form a closed interior area 2006 at the top portion of the body 2002 and extending downward at least a portion of the height 2003. This closed interior area region at the top portion can be useful in providing guidance within the closed interior area region at the top portion for tools or implants being advanced into the interior area 2006.

The implant guide sleeve 2000, for instance at the body 2002, can also include one or more guide legs 2012. The guide legs 2012 can be located at a bottom portion of the body 2002 such that the guide legs 2012 can be configured to serve as the anatomical contact surface of the implant guide sleeve 2000. The illustrated embodiment of the body 2002 includes four guide legs 2012 each spaced apart from one another, with two such guide legs 2012 at one end of the body's length 2007 and two such guide legs 2012 at another, opposite end of the body's length 2007. In this configuration, as shown at FIG. 11A, the implant guide sleeve 2000 can be positioned such that two guide legs 2012 at the one end of the body's length 2007 contact, or are placed over, the first bone 1604 while two guide legs 2012 at the other, opposite end of the body's length 2007 contact, or are placed over, the second bone 1606. The non-continuous configuration of the bottom portion of the body 2002 formed by the spaced apart legs 2012 can be useful in creating windows 2014 that are defined in the body 2002 to enable visualization of the target anatomy while the body 2002 is placed at the target anatomy. For instance, the windows 2014 can be configured to enable visualization of the first bone 1604, the second bone 1606, and the separation 1602 while the body 2002 is placed at the first and second bones 1604, 1606 and across the separation 1602. Moreover, because devices guided by the implant guide sleeve 2000 will typically be placed into the interior area 2006 from the top portion of the body 2002, the windows 2014 can enable visualization of the first bone 1604, the second bone 1606, and the separation 1602 while the device(s) is being advanced downward from the top portion of the body 2002.

The implant guide sleeve 2000, for instance at the body 2002, can further include a first end portion bottom surface 2020, a second end portion bottom surface 2021, a first end portion top surface 2022, and a second end portion top surface 2023. The second end portion bottom surface 2021 can be spaced apart from the first end portion bottom surface 2020. For instance, the first end portion bottom surface 2020 can be at a first end of the length 2007 and the second end portion bottom surface 2021 can be at a second, opposite end of the length 2007. The first end portion top surface 2022 can be aligned with (e.g., relative to the height 2003) the first end portion bottom surface 2020, and the second end portion top surface 2023 can be aligned with the second end portion bottom surface 2021 (e.g., relative to the height 2003) and spaced apart from the first end portion top surface 2022. For instance, the first end portion top surface 2022 can be at the first end of the length 2007 and the second end portion top surface 2023 can be at the second, opposite end of the length 2007. In the illustrated embodiment, the first and second end portion top surfaces 2022, 2023 can be formed by the top wall 2011, while the first end portion bottom surface 2020 can be formed by the legs 2012 at, or over, the first bone 1604 and the second end portion bottom surface 2021 can be formed by the legs 2012 at, or over, the second bone 1606.

Additionally, the implant guide sleeve 2000, for instance at the body 2002, can include one or more structures configured to help secure the implant guide sleeve 2000 at one or more bones. For example, the implant guide sleeve 2000 can include at the body 2002 one or more pin apertures that are configured, respectively, to receive a pin therethrough and into an interfacing bone. The illustrated embodiment of the implant guide sleeve 2000 includes a first pin aperture 2026 and a second pin aperture 2028. The first pin aperture 2026 is configured to receive a first pin positioned therethrough and into the first bone 1604 to fixate the implant guide sleeve 2000 to the first bone 1604. The second pin aperture 2028 is configured to receive a second pin positioned therethrough and into the second bone 1606 to fixate the implant guide sleeve 2000 to the second bone 1606.

Figure 11B:
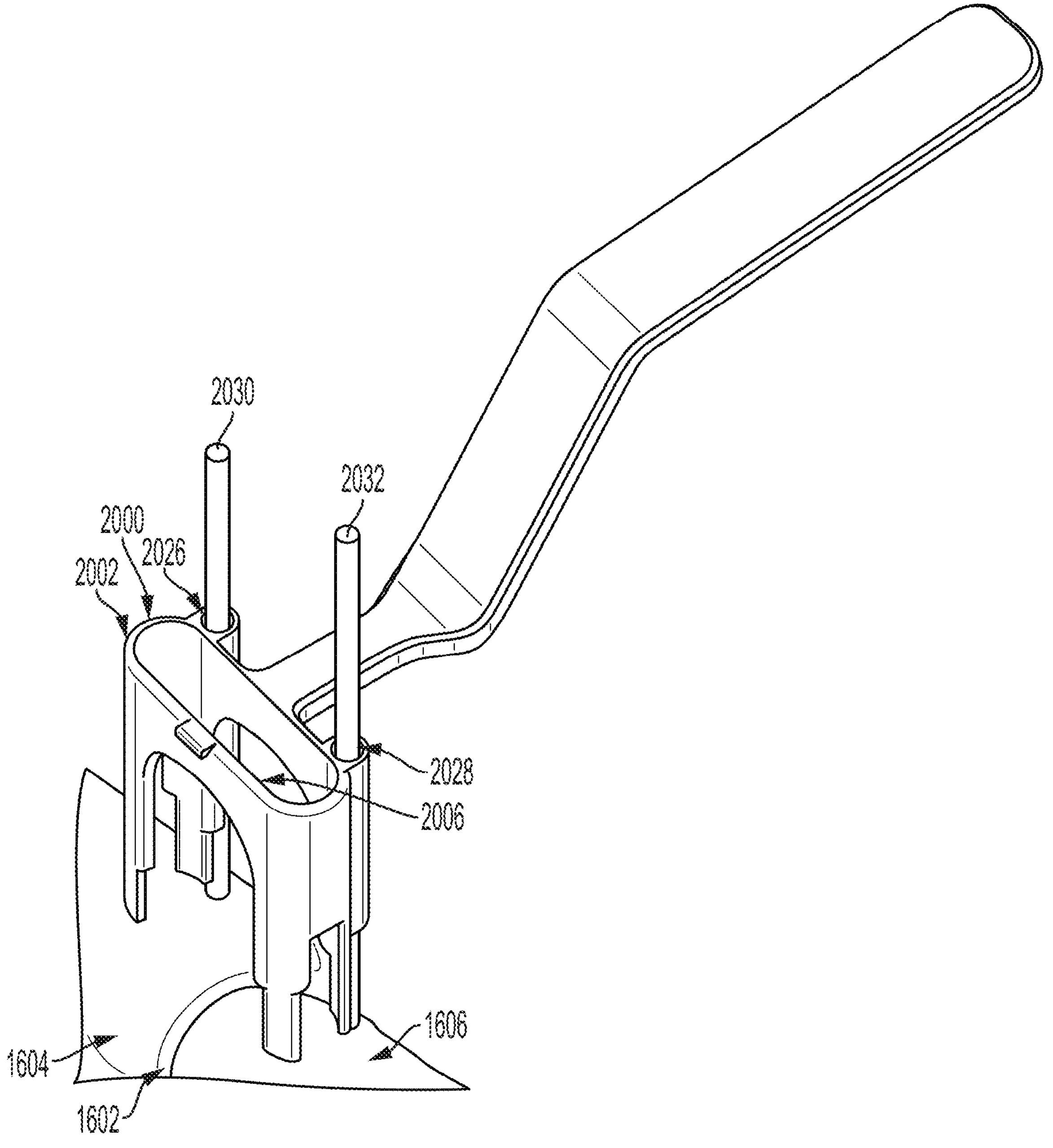

FIG. 11B is a perspective view of the implant guide sleeve 2000 secured to the first bone 1604 and the second bone 1606. As noted, the implant guide sleeve 2000 can be positioned at (e.g., in contact with; over and in contact with overlaying skin) the first bone 1604 and the second bone 1606 and across the separation 1602 between the first and second bones 1604, 1606. In instances where the implant guide sleeve 2000 is to be secured to the bones 1604, 1606, the implant guide sleeve 2000 can be fixated to each of the first bone 1604 and the second bone 1606 after the implant guide sleeve 2000 is positioned at the first bone 1604 and the second bone 1606 but before advancing the inserter to position the implant.

For the illustrated embodiment, the implant guide sleeve 2000 can be secured to the bones 1604, 1606 using the pin apertures 2026, 2028 at the body 2002. Fixating the implant guide sleeve 2000 to the first bone 1604 can include inserting a first pin 2030 through the first pin aperture 2026 at the implant guide sleeve 2000 and into the first bone 1604. And, fixating the implant guide sleeve 2000 to the second bone 1606 can include inserting a second pin 2032 through a second pin aperture 2028 at the implant guide sleeve 2000 and into the second bone 1606. The implant guide sleeve 2000 can be locationally fixated at the first and second bones 1604, 1606 such that the interior area 2006, defined at the body 2002, is positioned over at least a portion of the first bone 1604, over at least a portion of the second bone 1606, and over at least a portion of the separation 1602.

Figure 11C:
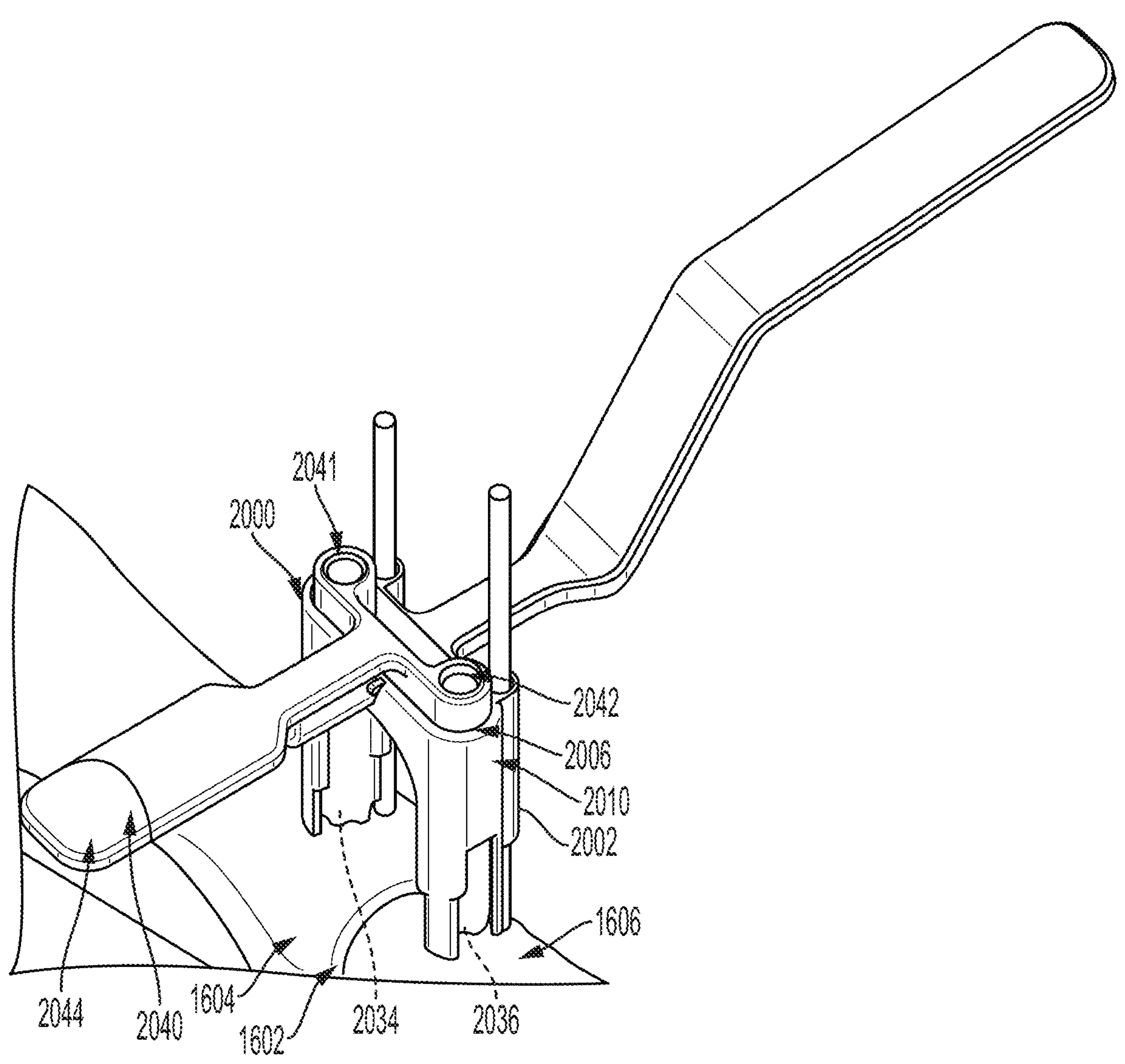

FIG. 11C is a perspective view of the implant guide sleeve 2000 used for guiding creation of implant holes. For example, the implant guide sleeve 2000 can be configured to guide creation of a first implant hole 2034 in the first bone 1604 and to guide creation of a second implant hole 2036 in the second bone 1606.

In a variety of embodiments, using the implant guide sleeve 2000 to guide creation of the first implant hole 2034 in the first bone 1604 and to guide creation of the second implant hole 2036 in the second bone 1606 can include using the implant guide sleeve 2000 to guide placement of a drill at the first bone 1604 and at the second bone 1606 for creating the first and second implant hole 2034, 2036. As such, the interior area 2006 of the implant guide sleeve 2000 can be configured to receive therein a drill. In this way, using the implant guide sleeve 2000 to guide placement of the drill at the first bone 1604 and at the second bone 1606 can include using an interior area 2006 defined by the implant guide sleeve 2000 to guide placement of the drill at the first bone 1604 for creating the first implant hole 2034 and to guide placement of the drill at the second bone 1606 for creating the second implant hole 2036.

In some such embodiments, a drill guide 2040 can be used with the implant guide sleeve 2000 to provide additional guidance in creating the implant holes 2034, 2036. For such embodiments, using the implant guide sleeve 2000 to guide creation of the first implant hole 2034 in the first bone 1604 and to guide creation of the second implant hole 2036 in the second bone 1606 can include inserting the drill guide 2040 into the implant guide sleeve 2000 and drilling the first implant hole 2034 in the first bone 1604 and the second implant hole 2036 in the second bone 1606 through the drill guide 2040 inserted into the implant guide sleeve 2000.

The drill guide 2040 can include a handle 2044 and one or more drill guide sleeves 2041, 2042. For example, the handle 2044 can be at a proximal end of the drill guide 2040 and the one or more drill guide sleeves 2041, 2042 can be at an opposite distal end portion of the drill guide 2040. The illustrated embodiment of the drill guide 2040 includes a first drill guide sleeve 2041 and a second drill guide sleeve 2042. Each of the first and second drill guide sleeves 2041, 2042 can be configured to receive therein a drill. And, the first drill guide sleeve 2041 can be used to drill the first implant hole 2034 in the first bone 1604 and the second drill guide sleeve 2042 can be used to drill the second implant hole 2036 in the second bone 1606.

The illustrated embodiment of the implant guide sleeve 2000 can be configured to receive the drill guide 2040 thereat. As one such example, the interior area 2006 of the implant guide sleeve 2000 can be configured to receive therein at least one of the drill guide sleeves 2041, 2042. As illustrated at FIG. 11C, the interior area 2006 of the implant guide sleeve 2000 is configured to receive therein both of the drill guide sleeves 2041, 2042. To facilitate placement of both drill guide sleeves 2041, 2042 at the interior area 2006, the drill guide 2040 can define a size and shape that fits within the interior area 2006. For instance, the drill guide 2040 can define an outer perimeter size and shape, at the distal end of the drill guide 2040 where the drill guide sleeves 2041, 2042 are located, indexed to the interior area 2006 of the implant guide sleeve 2000 so that the distal end of the drill guide 2040 where the drill guide sleeves 2041, 2042 are located can be placed at the interior area 2006. As shown for the illustrated embodiment, the drill guide sleeves 2041, 2042 can have an outer perimeter contour (e.g., curved contour) that substantially matches or is complementary to an adjacent wall 2010 of the implant guide sleeve 2000 defining the interior area 2006. When the interior area 2006 of the implant guide sleeve is placed over the first bone 1604 and the second bone 1606, placing the drill guide sleeves 2041, 2042 at this so positioned interior area 2006 can result in the drill guide sleeves 2041, 2042 guiding the drill therethrough, respectively, to contact the first bone 1604 and the second bone 1606.

For such embodiments where the implant guide sleeve 2000 is configured to receive the drill guide 2040 thereat, prior to creating the implant holes using the drill guide sleeves 2041, 2042 and guidance from the interior area 2006, the drill guide 2040 can be aligned with the implant guide sleeve 2000 and the drill guide 2040 can then be placed at the implant guide sleeve 2000. This can include placing the drill guide sleeves 2041, 2042 of the drill guide 2040 over the top portion of the body 2002 and aligned with the interior area 2006 and then moving the drill guide sleeves 2041, 2042 toward and ultimately into the interior area 2006. As such, placing the drill guide 2040 at the implant guide sleeve 2000 can include placing the first drill guide sleeve 2041 within the interior area 2006 defined by the implant guide sleeve 2000 and placing the second drill guide sleeve 2042 within the interior area 2006 defined by the implant guide sleeve 2000 and also placing the handle 2044 of the drill guide 2040 at least partially outside of the interior area 2006 defined by the implant guide sleeve 2000.

Figure 11D:
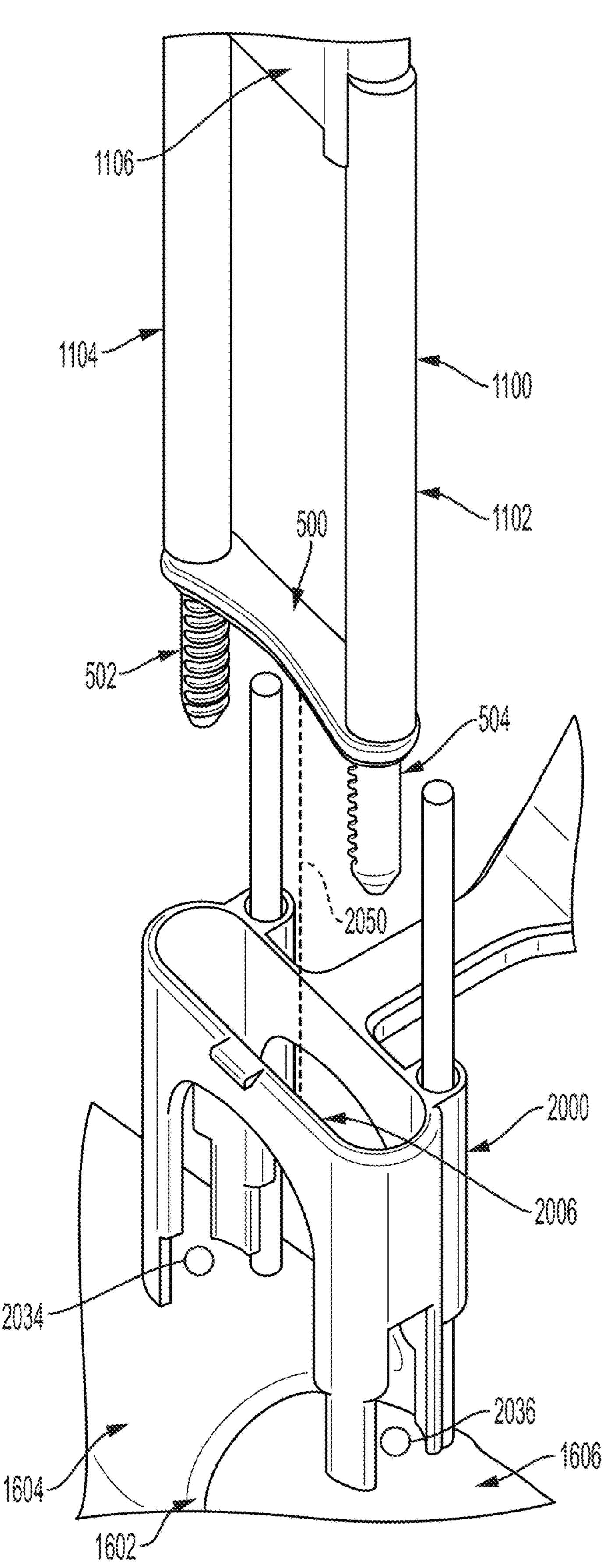

FIG. 11D is a perspective view of the implant guide sleeve 2000 used for aligning the inserter 1100, operatively connected to the staple 500, with the implant guide sleeve 2000.

As one example, aligning the staple 500, operatively connected to the inserter 1100, with the implant guide sleeve 2000 can include aligning the staple 500 (e.g., and the inserter 1100) on a common axis 2050 with the interior area 2006 of the implant guide sleeve 2000. With this common axis alignment between the interior area 2006 and at least the staple 500, the staple 500 can be moved, for instance via the inserter 1100, along the common axis 2050 into the interior area 2006 of the implant guide sleeve 2000. For instance, as shown, the common axis 2050 can extend in the plantar-dorsal direction and perpendicular to a longitudinal axis of the first and/or second bones 1604, 1606. More specifically, at least the staple 500 can be aligned with the interior area 2006 by aligning at least the staple 500 to be between the first end portion top surface 2022 and the second end portion top surface 2023 of the body 2002 while on the axis 2050.

As described previously herein, the inserter 1100 can include the first coupling shaft 1102 connected to the first side of the staple 500 and the second coupling shaft 1104 connected to the second side of the staple 500. As also described previously herein, the inserter 1100 can further include the connector 1106. When aligning the inserter 1100 with the implant guide sleeve 2000, the connector 1106 can be assembled at the inserter 1100 so as to join the first coupling shaft 1102 and the second coupling shaft 1104. When the connector 1106 so joins the first coupling shaft 1102 and the second coupling shaft 1104, the first coupling shaft 1102 and the second coupling shaft 1104 can be biased toward each other to apply the load force to the staple 500. As such, when the connector 1106 so joins the first coupling shaft 1102 and the second coupling shaft 1104 as the inserter 1100 is aligned with the implant guide sleeve 2000, the legs 502, 504 of the staple 500 can be generally parallel to one another as a result of the applied load force.

Figure 11E:
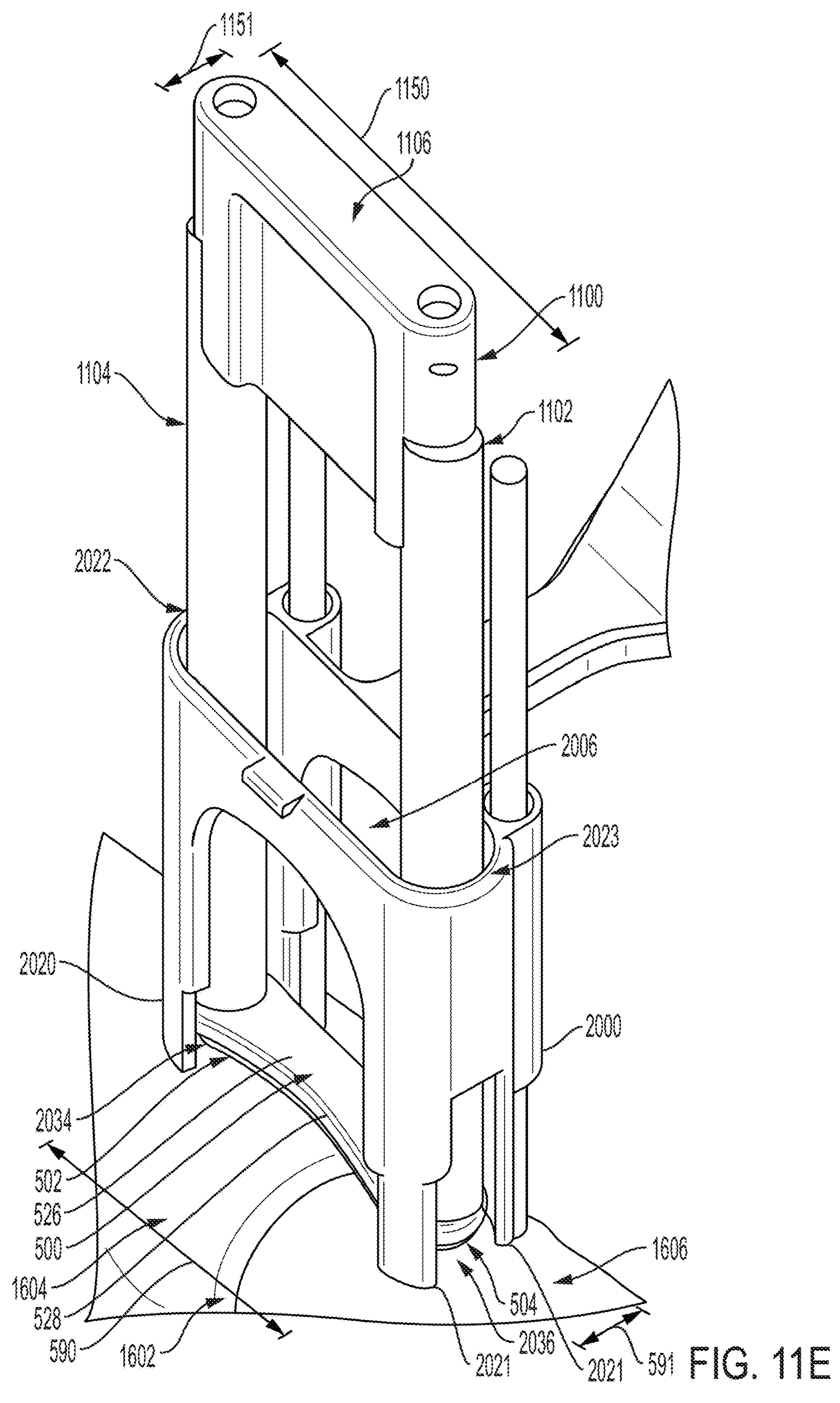

FIG. 11E is a perspective view of the implant guide sleeve 2000 used for advancing the inserter 1100, relative to the implant guide sleeve 2000, to position the staple 500 at the first bone 1604 and the second bone 1606.

The inserter 1100 can be advanced, relative to the implant guide sleeve 2000, to position the staple 500 in contact with the first bone 1604 and the second bone 1606 with the staple 500 bridging between the first bone 1604 and the second bone 1606 (e.g., bridging the separation 1602). More specifically, the inserter 1100 can be advanced, relative to the implant guide sleeve 2000, to position the staple 500 in the first implant hole 2034 in the first bone 1604, in the second implant hole 2036 in the second bone 1606, and across the separation 1602. Positioning the staple 500 at the first and second implant holes 2034, 2036 can include positioning the leg 502 of the staple 500 at (e.g., in) the first implant hole 2034 and positioning the leg 504 of the staple 500 at (e.g., in) the second implant hole 2036. Using the same implant guide sleeve 2000, at the same general orientation relative to the bones 1604, 1606, for guiding both the implant hole creation at the bones 1604, 1606 and guiding the implant (e.g., staple 500) placement at those previously created implant holes can be useful in maintaining a common reference throughout these sequential steps so as to increase the speed and convenience at which the implant (e.g., staple 500) can be placed at the bones 1604, 1606.

To advance the staple 500 (e.g., via the inserter 1100) relative to the implant guide sleeve 2000 to position the staple 500 at the bones 1604, 1606, the staple 500, and thus the inserter 1100 operatively coupled to the staple 500, can be advanced relative to the interior area 2006 of the implant guide sleeve 2000. To accommodate advancement of the inserter 1100 relative to the implant guide sleeve 2000, an overall length 1150 of the inserter 1100 (e.g., outer-most length envelop defined by the assembled inserter 1100) can be less than the length 2007 of the body 2002 and an overall width 1151 of the inserter 1100 (e.g., outermost width envelop defined by the assembled inserter 1100) can be less than the width 2009 of the body 2002. Likewise, to accommodate advancement of the staple 500 relative to (e.g., and within) the implant guide sleeve 2000 (e.g., within the interior area 2006), an overall length 590 of the staple 500 can be less than the length 2007 of the body 2002 and an overall width 591 of the staple 500 can be less than the width 2009 of the body 2002. More specifically, to accommodate advancement of the inserter 1100 and staple 500 relative to, and within, the interior area 2006 of the implant guide sleeve 2000, the interior area 2006 is larger than the corresponding envelop area defined by the assembled inserter 1100 and operatively coupled staple 500.

Advancing the inserter 1100, and thus the staple 500 operatively coupled to the inserter 1100, relative to the interior area 2006 can include advancing the staple 500, followed by the inserter 1100, between the first end portion top surface 2022 and the second end portion top surface 2023 of the implant guide sleeve 2000. It can then be followed by advancing the staple 500, and trailing inserter 1100, toward the first end portion bottom surface 2020 and the second end portion bottom surface 2021 such that the staple 500 is brought to a position adjacent the first end portion bottom surface 2020 and the second end portion bottom surface 2021 when the staple 500 is in contact with the first bone 1604 and the second bone 1606 with the staple 500 bridging between the first bone 1604 and the second bone 1606.

In guiding by the implant guide sleeve 2000 to position the staple 500 in contact with the bones 1604, 1606, the inserter 1100 can be configured to position the staple 500 generally into flush contact with the bones 1604, 1606. The staple 500 includes the top surface 526 and the bottom surface 528. The inserter 1100 is operatively connected to the staple 500 at a location on the staple 500 spaced apart from the bottom surface 528. As a result of this operative connection spaced apart from the bottom surface 528 of the staple 500, advancing the inserter 1100, relative to the implant guide sleeve 2000, to position the staple 500 in contact with the first bone 1604 and the second bone 1606 can include contacting the first bone 1604 and the second bone 1606 with the bottom surface 528 of the staple. More specifically, as a result of this operative connection spaced apart from the bottom surface 528 of the staple 500, the inserter 1100 is operatively connected to the staple 500 at a location on the staple 500 between the top surface 526 and the bottom surface 528 such that contacting the first bone 1604 and the second bone 1606 with the bottom surface 528 of the staple 500 includes contacting the first bone 1604 flush with the bottom surface 528 and contacting the second bone 1606 flush with the bottom surface 528.

Figure 11F:
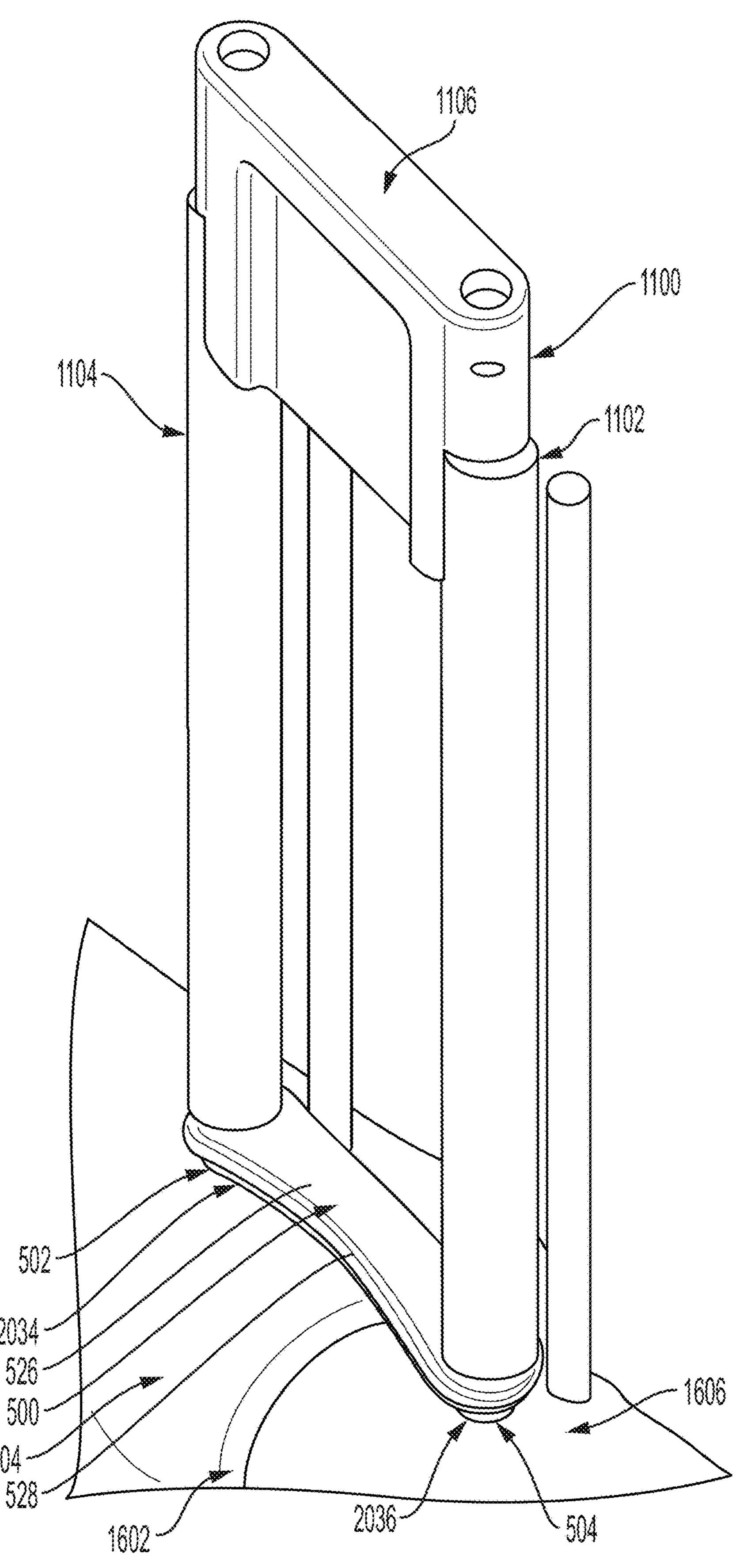

FIG. 11F is a perspective view of the inserter 1100 with the staple 500 positioned in contact with the first bone 1604 and the second bone 1606 after the implant guide sleeve has been used to help guide positioning of the staple 500 at the first and second bones 1604, 1606 and the implant guide sleeve 2000 is removed. The implant guide sleeve can be used to guide the creation of the implant hole(s) and/or to guide positioning of the staple 500 at the bone(s) 1604, 1606 and then after the staple 500 has been positioned at the bone(s) 1604, 1606 as desired, the implant guide sleeve can be removed. As shown at the example of FIG. 11F, when the implant guide sleeve is removed, the staple legs 502, 504 can be positioned in the implant holes 2034, 2036, respectively. And, with the implant guide sleeve removed, the inserter 1100 can be better accessed to remove the load force applied to the staple 500 and thereby cause the staple to apply a compressive force at the bones 1604, 1606 to urge the bones 1604, 1606 toward the separation 1602.

FIGS. 12A-12D illustrate another embodiment of an implant guide sleeve 3000. The implant guide sleeve 3000 can be used, as one example, to help carry out one or more of the steps of the method 1500 described previously. Thus, in one exemplary application, the implant guide sleeve 3000 can be used in a surgical technique for positioning an implant, such as a staple, to fixate bones for fusion, and one or more aspects described and/or illustrated with respect to the implant guide sleeve 3000 can be applied in the method 1500.

Figure 12A:
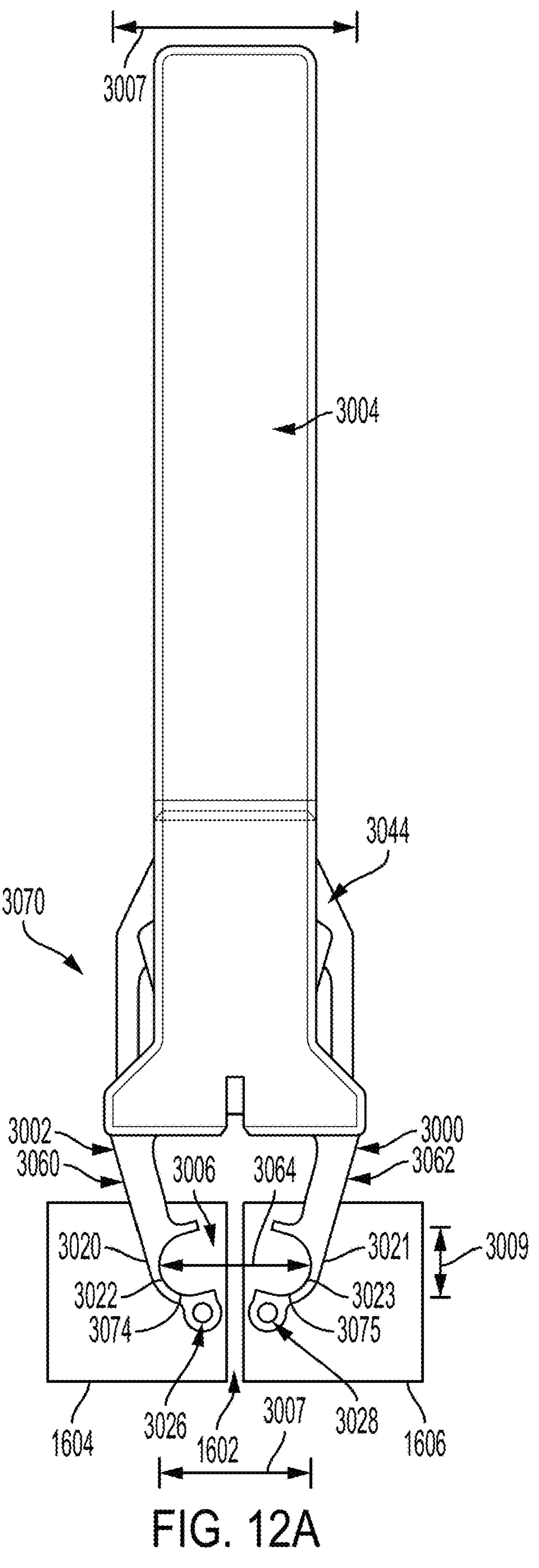
FIGS. 12A-12D illustrate another embodiment of an implant guide sleeve (e.g., that can be used for an embodiment of a surgical technique for positioning an implant to fixate bones for fusion).

FIG. 12A is a top plan view of the implant guide sleeve 3000 positioned at the first bone 1604, the second bone 1606, and across the separation 1602 between the first bone 1604 and the second bone 1606. As with the previously illustrated embodiment of the implant guide sleeve 2000, in the illustrated example, the first bone 1604 is a metatarsal, more specifically the first metatarsal, the second bone 1606 is a cuneiform, more specifically the medial cuneiform, and the separation 1602 is a joint space, more specifically the tarsometatarsal (TMT) joint space, between the first and second bones 1604, 1606. Though as described elsewhere herein, embodiments disclosed herein can be applied similarly to other bones in the foot or hand or other (e.g., small) bones more generally.

The implant guide sleeve 3000 can be configured to be placed at one or more bones, such as the first and second bones 1604, 1606, to guide creation of implant holes at such one or more bones and/or to guide placement of an implant, such as a staple, at the one or more bones 1604, 1606. For example, the implant guide sleeve 3000 can be configured to be placed at the first and second bones 1604, 1606 and configured to (i) guide creation of a first implant hole at the first bone 1604 and to guide creation of a second implant hole at the second bone 1606, and (ii) then guide placement of an implant at those previously created first and second implant holes. With the implant guide sleeve 3000 configured to sequentially guide implant hole creation followed by implant placement using the same implant guide sleeve 3000 (e.g., the same implant guide sleeve 3000 maintained at the same general orientation relative to the bones 1604, 1606 for both the implant hole creation and the implant placement), the implant guide sleeve 3000 can be useful in facilitating more accurate and efficient implant procedures. This can be especially useful in applications involving relatively small bones of the foot or hand where the location of previously created implant holes in such small bones can otherwise be difficult to discern when attempting to position the implant at these relatively small implant holes.

The implant guide sleeve 3000 can include a guide sleeve body 3002 and a handle 3004. The body 3002 can have a height (in a direction into/out of the plane view viewing angle of the illustration at FIG. 12A) that extends in a direction away from bones 1604, 1606 when the body 3002 is placed at the bones 1604, 1606. This height of the body 3002 can be sufficiently tall to provide the guiding functions described herein but yet not too tall to impede workflow in the region of the bones 1604, 1606. The body 3002 can have a length 3007 that extends in a direction generally parallel to the longitudinal axis of at least one of bones 1604, 1606, and the length 3007 can range from one to twelve inches, such as ranging from one to six inches. The length 3007 can be configured so as to accommodate therein a corresponding length of one or more tools or devices used in creating implant holes in the bones 1604, 1606 (e.g., drill) and positioning an implant at the bones 1604, 1606 (e.g., inserter and staple). And the body 3002 can have a width 3009 that extends in a direction generally perpendicular to the longitudinal axis of at least one of bones 1604, 1606, and the width 3009 can range from one-tenth of an inch to six inches, such as ranging from one-tenth of an inch to one inch. The width 3009 can be configured so as to accommodate therein a corresponding width of one or more tools or devices used in creating implant holes in the bones 1604, 1606 (e.g., drill) and positioning an implant at the bones 1604, 1606 (e.g., inserter and staple). The handle 3004 can extend outward from the body 3002. The handle 3004 can be configured to be gripped with a hand of a user to move and place the body 3002. As illustrated, the implant guide sleeve 3000 can be configured such that when the body 3002 is positioned at the first and second bones 1604, 1606, the handle 3004 can extend away from the bones 1604, 1606.

The illustrated embodiment of the implant guide sleeve 3000 can define an interior area 3006 that can be configured to guide implant hole creation and/or implant placement. As one example, the interior area 3006 can be an internal volume defined by the body 3002. In this example, the interior area 3006 can be defined as the area equal to the length 3007 multiplied by the width 3009 and the internal volume can be defined as the volume equal to the length 3007 multiplied by the width 3009 multiplied by the height (measured in a direction into/out of the page in the illustrated plan view angle at FIG. 12A). The interior area 3006 can be configured to receive therein one or more tools for creating implant holes at the bones 1604, 1606 and/or to receive therein one or more implants being placed at the bones 1604, 1606. For the illustrated example, the interior area 3006 can be configured to both receive therein a drill to create a first implant hole at the first bone 1604 and to create a second implant hole at the second bone 1606 while the drill is within the interior area 3006. Also for the illustrated example, the interior area 3006 can be configured to receive therein an inserter and implant that is operatively coupled to the inserter.

The implant guide sleeve 3000, for instance at the body 3002, can further include a first end portion bottom surface 3020, a second end portion bottom surface 3021, a first end portion top surface 3022, and a second end portion top surface 3023. The second end portion bottom surface 3021 can be spaced apart from the first end portion bottom surface 3020. For instance, the first end portion bottom surface 3020 can be at a first end of the length 3007 and the second end portion bottom surface 3021 can be at a second, opposite end of the length 3007. The first end portion top surface 3022 can be aligned with (e.g., relative to the height) the first end portion bottom surface 3020, and the second end portion top surface 3023 can be aligned with the second end portion bottom surface 3021 (e.g., relative to the height) and spaced apart from the first end portion top surface 3022. For instance, the first end portion top surface 3022 can be at the first end of the length 3007 and the second end portion top surface 3023 can be at the second, opposite end of the length 3007.

Additionally, the implant guide sleeve 3000, as shown for the illustrated embodiment, can include a first guide arm 3060 and a second guide arm 3062. The first guide arm 3060 and the second guide arm 3062 can be movable. For instance, each guide arm 3060, 3062 can be movable relative to the handle 3004. As one example, the first guide arm 3060 and the second guide arm 3062 can be rotationally coupled to the handle 3004 such that moving the first guide arm 3060 includes rotating the first guide arm 3060 relative to the handle 3004 and moving the second guide arm 3062 includes rotating the second guide arm 3062 relative to the handle 3004. As one example, the interior area 3006 can be the area between the first guide arm 3060 and the second guide arm 3062 such that moving the first and second guide arms 3060, 3062 can change the size of the interior area 3006. For instance, as shown at FIG. 12A, the first guide arm 3060 and the second guide arm 3062 are spaced apart by a first guide arm distance 3064. For embodiments that include the first and second guide arms 3060, 3062, the width 3009 can be the distance defined by a distance between an outer diameter of the guide arms 3060, 3062 and the guide arm distance (e.g., the first guide arm distance 3064) can be defined by a distance between an inner diameter of the guide arms 3060, 3062.

The implant guide sleeve 3000, for instance at the body 3002, can also include one or more structures configured to help secure the implant guide sleeve 3000 at one or more bones. For example, the implant guide sleeve 3000 can include at the body 3002 one or more pin apertures that are configured, respectively, to receive a pin therethrough and into an interfacing bone. The illustrated embodiment of the implant guide sleeve 3000 includes a first pin aperture 3026 and a second pin aperture 3028. The first pin aperture 3026 is configured to receive a first pin positioned therethrough and into the first bone 1604 to fixate the implant guide sleeve 3000 to the first bone 1604. The second pin aperture 3028 is configured to receive a second pin positioned therethrough and into the second bone 1606 to fixate the implant guide sleeve 3000 to the second bone 1606. The first pin aperture 3026 can be at the first guide arm 3060 and the second pin aperture 3028 can be at the second guide arm 3062 such that as the first and second guide arms 3060, 3062 move relative to the handle 3004 the first and second pin apertures 3026, 3028 also move relative to the handle 3004.

Figure 12B:
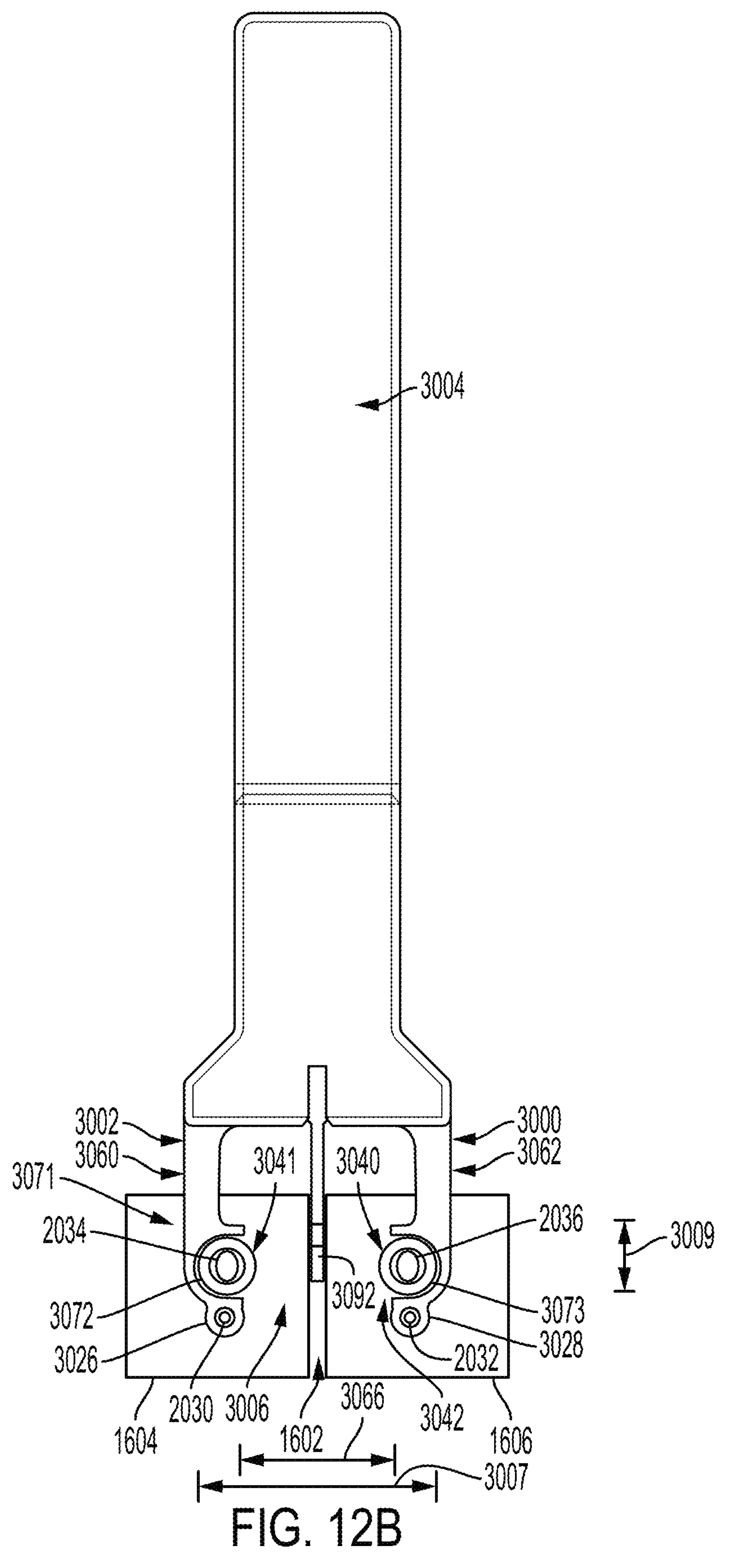

FIG. 12B is a top plan view of the implant guide sleeve 3000 secured to the first bone 1604 and the second bone 1606 and used for guiding creation of implant holes 2034, 2036.

As noted previously, the size of the implant guide sleeve 3000 can be adjusted. For instance, FIG. 12B shows the implant guide sleeve 3000 in a second size configuration, while FIG. 12A shows the implant guide sleeve 3000 in a first, smaller size configuration. The implant guide sleeve 3000 can be configured to adjust between at least the first, smaller size configuration and the second, larger size configuration. The first size configuration of the implant guide sleeve 3000 and the second size configuration of the implant guide sleeve can define different cross-sectional areas. For example, the first size configuration of the implant guide sleeve 3000 can define a first interior cross-sectional area at the interior area 3006 and bound by the implant guide sleeve 3000 while the second size configuration of the implant guide sleeve 3000 can define a second interior cross-sectional area at the interior area 3006 and bound by the implant guide sleeve 3000. The second interior cross-sectional area can be larger than the first interior cross-sectional area.

As one example, the size of the implant guide sleeve 3000 can be adjusted by moving the first guide arm 3060 and/or the second guide arm 3062. In particular, adjusting the size of the implant guide sleeve 3000 between the first size configuration and the second size configuration can include rotating the first guide arm 3060 relative to the handle 3004 and rotating the second guide arm 3062 relative to the handle 3004. In the first size configuration, the first guide arm 3060 and the second guide arm 3062 can spaced apart by the first guide arm distance 3064 (shown at FIG. 12A and, e.g., measured between the guide arms 3060, 3062 at the interior area 3006), and in the second size configuration the first guide arm 3060 and the second guide arm 3062 can be spaced apart by a second guide arm distance 3066 (shown at FIG. 12B and, e.g., measured between the guide arms 3060, 3062 at the interior area 3006). The second guide arm distance 3066 can be greater than the first guide arm distance. As one example, the first guide arm distance 3064 can be smaller than a length of the implant (e.g., smaller than the length 590 of the staple 500) to be guided and positioned using the implant guide sleeve 3000 (e.g., using the interior area 3006), while the second guide arm distance 3066 can be larger than the length of the implant (e.g., smaller than the length 590 of the staple 500) to be guided and positioned using the implant guide sleeve 3000 (e.g., using the interior area 3006). In this example, then, the guide arm distance needs to be adjusted to the larger second guide arm distance 3066 before the implant can be positioned with guidance from the implant guide sleeve 3000.

The ability to adjust the size of the implant guide sleeve 3000 can be useful in allowing for a smaller access site (e.g., smaller incision size over the bones 1604, 1606). Namely, the implant guide sleeve 3000 can be in the first, smaller size configuration (e.g., shown at FIG. 12A) when the implant guide sleeve 3000 is being moved through the access site (e.g., through an incision) toward the bones 1604, 1606 and while the implant guide sleeve 3000 is being positioned at the bones 1604, 1606 and across the separation 1602. Then, after the implant guide sleeve 3000 has been moved through the access site (e.g., through an incision) and placed at, or over, the bones 1604, 1606, the implant guide sleeve 3000 can be adjusted to the second, larger size configuration (e.g., shown at FIG. 12B). Thus, prior to positioning the implant guide sleeve 3000 at the first bone 1604, the second bone 1606, and across the separation 1602, the implant guide sleeve 3000 can be inserted, in the first size configuration, through an incision that exposes at least a portion of each of the first bone 1604, the second bone 1606, and the separation 1602. And, after inserting the implant guide sleeve 3000, in the first size configuration, through the incision, the size of the implant guide sleeve 3000 can be adjusted from the first size configuration to the second size configuration. In addition, in a further embodiment, the implant guide sleeve 3000 can be adjusted from the first size configuration to the second size configuration before advancing the inserter 1100 relative to the implant guide sleeve 3000. And, in yet a further embodiment, the implant guide sleeve 3000 can be fixated to each of the first bone 1604 and the second bone 1606 after adjusting the implant guide sleeve 3000 from first size configuration to the second size configuration and before advancing the inserter 1100 relative to the implant guide sleeve 3000.

FIG. 12B shows the implant guide sleeve 3000 secured to the first bone 1604 and the second bone 1606. As noted, the implant guide sleeve 2000 can be positioned at (e.g., in contact with; over and in contact with overlaying skin) the first bone 1604 and the second bone 1606 and across the separation 1602 between the first and second bones 1604, 1606. In instances where the implant guide sleeve 3000 is to be secured to the bones 1604, 1606, the implant guide sleeve 3000 can be fixated to each of the first bone 1604 and the second bone 1606 after the implant guide sleeve 3000 is positioned at the first bone 1604 and the second bone 1606 but before advancing the inserter to position the implant.

For the illustrated embodiment, the implant guide sleeve 3000 can be secured to the bones 1604, 1606 using the pin apertures 3026, 3028 at the body 3002. Fixating the implant guide sleeve 3000 to the first bone 1604 can include inserting first pin 2030 through the first pin aperture 3026 at the implant guide sleeve 3000 and into the first bone 1604. And, fixating the implant guide sleeve 3000 to the second bone 1606 can include inserting second pin 2032 through the second pin aperture 3028 at the implant guide sleeve 3000 and into the second bone 1606. The implant guide sleeve 3000 can be locationally fixated at the first and second bones 1604, 1606 such that the interior area 3006, defined at the body 3002 (e.g., between the guide arms 3060, 3062), is positioned over at least a portion of the first bone 1604, over at least a portion of the second bone 1606, and over at least a portion of the separation 1602

The implant guide sleeve 3000 can further include a drill guide 3040 to provide guidance in creating implant holes 2034, 2036. Using the implant guide sleeve 3000 to guide creation of the first implant hole 2034 in the first bone 1604 and to guide creation of the second implant hole 2036 in the second bone 1606 can include inserting the drill guide 3040 into the implant guide sleeve 3000 and drilling the first implant hole 2034 in the first bone 1604 and the second implant hole 2036 in the second bone 1606 through the drill guide 3040 inserted into the implant guide sleeve 3000. More specifically, as one example, the drill guide 3040 can be inserted into the interior area 3006 and between the guide arms 3060, 3062, and, in such example, the interior area 3006, with the inserted drill guide 3040, can be used to guide placement of a drill at the first bone 1604 and to guide creation of the first implant hole 2034 and to guide placement of a drill at the second bone 1606 and to guide creation of the second implant hole 2036.

The drill guide 3040 can include a handle 3044 (seen best at FIG. 12D) one or more drill guide sleeves 3041, 3042. For the illustrated embodiment, as described further in reference to FIG. 12D, the drill guide 3040, including the one or more drill guide sleeves 3041, 3042, can be integrated with the implant guide sleeve 3000. For example, the handle 3044 can be at a proximal end of the drill guide 3040 and the one or more drill guide sleeves 3041, 3042 can be at an opposite distal end portion of the drill guide 3040. The illustrated embodiment of the drill guide 3040 includes a first drill guide sleeve 3041 and a second drill guide sleeve 3042. Each of the first and second drill guide sleeves 3041, 3042 can be configured to receive a drill therein. And, the first drill guide sleeve 3041 can be used to drill the first implant hole 2034 in the first bone 1604 and the second drill guide sleeve 3042 can be used to drill the second implant hole 2036 in the second bone 1606.

The implant guide sleeve 3000 can be configured to receive the drill guide 3040 thereat. As one such example, the interior area 3006 of the implant guide sleeve 3000 can be configured to receive therein at least one of the drill guide sleeves 3041, 3042. As illustrated at FIG. 12B, the interior area 3006 of the implant guide sleeve 3000 is configured to receive therein both of the drill guide sleeves 3041, 3042. To facilitate placement of both drill guide sleeves 3041, 3042 at the interior area 3006, the drill guide 3040 can define a size and shape that fits within the interior area 3006. For instance, the drill guide 3040 can define an outer perimeter size and shape, at the distal end of the drill guide 3040 where the drill guide sleeves 3041, 3042 are located, indexed to the interior area 3006 of the implant guide sleeve 3000 so that the distal end of the drill guide 3040 where the drill guide sleeves 3041, 3042 are located can be placed at the interior area 3006. As shown for the illustrated embodiment, the drill guide sleeves 3041, 3042 can have an outer perimeter contour (e.g., curved contour) that substantially matches or is complementary to the interior perimeter contour (e.g., curved contour) of the adjacent guide arms 3060, 3062, respectively, defining the interior area 3006. When the interior area 3006 of the implant guide sleeve is placed over the first bone 1604 and the second bone 1606, placing the drill guide sleeves 3041, 3042 at this so positioned interior area 3006 can result in the drill guide sleeves 3041, 3042 guiding the drill therethrough, respectively, to contact the first bone 1604 and the second bone 1606.

The drill guide 3040 for the illustrated embodiment can be movably coupled to the implant guide sleeve 3000. The drill guide 3040 can be moved relative to the implant guide sleeve 3000 after inserting the implant guide sleeve 3000 (e.g., in the first size configuration) through an incision that exposes at least a portion of each of the first bone 1604, the second bone 1606, and the separation 1602 but prior to creating the implant holes using the drill guide sleeves 3041, 3042 and guidance from the interior area 3006. Furthermore, this can include moving the drill guide 3040 relative to the implant guide sleeve 3000 after adjusting the size of the implant guide sleeve 3000 between the first size configuration and the second size configuration (e.g., after adjusting the size of the implant guide sleeve 300 from the first size configuration to the second size configuration).

Moving the drill guide 3040 relative to the implant guide sleeve 3000 can include moving the first drill guide sleeve 3041 and/or the second drill guide sleeve 3042 relative to the implant guide sleeve 3000. As one example, the drill guide 3040 can be movable, relative to the implant guide sleeve 3000, between a retracted position 3070 (e.g., shown at FIG. 12A) and an extended position 3071 (e.g., shown at FIG. 12B). In the retracted position 3070, each of the first drill guide sleeve 3041 and the second drill guide sleeve 3042 can be retracted relative to the implant guide sleeve 3000. For instance, the first drill guide sleeve 3041 and the second drill guide sleeve 3042 can be retracted relative to the implant guide sleeve 3000 such that each of the first drill guide sleeve 3041 and the second drill guide sleeve 3042 is retracted outside of the interior area 3006 in a direction toward the handle 3004. When the first drill guide sleeve 3041 and the second drill guide sleeve 3042 are in the retracted position, the guide arms 3060, 3062 can be enabled to move between the different size configurations defined at the interior area 3006. In the extended position 3071, each of the first drill guide sleeve 3041 and the second drill guide sleeve 3042 can be aligned with the implant guide sleeve 3000. For instance, the first drill guide sleeve 3041 and the second drill guide sleeve 3042 can be extended relative to the handle 3004 such that each of the first drill guide sleeve 3041 and the second drill guide sleeve 3042 is extended to be positioned and sit within the interior area 3006. More particularly, in one example, in the extended position 3071, the first drill guide sleeve 3041 can nest at an interior surface 3072 of the first drill guide sleeve 3041 and the second drill guide sleeve 3042 can nest at an interior surface 3073 of the second drill guide sleeve 3042. To accommodate such nesting, for instance, an interior surface 3074 of the guide arm 3060 defining the interior area 3006 can have a first geometric shape that is complementary to an exterior surface 3072 of the first drill guide sleeve 3041 and an interior surface 3075 of the guide arm 3062 defining the interior area 3006 can have a second geometric shape that is complementary to an exterior surface 3073 of the second drill guide sleeve 3042. With these complementary surfaces, in the extended position 3071, the first drill guide sleeve 3041 can nest at the interior surface 3074 of the guide arm 3060 and the second drill guide sleeve 3042 can nest at the interior surface 3075 of the guide arm 3062. Furthermore, when the first drill guide sleeve 3041 and the second drill guide sleeve 3042 are in the extended position, the guide arms 3060, 3062 may be impeded from moving between the different size configurations defined at the interior area 3006.

To help facilitate movement of the drill guide 3040, the implant guide sleeve 3000 can include an actuator 3080 (best illustrated at FIG. 12D) that is configured to move the drill guide 3040. For the illustrated embodiment, the actuator 3080 is included at the handle 3044 of the drill guide 3040. The actuator 3080 can be configured such that, when actuated, the actuator 3080 causes the drill guide 3040 to move, relative to the implant guide sleeve 3000, from the retracted position 3070 to the extended position 3071. For example, the drill guide 3040 can be maintained at the extended position 3071 while an actuation input is being applied at the actuator 3080 and when the actuation input is removed from the actuator 3080 the drill guide 3040 can move back to the retracted position 3070. For the illustrated embodiment, the actuation input at the actuator 3080 can be a force applied by a hand (e.g., finger) of a user to cause the drill guide sleeves 3041, 3042 to move into the interior area 3006 of the implant guide sleeve 3000.

The drill guide 3040 can further include a visual marker 3082. The visual marker 3082 can be configured to help assist with alignment at the separation 1602 between the first bone 1604 and the second bone 1606. The visual marker 3082 can be movable with the drill guide 3040. As such, the in the retracted position 3070 of the drill guide 3040, the visual marker 3082 can be retracted relative to the implant guide sleeve 3000 and the interior area 3006. On the other hand, in the extended position 3071 of the drill guide 3040, the visual marker 3082 can extend out, relative to the handle 3004, and be aligned with the implant guide sleeve 3000 and the interior area 3006. The presence of the visual marker 3082 when extended into the interior area 3006 can help to provide a reference relative to the separation 1602, first bone 1604, and second bone 1606, for instance, when creating the implant holes 2034, 2036.

Figure 12C:
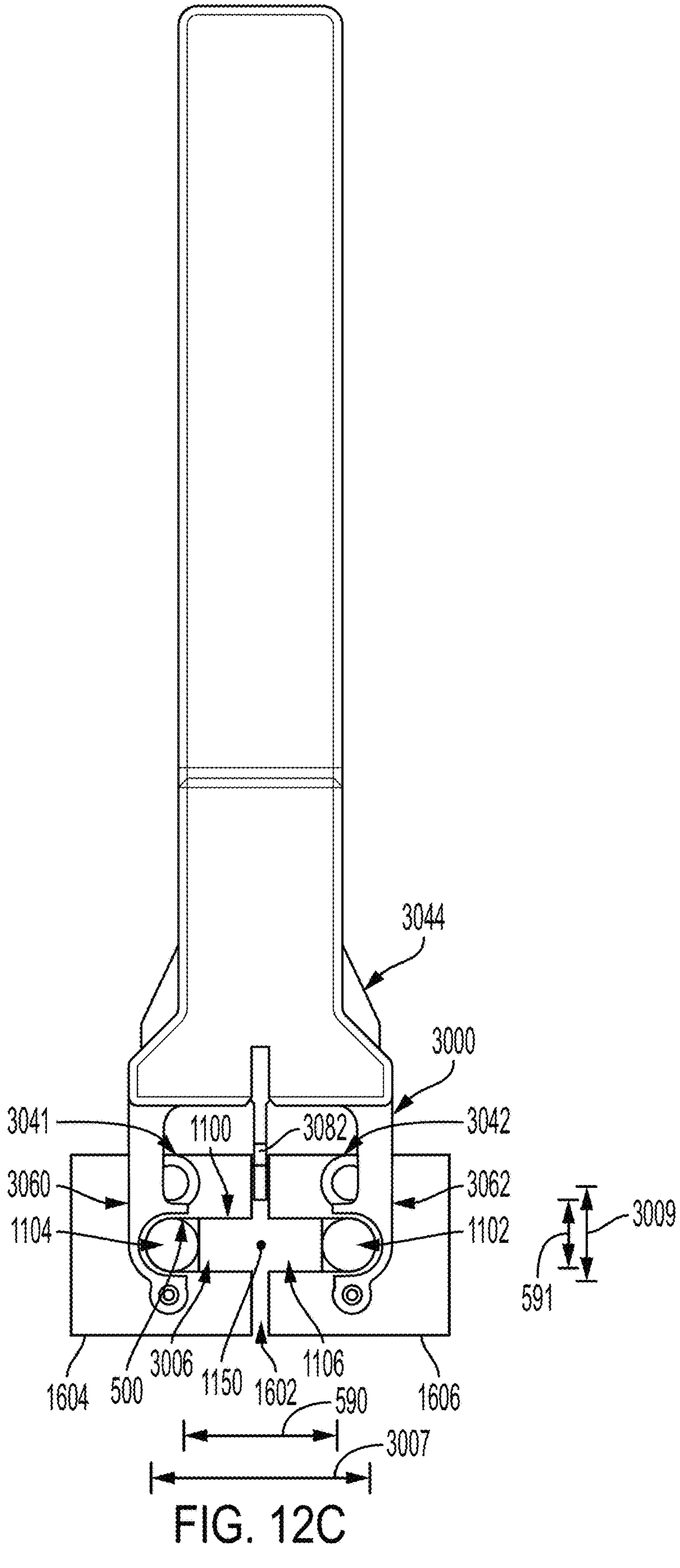

FIG. 12C is a top plan view of the implant guide sleeve 3000 used for aligning the inserter 1100. The inserter 1100 is shown here operatively connected to the staple 500. The staple 500, and associated inserter 1100, can be aligned with the implant guide sleeve 3000 and the implant guide sleeve 3000 can be used for advancing the staple 500, via advancement of the inserter 1100, relative to the implant guide sleeve 3000, to position the staple 500 at the first bone 1604 and the second bone 1606. Using the implant guide sleeve 3000 for guiding positioning of the staple 500 in contact with the first and second bones 1604, 1606 can be similar to the description set forth previously herein with respect to aligning and advancing the staple 500, and associated inserter 1100, using the implant guide sleeve 2000 (e.g., in reference to FIGS. 11D-11F).

As one example, aligning the inserter 1100, operatively connected to the staple 500, with the implant guide sleeve 3000 can include aligning the staple 500 (e.g., and the inserter 1100) on the common axis 2050 with the interior area 3006 of the implant guide sleeve 3000. With this common axis alignment between the interior area 3006 and at least the staple 500, the staple 500 can be moved, for instance via the inserter 1100, along the common axis 2050 into the interior area 3006 of the implant guide sleeve 3000. For instance, as shown, the common axis 2050 can extend in the plantar-dorsal direction and perpendicular to a longitudinal axis of the first and/or second bones 1604, 1606. In some instances, this can include at least the staple 500 being aligned with the interior area 3006 by aligning at least the staple 500 to be between the first end portion top surface 3022 and the second end portion top surface 3023 of the body 3002 while on the axis 2050. Similarly, in some instances, this can include at least the staple 500 being aligned with the interior area 3006 by aligning at least the staple 500 to be between the first guide arm 3060 and the second guide arm 3062. For example, the staple 500 can be aligned with the interior area 3006 by aligning the staple 500 on the common axis 1150 with the length and width of the staple 500 inside of the span between the guide arms 3060, 3062 (e.g., inside of the second guide arm distance 3066) and the width between the guide arms 3060, 3062 (e.g., inside of the width 3009). To facilitate this staple 500 alignment with the implant guide sleeve 3000, the implant guide sleeve 3000 can be in the second, larger size configuration when the staple 500 is being aligned with the implant guide sleeve 3000 and/or when the staple 500 is being advanced relative to the implant guide sleeve 3000 to position the staple 500 at the bones 1604, 1606. As such, it an be the case in various embodiments that the size of the implant guide sleeve 3000 is adjusted to be a larger size (e.g., adjusted to have a larger interior area 3006) prior to advancing the staple 500, relative to the implant guide sleeve 3000, to position the staple 500 at the bones 1604, 1606.

With the staple 500 aligned with the implant guide sleeve 3000, the staple 500 can be advanced, relative to the implant guide sleeve 3000, to position staple 500 in contact with the first bone 1604 and the second bone 1606 with the staple 500 bridging between the first bone 1604 and the second bone 1606 (e.g., bridging the separation 1602). More specifically, the staple 500 can be advanced (e.g., via the inserter 1100), relative to the implant guide sleeve 3000, to position the staple 500 in the first implant hole 2034 in the first bone 1604, in the second implant hole 2036 in the second bone 1606, and across the separation 1602. Positioning the staple 500 at the first and second implant holes 2034, 2036 can include positioning the leg 502 of the staple 500 at (e.g., in) the first implant hole 2034 and positioning the leg 504 of the staple 500 at (e.g., in) the second implant hole 2036. As described previously herein, using the same implant guide sleeve 3000, at the same general orientation relative to the bones 1604, 1606, for guiding both the implant hole creation at the bones 1604, 1606 and guiding the staple 500 placement at those previously created implant holes can be useful in maintaining a common reference throughout these sequential steps.

To advance the staple 500 (e.g., via the inserter 1100) relative to the implant guide sleeve 3000 to position the staple 500 at the bones 1604, 1606, the staple 500, and thus the inserter 1100 operatively coupled to the staple 500, can be advanced relative to the interior area 3006 of the implant guide sleeve 3000. To accommodate advancement of the staple 500 relative to (e.g., and within) the implant guide sleeve 3000 (e.g., within the interior area 3006), the overall length 590 of the staple 500 can be less than the length 3007 of the body 3002 (e.g., less than the larger second guide arm distance 3066) and the overall width 591 of the staple 500 can be less than the width 3009 of the body 3002 (e.g., less than width defined by the interior surfaces 3074, 3075 of the guide arms 3060, 3062, respectively). Indeed, as the staple 500 can be advanced through the same interior area 3006 at which the drill guide sleeves 3041, 3042 are positioned (e.g., when creating the implant holes prior to advancing the staple 500), the staple 500 can have a width similar to a width of those drill guide sleeves 3041, 3042. Likewise, to accommodate advancement of the inserter 1100 relative to the implant guide sleeve 3000, the overall length 1150 of the inserter 1100 (e.g., outer-most length envelop defined by the assembled inserter 1100) can be less than the length 3007 of the body 3002 and the overall width 1151 of the inserter 1100 (e.g., outermost width envelop defined by the assembled inserter 1100) can be less than the width 3009 of the body 3002. More specifically, to accommodate advancement of the staple 500 and accompanying inserter 1100 relative to, and within, the interior area 3006 of the implant guide sleeve 3000, the interior area 3006 can be larger than the corresponding envelop area defined by the assembled inserter 1100 and operatively coupled staple 500.

Advancing the staple 500, and thus the inserter 1100 operatively coupled to the staple 500, relative to the interior area 3006 can include advancing the staple 500, followed by the inserter 1100, between the first end portion top surface 3022 and the second end portion top surface 3023 of the implant guide sleeve 3000. It can then be followed by advancing the staple 500, and trailing inserter 1100, toward the first end portion bottom surface 3020 and the second end portion bottom surface 3021 such that the staple 500 is brought to a position adjacent the first end portion bottom surface 3020 and the second end portion bottom surface 3021 when the staple 500 is in contact with the first bone 1604 and the second bone 1606 with the staple 500 bridging between the first bone 1604 and the second bone 1606.

As described previously with respect to advancement of the staple 500 relative to the implant guide sleeve 2000, the implant guide sleeve 3000 can likewise guide advancement of the staple 500 to position the staple 500 in contact with the bones 1604, 1606. Namely, when guiding placement of the staple 500 using the implant guide sleeve 3000, the inserter 1100 can be configured to position the staple 500 generally into flush contact with the bones 1604, 1606, as the inserter 1100 can be operatively connected to the staple 500 at a location on the staple 500 spaced apart from the bottom surface 528 of the staple 500 such that advancing the inserter 1100, relative to the implant guide sleeve 3000, to position the staple 500 in contact with the first bone 1604 and the second bone 1606 can include contacting the first bone 1604 and the second bone 1606 with the bottom surface 528 of the staple (e.g., contacting the first bone 1604 flush with the bottom surface 528 and contacting the second bone 1606 flush with the bottom surface 528).

Figure 12D:
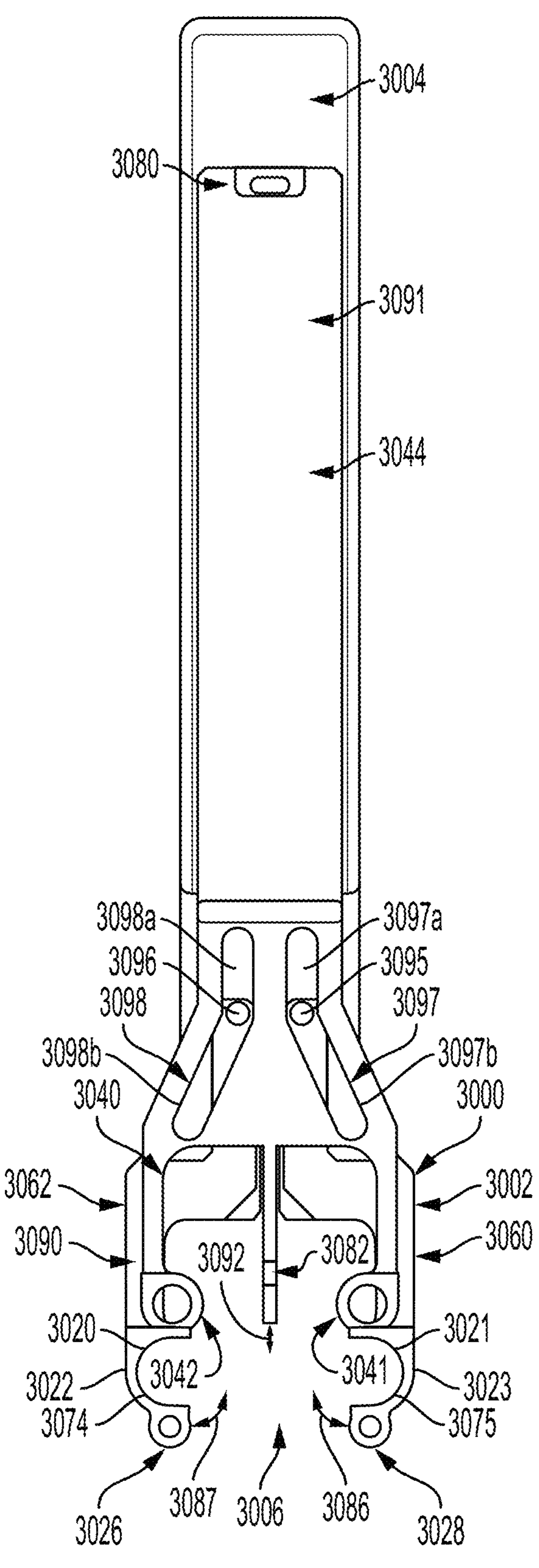

FIG. 12D is a bottom plan view of the implant guide sleeve 3000 in isolation. In particular, FIG. 12D illustrates an exemplary configuration of the drill guide 3040 at the implant guide sleeve 3000, for instance, with the drill guide 3040 integrated with the implant guide sleeve 3000. The illustrated embodiment of the drill guide 3040 includes the first drill guide sleeve 3041, the second drill guide sleeve 3042, and the handle 3044. The first and second drill guide sleeves 3041, 3042 can be at a distal end portion 3090 of the drill guide 3040 and the handle 3044 can be at a proximal end portion 3091 of the drill guide.

As noted previously, the drill guide 3040 can be movably coupled to the implant guide sleeve 3040, for instance, such that the drill guide 3040 is movable relative to the handle 3004 in the direction 3092. The drill guide 3040 can be movably coupled to the implant guide sleeve 3040 in any of a variety of manners, including a suitable type of mechanical translation coupling (e.g., a track receiving a sliding element). The drill guide 3040 being movably coupled to the implant guide sleeve 3000 can include the first drill guide sleeve 3041 and the second drill guide sleeve 3042 being movable relative to the implant guide sleeve 3040. For instance, the first and second drill guide sleeves 3041, 3042 can be movably coupled to the implant guide sleeve 3040 such that the first and second drill guide sleeves 3041, 3042 are movable relative to the handle 3004 in the direction 3092. As noted previously, the drill guide 3040 can be movable, relative to the implant guide sleeve 3000 (e.g., relative to the handle 3004), in the direction 3092 between the retracted position 3070 (e.g., shown at FIG. 12A, 12D) and the extended position 3071 (e.g., shown at FIG. 12B). In the retracted position 3070, each of the first drill guide sleeve 3041 and the second drill guide sleeve 3042 can be retracted relative to the implant guide sleeve 3000 (e.g., relative to the handle 3004), such as being retracted outside of the interior area 3006. To help execute movement of the drill guide 3040, the implant guide sleeve 3000 can include the actuator 3080, as described previously herein.

As shown for the illustrated embodiment, the drill guide 3040 can further include the visual marker 3082. The visual marker 3082 can be configured, for example, to help assist with alignment relative to a target anatomy. As one such example, the visual marker 3082 can be configured to help assist with alignment relative to a separation between bones. The visual marker 3082 can be movable with the drill guide 3040 such that in the drill guide's retracted position the visual marker 3082 can be retracted relative to the implant guide sleeve 3000 and the interior area 3006, while in the drill guide's extended position the visual marker 3082 can extend out, relative to the handle 3004, and be aligned with the implant guide sleeve 3000 and the interior area 3006.

In addition to the drill guide 3040 being movable, the first and second guide arms 3060, 3062 of the implant guide sleeve 3000 can be movable, as described previously herein. In one embodiment, the first and second guide arms 3060, 3062 can be movably coupled to the implant guide sleeve 3000 so as to be independently movable relative to the handle 3004, while in another embodiment the first and second guide arms 3060, 3062 can be movably coupled to the implant guide sleeve 3000 so as to be movable in tandem relative to the handle 3004.

FIG. 12D illustrates an exemplary embodiment of a movable coupling of the first and second guide arms 3060, 3062 at the implant guide sleeve 3000. The first guide arm 3060 can be movably coupled to the implant guide sleeve 3000 via a first pivot coupling 3095, and the second guide arm 3062 can be movably coupled to the implant guide sleeve 3000 via a second pivot coupling 3096. FIG. 12D illustrates a pivotable pinned coupling of each of the guide arms 3060, 3062 at the handle 3004, though other embodiments within the scope of this disclosure can include other types of movable couplings between the guide arms 3060, 3062 and the implant guide sleeve 3000.

For the illustrated embodiment, the guide arms 3060, 3062 can be configured to move (e.g., rotate relative to the handle 3004) as a result of movement of the drill guide 3040. For the illustrated embodiment, the drill guide 3040 includes a first guide arm track 3097 and a second guide arm track 3098. Each of the first and second guide arm tracks 3097, 3098 can be defined along more than one axis. For instance, the first guide arm track 3097 can include a first guide arm track first portion 3097*a* extending along a first axis and a first guide arm track second portion 3098*b* extending along a second axis that is different than the first axis, and the second guide arm track 3098 can include a second guide arm track first portion 3098*a* extending along a third axis (e.g., the third axis is parallel to the first axis and skewed relative to the second axis) and a second guide arm track second portion 3098*b* extending along a fourth axis that is different than the third axis (e.g., the four axis is parallel to the second axis and skewed relative to the first axis). For the embodiment shown here, the first and second guide arm tracks 3097, 3098 are mirror images of one another. The first and second guide arm tracks 3097, 3098 can be located between the proximal end portion 3091 and the distal end portion 3090 and, for instance, proximal to the drill guide sleeves 3041, 3042.

As the drill guide 3040 is moved in the direction 3092, the first and second guide arm tracks 3097, 3098 can be configured to transfer a motive force from the drill guide 3040 to the guide arms 3060, 3062. For example, the first pivot coupling 3095 of the first guide arm 3060 can intersect the first guide arm track 3097, and the second pivot coupling 3096 can intersect the second guide arm track 3098. Thus, as the drill guide 3040 is moved in the direction 3092, the first guide arm track 3097 will move relative to the first pivot coupling 3095 and the second guide arm track 3098 will move relative to the second pivot coupling 3096. This relative movement of the respective track 3097, 3098 and pivot coupling 3095, 3096 can act to cause the first guide arm 3060 to move in a direction 3086 and the second guide arm 3062 to move in a direction 3087. Accordingly, as the drill guide 3040 is moved in the direction 3092 this can cause the first and second guide arms 3060, 3062 to move in the directions 3086, 3087, respectively. In this way, the guide arms 3060, 3062 can be moved to change the size of the interior area 3006 to accommodate drill guide sleeves 3041, 3042 as the drill guide sleeves are being moved to the extended position. This can provide an automatic adjustment of the interior area 3006 to an extent needed to receive the drill guide sleeves 3041, 3042 at that interior area 3006.

Figure 12E:
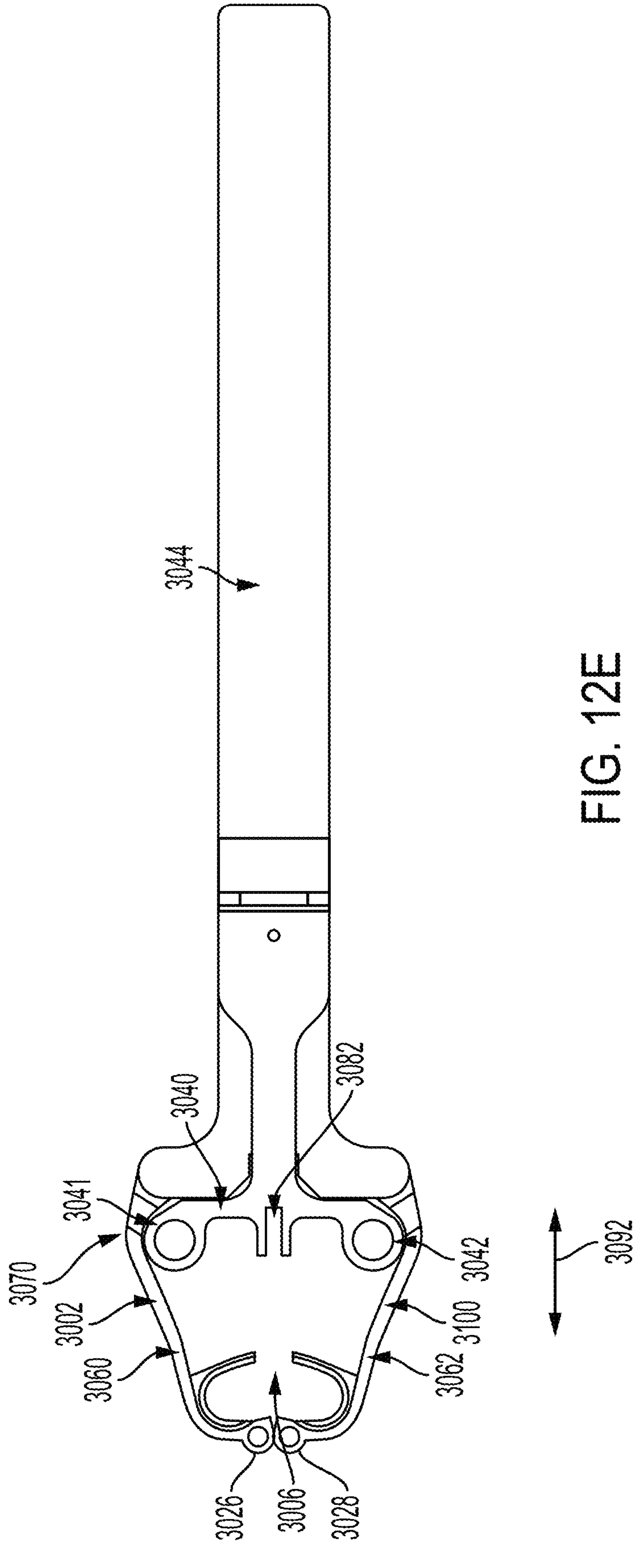
FIGS. 12E-12I illustrate another embodiment of an implant guide sleeve (e.g., that can be used for an embodiment of a surgical technique for positioning an implant to fixate bones for fusion).
Figure 12F:
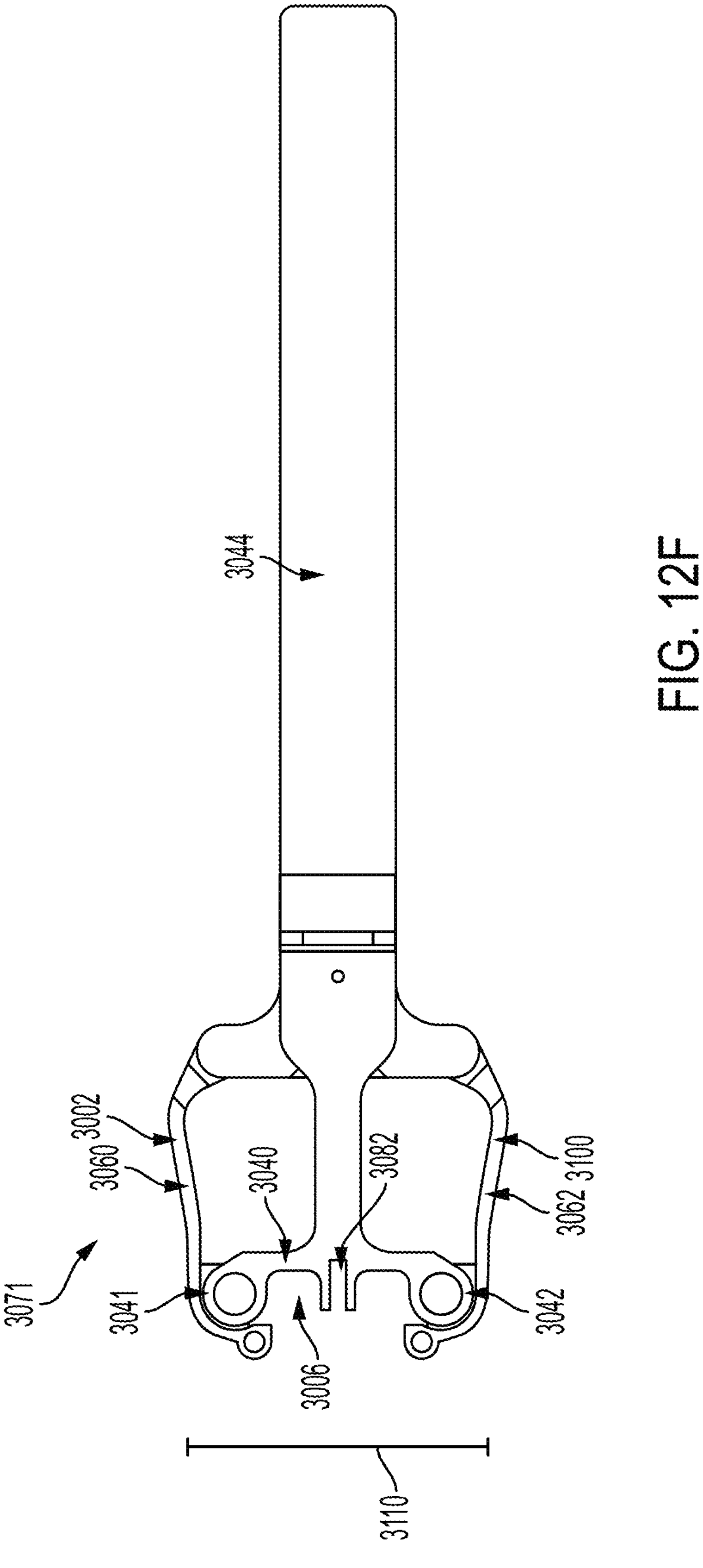
Figure 12G:
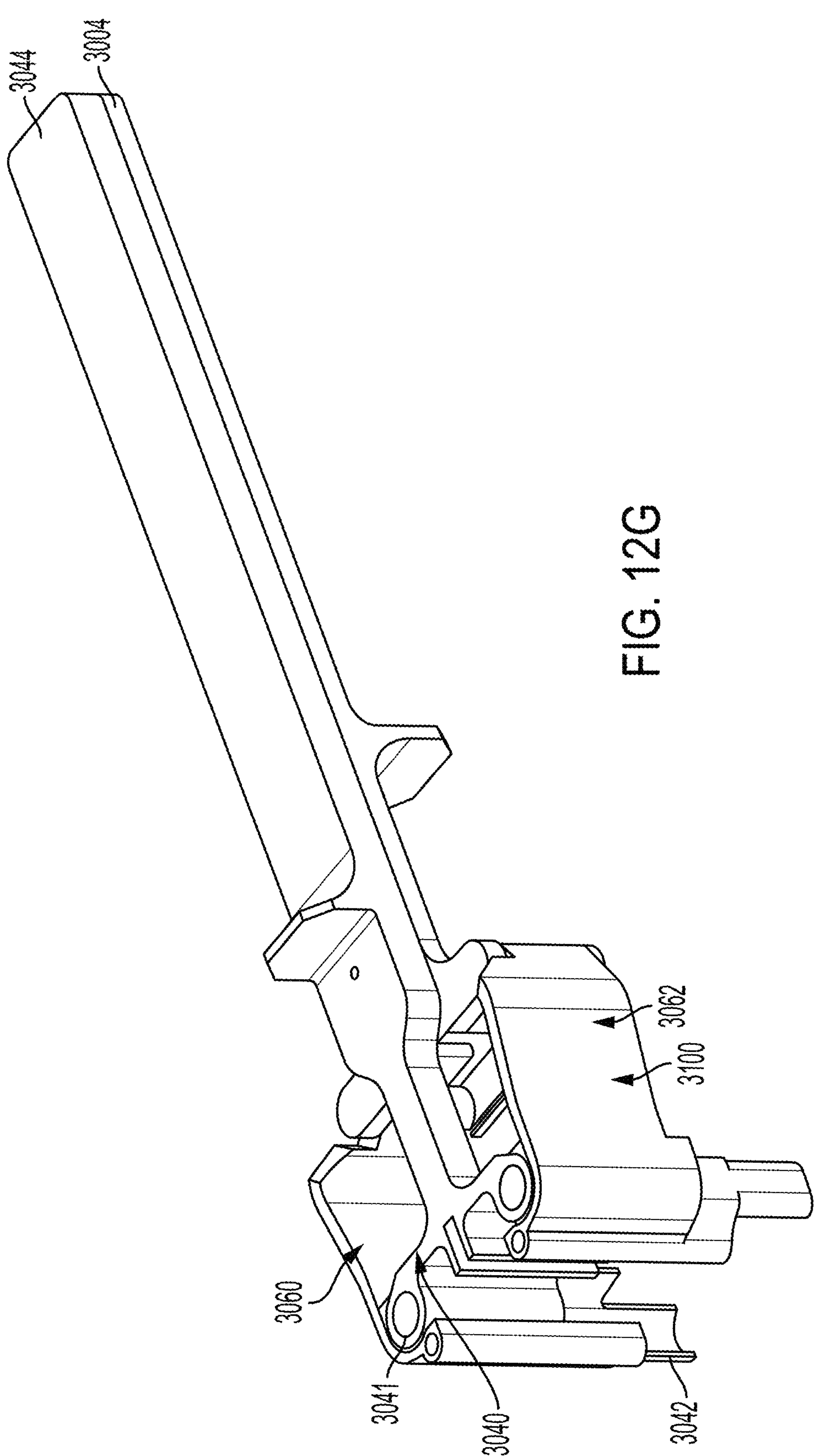

FIGS. 12E-12G illustrate another embodiment of an implant guide sleeve 3100. The implant guide sleeve 3100 can be similar to, or the same as, the implant guide sleeve 3000 disclosed with respect to FIGS. 12A-12D. In one example, the implant guide sleeve 3100 can be the same as the implant guide sleeve 3000 described in reference to FIGS. 12A-12D except as otherwise noted here with respect to FIGS. 12E-12G. FIG. 12E illustrates a top plan view of the implant guide sleeve 3100 at the first size configuration, while FIGS. 12F and 12G illustrate, respectively, top plan and perspective views of the implant guide sleeve 3100 at the second size configuration.

The implant guide sleeve 3100 can define the interior area 3006 between the first guide arm 3060 and the second guide arm 3062. And at least one of the first and second arms 3060, 3062 (e.g., each of the first and second arms 3060, 3062) can be movable to change the size of the interior area 3006. For example, each of the first and second arms 3060, 3062 can be movable between the first size configuration position, an example of which is illustrated at FIG. 12E, and the second size configuration position, an example of which is illustrated at FIG. 12F. Moving the first and second arms 3060, 3062 can adjust the interior area 3006, such as between the smaller interior area 3006 when the first and second arms 3060, 3062 are at the first size configuration position of FIG. 12E and the larger interior area 3006 when the first and second arms 3060, 3062 are at the second size configuration position of FIG. 12F.

The illustrated embodiment of the implant guide sleeve 3100 can be configured to move each of the first arm 3060 and the second arm 3062, and to thus change the size of the interior area 3006, by moving the handle 3044 of the drill guide 3040. In particular, the implant guide sleeve 3100 can be configured to move each of the first arm 3060 and the second arm 3062, to change the size of the interior area 3006, as a result of sliding the handle 3044 relative to the handle 3004. For example, the handle 3044 of the drill guide 3040 can be slidable, relative to the handle 3044 and thus relative to the arms 3060, 3062, in the direction 3092 between the retracted position 3070, an example of which is shown at FIG. 12E, and the extended position 3071, an example of which is shown at FIGS. 12F and 12G. The handle 3044 of the drill guide 3040 can generally overlay the handle 3004. For the illustrated embodiment, when the implant guide sleeve 3100 is positioned at one or more bone portions, the handle 3004 can face the one or more bones at which the implant guide sleeve 3100 is positioned while the handle 3044 can overlay the handle 3004 and thus face away from the one or more bones at which the implant guide sleeve 3100 is positioned. As such, the slidable handle 3044 can face away from the one or more bones and generally cover the handle 3004 (e.g., cover a majority of the surface area of the handle 3004 at a side of the handle 3004 interfacing with the handle 3044). This can be useful in helping to prevent snagging or catching of objects (e.g., a glove worn by a user) at the stationary handle 3004 and/or between the movable handle 3044 and the stationary handle 3004.

In one particular such embodiment, the handle 3044 can be coupled to a biasing member, such as a spring, configured to bias the handle 3044 at one of the retracted position 3070 and the extended position 3071. And, when that bias at the handle 3044 is overcome, the handle 3044 can move, for instance as a result of user applied force and/or a plunger member acting on the handle 3044, the handle 3044 can be moved from the one of the retracted position 3070 and the extended position 3071 biased position to the other of the retracted position 3070 and the extended position 3071. In such an example, the handle 3004 can be stationary and include first and second detent members, with the first detent member associated with the retracted position 3070 of the handle 3044 and the second detent member associated with the extended position 3071 of the handle 3044. In this example, when the bias at the handle 3044 is overcome, the handle 3044 can move the plunger out from engagement at the first detent member and to engagement at the second detect member to thereby move the handle 3044, and thus the drill guide 3040, from the retracted position 3070 and the extended position 3071 which in turn can cause the arms 3060, 3062 to move and expand the interior area 3006.

The illustrated embodiment of the implant guide sleeve 3100 can include the first guide arm 3060 and the second guide arm 3062 sized so that, when the arms 3060, 3062 are in the second size configuration, the arms 3060, 3062 can approximate (e.g., equal) the size of the drill guide 2040. For example, the drill guide 2040 can define a drill guide envelop at the area at which the drill guide is positioned at one or more bone portions, and the arms 3060, 3062 can define a guide sleeve arm envelop 3110 when the arms 3060, 3062 are in the second size configuration (e.g., defining the relatively larger interior area 3006 as compared to the interior area associated with the first size configuration and when the drill guide is at the extended position 3071). In certain embodiments, the guide sleeve arm envelop 3110 can approximate (e.g., equal) the drill guide envelop. In one application, the guide sleeve arm envelop 3110 can be sized so as to fit at (e.g., and partially through) a 1.75 cm, 2.0 cm, or 2.25 cm incision. To help define this guide sleeve arm envelop 3110, the arms 3060, 3062 of the implant guide sleeve 3100 can be reduced in wall thickness as compared to the wall thickness of the arms 3060, 3062 of the implant guide sleeve 3000.

Figure 12H:
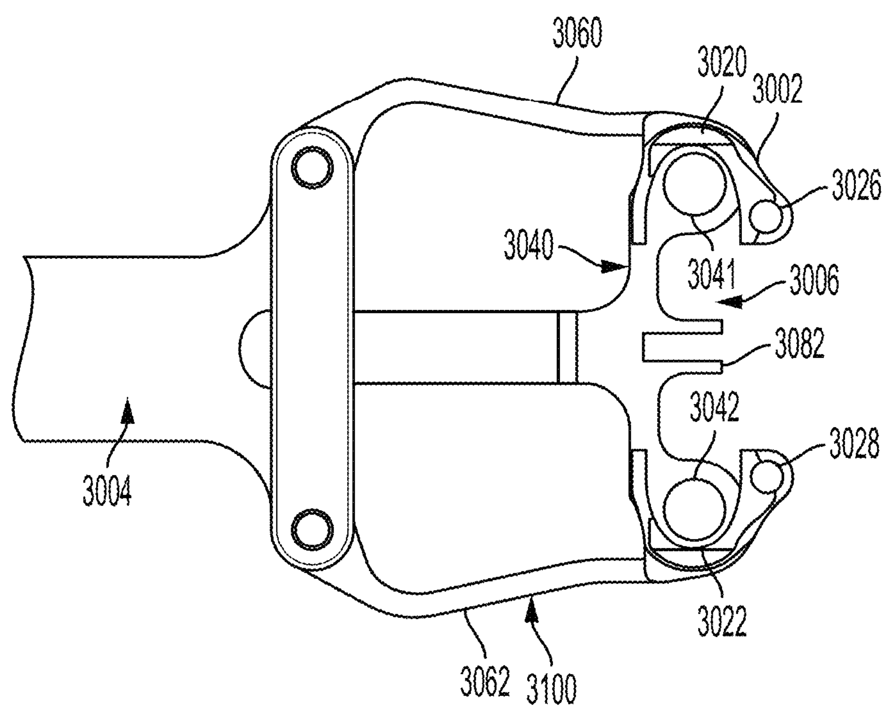
Figure 12I:
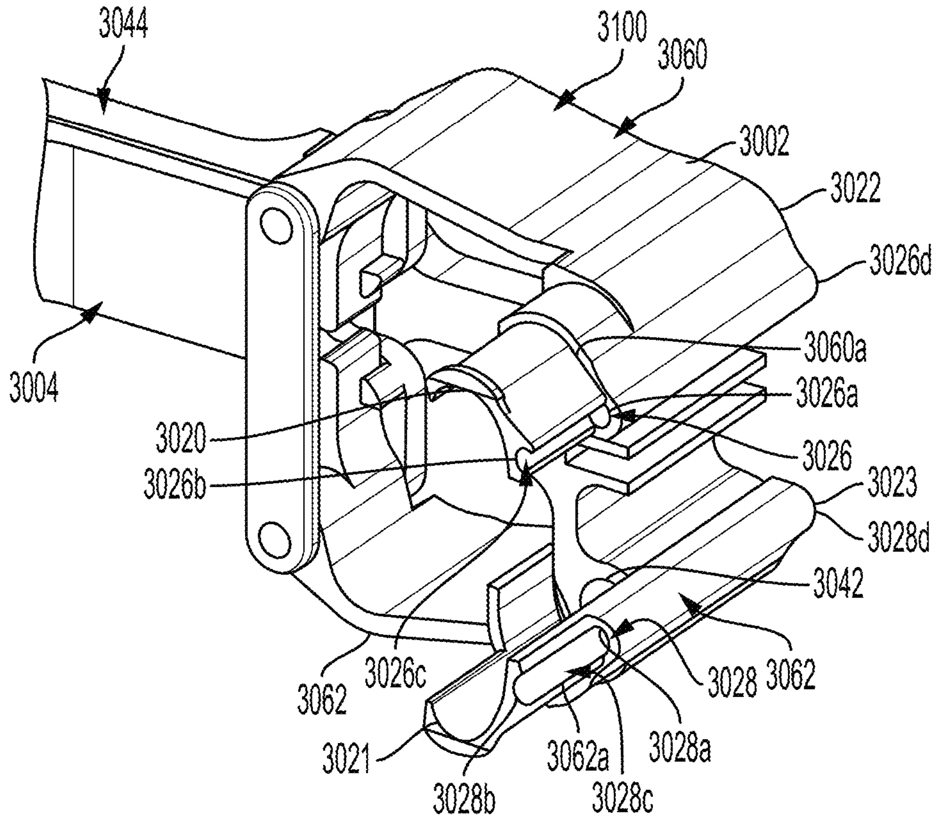

FIGS. 12H-12I illustrate the implant guide sleeve 3100 of FIGS. 12E-12G but with a modified guide sleeve profile, for instance, to help minimize incision size needed in using the implant guide sleeve 3100. FIG. 12H is a bottom plan view of a bone facing side of the implant guide sleeve 3100 at the second size configuration, and FIG. 12I is a perspective view of the bone facing side of the implant guide sleeve 3100 at the second size configuration.

The implant guide sleeve 3100 shown at FIGS. 12H and 12I can have a modified guide sleeve profile relative to the guide sleeve profile shown at FIGS. 12E-12G. The implant guide sleeve 3000, for instance at the body 3002, can include the first end portion bottom surface 3020, the second end portion bottom surface 3021, the first end portion top surface 3022, and the second end portion top surface 3023. The first end portion bottom surface 3020 can be a bone facing surface that defines a bone facing end of the first guide arm 3060 and the first end portion bottom surface 3022 can be opposite the first end portion bottom surface 3020 at the first guide arm 3060. Also at the first guide arm 3060 can be the first pin aperture 3026. Likewise, the second end portion bottom surface 3021 can be a bone facing surface that defines a bone facing end of the second guide arm 3062 and the second end portion top surface 3023 can be opposite the second end portion bottom surface 3021 at the second guide arm 3062. Also at the second guide arm 3062 can be the second pin aperture 3028. As will be described further, the implant guide sleeve 3100 shown at FIGS. 12H and 12I can have a modified guide sleeve profile at the first guide arm 3060 and/or the second guide arm 3062.

As shown at the example of FIGS. 12H and 12I, the implant guide sleeve 3100 can have a modified guide sleeve profile at the first guide arm 3060 and/or the second guide arm 3062, for instance, that can help to minimize incision size needed when using the implant guide sleeve 3100. As one example, the first pin aperture 3026 at the first guide arm 3060 can have a reduced profile (e.g., reduced width) at or near a bone facing portion of the first guide arm 3060. The illustrated example at FIGS. 12H-12I shows that the first pin aperture 3026 can have a bone facing portion 3026*c* that has a width less than an opposite, top side portion 3026*d* of the first pin aperture 3026. In particular, this example shows the bone facing portion 3026*c* of the first pin aperture 3026 as a partially open channel, for instance, in the form of a semi-circular open channel, while the opposite, top side portion 3026*d* of the first pin aperture 3026 is an enclosed, circular channel with a width greater than the bone facing portion 3026*c* of the first pin aperture 3026. Thus, the first pin aperture 3026 can define an enclosed channel extending from the top side portion 3026*d* of the first pin aperture 3026 and define an open channel extending from the bone facing portion 3026*c* of the first pin aperture 3026. The first pin aperture 3026 can have a channel transition 3026*a* where the first pin aperture 3026 transitions between the two different widths defined by the first pin aperture 3026 such that the greater width (e.g., closed) portion of the first pin aperture 3026 extends from the top side portion 3026*d* to the channel transition 3026*a*, and the less width (e.g., open) portion of the first pin aperture 3026 extends from the channel transition 3026*a* to a bone facing end 3026*b* of the first pin aperture 3026. Likewise, the second pin aperture 3028 at the second guide arm 3062 can have a reduced profile (e.g., reduced width) at or near a bone facing portion of the second guide arm 3062. The illustrated example at FIGS. 12H-12I shows that the second pin aperture 302 can have a bone facing portion 3028*c* that has a width less than an opposite, top side portion 3028*d* of the second pin aperture 3028. In particular, this example shows the bone facing portion 3028*c* of the second pin aperture 3028 as a partially open channel, for instance, in the form of a semi-circular open channel, while the opposite, top side portion 3028*d* of the second pin aperture 3028 is an enclosed, circular channel with a width greater than the bone facing portion 3028*c* of the second pin aperture 3028. Thus, the second pin aperture 3028 can define an enclosed channel extending from the top side portion 3028*d* of the second pin aperture 3028 and define an open channel extending from the bone facing portion 3028*c* of the second pin aperture 3028. The second pin aperture 3028 can have a channel transition 3028*a* where the second pin aperture 3028 transitions between the two different widths defined by the second pin aperture 3028 such that the greater width (e.g., closed) portion of the second pin aperture 3028 extends from the top side portion 3028*d* to the channel transition 3028*a*, and the less width (e.g., open) portion of the second pin aperture 3028 extends from the channel transition 3028*a* to a bone facing end 3028*b* of the second pin aperture 3028. The lesser width portion 3026*c*, 3028*c* of the respective first and second pin apertures 3026, 2028 can face away from the interior area 3006 and thus be at an outer perimeter of the implant guide sleeve 3100. As such, this can help to reduce the size of an incision needed for the implant guide sleeve 3100 to access bones through the incision.

As another additional or alternative example shown at FIGS. 12H and 12I, the implant guide sleeve 3100 can have a modified guide sleeve profile at the first guide arm 3060 and/or the second guide arm 3062 in the form of a reduced width at one or more bone facing portions of the first guide arm 3060 and/or the second guide arm 3062. For example, the first guide arm 3060 can have a reduced width bone facing portion that extends from the first end portion bottom surface 3020 to a first guide width transition 3060*a*. The first guide width transition 3060*a* can be at a same height along the implant guide sleeve 3100 as the channel transition 3026*a* such that the channel transition 3026*a* and the first guide width transition 3060*a* are coplanar. Likewise, the second guide arm 3062 can have a reduced width bone facing portion that extends from the second end portion bottom surface 3021 to a second guide width transition 3062*a*. The second guide width transition 3062*a* can be at a same height along the implant guide sleeve 3100 as the channel transition 3028*a* such that the channel transition 3028*a* and the second guide width transition 3062*a* are coplanar. In one further example, the channel transition 3026*a* and the first guide width transition 3060*a* at the first guide arm 3060 can be at a same height as the channel transition 3028*a* and the second guide width transition 3062*a* at the second guide arm 3062 such that each of the channel transition 3026*a*, the first guide width transition 3060*a*, the channel transition 3028*a* and the second guide width transition 3062*a* are coplanar. The lesser width portions of the respective first and second guide arms 3026, 3028 can face away from the interior area 3006 and thus be at an outer perimeter of the implant guide sleeve 3100. As such, this can help to reduce the size of an incision needed for the implant guide sleeve 3100 to access bones through the incision.

Figure 13:
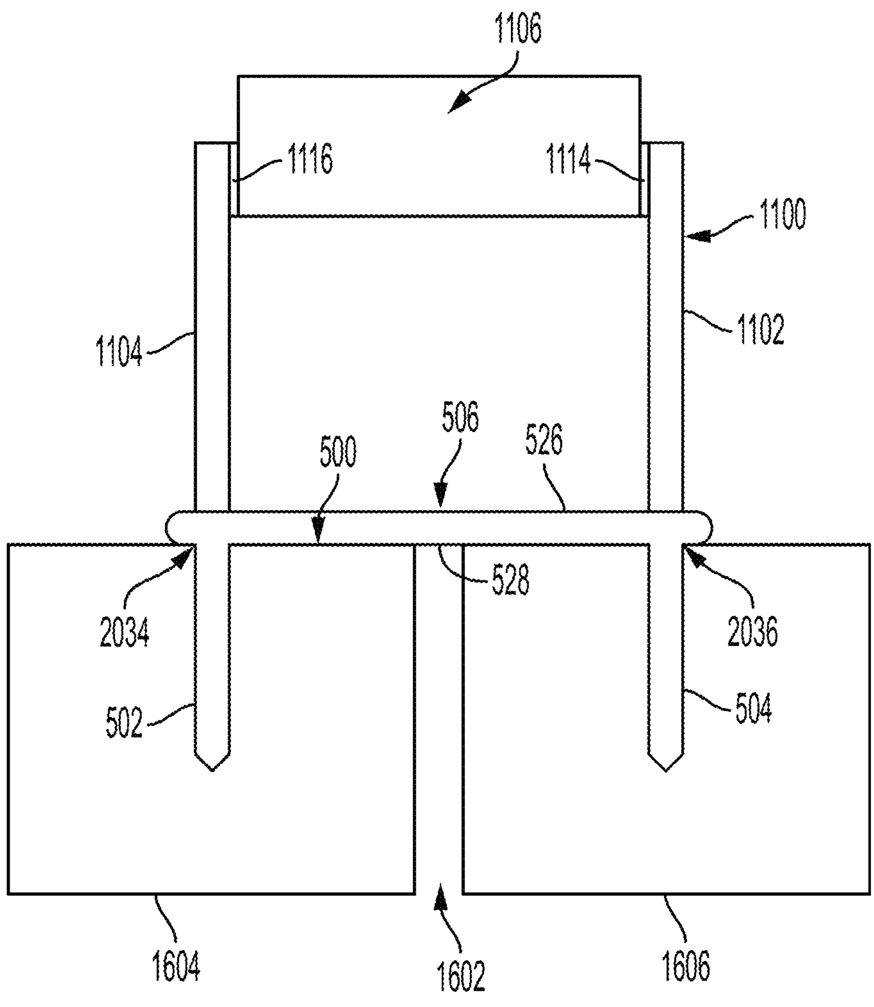
FIG. 13 is a side elevational view of an assembled inserter embodiment used to position a staple in contact with first and second bones.

The foregoing disclosure and accompanying illustrations has included descriptions of the use of an implant guide sleeve to guide creation of one or more implant holes and/or to guide placement of an implant. As noted, the staple 500 can be one such exemplary type of implant guided for placement using an implant guide sleeve. The following disclosure with respect to FIGS. 13 and 14 will describe aspects related to an implant once positioned at a target anatomy, according to various embodiments. FIG. 13 and specifically refer to the staple 500, though other embodiments within the scope of the present disclosure can include other staple configurations and/or other types of implants (e.g., bone plates, etc.).

FIG. 13 is a side elevational view of the staple 500 operatively coupled to the assembled inserter 1100 after the staple 500 has been positioned in contact with first and second bones 1604, 1606. As one such example, FIG. 13 can represent a point in time after the staple 500 has been so positioned using an implant guide sleeve to guide that positioning and the implant guide sleeve has been removed leaving the staple 500 and operatively connected inserter 1100 previously guided through an interior area of an implant guide sleeve.

FIG. 13 shows the staple 500 positioned in contact with the first bone 1604 and the second bone 1606 with the bridge 506 of the staple 500 bridging across the separation 1602 between the bones 1604, 1606. As also shown here, this can further include the first leg 502 positioned in the first implant hole 2034 in the first bone 1604 and the second leg 504 positioned in the second implant hole 2036 in the second bone 1606. This positioning of the staple 500 can also include contacting the first bone 1604 and the second bone 1606 with the bottom surface 528 of the staple 500. In one specific such example, contacting the first bone 1604 and the second bone 1606 with the bottom surface 528 of the staple 500 can include contacting the first bone 1604 generally flush with the bottom surface 528 and contacting the second bone 1606 generally flush with the bottom surface 528.

When the staple 500 is being positioned as such, the connector 1106 of the inserter 1100 can receive the first coupling shaft 1102 (e.g., at the first receptacle 1114 at the connector 1106) and the second coupling shaft 1104 (e.g., at the second receptacle 1116 at the connector 1106). When the first and second coupling shafts 1102, 1104 are received at the connector 1106, the staple 500 can be in the deformed insertion state, such as that shown at FIG. 13. As seen at the illustrated example, the deformed insertion state of the staple 500, when the connector 1106 joins the first and second coupling shafts 1102, 1104, the first leg 502 can be generally parallel to the second leg 504. This generally parallel configuration of the legs 502, 504 can be helpful to facilitate insertion of the legs 502, 504 at the respective bones 1604 1606 (e.g., at the respective implant holes 2034, 2036).

Figure 14:
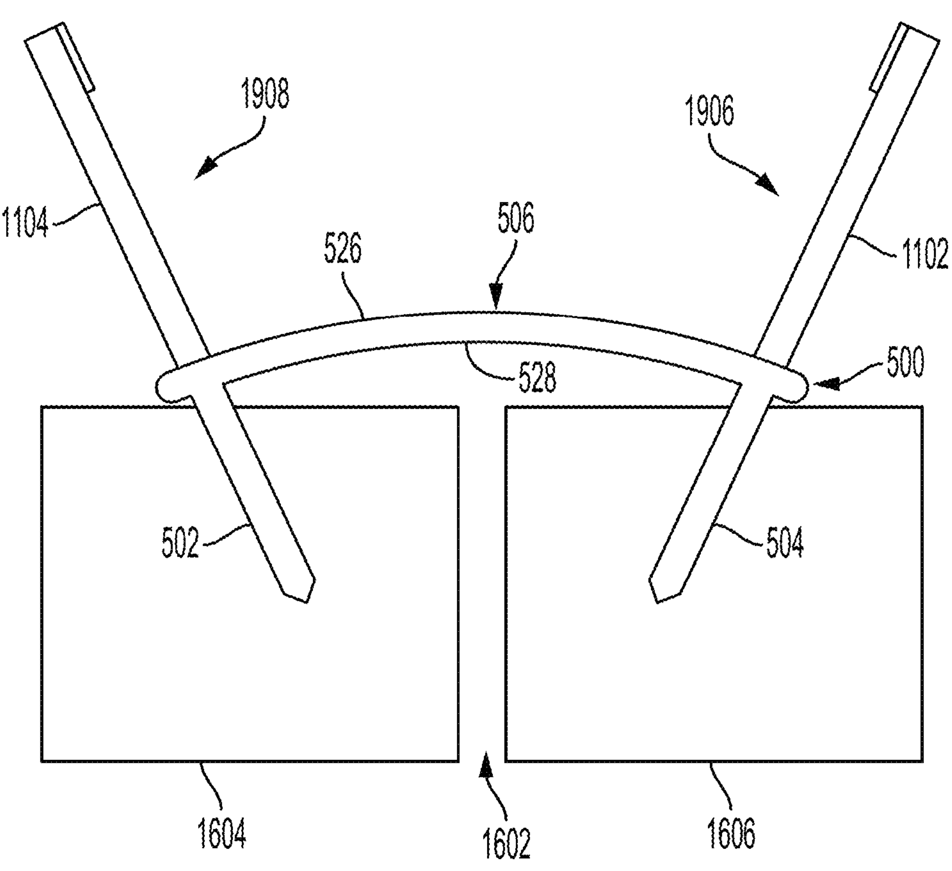
FIG. 14 is a side elevational view of the inserter of FIG. 13 but with the connector component removed such that the staple helps to fixate the first and second bones and applies a compression force at the first and second bones.

Once the staple 500 is positioned as desired at the target anatomy, the staple 500 can be configured to apply a compression force at that target anatomy. FIG. 14 is a side elevational view of the inserter 1100 of FIG. 13 but with the connector 1106 removed. In such embodiment, removing the connector 1106 can cause the staple 500 to transition from the deformed insertion state to a biased compression-inducing state. The biased compression-inducing state can cause the staple 500 to apply one or more compression force at the one or more bones 1604, 1606.

Removing the connector 1106 from the inserter 1100 can cause the load force previously applied by the connector 1106 to be removed from the staple 500. Removing the connector 1106 can cause the first coupling shaft 1102 and the second coupling shaft 1104 to move away from each other—the first coupling shaft 1102 can be caused to move in direction 1906 (e.g., opposite the direction in which the first coupling shaft 1102 is caused to move when the connector 1106 joins the first coupling shaft 1102 to the second coupling shaft 1104) and the second coupling shaft 1104 can be caused to move in a direction 1908 (e.g., opposite the direction in which the second coupling shaft 1104 is caused to move when the connector 1106 joins the second coupling shaft 1104 to the first coupling shaft 1102). In an additional example, the step of removing the connector 1106 from the inserter 1100 can occur before the first coupling shaft 1102 and the second coupling shaft 1104 are removed from the operative couplings to the staple 500.

In one example, to help remove the connector 1106 and prior to removing the connector 1106, the first coupling shaft 1102 and the second coupling shaft 1104 can be moved toward each other (e.g., the first coupling shaft 1102 can be moved in a direction opposite the direction 1906 and the second coupling shaft 1104 can be moved in a direction opposite the direction 1908) to help disengage the first and second coupling shafts 1102, 1104 from the connector 1106. For example, moving the first coupling shaft 1102 and the second coupling shaft 1104 toward each other can help to disengage a first retention feature, when so included at the first coupling shaft 1102, from the first receptacle 1114 and a second retention feature, when so included at the second coupling shaft 1104, from the second receptacle 1116.

When the connector 1106 is removed from the first and second coupling shafts 1102, 1104 that are operatively connected to the staple 500, the first leg 502 of the staple 500 and the second leg 504 of the staple 500 can return toward their natural biased compression-inducing state, such as shown at the example of FIG. 14. This can include the first and second legs 502, 504 being in a generally skewed arrangement such that a central longitudinal axis of the leg 502 and a central longitudinal axis of the leg 504 intersect. Moreover, as the connector 1106 is in the process of being removed from the first and second coupling shafts 1102, 1104 that are operatively connected to the staple 500, the first leg 502 and the second leg 504 can incrementally move toward one another as the connector 1106 is being removed. Removing connector 1106 can cause the legs 502, 504 of the staple 500 to return from their deformed position back toward their native position, e.g., with the bones in which the legs of the staple are inserted preventing the legs from returning fully to their native, undeformed position, thereby resulting in a compressive force being applied by the staple across the end faces of the bones.

In some embodiments, more than one implant can be positioned according to the teachings disclosed herein. For example, in one embodiment at least two staples (e.g., two staples 500) can be positioned in and across the bones 1604, 1606 according to the teachings disclosed herein. This could include, for instance, positioning one staple at a medial cuneiform, a first metatarsal, and across the TMT joint at a dorsal side and positioning another staple at a medial cuneiform, a first metatarsal, and across the TMT joint at a medial side. When positioning at least two such staples in and across the bones 1604, 1606 according to the teachings disclosed herein, the associated technique could further include, prior to positioning such staples at the bones 1604, 1606, making a first incision at a first anatomical location (e.g., adjacent the medial cuneiform, the first metatarsal, and across the TMT joint at the dorsal side) and making a second, different incision at a second, different anatomic location (e.g., adjacent the medial cuneiform, the first metatarsal, and across the TMT joint at the medial side).

Figure 15A:
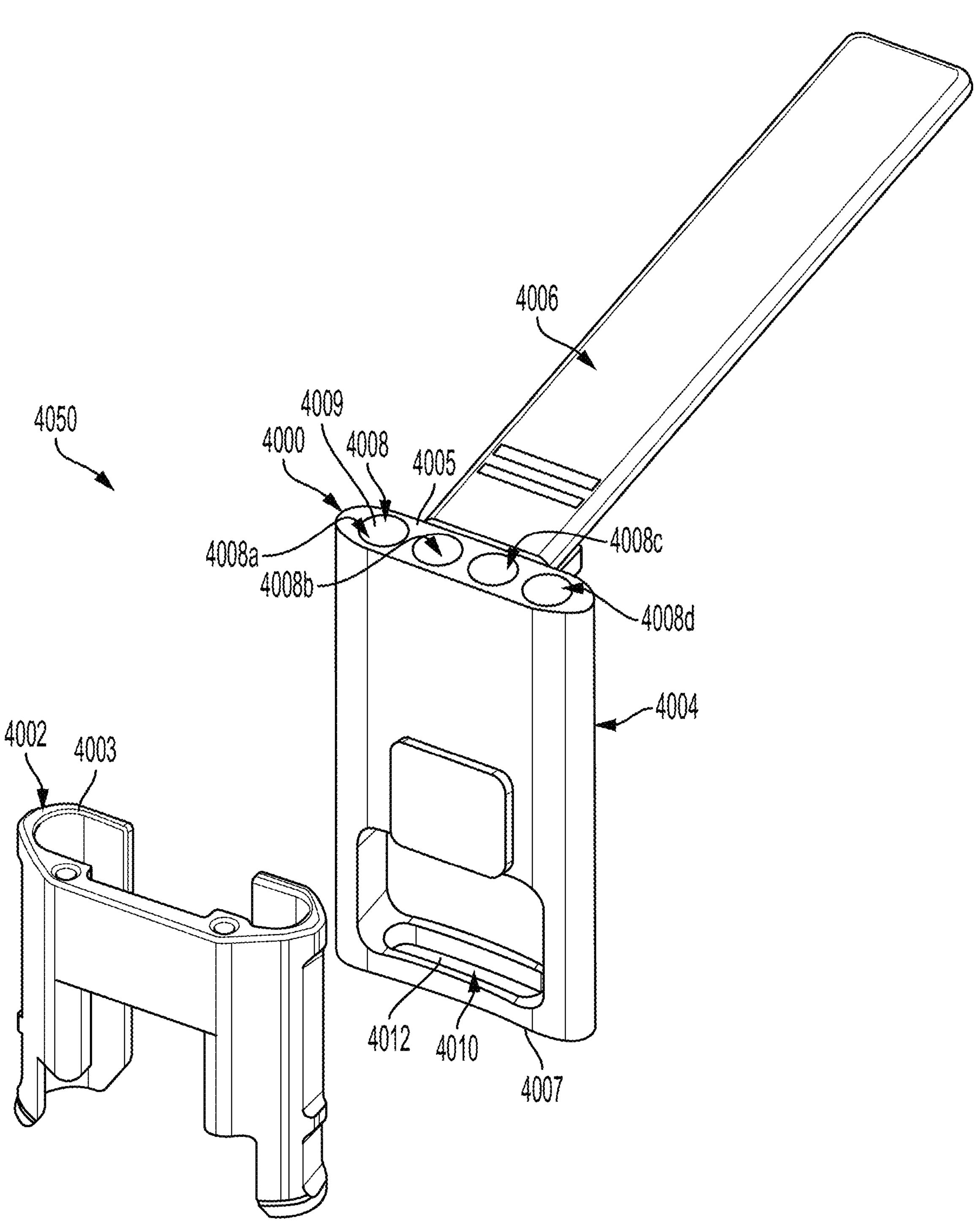
FIGS. 15A-15C illustrate an embodiment of a contour guide.
Figure 15B:
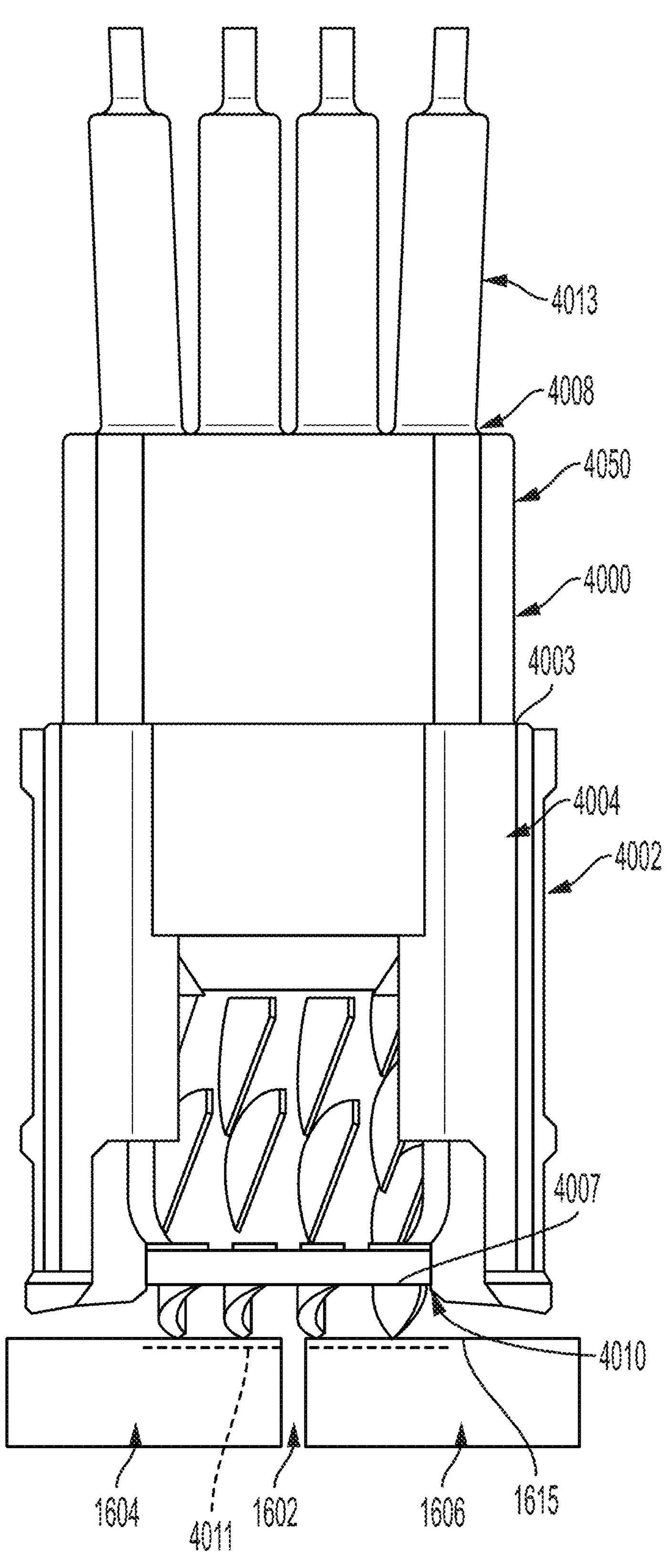
Figure 15C:
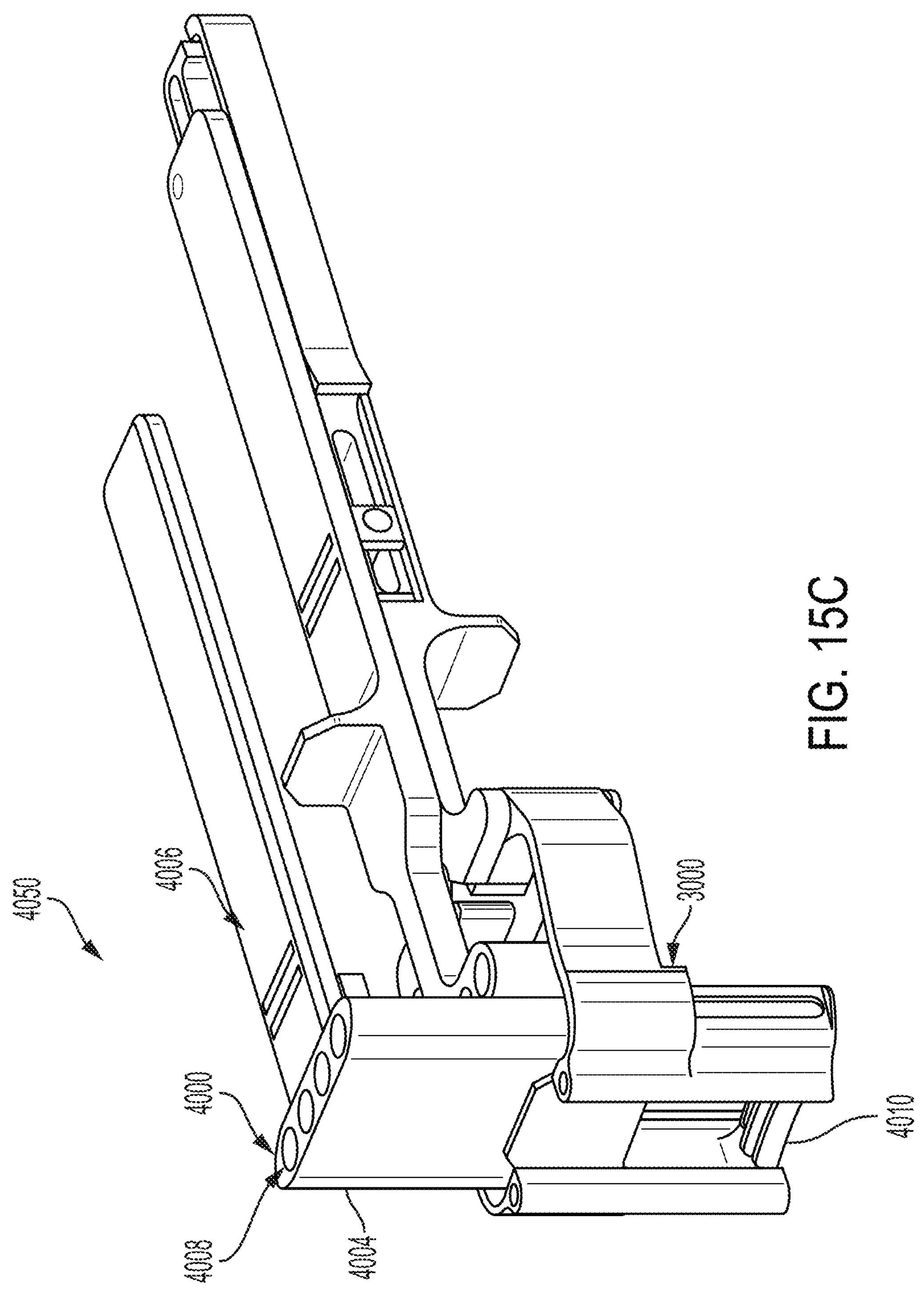

FIGS. 15A-15C illustrate an embodiment of a contour guide 4000. FIG. 15A is a perspective view of the contour guide 4000 along with an optional accompanying implant guide sleeve 4002, FIG. 15B is an elevational view of the contour guide 4000 placed at the implant guide sleeve 4002 to modify a surface of one or more bone portions 1604, 1606, and FIG. 15C is a perspective view of the contour guide 4000 placed at a different implant guide sleeve 3000. As will be described further, the contour guide 4000 can be configured to facilitate one or more surface modifications to one or more bone portions 1604, 1606. Use of the contour guide 4000 to create such one or more surface modifications can be useful, for instance, in creating a suitable, modified bone surface at which an implant can be positioned (e.g., and then fixated when so positioned at least at the modified bone surface). In one example, the contour guide 4000 can be configured to guide such one or more bone surface modifications at one or more surface regions, of the one or more bone portions 1604, 1606, that are to contact the implant to be placed thereat.

The contour guide 4000 includes a contour guide body 4004. The body 4004 has a top side 4005 and a bottom side 4007 that is opposite the top side 4005. The bottom side 4007 can be configured to interface with one or more bones 1604, 1606. For example, the bottom side 4007 can be configured to at least partially contact one or more bones 1604, 1606. In some such examples, such as that illustrated at FIG. 15B, the bottom side 4007 can be configured to interface with the first bone 1604, the second bone 1606, and the separation 1602 between the first bone 1604 and the second bone 1606. In one specific such example, the bottom side 4007 can be configured to contact at least a portion of a surface, such as a dorsal, medial, or lateral surface, at the first bone 1604 and configured to contact at least a portion of a surface, such as a dorsal, medial, or lateral surface, at the second bone 1606 while the bottom side bridges across the separation 1602.

The contour guide 4000 can include a guide slot 4010. The guide slot 4010 can define an opening at a portion of the body 4004 configured to interface with the one or more bones 1604, 1606. As shown for the illustrated embodiment of the contour guide 4000, the guide slot 4010 can be included at, or near, the bottom side 4007 of the body 4004 (e.g., opposite the top side 4005) such that the guide slot 4010 is configured to interface with one or more bone surfaces to be modified, using the contour guide 4000, at the one or more bones 1604, 1606. The guide slot 4010 can define a guide slot cross-sectional area 4012 (e.g., the cross-sectional area of the opening defined by the guide slot 4010 at, or near, the bottom side 4007). The guide slot cross-sectional area 4012 can be defined in a plane at the guide slot that extends transverse to a plane that extends between the top and bottom sides 4005, 4007. The guide slot cross-sectional area 4012 can be configured to receive one or more bone surface modification instruments 4013 to modify one or more surface regions 1615 of at least one of the first bone 1604 and the second bone 1606 to form a modified surface region 4011 at one or both of the first bone 1604 and the second bone 1606. For example, the guide slot 4010 can be configured to receive one or more bone surface modification instruments 4013 such that the one or more bone surface modification instruments 4013 are positioned within the guide slot 4010 (e.g., and extend out from the bottom side 4007 of the body 4004) and these one or more bone surface modification instruments 4013 contact the one or more surface regions 1615 of at least one of the first bone 1604 and the second bone 1606 so that the one or more bone surface modification instruments 4013 within the guide slot 4010 can form the modified surface region 4011. The illustrated embodiment shows an example of the guide slot 4010 that is configured to receive two or more bone surface modification instruments 4013 within the guide slot 4010.

The contour guide 4000 can be configured to facilitate modification to one or more surface regions 1615 at one or more bones 1604, 1606 along an extent (e.g., length and/or width) of the surface of those one or more bones 1604, 1606 at which an implant is to be placed. To do so, the guide slot 4010 can, for instance, define the cross-sectional area 4012 of the guide slot opening so that this opening cross-sectional area 4012 corresponds to a cross-sectional area of an implant (e.g., staple, plate) to be placed at the one or more bone portions 1604, 1606 after the contour guide 4000 has been used to create the modified surface region 4011 at the one or more bone portions 1604, 1606. For example, when the body 4004 is placed at the one or more bone portions 1604, 1606 (e.g., the bottom side 4007 is placed to interface with one or more bone portions 1604, 1606), the guide slot 4010 can be configured to approximate a surface area (e.g., length and/or width) at the one or more bone portions 1604, 1606 at which the implant will later be placed. Accordingly, the guide slot 4010 can be configured to define a bone surface modification area, via the cross-sectional area 4012, that corresponds to the size of the implant that is to subsequently be placed at that same bone surface modification area defined by the cross-sectional area 4012 of the guide slot 4010.

In some such examples, the cross-sectional area 4012 of the guide slot 4010 can correspond to the size of the implant that is to subsequently be placed at that same bone surface modification area defined by the cross-sectional area 4012 where the cross-sectional area 4012 is equal to or greater than a cross-sectional area of the implant (e.g., staple, plate, etc.) that is to subsequently be placed at the bone surface modification area defined by the cross-sectional area 4012. This can help to facilitate creation of the modified surface region 4011 that is at least equal in length and/or width to a length and/or width of the implant that is to subsequently be placed at the bone surface modification area defined by the cross-sectional area 4012. In other such examples, the cross-sectional area 4012 of the guide slot 4010 can be less than a cross-sectional area of the implant (e.g., staple, plate, etc.) that is to subsequently be placed at the bone surface modification area defined by the cross-sectional area 4012. Depending on the type and configuration of implant to be placed in various applications, this may help to facilitate creation of the modified surface region 4011 that is less than a length and/or width of the implant that is to be subsequently placed, for instance, in applications where only a portion of the bone surface area where the implant is to be placed is desired to be modified.

In some embodiments, the contour guide 4000 can further include at least one guide aperture 4008. The at least one guide aperture 4008 can be configured to at least partially receive one or bone surface modification instrument 4013. The at least one guide aperture 4008 can extend through at least a portion of the body 4004. For example, the at least one guide aperture 4008 can extend through at least a portion of the body from the top side 4005 and toward the bottom side 4007. The at least one guide aperture 4008 can be axially aligned with the guide slot 4010 such that when the least one guide aperture 4008 receives the bone surface modification instrument 4013, the bone surface modification instrument 4013 can be axially aligned with the guide slot 4010. Thus, as a result of the axial alignment between the at least one guide aperture 4008 and the guide slot 4010, as the bone surface modification instrument 4013 is placed within the guide aperture 4008, the bone surface modification instrument 4013 can be guided into the guide slot 4010 (e.g., while the bone surface modification instrument 4013 is also within the guide aperture 4008).

As one example, the illustrated embodiment of the contour guide 4000 includes a plurality of guide apertures 4008 each configured to receive a bone surface modification instrument 4013 thereat. The plurality of guide apertures 4008 as shown for the illustrated example can extend from the top side 4005 toward the bottom side 4007 but terminate prior to the bottom side 4007 and prior to the guide slot 4010. The illustrated embodiment of the contour guide 4000 includes a first guide aperture **4008*a*, a second guide aperture 4008*b*, a third guide aperture 4008*c*, and a fourth guide aperture 4008*d* each configured to receive a respective bone surface modification instrument 4013. In this example, the first, second, third, and fourth guide apertures 4008*a*-4008*d* are spaced apart from each other and are distinct apertures defined at the body 4004. In some examples, the guide apertures 4008*a*-4008*d* can extend through the body 4004 from the top side 4005 to define parallel guide apertures 4008*a*-4008*d* extending through the body 4004 from the top side 4005 toward the bottom side 4007. In other examples, the guide apertures 4008*a*-4008*d* can extend through the body 4004 from the top side 4005 to define at least a pair of non-parallel guide apertures 4008*a*-4008*d* extending through the body 4004 from the top side 4005 toward the bottom side 4007**.

As one example of at least a pair of non-parallel guide apertures **4008*a*-4008*d*, one or more of the guide apertures 4008*a*-4008*d* can extend through the body 4004 from the top side 4005 toward the bottom side 4007 in a first directional orientation and one or more others of the guide apertures 4008*a*-4008*d* can extend through the body 4004 from the top side 4005 toward the bottom side 4007 in a second, different directional orientation that is non-parallel to the first directional orientation. As one such example, one or more of the guide apertures 4008*a*-4008*d* can extend through the body 4004 from the top side 4005 toward the bottom side 4007 at a first skewed orientation and one or more others of the guide apertures 4008*a*-4008*d* can extend through the body 4004 from the top side 4005 toward the bottom side 4007** at a second, different skewed orientation. Referring to the illustrated embodiment, one or both of the guide apertures

4008*a*, 4008*b* can extend through the body 4004 from the top side 4005 toward the bottom side 4007 at a first skewed orientation while one or both of the guide apertures 4008*c*, 4008*d* can extend through the body 4004 from the top side 4005 toward the bottom side 4007 at a second, different skewed orientation. For instance, the guide apertures 4008*a* and/or 4008*b* can define a skewed opening through the body 4004 in a direction toward the guide apertures 4008*c* and/or 4008*d*, and the guide apertures 4008*c* and/or 4008*d* can define a skewed opening through the body 4004 in a direction toward the guide apertures 4008*a* and/or 4008*b*. Each of the plurality of guide apertures 4008 can be defined by the body 4004 as a distinct aperture open at the top side 4005 of the body 4004 and extending through at least a portion of the body 4004 toward the bottom side 4007.

A cross-sectional area 4009 of the one or more guide apertures 4008 and the cross-sectional area 4012 of the guide slot 4010 can each be configured to receive a bone surface modification instrument 4013. The cross-sectional area 4012 of guide slot 4010 can be equal to or greater than the cross-sectional area 4009 of the one or more guide apertures 4008. The cross-sectional area 4009 of the one or more guide apertures 4008 can be defined in a plane at the one or more guide apertures 4008 that extends transverse to a plane that extends between the top and bottom sides 4005, 4007. For example, the guide slot 4010 can define the opening thereat to have the cross-sectional area 4012 that is larger than the cross-sectional area 4009 of any one of the plurality of guide apertures 4008. As another example, the guide slot 4010 can define the opening thereat to have the cross-sectional area 4012 that is larger than the combined cross-sectional areas 4009 defined by each of the plurality of guide apertures 4008.

As noted, the contour guide 4000 (e.g., via the one or more guide apertures 4008 and/or the guide slot 4010) can be configured to receive thereat the bone surface modification instrument 4013. The bone surface modification instrument 4013 received at the contour guide 4000 can be configured to remove at least a portion of the surface 1615 at one or more bones 1604, 1606. For example, bone surface modification instrument 4013 received at the contour guide 4000 can be configured to break up bone at, or otherwise modify (e.g., smooth out the bone surface), the surface 1615 of the one or more bones 1604, 1606 to thereby create the modified surface region 4011. The illustrated embodiment shows one or more burr instruments as an example of a type of the bone surface modification instrument 4013 that can be received at, and guided by, the guide apertures 4008. Though other types of bone surface modification instruments 4013, including, e.g., a saw, configured to break up or otherwise modify a bone surface can be used.

In some embodiments, such as that illustrated here, the contour guide 4000 can include a handle 4006. The handle 4006 can extend out from the body 4004 to provide the user with an interface for handling and placing the body 4004 of the contour guide 4000 at the one or more bones 1604, 1606. Though in other embodiments the contour guide 4000 may not include any handle.

For embodiments that include an implant guide sleeve along with the contour guide 4000, a system 4050 can include the contour guide 4000 and the implant guide sleeve (e.g., implant guide sleeve 4002; implant guide sleeve 3000). In other embodiments, the contour guide 4000 can be used to modify one or more bone surfaces, as described herein, without an accompanying guide sleeve.

The implant guide sleeve 4002 can be similar to, or the same as, the implant guide sleeve 2000 disclosed elsewhere herein. In particular, as described elsewhere herein, the implant guide sleeve 4002 can be configured to be placed at one or more bone portions 1604, 1606 (e.g., two separate bones, such as in the foot; two portions of the same bone, such as in the foot) to guide creation of implant holes at such one or more bones and/or to guide placement of an implant, such as a staple, at the one or more bone portions 1604, 1606. As such, by placing the contour guide 4000 relative to the implant guide sleeve 4002, the contour guide 4000 can be guided for placement at the one or more bone portions 1604, 1606 at a location at the one or more bone portions 1604, 1606 corresponding to an intended implant location.

In some examples, to help facilitate reception of the contour guide 4000 at the implant guide sleeve 4002, the implant guide sleeve 4002 can define an interior cross-sectional area 4003 that is configured to receive and guide placement of the contour guide 4000 at one or more of the bones 1604, 1606. For instance, the interior cross-sectional area 4003 at the guide sleeve 4002 can be configured to receive and guide placement of at least the bottom side 4007 of the contour guide body 4004 to interface with the first bone 1604, the second bone 1606, and the separation 1603 between the first and second bones 604, 1606. The interior cross-sectional area 4003 at the guide sleeve 4002 can be greater than the cross-sectional area 4012 of the guide slot 4010 of the contour guide 4000 such that the interior cross-sectional area 4003 at the guide sleeve 4002 is configured to receive thereat at least the guide slot 4010. The interior cross-sectional area 4003 of the implant guide sleeve 4002 can, for example, be defined in a plane at the implant guide sleeve 4002 that extends transverse to a plane that extends between the top and bottom sides 4005, 4007.

In addition to receiving and guiding the guide slot 4010, the interior cross-sectional area 4003 of the implant guide sleeve 4002 can be configured, for instance as described elsewhere herein, to guide creation of one or more implant holes at one or more bones 1604, 1606 and/or to guide placement of one or more implants at the one or more bones 1604, 1606. For example, the interior cross-sectional area 4003 of the implant guide sleeve 4002 can be configured to guide creation of a first implant hole at the modified surface region 4011 at bone 1604 and a second implant hole at the modified surface region 4011 at bone 1606. As another additional or alternative example, the interior cross-sectional area 4003 of the implant guide sleeve 4002 can be configured to guide placement of a first leg of an implant (e.g., staple) at the first implant hole at the modified surface region 4011 at the bone 1604 and a second leg of the implant at the second implant hole at the modified surface region 4011 at the bone 1606. Thus, as one particular such example, the interior cross-sectional area 4003 of the implant guide sleeve 4002 can be configured to both: (i) guide creation of a first implant hole at the modified surface region 4011 at bone 1604 and a second implant hole at the modified surface region 4011 at bone 1606, and (ii) guide placement of a first leg of an implant (e.g., staple) at the first implant hole at the modified surface region 4011 at the bone 1604 and a second leg of the implant at the second implant hole at the modified surface region 4011 at the bone 1606.

FIG. 15C is a perspective view of the contour guide 4000 placed at a different implant guide sleeve 3000. The placement and use of the contour guide 4000 in conjunction with the implant guide sleeve 3000 can be similar to that described with respect to the implant guide sleeve 4002. And the implant guide sleeve 3000 can define an interior cross-sectional area that is the same as, or similar to, the interior cross-sectional area 4003 of the guide sleeve 4002 described previously. As such, the interior cross-sectional area of the implant guide sleeve 3000 can be configured to receive thereat at least the guide slot 4010 and guide placement of at least the guide slot 4010 of the contour guide 4000 at one or more of the bones 1604, 1606.

As noted and as will be described further here, the contour guide 4000 can be used in a method for making one or more surface modifications to one or more bones 1604, 1606 (e.g., to one or more bone portions 1604, 1606 of the same bone; to one or more different bones 1604, 1606).

Figure 15D:
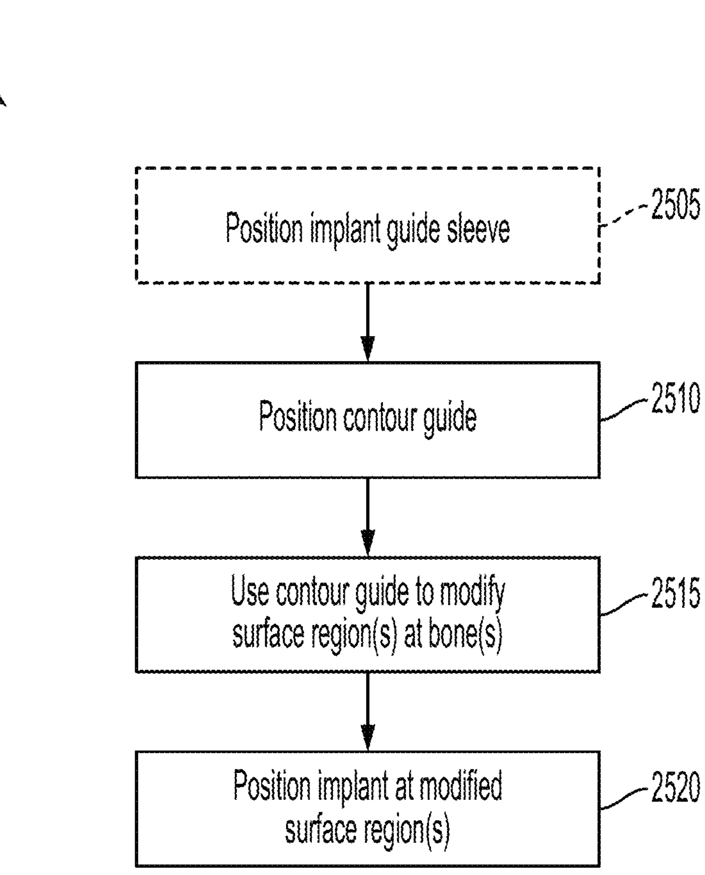
FIG. 15D is a flow diagram of an example surgical technique using a contour guide to modify a bone surface to receive an implant.

FIG. 15D is a flow diagram of an example surgical technique 2500 using a contour guide to modify a bone surface to receive an implant. In some embodiments, the technique 2500 can include use the of the contour guide 4000, as described elsewhere herein, to modify such bone surface(s) to receive an implant (e.g., a staple, a plate, etc.).

In some embodiments, the technique 2500 can include use of an implant guide sleeve. For those embodiments of the technique 2500 that do include use of an implant guide sleeve, the technique 2500 can include an optional step 2505 of positioning an implant guide sleeve.

At step 2505, the technique can include positioning an implant guide sleeve. The implant guide sleeve can be positioned at one or more bones. For example, referring to the example at FIG. 15B, the implant guide sleeve 4004 can be positioned at the first bone 1604 and the second bone 1606 and across the separation 1602 between the first bone 1604 and the second bone 1606. The guide sleeve positioned at one or more bones at step 2505 can be, for instance, the same as, or similar to, any one of the implant guide sleeve embodiments disclosed elsewhere herein (e.g., implant guide sleeve 4002; implant guide sleeve 3000).

As described previously, the implant guide sleeve positioned at one or more bones can be used to guide placement of one or more tools. For example, as described previously, the implant guide sleeve positioned at one or more bones can be used to guide placement of the contour guide 4000, to guide creation of one or more implant hole at one or more bones (e.g., at the modified surface region 4011 at bone 1604 modified using the contour guide 4000), and/or to guide placement of an implant at the one or more implant holes (e.g., placement of a staple's first leg at a first implant hole at the modified surface region 4011 at the bone 1604 and placement of the staple's second leg at a second implant hole at the modified surface region 4011 at the bone 1606). In examples where the implant guide sleeve is used and positioned at step 2505, the implant guide sleeve can be fixated at one or more bones prior to positioning the contour guide 4000 relative to the implant guide sleeve (e.g., fixating the implant guide sleeve using one or more wires or pins at the implant guide sleeve and at the one or more bones). As one particular such example, the implant guide sleeve can be fixated at the first bone 1604 and the second bone 1606 prior to positioning the contour guide at the first bone 1604 and the second bone 1606 and across the separation 1602 between the first bone 1604 and the second bone 1606 using the implant guide sleeve.

Other embodiments of the technique 2500 may not use an implant guide sleeve and for these embodiments the technique 2500 can be executed without the step 2505 of positioning an implant guide sleeve.

At step 2510, the technique 2500 can include positioning the contour guide 4000 to interface with one or more bones. For example, as shown at the illustrative exemplary application at FIG. 15B, the contour guide 4000 can be positioned at the first bone 1604 and the second bone 1606 and across the separation 1602 between the first bone 1604 and the second bone 1606. For instance, the contour guide 4000 can be so positioned by positioning the bottom side 4007 of the contour guide 4000 at the first bone 1604 and the second bone 1604 and across the separation 1602 between the first and second bones 1604, 1606. In one particular such example, the contour guide 4000 can be so positioned by positioning the guide slot 4010 of the contour guide 4000 over at least a portion of the first bone 1604 and over at least a portion of the second bone 1606 and across the separation 1602 between the first and second bones 1604, 1606.

In some examples, at step 2510, placing the contour guide 4000 to interface with one or more bones 1604, 1606 can include defining, at least in part via the contour guide 4000, the bone surface modification region at the one or more bones 1604, 1606. The bone surface modification region can be a region at the surface 1615 of the one or more bones 1604, 1606 that is to be modified, to create the modified surface region 4011, to receive thereat an implant (e.g., staple, plate, etc.). The bone surface modification region can be defined in whole or in part by the guide slot 4010 at the contour guide 4000 that is positioned at the one or more bones 1604, 1606. Thus, placing the contour guide 4000 to interface with one or more bones 1604, 1606 at step 2510 can include placing the guide slot 4010 to interface with at least a portion of a first surface 1615 at the first bone 1604 and to interface with at least a portion of a second surface 1615 at the second bone 1606. And the at least the portion of the first surface 1615 at the first bone 1604 and the at least the portion of the second surface 1615 at the second bone 1606 to which the guide slot 4010 is positioned to interface can define the bone surface modification region at the surfaces 1615 of bones 1604, 1606 that is to be modified to create the modified surface region 4011 to receive thereat the implant.

When the technique 2500 includes the step 2505 of positioning the implant guide sleeve at the one or more bones 1604, 1606, the contour guide 4000 can be positioned at the one or more bones 1604, 1606 at step 2510 using the implant guide sleeve. In such embodiments, the contour guide 4000 can be positioned at the one or more bones 1604, 1606 relative to the implant guide sleeve. In one example, this could include placing the contour guide 4000 relative to the implant guide sleeve by placing at least a portion of the body 4004 (e.g., placing at least the guide slot 4010) of the contour guide 4000 within the implant guide sleeve.

At step 2515, the technique 2500 can include using the contour guide to modify a surface region of at least one bone to form a modified surface region at the at least one bone.

As one such example, referring to the exemplary application illustrated at FIG. 15B, step 2515 can include using the contour guide 4000 to modify a region of the surface 1615 of at least one of the first bone 1604 and the second bone 1606 to form the modified surface region 4011 at one or more of the first bone 1604 and the second bone 1606. In one further such example, referring to the exemplary application illustrated at FIG. 15B, step 2515 can include using the contour guide 4000 to modify a first region of the surface 1615 at the first bone 1604 to form a modified first surface region 4011 along the first bone 1604 and a second region of the surface 1615 at the second bone 1606 to form a modified second surface region 4011 along the second bone 1606.

As described previously herein, the modified surface region 4011 at the first and/or second bones 1604, 1606 can include one or more modifications to the surface 1615 of the first and/or second bones 1604, 1606 at locations along the surface 1615 of the first and/or second bones 1604, 1606 where an implant is to be placed after creating the modified surface region 4011. As such, the contour guide can be used to help define a size of the bone surface modification region 4011 corresponding to a size of the implant to be placed at that bone surface modification region 4011. Because the contour guide 4000 can approximate the size of the implant to be placed (e.g., via the guide slot 4010), using the contour guide 4000 to define the bone surface modification region 4011 at which the surface of the one or more bones 1604, 1606 is modified can allow for creating a surface change at the one or more bone portions 1604, 1606 commensurate with the implant to be placed at that same surface that is modified using the contour guide 4000.

For example, the implant (e.g., staple, plate, etc.) to be placed subsequent to the bone surface modification(s) using the contour guide can have an implant length, and the modified surface region 4011 at the first and/or second bones 1604, 1606 can have a modified surface region length that is equal to or greater than the implant length. Referring to the exemplary application illustrated at FIG. 15B, the implant that is to be placed at the first bone 1604, the second bone 1606, and across the separation 1602 between the bones 1604, 1606 can have an implant length (e.g., staple length), and the modified first surface region 4011 at the first bone 1604 and the modified second surface region 4011 at the second bone 1606 can define a modified bone surface length along the first and second bone 1604, 1606 equal to or greater than the implant length (e.g., equal to or greater than the staple length).

In additional or alternative examples, the implant (e.g., staple, plate, etc.) to be placed subsequent to the bone surface modification(s) using the contour guide can have an implant width, and the modified surface region 4011 at the first and/or second bones 1604, 1606 can have a modified surface region width that is equal to or greater than the implant width. Referring to the exemplary application illustrated at FIG. 15B, the implant that is to be placed at the first bone 1604, the second bone 1606, and across the separation 1602 between the bones 1604, 1606 can have an implant width (e.g., staple width), and the modified first surface region 4011 at the first bone 1604 and the modified second surface region 4011 at the second bone 1606 can define a modified bone surface width along the first and second bone 1604, 1606 equal to or greater than the implant width (e.g., equal to or greater than the staple width).

In one further example, the implant (e.g., staple, plate, etc.) to be placed subsequent to the bone surface modification(s) using the contour guide can have an implant length and an implant width defining an implant cross-sectional area, and the modified surface region 4011 at the first and/or second bones 1604, 1606 can have a modified surface region length and a modified surface region width, defining a modified surface region cross-sectional area that is equal to or greater than the implant cross-sectional area. Referring to the exemplary application illustrated at FIG. 15B, the implant that is to be placed at the first bone 1604, the second bone 1606, and across the separation 1602 between the bones 1604, 1606 can have an implant length and an implant width defining an implant cross-sectional area, and the modified first surface region 4011 at the first bone 1604 and the modified second surface region 4011 at the second bone 1606 can define a modified bone surface length and a modified bone surface width, defining a modified surface region cross-sectional area, along the first and second bone 1604, 1606 equal to or greater than the implant cross-sectional area (e.g., equal to or greater than the staple cross-sectional area defined by the staple length and the staple width).

Using the contour guide to create the modified surface region 4011 at one or more of the first and second bones 1604, 1606 can include creating any one or more modifications to the surface 1615 of at least one of the first and second bones 1604, 1606. For example, using the contour guide to create the modified surface region 4011 at one or more of the first and second bones 1604, 1606 can include changing a contour at the surface 1615 of at least one of the first and second bones 1604, 1606. For instance, using the contour guide to create the modified surface region 4011 at one or more of the first and second bones 1604, 1606 by at least changing a contour at the surface 1615 of at least one of the first and second bones 1604, 1606 can include using the contour guide to change the surface 1615 of at least one of the first and second bones 1604, 1606 such that the surface 1615 of at least one of the first and second bones 1604, 1606 where the modification is created is flatter than that surfaced 1615 prior to the modification. In some applications, this can include using the contour guide to perform a bone surface subtraction technique to create the modified surface region 4011, such as breaking up bone at the surface 1615 of at least one of the first and second bones 1604, 1606. In some such exemplary applications, using the contour guide to create the modification at the surface 1615 of at least one of the first and second bones 1604, 1606 can include breaking up bone at the surface 1615 of at least one of the first and second bones 1604, 1606 to create an elevational change at the surface 1615 of at least one of the first and second bones 1604, 1606. For instance, modified surface region 4011 at one or more of the first and second bones 1604, 1606 created using the contour guide can be lower in elevation than the surface 1615 of at least one of the first and second bones 1604, 1606 prior to the modification using the contour guide.

Using the contour guide to create the modified surface region 4011 at one or more of the first and second bones 1604, 1606 can include placing a bone surface modification instrument at the contour guide and in contact with the surface 1615 of at least one of the first and second bones 1604, 1606. For example, the bone surface modification instrument 4013, placed at the contour guide 4000 and in contact with the surface region 1615 of at least one of the first bone and the second bone 1604, 1606, can be configured to break up bone at the surface region 1615 of at least one of the first bone and the second bone 1604, 1606 to form the modified surface region 4011. In some exemplary applications, the bone surface modification instrument, placed at the contour guide and in contact with the surface region of at least one of the first bone and the second bone, can include at least one of a burr and a saw.

Referring to the illustrated exemplary application at FIG. 15B, the contour guide 4000 can be configured to guide creation of the modified surface region 4011 at one or more of the first and second bones 1604, 1606. For example, the modified surface region 4011 at one or more of the first and second bones 1604, 1606 can be created using the guide slot 4010 at the contour guide 4000. For instance, the modified surface region 4011 can be created over an area at one or more of the first and second bones 1604, 1606 bounded by the guide slot 4010. This could include, for instance, creating the modified surface region 4011 at an area at each of the first and second bones 1604, 1606 bounded by the guide slot 4010.

The one or more bone surface modification instruments can be placed at the guide slot 4010 and, when placed at the guide slot 4010, used to create the modified surface region 4011 at least one of the first and second bones 1604, 1606 over an area at one or more of the first and second bones 1604, 1606 corresponding to an area at one or more of the first and second bones 1604, 1606 interfacing with the guide slot 4010.

In some examples, in addition to the guide slot 4010, the contour guide 4000 can include one or more guide apertures 4008 that can be used to guide placement of one or more bone surface modification instruments 4013 to create the modified surface region 4011. In one such example, using the contour guide 4000 to modify the surface 1615 of at least one of the first and second bones 1604, 1606 to form the modified surface region 4011 at one or more of the first and second bones 1604, 1606 can include placing at least one bone surface modification instrument 4013 at least partially in a guide aperture 4008, at least partially in the guide slot 4010, and in contact with the surface 1615 of at least one of the first and second bones 1604, 1606 to be modified. This can cause the one or more bone surface modification instruments 4013 to be guided to the surface 1615 that is to be modified using the one or more bone surface modification instruments 4013. In some cases where the configuration of the contour guide 4000 is such that the one or more guide apertures 4008 are aligned with the guide slot 4010, this can include, when the contour guide 4000 is positioned at the first and second bones 1604, 1606 and across the separation 1602, the bone surface modification instrument 4013 first being inserted through the guide aperture 4008, then being inserted through the guide slot 4010, and then being placed in contact with the surface 1615 of at least one of the first and second bones 1604, 1606 to modify that surface 1615 to create the modified surface region 4011.

For embodiments of the technique 2500 that do include the step 2505 of positioning the implant guide sleeve (e.g., implant guide sleeve 4002; implant guide sleeve 3000), the contour guide 400 can be used to create the modified surface region 4011 when the contour guide 4000 is positioned relative to the implant guide sleeve. As one such example, the contour guide 4000 can be used to modify the surface 1615 of at least one of the first and second bones 1604, 1606 to form the modified surface region 4011 by using the contour guide 4000 to create the modified surface region 4011 while the contour guide 4000 is positioned at least partially within the implant guide sleeve (e.g., implant guide sleeve 4002; implant guide sleeve 3000).

At step 2520, the technique 2500 can include positioning an implant in contact at least with the modified surface region 4011. In applications of the technique 2500 where the contour guide is used to create the first modified surface region 4011 at the first bone 1604 and to create the second modified surface region 4011 at the second bone 1606, at step 2520, the implant can be placed in contact at least with the first modified surface region 4011 at the first bone 1604 and the second modified second surface region 4011 at the second bone 1606. In one such exemplary application where the implant is a staple, the first bone 1604 is a metatarsal, the second bone 1606 is a cuneiform, and the separation 1602 between the first and second bones is a joint space between the metatarsal and the cuneiform, placing the implant in contact at least with the modified surface region 4011 at step 2520 can include placing a first leg of the staple through the first modified surface region 4011 at the metatarsal and placing a second leg of the staple through the second modified surface region 4011 at the cuneiform. Additionally for this exemplary application, step 2520 could further include placing the implant in contact with each of the first modified surface region 4011 at the first bone 1604 and the second modified surface region 4011 at the second bone 1606 and along with the implant bridging the separation 1602 between the first and second bones 1604, 1606.

For embodiments of the technique 2500 that do include the step 2505 of positioning the implant guide sleeve (e.g., implant guide sleeve 4002; implant guide sleeve 3000), after positioning the contour guide using the implant guide sleeve at step 2510 and after using the contour guide to modify the surface region of at least one of the first bone and the second bone to form the modified surface region at one or more of the first bone and the second bone at step 2515, step 2520 can include positioning the implant at the modified surface region relative to the implant guide sleeve. For example, after using the contour guide to modify the surface region of at least one of the first bone and the second bone to form the modified surface region at one or more of the first bone and the second bone at step 2515, the contour guide can be removed at the implant guide sleeve can remain fixed at one or both of the first and second bones. Then the implant can be guided to, and positioned at, the modified surface region at one or both of the first and second bones using the implant guide sleeve. In one particular such application, after positioning the contour guide using the implant guide sleeve at step 2510 and after using the contour guide to modify the surface region of at least one of the first bone and the second bone to form the modified surface region at one or more of the first bone and the second bone at step 2515, step 2520 can include positioning the implant at the modified surface region relative to the implant guide sleeve by advancing an inserter, operatively connected to the implant, relative to the implant guide sleeve to place the implant in contact at least with the modified surface region.

In some examples, use of the contour guide 4000, such as described here, can be incorporated into the method 1500. For example, use of the contour guide 4000, such as described here, can be incorporated into the method 1500 prior to steps 1540, 1550 at which the implant is positioned. In one specific such example, use of the contour guide 4000, such as described here, can be incorporated into the method 1500 after the implant guide sleeve is placed at step 1510 (e.g., and after the implant guide sleeve is secured if/when step 1520 is included) and prior to steps 1540, 1550.

Figure 16A:
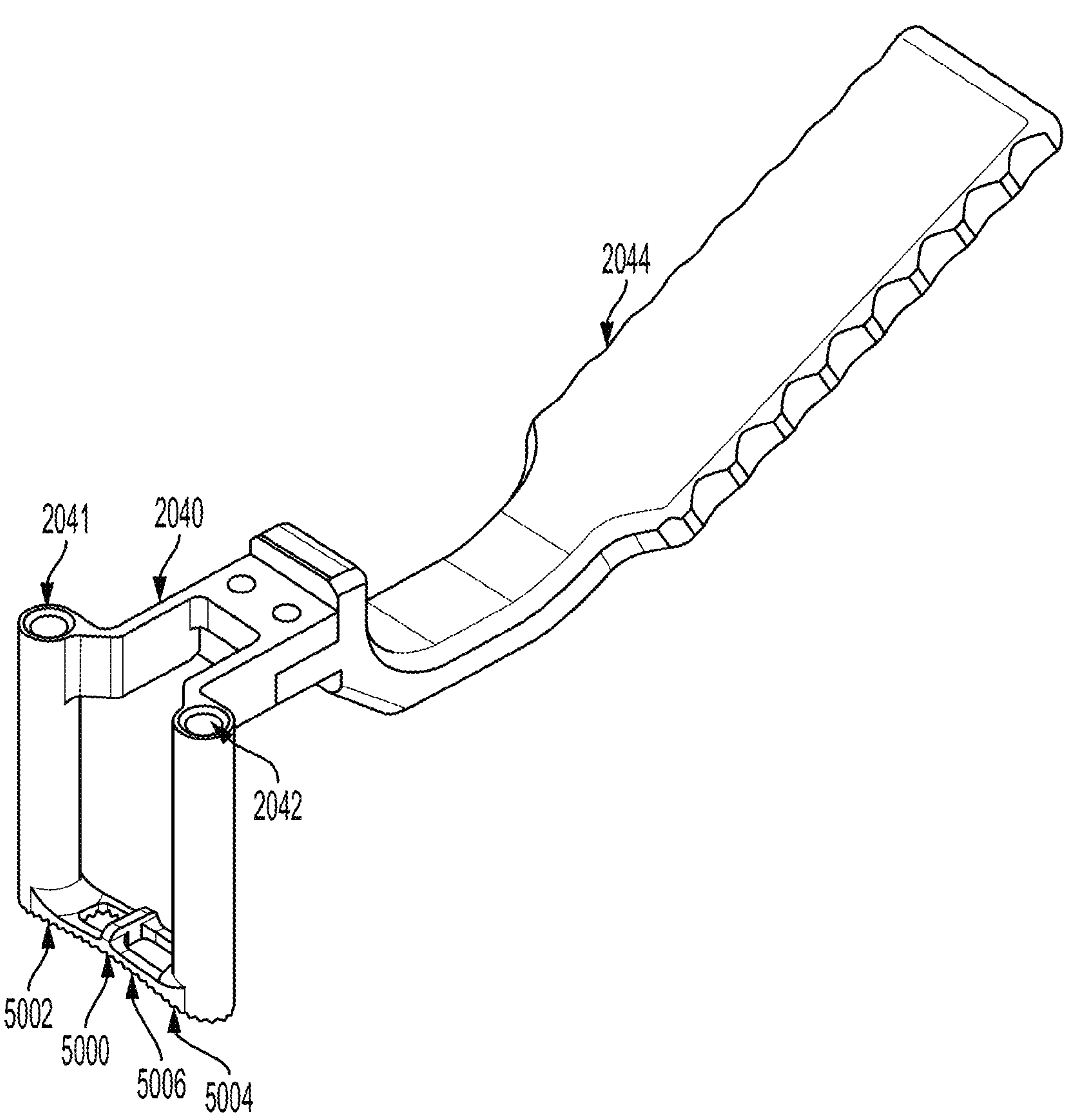
FIGS. 16A-16C illustrate one embodiment of a trialing member at a drill guide.
Figure 16B:
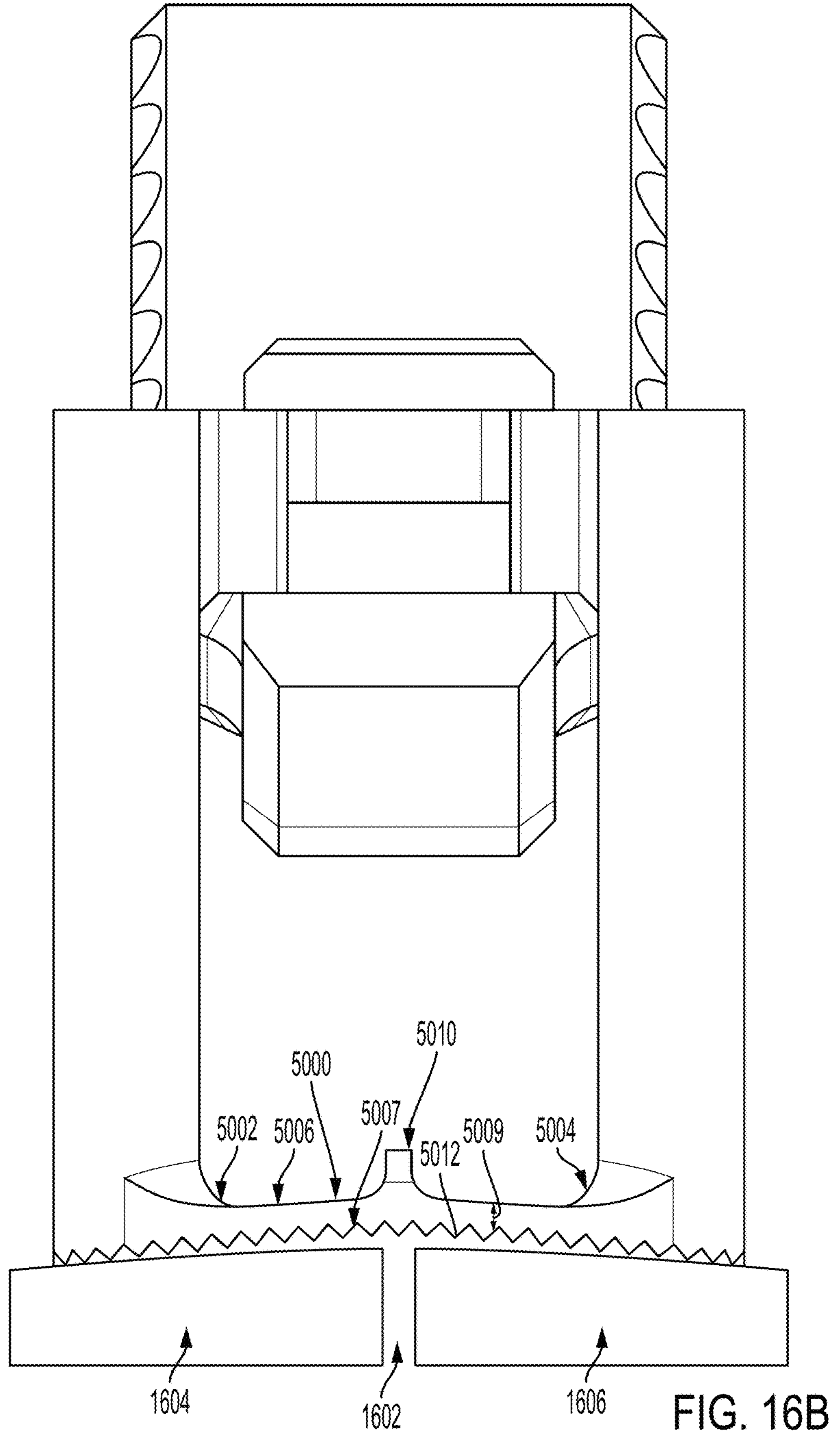
Figure 16C:
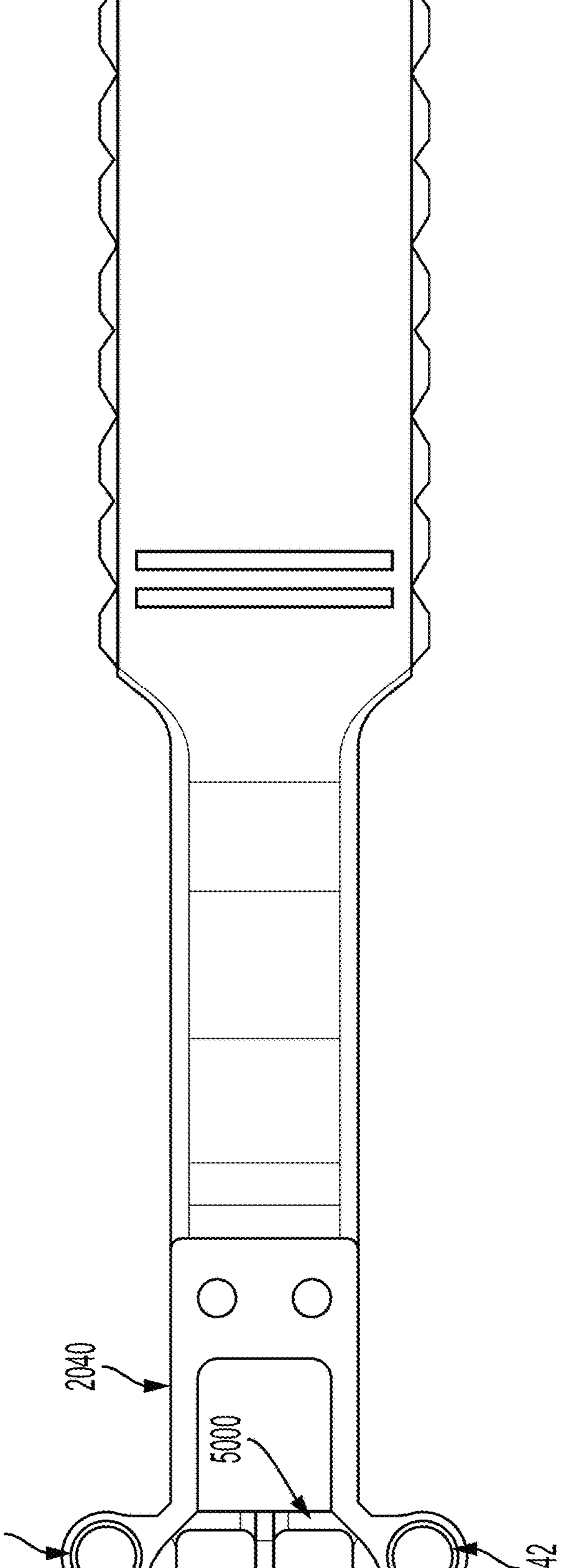

FIGS. 16A-16C illustrate one embodiment of a trialing member 5000. FIGS. 16A-16C show an embodiment where the trialing member 5000 is included at the drill guide 2040 which is described elsewhere herein. When the trialing member 5000 is included at the drill guide 2040, the trialing member 5000 can, for instance, extend between first and second drill guide sleeves 2041, 2042. Though other embodiments within the scope of this disclose can include the trialing member 5000 in isolation as a distinct, individual component. FIG. 16A is a perspective view of the trialing member 5000 at the drill guide 2040, FIG. 16B is an elevational view of the trialing member 5000 placed at one or more bone portions 1604, 1606, and FIG. 16C is a plan view of the trialing member 5000 at the drill guide 2040. The trialing member 5000 can be configured to approximate a size and/or shape of an implant, such as a staple, that is to be placed at one or more bone portions 1604, 1606 and, thereby, allow for a preview as to how such implant will sit on the one or more bone portions 1604, 1606. This can be useful, for example, in providing a preview as to how such implant will sit on the one or more bone portions 1604, 1606 before drilling, at the one or more bone portions 1604, 1606, one or more holes for use in securing the implant to the one or more bone portions 1604, 1606.

The trialing member 5000 can include one or more dimensions mimicking (e.g., approximating or matching) an implant to be placed at one or more bone portions 1604, 1606. For example, where the implant to be mimicked is a staple (e.g., staple 500, 600, 700, 800), the trialing member 5000 can include a first end portion 5002, a second end portion 5004, and a trialing bridge 5006 extending between the first and second end portions 5002, 5004. As best seen at FIG. 16B, the trialing bridge 5006 can include an arch 5007 and a thickness 5009 between the first and second end portions 5002, 5004. The arch 5007 can mimic (e.g., approximate, match) the curvature of a bridge of the staple to be subsequently placed, and, likewise, the thickness 5009 can mimic (e.g., approximate, match) the thickness of the bridge of the staple to be subsequently placed. Because the arch 5007 and/or thickness 5009 can mimic the contour and thickness of the staple to be subsequently placed at the one or more bone portions 1604 1606, the trialing member 5000 can be placed at the one or more bone portions 1604, 1606 before placing the staple thereat such that the trialing member 5000 can provide a preview as to the staple's fit relative to the surface of the one or more bone portions 1604, 1606.

In some embodiments, the trialing member 5000 can also include an alignment feature 5010. The alignment feature 5010 can be located at the bridge 5006. The alignment feature 5010 can be configured to provide an indication (e.g., visual indication) corresponding to a central region (e.g., centerline) of the trialing member 5000. When the trialing member 5000 is being placed at the one or more bone portions 1604, 1606, as shown at FIG. 16B, the alignment feature 5010 can be aligned with the separation 1602 (e.g., a joint space, such as a TMT joint space) between the bone portions 1604, 1606 and, thereby, help to provide a reference for placing the trialing member 5000 relative to the one or more bone portions 1604, 1606 in the same, or generally same, location at which the staple will be subsequently placed.

In certain embodiments, the trialing member 5000 can further include one or more friction elements 5012. The one or more friction elements 5012 can be configured to increase friction between a surface of the trialing element 5000 (e.g., a bottom surface that contacts the one or more bone portions 1604, 1606) and the one or more bone portions 1604, 1606 at which the trialing member 5000 is placed. This can be useful in helping to stabilize the relative positioning between the trialing member 5000 and the one or more bone portions 1604, 1606. The illustrated embodiment of the trialing member 5000 includes a plurality of friction elements 5012 in the form of teeth. Though in other embodiments other types of friction elements can be additionally or alternatively included.

As noted, the trialing member 5000 can be used in a method for placing an implant at one or more bone portions 1604, 1606.

At a first step, the trialing member 5000 is placed at (e.g., in contact with) one or more bone portions 1604, 1606. The trialing member 5000 can be placed at one or more bone portions 1604, 1606 such that the first end portion 5002 interfaces with one bone portion 1604 and the second end portion 5004 interfaces with another bone portion 1606. In instances where the trialing member 5000 includes the alignment feature 5010, this step can also include placing the trialing member 5000 at one or more bone portions 1604, 1606 such that the alignment feature 5010 interfaces with the separation 1602.

At a second step, a relative fit of the trialing member 5000 at the one or more bone portions 1604, 1606 can be determined. This can include, for instance, determining a fit of the arch 5007 relative to a curvature at the surface of the one or more bone portions 1604, 1606.

If the relative fit of the trialing member 5000 at the surface of the one or more bone portions 1604, 1606 is found suitable, one or more implant holes can then be created at the one or more bone portions 1604, 1606. This could include creating one or more implant holes at the one or more bone portions 1604, 1606 while the trialing member 5000 is placed at those same one or more bone portions 1604, 1606. As one example, one or more implant holes can be created using the drill guide 2040, for instance, by creating a first implant hole via the first drill guide sleeve 2041 adjacent the first end 5002 of the trialing member 5000 and creating a second implant hole via the second drill guide sleeve 2042 adjacent the second end 5004 of the trialing member 5000.

If the relative fit of the trialing member 5000 at the one or more bone portions 1604, 1606 is found unsuitable, then at least a portion of the surface of the one or more bones 1604, 1606 at which the trialing member 5000 was placed can be modified or the trialing member 5000 can be moved and placed at a different surface region at the one or more bone portions 1604, 1606 to mimic and evaluate the fit of a corresponding staple at that different surface regions. For embodiments where the surface of the bone portions 1604, 1606 is modified after the trialing member 5000 is placed at that surface, this could include modifying at least a portion of the surface of the one or more bone portions 1604, 1606 to alter a fit between the trialing member 5000 and that surface of the one or more bone portions 1604, 1606. As one particular such example, the contour guide 4000 can be used as disclosed elsewhere herein to modify the surface at the one or more bone portions 1604, 1606. Once the fit of the trialing member 5000 at the one or more bone portions 1604, 1606 is found to be suitable, one or more implant holes can then be created at the one or more bone portions 1604, 1606 as noted.

At a third step, the staple can be placed at the surface of the one or more bone portions 1604, 1606 at which the relative fit between the trialing member 5000 and that surface of the one or more bone portions 1604, 1606 was found suitable. This can include placing legs (e.g., tines) of the staple at the implant holes created using the drill guide sleeves adjacent the trialing member 5000.

Figure 16D:
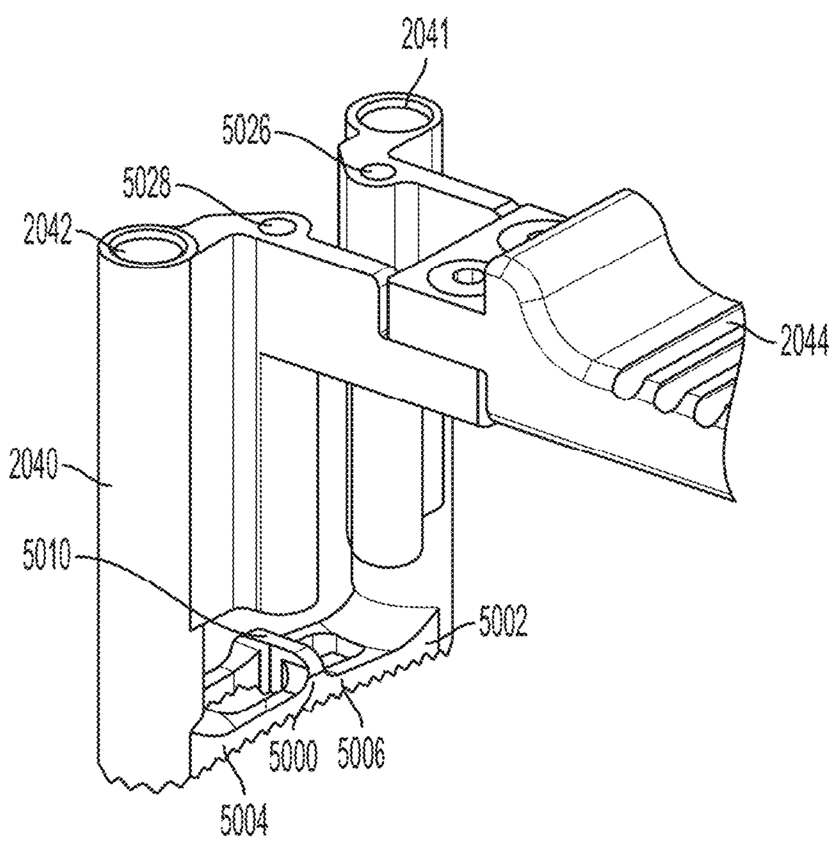
FIGS. 16D and 16E illustrate a further embodiment of the trialing member at the drill guide of FIGS. 16A-16C with one or more pin apertures included.
Figure 16E:
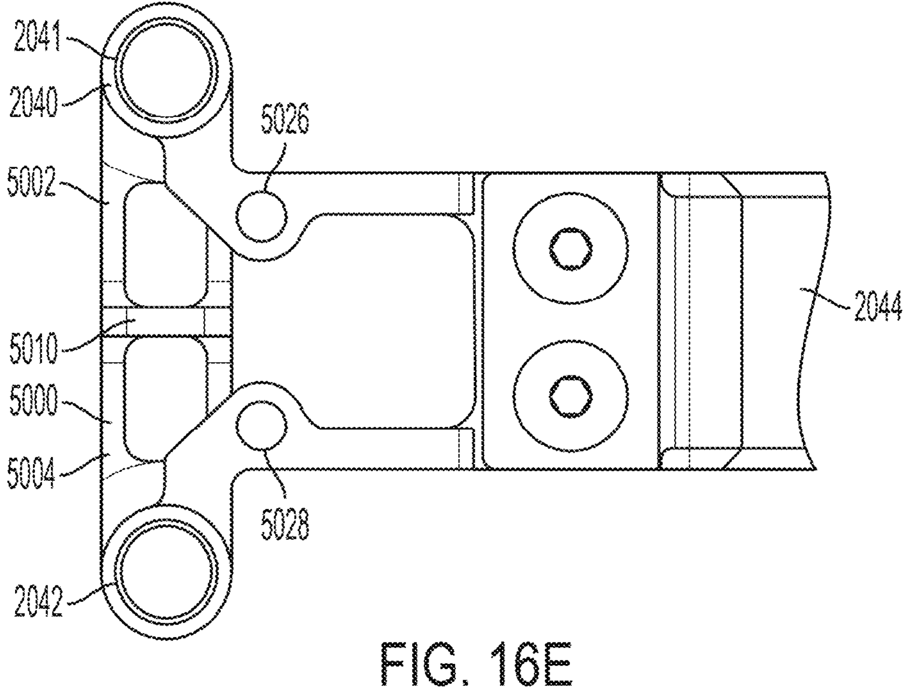

FIGS. 16D and 16E illustrate a further embodiment of the trialing member 5000 at the drill guide 2040 of FIGS. 16A-16C with one or more pin apertures 5026, 5028 included. FIG. 16D is a perspective view and FIG. 16E is a top plan view of the exemplary trialing member 5000 at the drill guide 2040 with one or more pin apertures 5026, 5028 included.

As illustrated for the example shown at FIGS. 16D and 16E, in addition to the trialing member 5000, the drill guide 2040 can include one or more pin apertures 5026, 5028. The illustrated embodiments shows the drill guide 2040 can include trialing member 5000, first drill guide sleeve 2041, second drill guide sleeve 2042, first pin aperture 5026, and second pin aperture 5028. The trialing member 5000, first drill guide sleeve 2041, and second drill guide sleeve 2042 can be as disclosed elsewhere herein. The first pin aperture 5026 can be configured to receive a pin or wire therethrough and into a bone, and the second pin aperture 5028 can be configured to receive another pin or wire therethrough and into a bone (e.g., the same or different bone as the first pin aperture 5026). As such, each of the first and second pin apertures 5026, 5028 can be open at a proximal end and open at an opposite distal, bone facing end. A pin or wire can be inserted through the first and/or second pin aperture 5026, 5028 to provide temporary fixation of the drill guide 2040 and trialing member 5000 at one or more bone portions (e.g., temporary fixation while the drill guide 2040 is utilized to drill one or more implant receiving holes and/or while the trialing member 5000 is used at one or more bone portions).

For applications where the drill guide 2040 and trialing member 5000 are to be used in conjunction with a procedure for placing an implant (e.g., staple) across bone portions, when the drill guide 2040 and trialing member 5000 are placed to interface with such bone portions the first pin aperture 5026 can be located at the drill guide 2040 so as to be positioned over a first bone portion and the second pin aperture 5028 can be located at the drill guide 2040 so as to be positioned over a second bone portion. As noted elsewhere herein since the first drill guide sleeve 2041 can be located at the drill guide 2040 so as to be positioned over the first bone portion, the first pin aperture 5026 can be located at the drill guide 2040 adjacent to the first drill guide sleeve 2041. Likewise, as noted elsewhere herein, since the second drill guide sleeve 2042 can be located at the drill guide 2040 so as to be positioned over the second bone portion, the second pin aperture 5028 can be located at the drill guide 2040 adjacent to the second drill guide sleeve 2042. For embodiments that include the alignment feature 5010, the first pin aperture 5026 and the first drill guide sleeve 2041 can be positioned at one side of the alignment feature 5010 and the second pin aperture 5028 and the second drill guide sleeve 2042 can be located at another, opposite side of the alignment feature 5010. Thus, the alignment feature 5010 can be located at the trialing member 5000 such that the alignment feature is configured to be positioned over the space 1602 between the first and second bone portions 1604, 1606, the first pin aperture 5026, the first drill guide sleeve 2041, and the first end portion 5002 of the trialing member 5000 can be located at the drill guide 2040 and trialing member 5000 such that each of the first pin aperture 5026, the first drill guide sleeve 2041, and the first end portion 5002 of the trialing member 5000 is configured to be positioned over the first bone portion 1604, and the second pin aperture 5028, the second drill guide sleeve 2042, and the second end portion 5004 of the trialing member 5000 can be located at the drill guide 2040 and trialing member 5000 such that each of the second pin aperture 5028, the second drill guide sleeve 2042, and the second end portion 5004 of the trialing member 5000 is configured to be positioned over the second bone portion 1606.

Figure 17A:
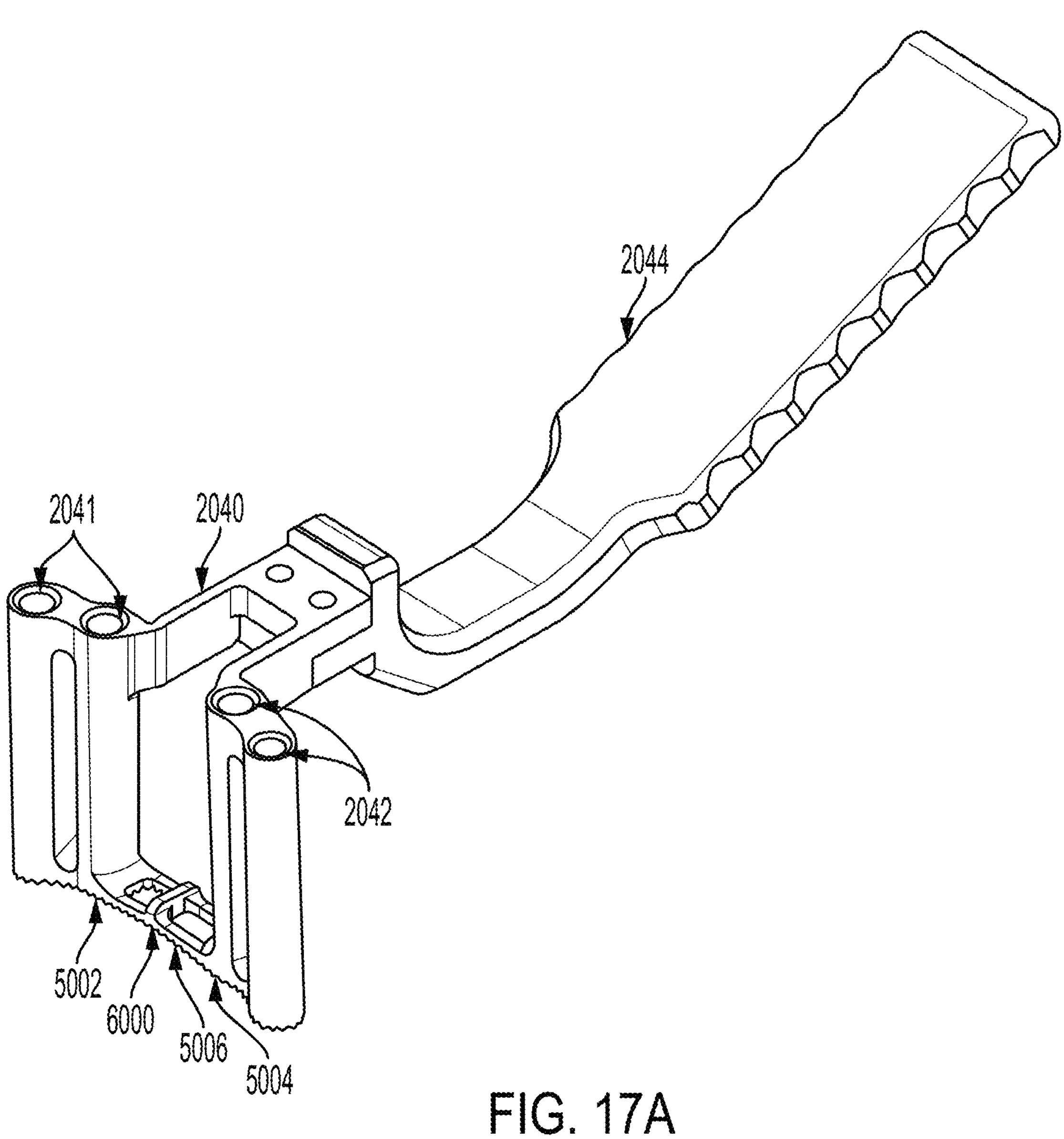
FIGS. 17A and 17B illustrate another embodiment of a trialing member at a drill guide.
Figure 17B:
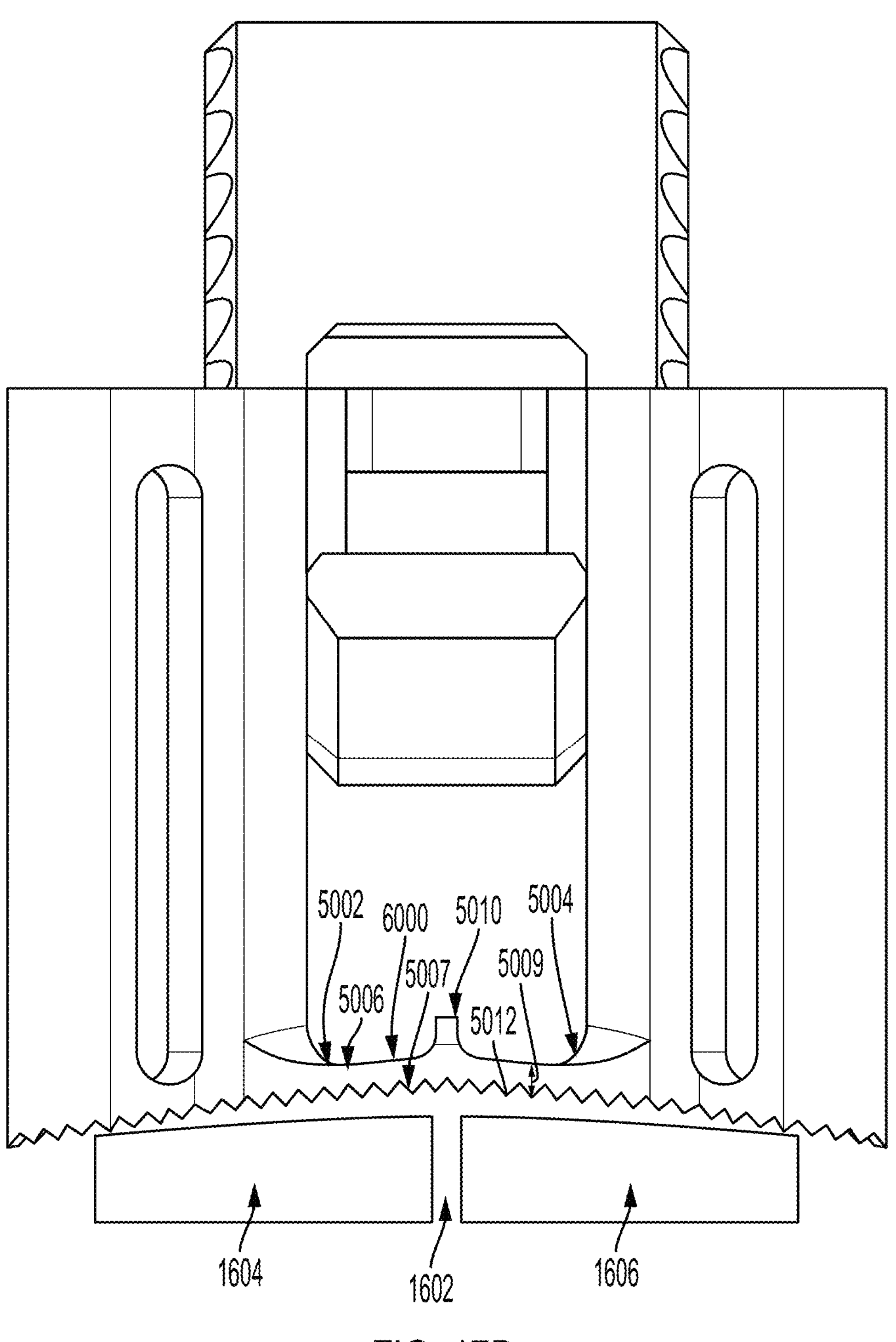

FIGS. 17A and 17B illustrate another embodiment of a trialing member 6000 at the drill guide 2040. FIG. 17A is a perspective view of the trialing member 6000 at the drill guide 2040, and FIG. 17B is an elevational view of the trialing member 6000 placed at one or more bone portions 1604, 1606. FIGS. 17A and 17B show an embodiment where the trialing member 6000 is included at the drill guide 2040 which is described elsewhere herein, though other embodiments within the scope of this disclose can include the trialing member 6000 in isolation as a distinct, individual component.

The trialing member 6000 can be similar to, or the same as, the trialing member 5000 disclosed previously except as otherwise noted here. Namely, the trialing member 6000 can be configured to mimic a different implant than the trialing member 5000. For example, the trialing member 5000 can be configured to mimic a first staple design whereas the trialing member 6000 can be configured to mimic a second, different staple design. In particular, as it relates to the illustrated embodiments, the trialing member 5000 can be configured to mimic a staple having two legs-one on each side of the bridge-whereas the trialing member 5000 can be configured to mimic a staple have four legs-two on each side of the bridge. Like the trialing member 5000, the trialing member 6000 can be configured to approximate a size and/or shape of a staple (e.g., having four legs) that is to be placed at one or more bone portions 1604, 1606 and, thereby, allow for a preview as to how such staple will sit on the one or more bone portions 1604, 1606. As shown for the example here, the drill guide 2040 can include more than one drill guide sleeve 2041 at one side of the drill guide 2040 (e.g., a side configured to be positioned over the first bone portion 1604) and can include more than one drill guide sleeve 2042 at another, opposite side of the drill guide 2040 (e.g., another, opposite side configured to be positioned over the second bone portion 1606).

Figure 17C:
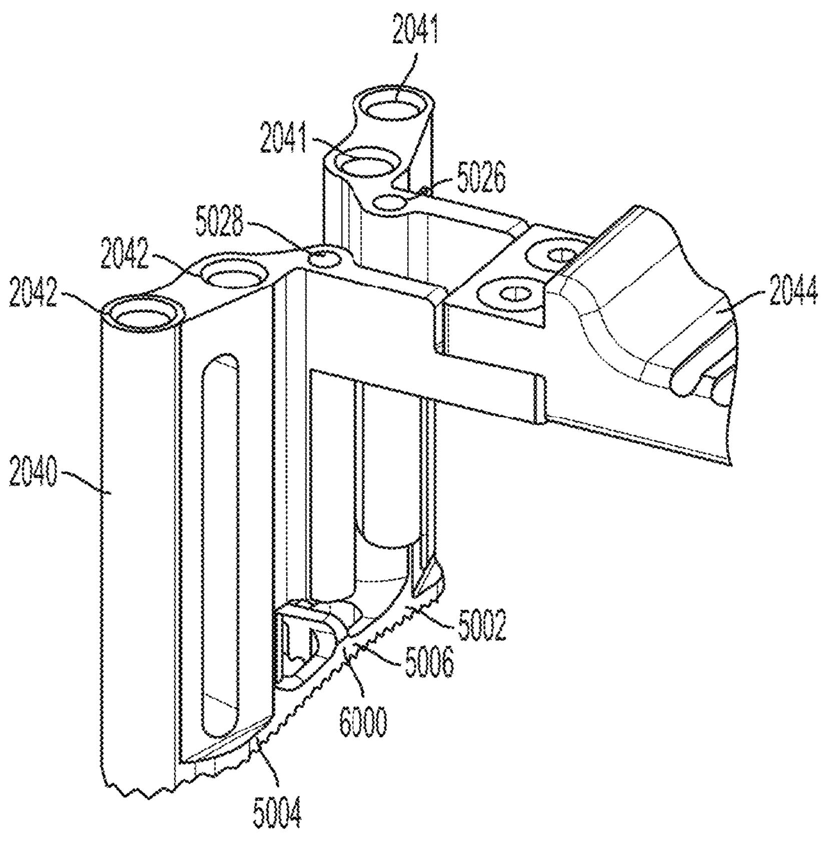
FIGS. 17C and 17D illustrate a further embodiment of the trialing member at the drill guide of FIGS. 17A-17B with one or more pin apertures included.
Figure 17D:
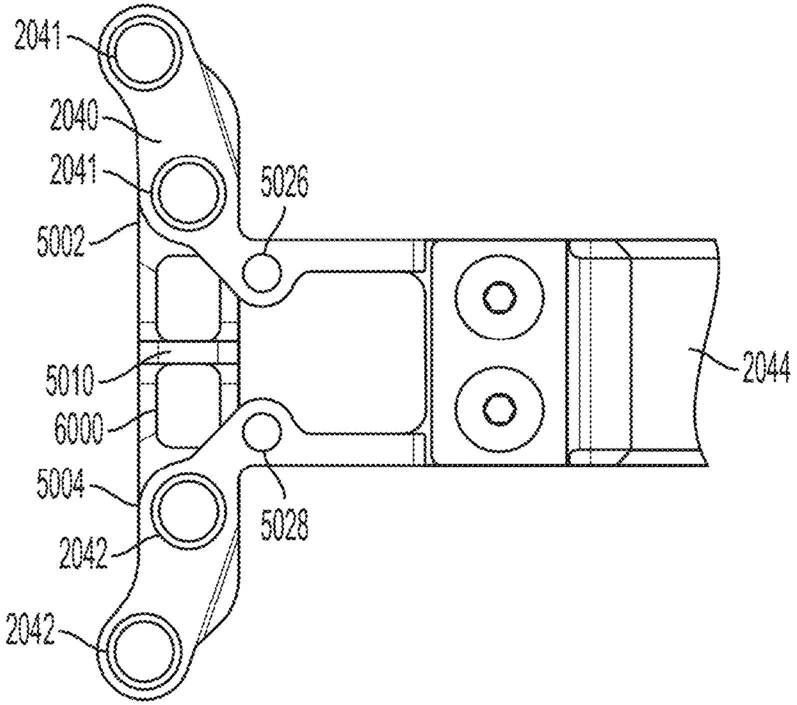

FIGS. 17C and 17D illustrate a further embodiment of the trialing member 6000 at the drill guide 2040 of FIGS. 17A-17B with one or more pin apertures 5026, 5028 included. FIG. 17C is a perspective view and FIG. 17D is a top plan view of the exemplary trialing member 6000 at the drill guide 2040 with one or more pin apertures 5026, 5028 included.

The illustrated for the example shown at FIGS. 17C and 17D, in addition to the trialing member 6000, the drill guide 2040 can include one or more pin apertures 5026, 5028, at least two drill guide sleeves 2041, and at least two drill guide sleeves 2042. The illustrated embodiments shows the drill guide 2040 can include trialing member 6000, two drill guide sleeves 2041, two drill guide sleeve 2042, first pin aperture 5026, and second pin aperture 5028. The trialing member 6000, drill guide sleeves 2041, drill guide sleeves 2042, first pin aperture 5026, and second pin aperture 5028 can be as disclosed elsewhere herein. A pin or wire can be inserted through the first and/or second pin aperture 5026, 5028 to provide temporary fixation of the drill guide 2040 and trialing member 6000 at one or more bone portions. For applications where the drill guide 2040 and trialing member 6000 are to be used in conjunction with a procedure for placing an implant (e.g., staple) across bone portions and where the alignment feature 5010 is included, when the drill guide 2040 and trialing member 6000 are placed to interface with such bone portions, the first pin aperture 5026 and the drill guide sleeves 2041 can be positioned at one side of the alignment feature 5010 and the second pin aperture 5028 and the drill guide sleeves 2042 can be located at another, opposite side of the alignment feature 5010. Thus, the alignment feature 5010 can be located at the trialing member 6000 such that the alignment feature 5010 is configured to be positioned over the space 1602 between the first and second bone portions 1604, 1606, the first pin aperture 5026, the drill guide sleeves 2041, and the first end portion 5002 of the trialing member 6000 can be located at the drill guide 2040 and trialing member 6000 such that each of the first pin aperture 5026, the drill guide sleeves 2041, and the first end portion 5002 of the trialing member 6000 is configured to be positioned over the first bone portion 1604, and the second pin aperture 5028, the drill guide sleeves 2042, and the second end portion 5004 of the trialing member 6000 can be located at the drill guide 2040 and trialing member 6000 such that each of the second pin aperture 5028, the drill guide sleeves 2042, and the second end portion 5004 of the trialing member 6000 is configured to be positioned over the second bone portion 1606.

Figure 18:
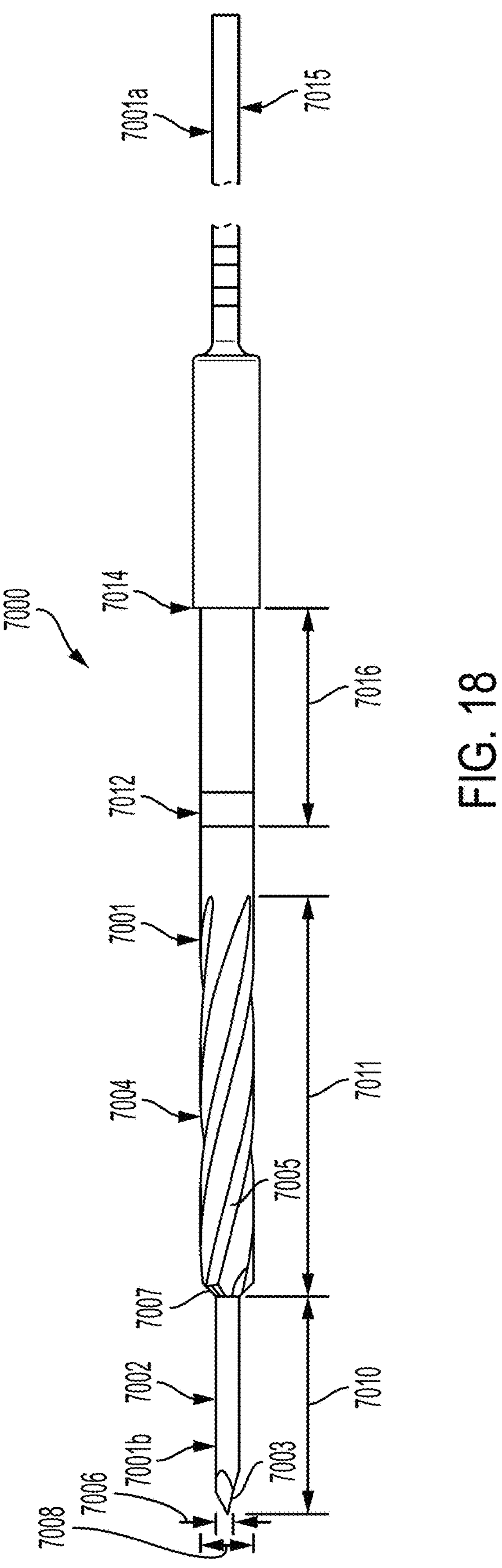
FIG. 18 is a side elevational view of an embodiment of a pinning and drilling instrument.

FIG. 18 illustrates a side elevational view of an embodiment of a pinning and drilling instrument 7000. The pinning and drilling instrument 7000 can be configured for evaluating a proposed implant receiving aperture location to be created (e.g., drilled) at a bone portion prior to actually creating that implant receiving aperture at the bone portion and, when the proposed implant receiving aperture location is determined to be suitable, the pinning and drilling instrument 7000 can be configured for creating the implant receiving aperture.

The pinning and drilling instrument 7000 can include a body 7001. The body 7001 can have a body proximal end 7001*a* and a body distal end 7001*b*. The body 7001 can include a pin portion 7002 and a drill portion 7004. The pin portion 7002 can be at, or near, the body distal end 7001*b* and can extend proximally along a pin portion length 7010 of the body 7001 toward the body proximal end 7001*a*. For the illustrated embodiment, the pin portion 7002 forms a distal-most end of the body 7001. The drill portion 7004 can be at the body 7001 proximal to the pin portion 7002 and can extend proximally along a drill portion length 7011 of the body 7001 toward the body proximal end 7001*a*. For the illustrated embodiment, the drill portion 7004 begins where the pin portion 7002 ends. For example, a distal end of the drill portion 7004 can begin where a proximal end of the pin portion 7002 terminates.

The pin portion 7002 and the drill portion 7004 can have different widths defined at the body 7001. The pin portion 7002 can have a pin width (e.g., diameter) 7006, and the drill portion 7004 can have a drill width (e.g., diameter) 7008. For the illustrated embodiment, the pin width 7006 is smaller than the drill width 7008. Accordingly, because the drill width 7008 can be greater than the pin width 7006, the width of the body 7001 of the pinning and drilling instrument 7000 can increase where the pin portion 7002 ends and the drill portion 7004 begins. The change in width at the body 7001 where the pin portion 7002 ends and the drill portion 7004 begins can create a shoulder 7007 at the body 7001 where the drill portion 7004 begins. Thus, the shoulder 7007 can trail the pin portion 7002 and the shoulder 7007 can be present at the distal end of the drill portion 7004. As will be described further herein, this shoulder 7007 can be configured to contact a bone portion following insertion of the pin portion 7002 at the bone portion and such contact between the bone portion and the shoulder 7007 can act to provide tactile feedback to a user indicating that the pin portion 7002 (e.g., pin portion length 7010) has been inserted into the bone portion. As such, in some applications where the pin portion 7002 positioning within the bone portion is to be evaluated (e.g., via imaging), insertion of the pin portion 7002 into the bone portion can be temporarily terminated when the shoulder 7007 contacts the bone portion to allow for such evaluation of the pin portion 7002 positioning within the bone portion.

The differential widths at the pin and drill portions 7002, 7004 can, in some embodiments, result in differential cross-sectional areas at the pin and drill portions 7002, 7004. In such embodiments, the pin portion 7002 can define a first cross-sectional area of the body 7001, and the drill portion 7004 can define a second cross-sectional area of the body 7001 different than the first cross-sectional area of the body 7001. For the exemplary illustrated embodiment, the second cross-sectional area defined at the body 7001 by the drill portion 7004 is greater than the first cross-sectional area defined at the body 7001 by the pin portion 7002.

As noted, the pin portion 7002 can be configured to be inserted into a bone portion. For example, the pin portion 7002 can be configured to create a tacking aperture at a bone. For the illustrated embodiment, the pin portion 7002 includes a pointed end 7003 that, when in contact with and advanced at a bone, can be configured to piece a surface of a bone and create a tacking aperture at a location at the bone where the pin portion 7002 is advanced.

The drill portion 7004 can be configured to create an implant receiving aperture at a bone. For example, the drill portion 7004 can include drill flutes 7005 that are configured to create the implant receiving aperture at the bone (e.g., for receiving a portion of an implant, such as a leg of a staple). For example, the pinning and drilling instrument 7000 can be rotationally driven to thereby cause the drill flutes 7005 to break up bone and create the implant receiving aperture. The drill flutes 7005 can begin generally where the pin portion 7002 ends, for instance, such that the drill flutes 7005 can begin at the shoulder 7007 and extend proximally therefrom along the body 7001. With the pinning and drilling instrument 7000 having the drill portion 7004 proximal to, and trailing, the pin portion 7002, the drill portion 7004 can be configured to create the implant receiving aperture at the bone at least at the location at the bone where the tacking aperture was previously created by the leading pin portion 7002. Thus, the pinning and drilling instrument 7000, when placed into contact with a bone and advanced into the bone, can be configured to first create a tacking aperture at the bone via the pin portion 7002 and then, as the pinning and drilling instrument 7000 is further advanced into the bone, the pinning and drilling instrument 7000 can be configured to create an implant receiving aperture, via the drill portion 7004, at least at the same location at the bone where the tacking aperture was previously created by the pin portion 7002. The tacking aperture can have a smaller diameter than the implant receiving aperture. For example, because the pin width 7006 can be smaller than the drill width 7008, the tacking aperture created by the pin portion 7002 can be smaller in diameter than the implant receiving aperture subsequently created by the drill portion 7004.

The pin portion 7002 can be configured to help evaluate a proposed positioning of an implant at one or more bone portions. Certain applications involving placement of an implant at one or more bone portions can include creation of an implant receiving aperture at a bone portion to receive within the bone, at the implant receiving aperture, at least a portion of an implant. For such applications, the pin portion 7002 can be configured to help evaluate a proposed positioning of an implant before creating the implant receiving aperture at the bone portion using the drill portion 7004. For example, the pin portion 7002 can have the pin length 7010 that is equal to a length of an implant portion that is to be implanted at (e.g., within) the bone, and, as such, the pin portion 7002 can provide a visual indication (e.g., via imaging) as to what the positioning of the implant within the bone will be. In particular, in some such applications, the pin portion 7002 can be configured to simulate a proposed implant receiving aperture location to be created (e.g., drilled using the drill portion 7004) at a bone portion, which in turn can serve as a proxy for the positioning of the implant to be later placed at the proposed implant receiving aperture, prior to actually creating that implant receiving aperture at the bone portion. This can allow for evaluation and either (i) confirmation that the implant receiving aperture location to receive the implant is suitable or (ii) determination that the implant receiving aperture location to receive the implant is unsuitable and should be moved in which case the pin portion 7003 can be removed from that location at the bone portion and repositioned at a new location at the same bone portion, or a different bone portion, for new evaluation.

For embodiments where the implant to be placed at the one or more bone portions is a staple, the pin portion 7002 can be configured to help evaluate a proposed positioning of a staple leg at (e.g., within) a bone portion. For example, the pin portion 7002 can have the pin length 7010 that is equal to a leg length of the staple that is to be implanted. For instance, certain staple designs have a leg length of 12 mm, 13 mm, or 16 mm. When the staple to be placed at the bone portion has a leg length of 12 mm, the pin length 7010 can be 12 mm; when the staple to be placed at the bone portion has a leg length of 13 mm, the pin length 7010 can be 13 mm; and when the staple to be placed at the bone portion has a leg length of 16 mm, the pin length 7010 can be 16 mm. Accordingly, in this example, visually ascertaining (e.g., via imaging) the position of the pin length 7010 at the bone portion can help to evaluate what the positioning of the staple leg will be if the staple leg is inserted at the location of the pin length 7010. To do so, the pin length 7010 of the pin portion 7002 can be inserted into the bone portion and image data (e.g., fluoroscopic image data) can be generated to visually capture the location of the pin length 7010 within the bone portion. If the location of the pin length 7010 within the bone portion is determined to be suitable for placing a leg of the staple at that location, then the pinning and drilling instrument 7000 can be further inserted into that bone portion to cause the drill portion 7004 to create the implant receiving aperture at the same location where the pin length 7010 positioning within the bone portion was determined to be suitable. On the other hand, if the location of the pin length 7010 within the bone portion is determined to be suitable for placing a leg of the staple at that location, then the pin portion 7002 can be removed from that location at the bone portion and the pin portion 7002, including the pin length 7010 simulating the staple leg, can be inserted at a different bone portion location for new positioning evaluation. Accordingly, the pinning and drilling instrument 7000 can help to both initially simulate a location of a staple leg-via the pin length 7010 of the pin portion 7002—and then subsequently create the implant receiving aperture-via the drill portion 7004—at that simulated staple leg location for placement of the staple leg at that location.

Figure 22A:
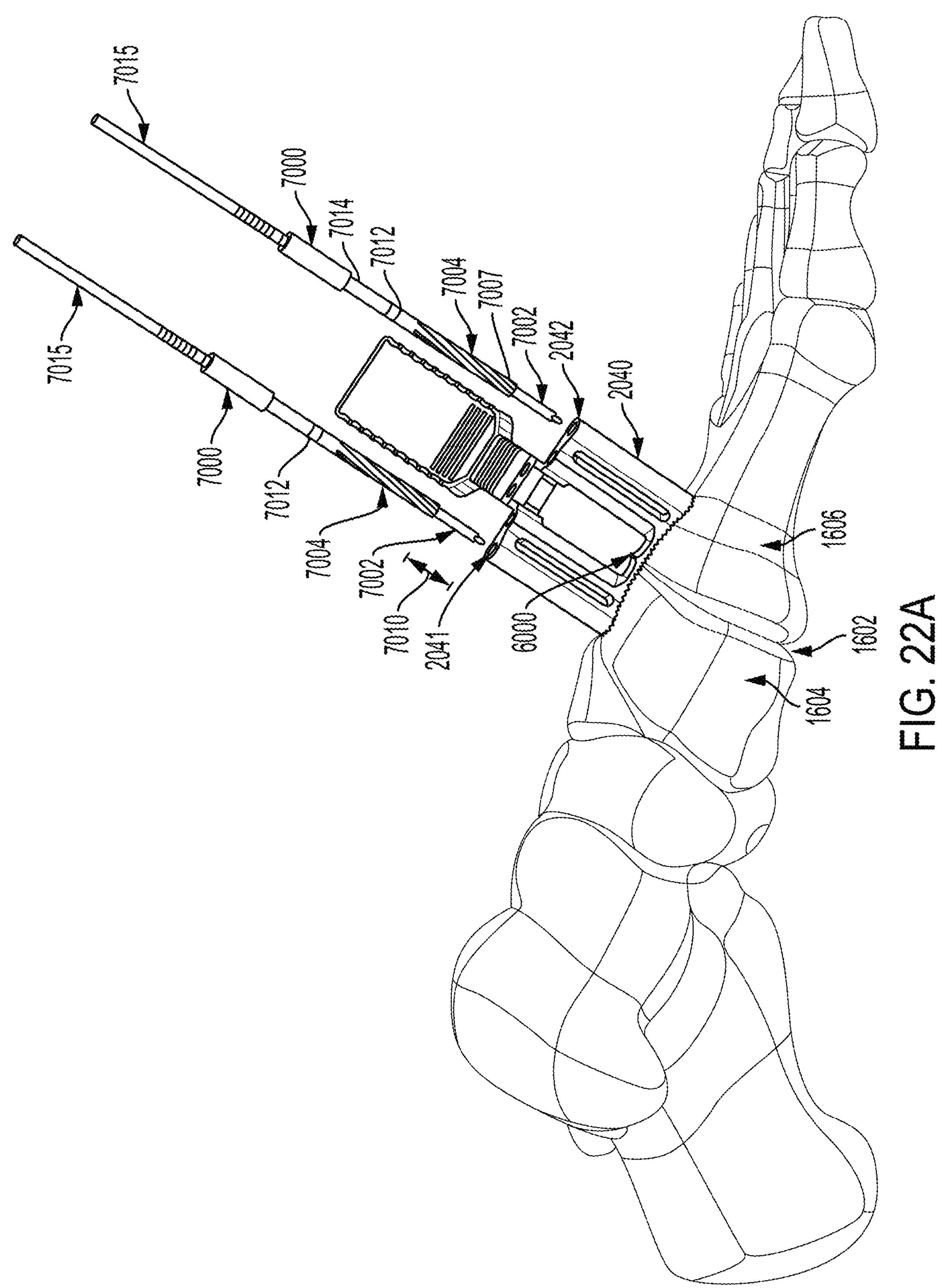
FIGS. 22A-22C illustrate an exemplary sequence of using a pinning and drilling instrument to create an implant receiving aperture at which an implant can be placed.
Figure 22B:
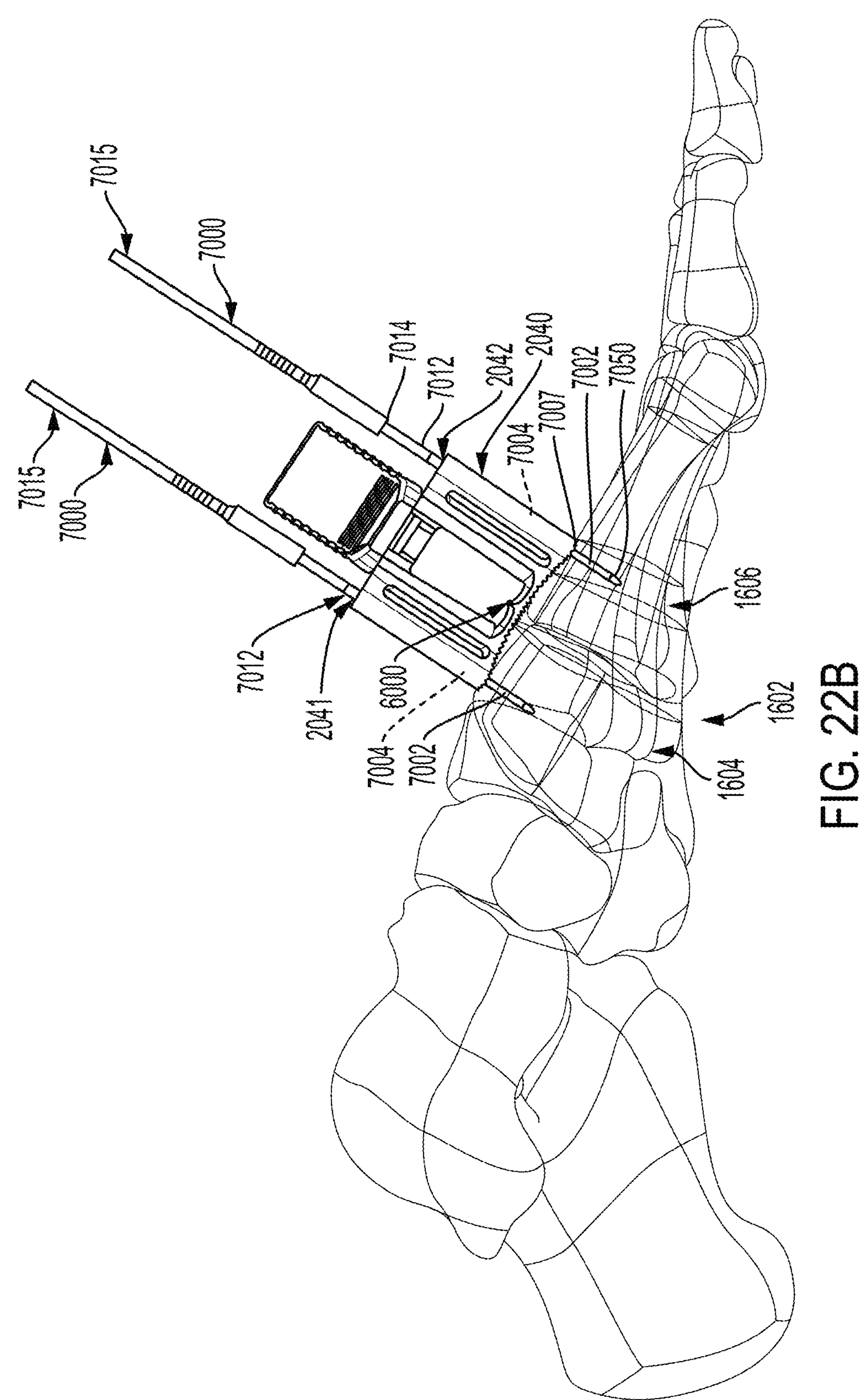

In some embodiments, such as that illustrated here, the pinning and drilling instrument 7000 can include a visual indicator 7012 and an interference stop 7014 at the body 7001. The visual indicator 7012 can be located at the body 7001 proximal to the pin portion 7002 and proximal to the drill portion 7004. In addition, the visual indicator 7012 can be located at a location along a length of the body 7001 corresponding to a fully inserted positioning of the pin portion 7002 at the bone. For example, in applications, such as that example shown at FIG. 22B, where the pinning and drilling instrument 7000 is inserted into the bone in conjunction with a drill guide (e.g., drill guide 2040) that includes a drill guide sleeve 2041, 2042 for receiving the pinning and drilling instrument 7000, a length between the distal, leading end of the drill portion 7004 and the visual indicator 7012 (e.g., a length between the shoulder 7007 and the visual indicator 7012) can be equal to a length of the drill guide sleeve 2041, 2042. Accordingly, as the pinning and drilling instrument 7000 is inserted into the bone and the visual indicator 7012 is moved adjacent to (e.g., intersects) the distal end of the drill guide sleeve 2041, 2042, such as shown at FIG. 22B, this can provide a user with an indication (e.g., visual indication) that the pin portion 7002 is fully inserted into the bone (e.g., the shoulder 7007 is contacting an outer surface of the bone).

Also, in some embodiments, a length 7016 defined between the visual indicator 7012 and the interference stop 7014 can be equal to the pin length 7010, and thus can be equal to a length of an implant portion that is to be placed within the bone portion. For applications where the implant is a staple, the length 7016 defined between the visual indicator 7012 and the interference stop 7014 can be equal to the pin length 7010, and thus can be equal to a leg length of the staple to be implanted. Accordingly, this length 7016 between the visual indicator 7012 and the interference stop 7014 can serve as a visual reference when inserting the drill portion 7004 into the bone portion to guide a length of drill portion 7004 insertion into the bone corresponding to the length 7016 which simulates a length of a staple leg. In other words, the visual indicator 7012 can provide an indication as to when the pin length 7010 is inserted into the bone and, because the pin length 7010 can correspond to the staple leg length, provide an indication that the pin length 7010 inserted into the bone simulates a length of a staple leg to be inserted at that same location within the bone.

For embodiments where it may be desirable to insert at least some of the pinning and drilling instrument 7000 into a bone portion using a driving tool, the pinning and drilling instrument 7000 can include a driver engagement portion 7015. The driver engagement portion 7015 can be proximal to the drill portion 7004. The illustrated embodiment shows the driver engagement portion 7015 at a distal end portion of the body 7001. The driver engagement portion 7015 can be configured (e.g., sized and/or shaped) for insertion into a powered driver. The driver engagement portion 7015 may have a length and diameter that allows the driver engagement portion 7015 to be inserted into a powered driver to a depth appropriate for the powered driver to then act on the pinning and drilling instrument 7000 for driving (e.g., rotationally driving) the pinning and drilling instrument 7000 a surgical procedure. For example, the pinning and drilling instrument 7000 can be coupled to a powered driver at the driver engagement portion 7015, and the pinning and drilling instrument 7000 can be rotationally driven by the powered driver to cause the drill portion 7004 to create the implant receiving aperture.

Figures 19A, 19B:
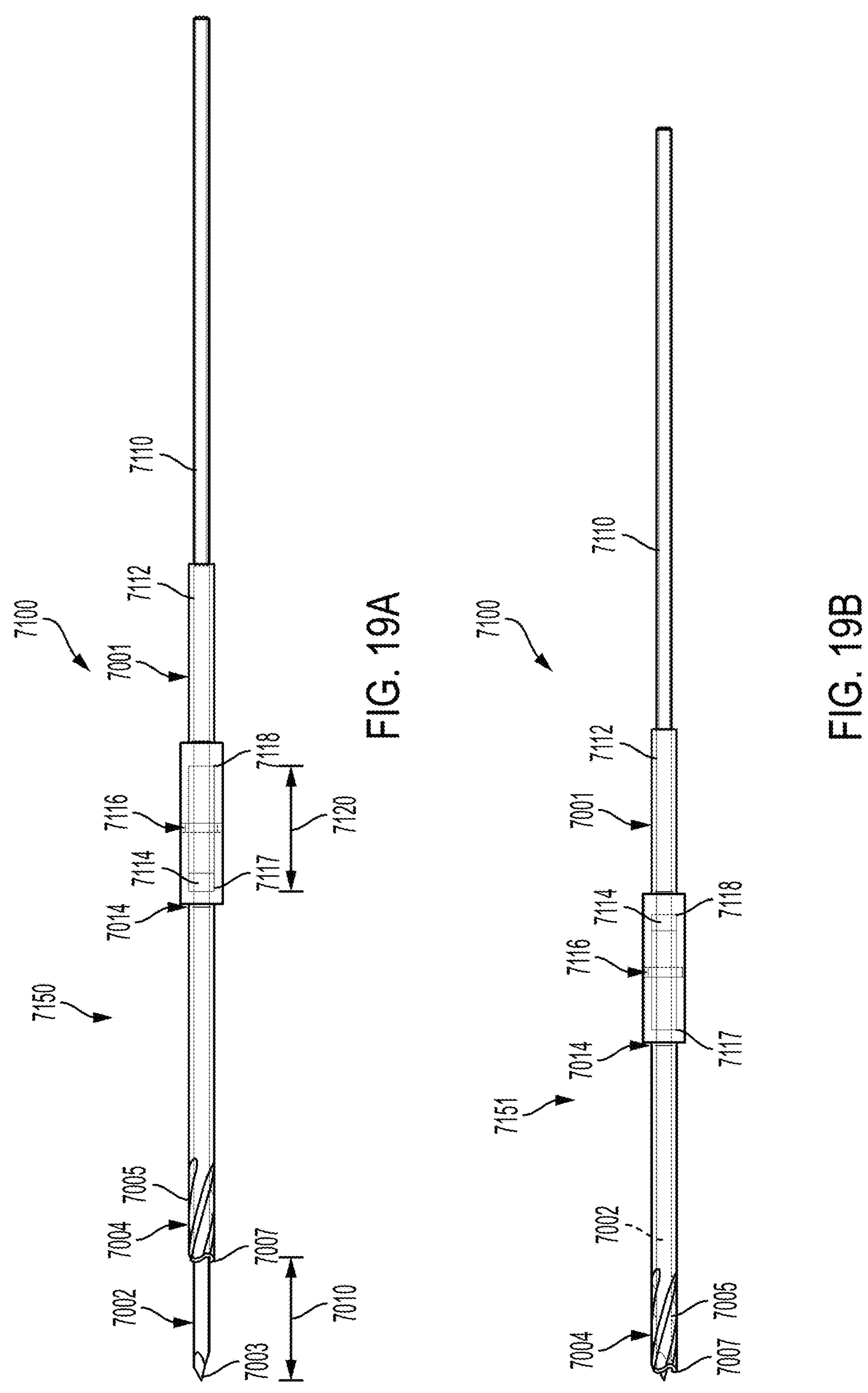
FIGS. 19A-19B illustrate another embodiment of a pinning and drilling instrument with movable and coupled portions.

FIGS. 19A-19B illustrate another embodiment of a pinning and drilling instrument 7100. The pinning and drilling instrument 7100 can be the similar to, or the same as, the pinning and drilling instrument 7000 described elsewhere herein except as otherwise disclosed here with respect to FIGS. 19A-19B. FIG. 19A is a side elevational view of the pinning and drilling instrument 7100 in an exemplary pinning configuration 7150. And FIG. 19B is a side elevational view of the pinning and drilling instrument 7100 in an exemplary drilling configuration 7151.

The pinning and drilling instrument 7100 can be adjustable between the pinning configuration 7150 and the drilling configuration 7151. In the pinning configuration 7150 the pin portion 7002 (e.g., pointed end 7003) can extended out from the drill portion 7004 further than the pin portion 7002 (e.g., pointed end 7003) extends out from the drill portion 7004 in the drilling configuration 7151. As one such example of the pinning configuration 7150, the pin portion 7002 can extend out from the shoulder 7007 the pin portion length 7010 that is equal to a portion of an implant (e.g., staple leg) that is to be later implanted at the location where the pin portion length 7010 is inserted within a bone. And as one such example of the drilling configuration 7151, the pin portion 7002 can extend out from the shoulder 7007 a distance less than the pin portion length 7010. For example, as shown for the illustrated embodiment, in the drilling configuration 7151, at least some of the pin portion length 7010 that was extended out in the pinning configuration 7150 can be nested inside of the drill portion 7004.

To facilitate adjustment between such configurations, the pinning and drilling instrument 7100 can include portions that are coupled together and movable relative to one another, at least in part, to change the pinning and drilling instrument 7100 between the pinning configuration 7150 and the drilling configuration 7151. The illustrated embodiment of the pinning and drilling instrument 7100 can include a pin shaft 7110 having the pin portion 7002 (e.g., at a distal end of the pin shaft 7110) and a drill shaft 7112 having the drill portion 7004 (e.g., at a distal end of the drill shaft 7112). The pin shaft 7110 and the drill shaft 7112 can be movable independent from one another, at least over a predefined range of movement, to adjust the pinning and drilling instrument 7100 between the pinning configuration 7150 and the drilling configuration 7151. For example, the pin shaft 7112, and thus the pin portion 7002, and the drill shaft 7110, and thus the drill portion 7004, can be movable independent from one another over a first range of movement but be movable together over a second, different range of movement. For instance, the pin shaft 7112, and thus the pin portion 7002, and the drill shaft 7110, and thus the drill portion 7004, can be movable independent from one another over a first range of movement that includes inserting the pin portion 7002 into a bone and then inserting at least a portion of the drill portion 7004 into the bone. Yet, the pin shaft 7112, and thus the pin portion 7002, and the drill shaft 7110, and thus the drill portion 7004, can be movable together over a second range of movement that includes further inserting the drill portion 7004 into the bone beyond the extend of drill portion 7004 insertion over the first range of movement.

To facilitate adjustment between the pinning configuration 7150 and the drilling configuration 7151, for the illustrated embodiment of the pinning and drilling instrument 7100, the pin shaft 7110 can include a step 7114 (e.g., proximal to the pin portion 7002) and the drill shaft 7112 can include a chamber 7116 (e.g., proximal to the drill portion 7004). The chamber 7116 can include a distal step stop 7117 and a proximal step stop 7118. The step 7114 of the pin shaft 7110 can be positioned within the chamber 7116 and movable over a range of movement 7120 between the distal step stop 7117 and the proximal step stop 7118 as the pin shaft 7110 and the drill shaft 7112 are moved relative to one another. Yet, when the step 7114 of the pin shaft 7110 is moved into contact with the distal step stop 7117 and/or the proximal step stop 7118, engagement between the step 7114 and the step stop 7117 and/or 7118 can cause relative movement between the pin shaft 7110 and the drill shaft 7112 to be arrested and, thereby, act to cause the pin shaft 7112, and thus the pin portion 7002, and the drill shaft 7110, and thus the drill portion 7004, to be movable together. For example, as seen at FIG. 19A, when the step 7114 is spaced apart from the proximal step stop 7118, the pin shaft 7110, and thus the pin portion 7002, can be movable independent of the drill shaft 7112, and thus the drill portion 7004, to extend the pin portion 7002 out the pin portion length 7010. For instance, a user can engage the drill shaft 7112 and apply a motive force to translate the drill shaft 7112 relative to and toward the pin portion 7002 that is inserted within the bone. Then, as seen at FIG. 19B, when the step 7114 is brought into engagement at the proximal step stop 7118 as a result of the drill shaft 7112 movement relative to the pin shaft 7110, the pin shaft 7110, and thus the pin portion 7002, can be movable together (e.g., with a majority of the pin portion length 7010 nested within the drill shaft 7112) while the step 7114 engages the proximal step stop 7118 at the drill shaft 7112.

Figures 20A, 20B:
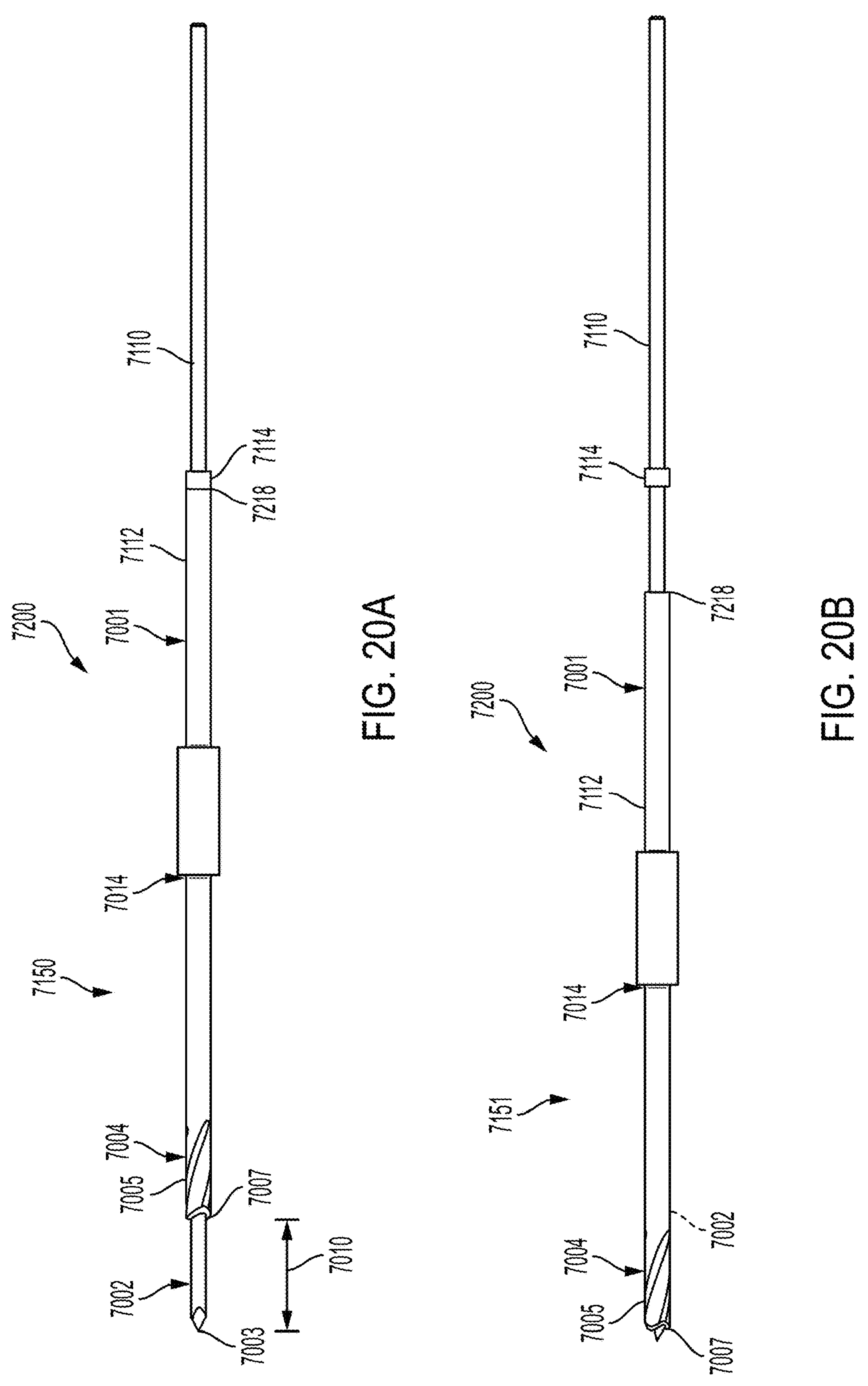
FIGS. 20A-20B illustrate another embodiment of a pinning and drilling instrument with movable and decoupled portions.

FIGS. 20A-20B illustrate another embodiment of a pinning and drilling instrument 7200. The pinning and drilling instrument 7200 can be the similar to, or the same as, the pinning and drilling instruments 7000, 7100 as described elsewhere herein except as otherwise disclosed here with respect to FIGS. 20A-20B. FIG. 20A is a side elevational view of the pinning and drilling instrument 7200 in the pinning configuration 7150. FIG. 20B is a side elevational view of the pinning and drilling instrument 7200 in the drilling configuration 7151.

Like the pinning and drilling instrument 7100, the pinning and drilling instrument 7200 can be adjustable between the pinning configuration 7150 and the drilling configuration 7151. The pinning and drilling instrument 7100, as disclosed previously, includes the pin shaft 7110 and the drill shaft 7112 coupled together via the chamber 7116 and thus limits relative, independent movement between the pin shaft 7110 and the drill shaft 7112 over the distance 7120 between the step stops 7117, 7118. Whereas the pinning and drilling instrument 7200 includes the pin shaft 7110 and the drill shaft 7112 decoupled from one another and, thus, the pinning and drilling instrument 7200 can be configured to allow relative movement between the pin shaft 7110 and the drill shaft 7112 over a wider range constrained by stop 7218. Stop 7128 can be included at the drill shaft 7112. When the step 7114 is spaced from the stop 7128, the pin shaft 7110 and the drill shaft 7112 can be movable independent of one another, but when the step 7114 is engaged at the stop 7128 the pin shaft 7110 and the drill shaft 7112 can be movable together.

The pinning and drilling instrument 7200 can be used in the pinning configuration 7150 and in the drilling configuration 7151 as disclosed elsewhere herein with respect to the pinning and drilling instruments 7000, 7100. As one example disclosed elsewhere herein, the pinning and drilling instrument 7000, 7100, 7200 can be used for a method of simulating and, upon confirmation of the simulated position of the implant using the pinning and drilling instrument 7000, 7100, 7200 (e.g., using the pin length 7010 of the pin portion 7002), creating an implant receiving aperture at that simulated position.

Figure 21:
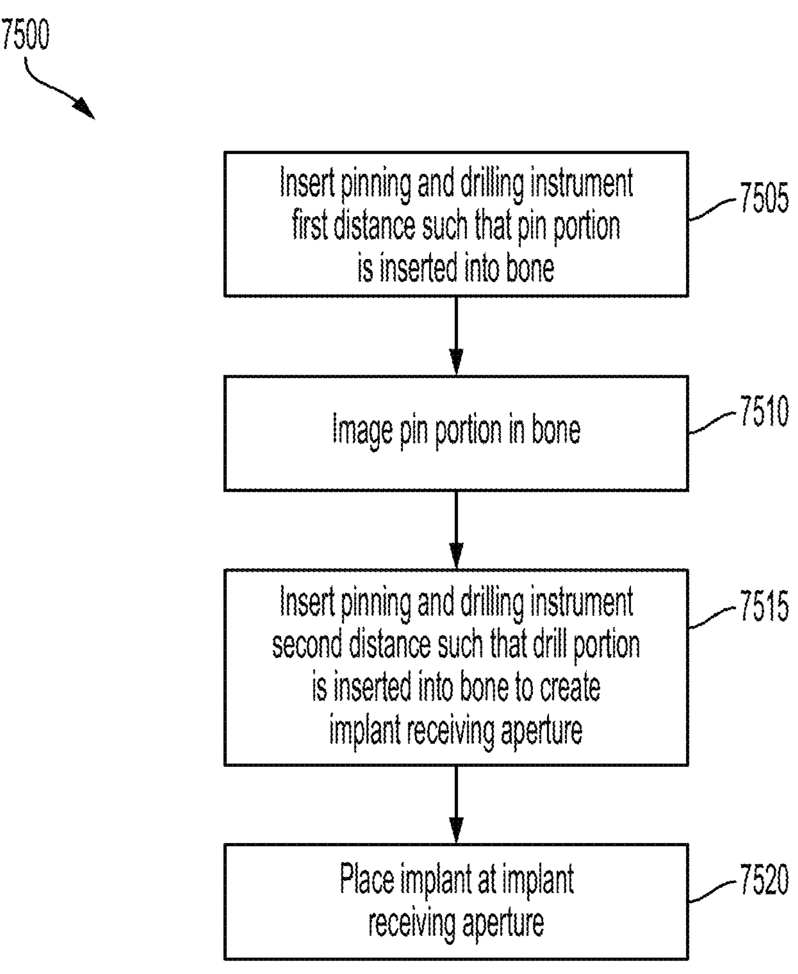
FIG. 21 is a flow diagram of an example surgical technique using a pinning and drilling instrument to create an implant receiving aperture at which an implant can be placed.
Figure 22C:
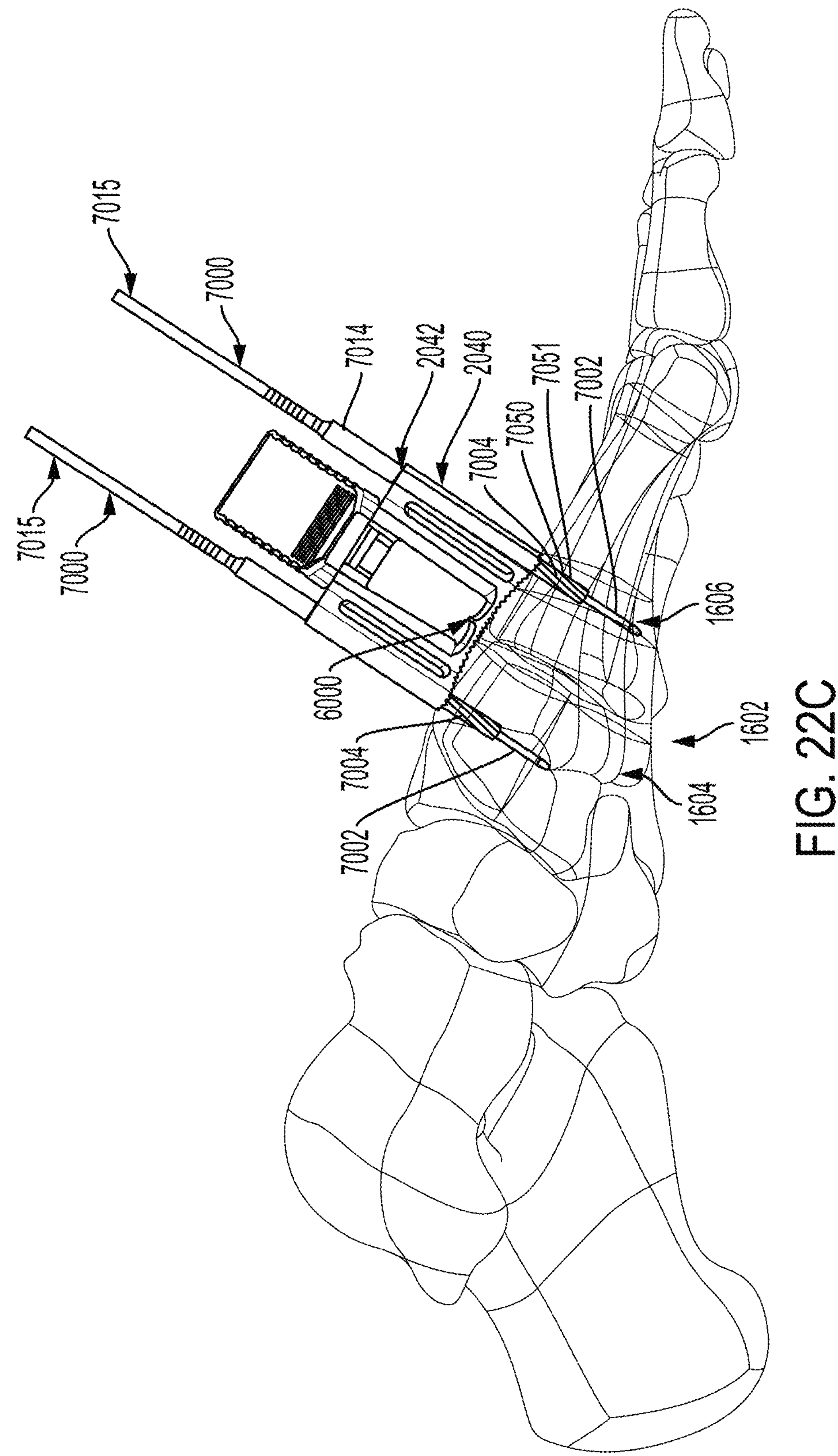

FIG. 21 is a flow diagram of an example surgical technique 7500 using a pinning and drilling instrument to create an implant receiving aperture at which an implant can be placed. FIGS. 22A-22C will be referenced for exemplary, illustrative purposes in the following disclosure relating to the technique 7500. Namely, FIGS. 22A-22C illustrate an exemplary sequence of using a pinning and drilling instrument to create an implant receiving aperture at which an implant can be placed.

FIG. 22A shows a side elevational view of two pinning and drilling instruments 7000 being advanced toward an exemplary drill guide 2040 that is placed at bone portions 1604, 1606 of a foot. FIG. 22A illustrates one exemplary application of the technique 2500 at one or more bones of a foot and using the drill guide 2040 and two pinning and drilling instrument 7000. Though other applications of the technique 2500 can be carried out at one or more bones at other parts of the anatomy, with or without using a drill guide, with just one pinning and drilling instrument 7000, with more than two pinning and drilling instruments 7000, and/or with other pinning and drilling instrument embodiments, such as the pinning and drilling instrument 7100 and/or 7200.

In various applications of the technique 2500, the one or more bone portions 1604, 1606 can be bone portions of the same bone or different bones. For example, the one or more bone portions can include a first bone 1604 and a second bone 1606 separated by a joint space 1602. For the illustrated application of the technique 2500, the bone portion 1604 is a cuneiform (e.g., medial cuneiform), the bone portion 1604 is a metatarsal (e.g., first metatarsal), and the space 1602 between the cuneiform and the metatarsal is a tarsometatarsal joint space.

For applications of the technique 2500 that do use a drill guide, the technique 2500 can include a step of placing a drill guide at the one or more bone portions 1604, 1606. As shown at the exemplary application of FIG. 22A, before step 7505, the technique 7500 can include a step of placing the drill guide 2040 at the one or more bone portions 1604, 1606. The drill guide 2040, as disclosed elsewhere herein, can include trialing member 6000 that simulates at least one dimension of the implant (e.g., staple) to be placed at step 7520. Placing the drill guide 2040 at the first bone 1604 and the second bone 1606 can include, as shown at FIG. 22A, placing the trialing member 6000 at the first bone 1604, at the second bone 1606, and across the joint space 1602 separating the first and second bones 1604, 1606.

At step 7505, the technique 7500 can include inserting the pinning and drilling instrument a first distance into one or more bone portions. FIG. 22B illustrates an exemplary application of step 7505, showing a side elevational view of two pinning and drilling instruments 7000 each inserted into the respective bone portion 1604, 1606. The pinning and drilling instrument 7000 can be inserted, at step 7505, the first distance into bone portion 1604 or 1606 at a location at respective bone portion 1604, 1606 such that the pin portion 7002 of the pinning and drilling instrument 7000 is inserted into the one or more bone portions at the location at respective bone portion 1604, 1606.

Inserting the pinning and drilling instrument 7000 the first distance into the respective bone portion 1604, 1606 can include inserting the pin portion length 7010 into the respective bone portion 1604, 1606. As one example, the pin portion length 7010 can be equal to a length of an implant portion that is to be implanted at (e.g., within) the respective bone portion 1604, 1606. In this example, the pin portion 7002 inserted the pin portion length 7010 into the respective bone portion 1604, 1606 can provide a visual indication (e.g., via imaging) as to what the positioning of the implant within the respective bone portion 1604, 1606 will be. For instance, in applications where the implant is a staple, the pin portion length 7010 can be equal to a length of a leg of the staple, and inserting the pin portion 7002 into the respective bone portion 1604, 1606 can include inserting the pin portion length 7010, in this instance equal to the length of the leg of the staple to be later implanted at that same location, into the respective bone portion.

Inserting the pin portion 7002 (e.g., the pin portion length 7010) the first distance into the respective bone portion 1604, 1606 at step 7505 can include creating a tacking aperture 7050 at the bone portion 1604, 1606 at the location where the pin portion 7002 is inserted. For example, the tacking aperture 7050 can be created by inserting the pin portion 7002 into the respective bone portion 1604, 1606 and, as such, the tacking aperture 7050 can have a diameter equal to the diameter of the pin portion and the tacking aperture 7050 can extend into the respective bone portion 1604, 1606 a distance equal to a length of the pin portion 7002 inserted into the respective bone portion 1604, 1606. For instance, where the pin portion length 7010 is inserted into the respective bone portion 1604, 1606, the tacking aperture 7050 can have a length extending into the respective bone portion 1604, 1606 equal to the pin portion length 7010. And, thus, where the pin portion length 7010 equals a length of an implant portion (e.g., staple leg) that is to be implanted within the respective bone portion 1604, 1606, the tacking aperture 7050 created at step 7505 by inserting the drill portion 7002 into the respective bone portion 1604, 1606 can extend into the respective bone portion 1604, 1606 a distance equal to the length of an implant portion (e.g., staple leg) that is to be implanted within the respective bone portion 1604, 1606.

As illustrated for the exemplary application of the technique 7500, the drill guide 2040, or other guide component, can be used, at step 7505, to help guide insertion of the pinning and drilling instrument 7000 the first distance into the respective bone portion 1604, 1606. For example, as seen at the exemplary illustrations of FIGS. 22A and 22B, the pinning and drilling instrument 7000 can be inserted, at step 7505, the first distance into the respective bone portion 1604, 1606 by inserting the pinning and drilling instrument 7000 relative to the drill guide 2040. As one particular such example, as seen at the exemplary illustrations of FIGS. 22A and 22B, the pinning and drilling instrument 7000 can be inserted, at step 7505, the first distance into the respective bone portion 1604, 1606 by inserting the pinning and drilling instrument 7000 through a respective guide sleeve 2041, 2041 and into the respective bone portion 1604, 1606 the first distance. This could include inserting the pinning and drilling instrument 7000 through a respective guide sleeve 2041, 2041 and into the respective bone portion 1604, 1606 the first distance so as to provisionally fixate the drill guide 2040 at the respective bone portion 1604, 1606 using the pinning and drilling instrument 7000. For the example of FIGS. 22A and 22B, this includes inserting one pinning and drilling instrument 7000 at the drill guide 2040 (e.g., through one guide sleeve 2041) and into one bone 1604 the first distance (e.g., a distance equal to the pin portion length 7010) and inserting another pinning and drilling instrument 7000 at the drill guide 2040 (e.g., through another guide sleeve 2042) and into another bone 1606 the first distance (e.g., a distance equal to the pin portion length 7010). For instance, one pinning and drilling instrument 7000 can be inserted at the guide sleeve 2041 and into the bone 1604 the first distance equal to the pin portion length 7010 which is equal to a first leg of a staple at a first side of the staple bridge and another pinning and drilling instrument 7000 can be inserted at the guide sleeve 2042 and into the bone 1606 the first distance equal to a second leg of the staple at a second side of the staple bridge.

Inserting the pinning and drilling instrument the first distance into a bone portion such that the pin portion is inserted into the bone at step 7505 can terminate, for example, when a length of the pin portion 7002 inserted into the bone at least approximates a length of an implant that is intended to later be placed into the pin at the same location where a length of the pin portion 7002 is inserted. As one example, inserting the pinning and drilling instrument the first distance into a bone portion such that the pin portion is inserted into the bone at step 7505 can terminate, for example, when the pin portion length 7010, equal to the length of the implant portion to be implanted within the bone at that same location, is inserted into the bone. In some examples, to help provide the user with feedback as to when to terminate insertion of the pin portion the first distance into the bone at step 7505, contact between the shoulder 7007 and the bone at which the pin portion is inserted can be used as an indication to terminate insertion of the pin portion at step 7505. For instance, insertion of the pin potion the first distance into the bone at step 7505 can be temporarily terminated when the shoulder 7007 comes into contact with the respective bone 1604, 1606, such as shown at FIG. 22B. In an example where the shoulder 7007 defines a leading edge of a second cross-sectional area at the drill portion 7004 of the body 7001 larger than a first cross-sectional area of the pin portion 7002 at the body 7001, insertion of the pin potion the first distance into the bone at step 7505 can be temporarily terminated when that second-cross-sectional area contacts the bone portion within which the pin portion 7002 is inserted.

To help assist with determining when to terminate insertion of the pin portion 7002 to allow for evaluating the pin portion 7002 position within the bone, when so included, the visual indicator 7012 can be used. For example, the visual indicator 7012 can be at a location along a length of the body 7001 to correspond to a fully inserted position of the pin portion 7002 at the bone. As such, when the visual indicator 7012 has been moved to a predetermined position, this can provide an indication to a user that the pin portion 7002 (e.g., the pin portion length 7010) has been fully inserted into the bone. For the illustrated example application shown at FIG. 22B, inserting the pinning and drilling instrument the first distance into a bone portion such that the pin portion is inserted into the bone at step 7505 can be terminated when the visual indicator 7012 is moved to a predetermined position relative to the drill guide 2040. As one such example according to FIG. 22B, inserting the pinning and drilling instrument the first distance into a bone portion such that the pin portion is inserted into the bone at step 7505 can be terminated when the visual indicator 7012 is moved to a predetermined position relative to the guide sleeve 2041 or 2042 of the drill guide. For instance, when the visual indicator 7012 is moved adjacent to, or into at least partial alignment with, the respective guide sleeve 2041, 2042, insertion of the pin portion 7002 can be considered accomplished and further insertion of the pinning and drilling instrument 7000 into the bone can be temporarily terminated to evaluate the position of the pin portion 7002 in the bone.

At step 7510, the technique 7500 can include imaging at least a portion of the pin portion of the pinning and drilling instrument inserted in the bone portion. Imaging the position of the pin portion within the one or more bone portions at step 7510 can occur after inserting the pinning and drilling instrument 7000 the first distance (e.g., the pin portion length 7010) into the one or more bone portions and before creating an implant receiving aperture at that location by further inserting the pinning and drilling instrument the second further distance into the one or more bone portions. When the pinning and drilling instrument 7000 is inserted into the bone portion the first distance to approximate and simulate a distance that a portion of an implant would be inserted into the bone portion (e.g., when the pinning and drilling instrument is inserted into the bone portion the pin portion length 7010 equal to a length of a staple leg) at step 7505, imaging the position of the pin portion 7002 inserted into the bone portion can capture image data using the inserted pin portion 7002 to represent what could be a subsequent location for inserting an implant portion (e.g., staple leg). And this can thus allow for evaluating to proposed location of the to-be-inserted implant portion (e.g., staple leg), via the captured image data of the pin portion inserted into the bone portion, to determine if such location is suitable for then actually placing the implant portion there.

The imaging at step 7510 can include generating or otherwise acquiring image data that represents the position of the pin portion inserted the first distance within the bone portion. A variety of imaging modalities can be used to execute the imaging at step 7510. As one example, imaging at step 7510 can include generating or otherwise acquiring fluoroscopic image data that represents the position of the pin portion inserted the first distance within the bone portion. For applications of the technique 7500 where the bone portion 1604 is a first bone (e.g., cuneiform), the bone portion 1606 is a second bone (e.g., metatarsal), and the space 1602 is a joint space (e.g., tarsometatarsal joint) between the first and second bones, imaging the position of the pin portion 7002 within one of the first bone and the second bone can include imaging the position of the pin portion 7002 within one of the first bone and the second bone relative to the joint space. For example, it can in some applications be useful to evaluate the proposed position of the implant portion to-be-inserted into the bone, using captured image data of the pin portion within that bone as a proxy, to evaluate this proposed position relative to the joint space using the captured image data. If the proposed position of the implant portion to-be-inserted into the bone, using captured image data of the pin portion within that bone as a proxy, relative to the joint space is determined to be suitable, then the technique can proceed to step 7515. As one example, when it is determined, from the imaged position of the pin portion 7002, that the pin portion 7002 is spaced apart from the joint space adjacent the one or more bones, the implant receiving aperture can be created at the location by further inserting the pinning and drilling instrument (e.g., inserting the drill portion) into the one or more bone portions. On the other hand, if the proposed position of the implant portion to-be-inserted into the bone, using captured image data of the pin portion within that bone as a proxy, relative to the joint space is determined to be unsuitable, the pin portion can be removed from that location within the bone portion and steps 7505 and 7510 can be repeated at a new location at the bone portion relative to the joint space.

At step 7515, the technique 7500 can include creating an implant receiving aperture 7051. The implant receiving aperture 7051 can be created at step 7515 using the drill portion 7004 of the pinning and drilling instrument 7000. For example, the implant receiving aperture 7051 can be created at the location where the pin portion 7002 has been inserted by further inserting the pinning and drilling instrument 7000 a second further distance into the respective bone portion at that location at the bone portion where the pin portion 7002 has been inserted such that the drill portion 7004 of the pinning and drilling instrument 7000 is inserted into the bone portion to create the implant receiving aperture 7051 at that location. The implant receiving aperture 7051 can be created at step 7515 using the drill portion 7004 of the pinning and drilling instrument 7000 after inserting the pinning and drilling instrument 7000 (e.g., the pin portion 7002) the first distance (e.g., equal to the pin portion length 7010) into the same bone portion at step 7505. Thus, in such applications of the technique 7500, the tacking aperture 7050 can be created as the pin portion 7002 is inserted into the bone portion and then, when the position of the pin portion within the bone portion is determined to be a suitable position for placing at least a portion of an implant (e.g., using image data from step 7510), the implant receiving aperture can be subsequently created at step 7515 by further inserting the same pinning and drilling instrument into the same bone portion location where the pin portion 7002 was positioned so as to cause the drill portion 7004 to be inserted into that same location at the bone portion to create the implant receiving aperture 7051.

FIG. 22C is a side elevational view of two pinning and drilling instruments 7000 each inserted a second, further distance into the respective bone portion 1604, 1606 after each pinning and drilling instrument 7000 has had its respective pin portion inserted the first distance into the respective bone portion 1604, 1606. Inserting each pinning and drilling instruments 7000 the second, further distance into the respective bone portion 1604, 1606 such that the drill portion 7004 of the respective pinning and drilling instrument 7000 is inserted into the respective bone portion 1604, 1606 can create two implant receiving apertures 7051—one implant receiving aperture at the bone portion 1604 using the drill portion 7004 of one of the pinning and drilling instruments 7000 and another implant receiving aperture at the bone portion 1606 using the drill portion 7004 of the other pinning and drilling instruments 7000. The distance that the one created implant receiving aperture at the bone portion 1604 extends into the bone can generally be equal to or otherwise approximate a length of a first leg of a staple at a first side of the bridge of the staple, and the distance that the other created implant receiving aperture at the bone portion 1606 extends into the bone can generally be equal to or otherwise approximate a length of a second leg of a staple at a second side of the bridge of the staple.

At step 7515, the implant receiving aperture 7051 can be created at the location where the pin portion 7002 was inserted at the bone by further inserting the pinning and drilling instrument 7000 the second further distance into the bone while the pin portion 7002 is at the bone. For example, further inserting the pinning and drilling instrument 7000 the second further distance into the bone can cause the drill portion 7004 to contact the bone where the pin portion 7002 was previously contacting the bone (e.g., at the tacking aperture 7050) while causing the pin portion 7002 to be further inserted into the bone. As described previously, in some examples, the drill portion 7004 can include drill flutes that begin where the pin portion 7002 ends, and, in such examples, further inserting the pinning and drilling instrument 7000 the second further distance into the bone at step 7515 can include rotationally driving the drill flutes of the pin portion 7004 into the location at the bone where the pin portion was inserted into the bone (rotationally driving the drill flutes at the tacking aperture 7050). For those embodiments where the drill portion 7004 includes a larger diameter than the pin portion 7002, creating the implant receiving aperture 7051 at the location where the pin portion 7002 was inserted by rotationally driving the drill flutes of the drill portion into that location at the bone can include creating the implant receiving aperture 7051 of a second diameter that extends into the bones at the location where the pin portion 7002 was inserted and thus where the tacking aperture 7050 of a first diameter was created, where that second diameter of the implant receiving aperture 7051 is greater than that first diameter of the tacking aperture 7050.

The example application of step 7515 of the technique 7500 shown at FIG. 23C uses the drill guide 2040 placed at the bone portions 1604, 1606. In such an example, step 7515 can be executed to create the implant receiving aperture 7051 at the location where the pin portion 7002 was inserted by further inserting the pinning and drilling instrument 7000 through the drill guide 2040 the second further distance into the bone portion so that the drill portion 7004 is extended out from the drill guide 2040. This could include creating the implant receiving aperture 7051 at the location where the pin portion 7002 was inserted by further inserting the pinning and drilling instrument 7000 through the guide sleeve 2041 or 2042 of the drill guide 2040 the second further distance into the bone portion so that the drill portion 7004 is extended out from the guide sleeve 2041 or 2042.

At step 7520, the technique 7500 includes placing an implant at the implant receiving aperture 7051. Placing the implant at the implant receiving aperture 7051 can include placing at least a portion of the implant within the implant receiving aperture 7051. For example, the at least the portion of the implant placed within the implant receiving aperture 7051 can have an implant portion length that is equal to a length of the implant receiving aperture 7051 created at step 7515 using the drill portion 7004 (e.g., the implant portion length can be equal to a length of the drill portion 7004). As an additional example, the at least the portion of the implant placed within the implant receiving aperture 7051 can be larger than the first diameter of the tacking aperture 7050 created at step 7505 using the pin portion 7002 but smaller than the implant receiving aperture 7051 created at step 7515 using the drill portion 7004.

As one example for executing step 7520, the implant can be a staple having a first leg, a second leg, and a bridge that bridges between the first and second legs, and the bone portion 1604 can be a first bone (e.g., metatarsal) and the bone portion 1606 can be a second bone (e.g., cuneiform). In this example, the first implant receiving aperture can be created at step 7515 so as to have a length generally equal to the length of the first leg of the staple and a diameter larger than the diameter of the first leg of the staple. Likewise in this example, the second implant receiving aperture can be created at step 7515 so as to have a length generally equal to the length of the second leg of the staple and a diameter larger than the diameter of the second leg of the staple. Then, in this example, placing the staple at step 7520 can include placing the first leg of the staple at the first implant receiving aperture created using the drill portion 7004 of one of the pinning and drilling instruments 7000 and placing the second leg of the staple at the second implant receiving aperture created using the drill portion 7004 of the other of the pinning and drilling instruments 7000.

Figure 23:
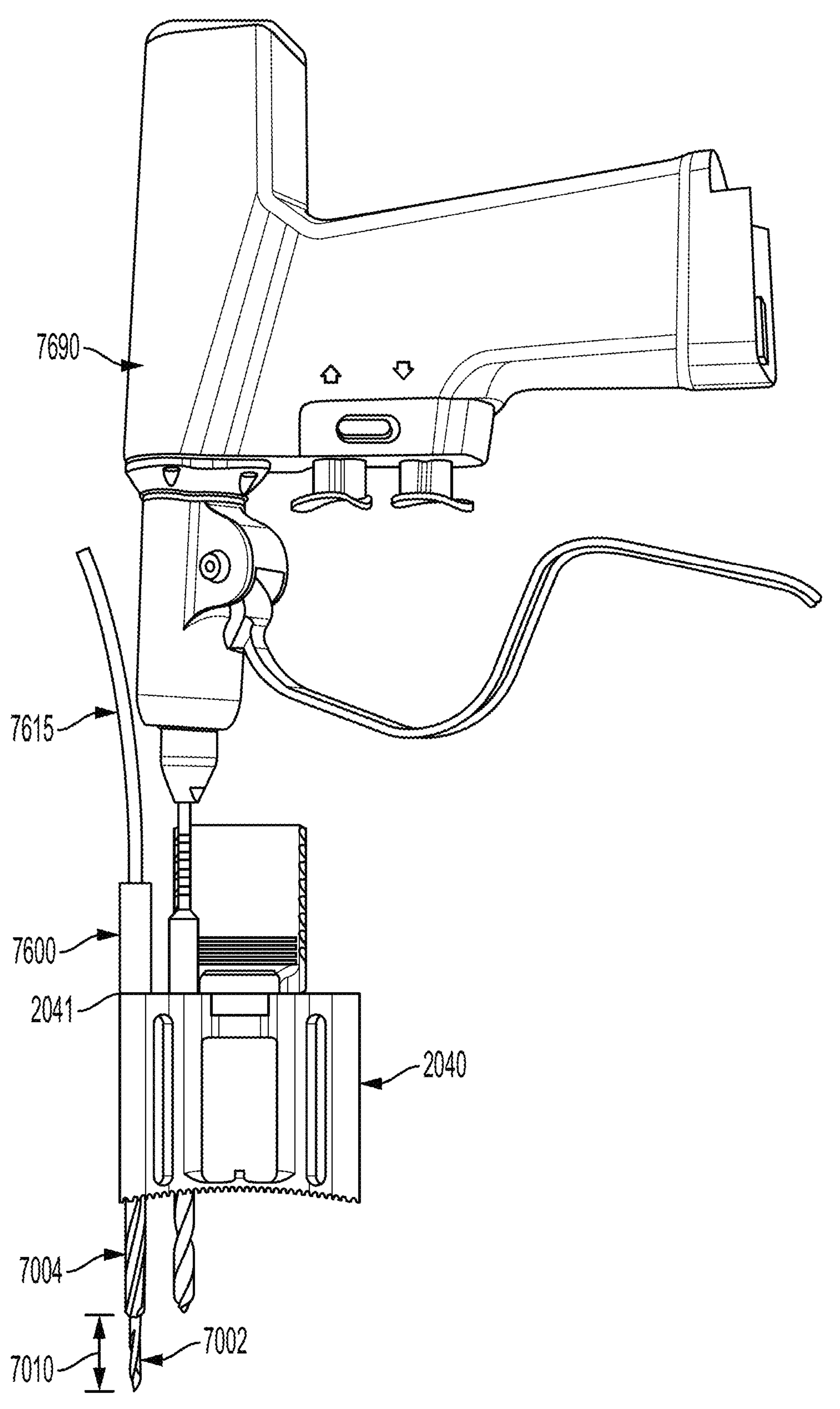
FIG. 23 is an elevational view of another embodiment of a pinning and drilling instrument shown as used in conjunction with a powered driver tool and a drill guide.

FIG. 23 is an elevational view of another embodiment of a pinning and drilling instrument 7600 used in conjunction with a powered driver (e.g., powered drill) 7690 and drill guide 2040. The pinning and drilling instrument 7600 can be similar to, or the same as, the pinning and drilling instrument 7000 disclosed elsewhere herein except as otherwise noted here.

For example, the pinning and drilling instrument 7600 can have one or more of the features disclosed elsewhere herein with respect to the pinning and drilling instrument 7000 except that the pinning and drilling instrument 7600 can have a variable stiffness along its length. In particular, the pinning and drilling instrument 7600 can have one end portion that is less stiff, and thus more flexible, than an opposite end portion. For instance, the pinning and drilling instrument 7600 can have a proximal portion that is less stiff, and thus more flexible, than a distal portion of the pinning and drilling instrument 7600. The illustrated embodiment of the pinning and drilling instrument 7600 shows a driver engagement portion 7615 that is proximal to the drill portion 7004 and proximal to the pin portion 7002, and the illustrated embodiment shows that the driver engagement portion 7615 can have a lesser stiffness, and thus be more flexible, than the drill portion 7004 and/or the pin portion 7002 (e.g., the drill portion 7004 and the pin portion 7002 have a greater flexural modulus than the driver engagement portion 7615). Thus, the distal end portion of the body of the pinning and drilling instrument 7600 having the driver engagement portion 7615 can be less stiff, and thus more flexible, than the proximal end portion of the body of the pinning and drilling instrument 7600 having the pin and/or drill portions 7002, 7004.

The variable stiffness along a length of the pinning and drilling instrument 7600 can be useful in creating clearance space for a user to operate during a procedure involving the pinning and drilling instrument 7600. FIG. 23 shows the pinning and drilling instrument 7600 at the drill guide 2040 and adjacent to the powered driver 7690 engaged to an adjacent drill piece also at the drill guide 2040. As seen here, the more flexible distal end portion of the body of the pinning and drilling instrument 7600 having the driver engagement portion 7615 can be configured to bend and flex away from the powered driver 7690 that is engaged to an adjacent drill piece also at the drill guide 2040. As also seen at FIG. 23, while the more flexible distal end portion of the body of the pinning and drilling instrument 7600 bends and flexes away from the powered driver 7690, the stiffer proximal end portion of the body of the pinning and drilling instrument 7600 having the pin portion 7002 and the drill portion 7004 can be configured to maintain a linear, straight orientation. Thus, the stiffer proximal end portion of the body of the pinning and drilling instrument 7600 having the pin portion 7002 and the drill portion 7004 can extend along one longitudinal axis while the less stiff distal end portion of the body of the pinning and drilling instrument 7600 having the driver engagement portion 7615 can extend along another longitudinal axis that is at a skewed orientation relative to the longitudinal axis along which the pin portion 7002 and the drill portion 7004 can extend.

In addition to the variable stiffness along a length of the pinning and drilling instrument 7600, the pinning and drilling instrument 7600 can define a same diameter at the pin portion 7002 as at the driver engagement portion 7615. This common diameter at the pin portion and at the driver engagement portion 7615 of the pinning and drilling instrument 7600 can be useful in reducing or eliminating a need to switch collet connection components at the powered driver 7690.

Figure 24:
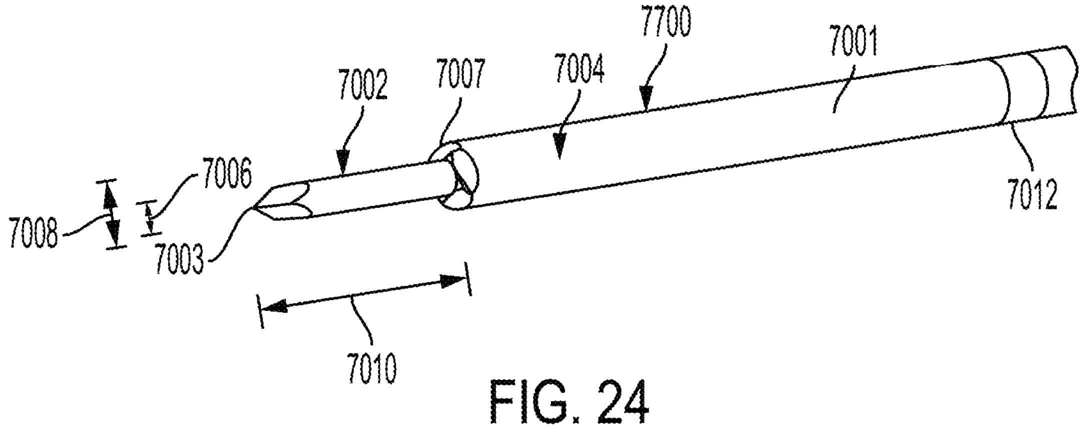
FIG. 24 is a perspective view of an end portion of an additional embodiment of a pinning and drilling instrument.
Figure 25:
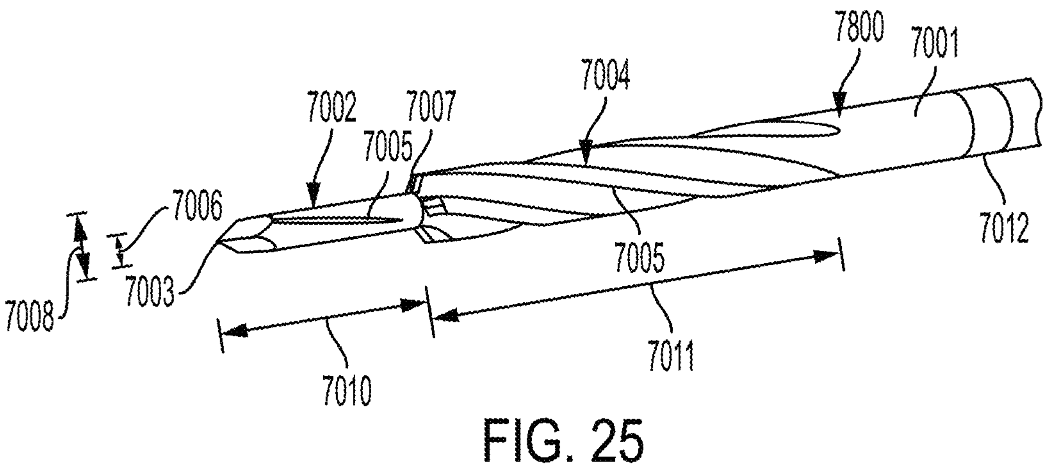
FIG. 25 is a perspective view of an end portion of a further embodiment of a pinning and drilling instrument.
Figure 26:
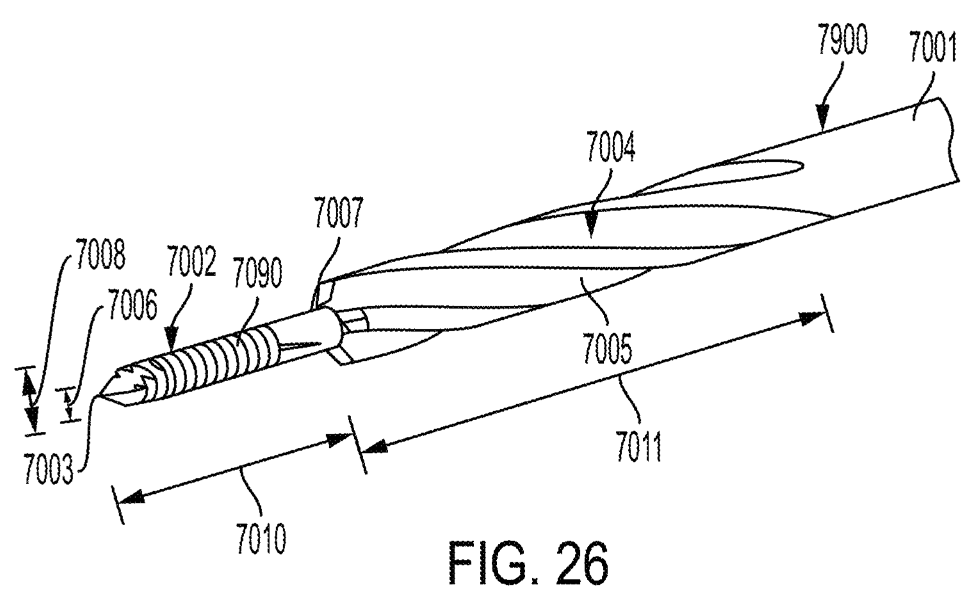
FIG. 26 is a perspective view of an end portion of another embodiment of a pinning and drilling instrument.

FIGS. 24-26 show further embodiments of a pinning and drilling instrument with various pin and drill portion configurations. Any of the pin and drill portion configurations shown at the examples of FIGS. 24-26 can be used with any other pinning and drilling instrument embodiments disclosed herein.

FIG. 24 is a perspective view of a distal end portion of an additional embodiment of a pinning and drilling instrument 7700. The pinning and drilling instrument 7700 can be similar to, or the same as, any other pinning and drilling instrument embodiment disclosed elsewhere herein (e.g., the pinning and drilling instrument 7000; the pinning and drilling instrument 7600) except as otherwise noted here.

At the illustrated distal end portion of FIG. 24, the pinning and drilling instrument 7700 can have the pin potion 7002 and the drill portion 7004. The illustrated pinning and drilling instrument 7700 can be similar to or the same as the pinning and drilling instrument 7000 described previously herein except that, as shown at the example of FIG. 24, the pinning and drilling instrument 7700 can lack any flutes at the drill portion 7004. In particular, the pinning and drilling instrument 7700 can have both the pin portion 7002 and the drill portion 7004 without any flutes. Thus, the pin portion 7002 of the pinning and drilling instrument 7700 can include a planar, flute-free surface extending circumferentially around an outer perimeter of the pin portion 7002, and the drill portion 7004 of the pinning and drilling instrument 7700 can include a planar, flute-free surface extending circumferentially around an outer perimeter of the drill portion 7004. Without flutes at the drill portion 7004 of the pinning and drilling instrument 7700, the drill portion 7004 of the pinning and drilling instrument 7700 may not be configured to drill an implant receiving hole at bone but instead the pinning and drilling instrument 7700 can be configured to provide a tacking function using the drill portion 7002.

FIG. 25 is a perspective view of a distal end portion of a further embodiment of a pinning and drilling instrument 7800. The pinning and drilling instrument 7800 can be similar to, or the same as, any other pinning and drilling instrument embodiment disclosed elsewhere herein (e.g., the pinning and drilling instrument 7000; the pinning and drilling instrument 7600) except as otherwise noted here.

At the illustrated distal end portion of FIG. 25, the pinning and drilling instrument 7800 can have the pin potion 7002 and the drill portion 7004. The illustrated pinning and drilling instrument 7800 can be similar to or the same as the pinning and drilling instrument 7000 described previously herein except that, as shown at the example of FIG. 25, the pinning and drilling instrument 7800 can include one or more flutes 7005 at each of the pin portion 7002 and the drill portion 7004. As illustrated at FIG. 25, the pin portion 7002 of the pinning and drilling instrument 7800 can include one or more flutes 7005 extending along at least a portion of the length 7010 of the pin portion 7002. The one or more flutes 7005 at the pin portion 7002 can extend both along at least a portion of the length 7010 of the pin portion 7002 and around at least a portion of the outer perimeter (e.g., circumference) of the pin portion 7002. With one of more flutes 7005 thereat, in addition to a tacking function, the pin portion 7002 of the pinning and drilling instrument 7800 can be configured to help create the implant receiving aperture at the bone (e.g., for receiving a portion of an implant, such as a leg of a staple) by breaking up portions of that bone if/when the pinning and drilling instrument 7800 is rotationally driven when the pin portion 7002 is in contact with that bone. And, as also illustrated at FIG. 25, the drill portion 7004 of the pinning and drilling instrument 7800 can include one or more flutes 7005 extending along the length 7011 of the drill portion 7004 and around at least a portion of the outer perimeter (e.g., circumference) of the drill portion 7004. Accordingly, when the pinning and drilling instrument 7800 is rotationally driven when the drill portion 7004 is in contact with the bone, the drill portion 7004 can be configured to break up portions of that bone using the flutes 7005 to help create the implant receiving aperture at that bone.

FIG. 26 is a perspective view of a distal end portion of another embodiment of a pinning and drilling instrument 7900. The pinning and drilling instrument 7900 can be similar to, or the same as, any other pinning and drilling instrument embodiment disclosed elsewhere herein (e.g., the pinning and drilling instrument 7000; the pinning and drilling instrument 7600) except as otherwise noted here.

At the illustrated distal end portion of FIG. 26, the pinning and drilling instrument 7900 can have the pin potion 7002 and the drill portion 7004. The illustrated pinning and drilling instrument 7900 can be similar to or the same as the pinning and drilling instrument 7000 described previously herein except that the pinning and drilling instrument 7900 can include one or more flutes 7005 at the pin portion 7002 and/or the drill portion 7004 and can include one or more threads 7090 at the pin portion 7002 and/or the drill portion 7004. As illustrated at FIG. 26, the pin portion 7002 of the pinning and drilling instrument 7900 can include one or more threads 7090. The threads 7090 at the pin portion 7002 can extend along at least a portion of the length 7010 of the pin portion 7002 (e.g., along at least half of the length 7010) and around at least a portion of the outer perimeter (e.g. circumference) of the pin portion 7002. The threads 7090 at the pin portion 7002 can be configured to create a threaded surface at the bone if/when the pinning and drilling instrument 7900 is rotationally driven when the pin portion 7002 is in contact with that bone, for instance, at a location at that bone where an implant is to be placed after use of the pinning and drilling instrument 7900. In certain examples, in addition to the one or more threads 7090, the pin portion 7002 of the pinning and drilling instrument 7900 can include one or more flutes 7005. As also illustrated at FIG. 26, the drill portion 7004 of the pinning and drilling instrument 7900 can include one or more flutes 7005 extending along the length 7011 of the drill portion 7004 and around at least a portion of the outer perimeter (e.g., circumference) of the drill portion 7004. Accordingly, when the pinning and drilling instrument 7900 is rotationally driven when the drill portion 7004 is in contact with the bone, the drill portion 7004 can be configured to break up portions of that bone using the flutes 7005 to help create the implant receiving aperture at that bone.

A staple as described herein may be used alone or in combination with one or other bone fixation devices to fixate a joint between opposed bone portions for fusion. Other types of bone fixation devices that can be used include, but are not limited to, a bone screw (e.g., a compressing bone screw), a bone plate, an external fixator, a pin (e.g., an intramedullary implant), and/or combinations thereof. A staple according to the disclosure can be attached before or after installing the one or more other bone fixation devices (when used) to the bone portions being fixated.

Various examples have been described. These and other examples are within the scope of the following claims.

What is claimed is:

1. A method of modifying a bone surface for receiving an implant, the method comprising:

positioning a contour guide at a first bone and a second bone and across a separation between the first bone and the second bone;

using the contour guide to modify a surface region of at least one of the first bone and the second bone to form a modified surface region at one or both of the first bone and the second bone where a bridge of an implant is configured to be positioned;

positioning the bridge of the implant in contact at least with the modified surface region.

2. The method of claim 1, wherein using the contour guide to modify the surface region of at least one of the first bone and the second bone comprises using the contour guide to modify a first surface region at the first bone to form a modified first surface region along the first bone and a second surface region at the second bone to form a modified second surface region along the second bone, and wherein positioning the implant in contact at least with the modified surface region comprises placing the implant in contact with each of the modified first surface region and the modified second surface region.

3. The method of claim 2, wherein the implant has an implant length, wherein the modified first surface region and the modified second surface region define a modified bone surface length along the first bone and the second bone, and wherein the modified bone surface length is equal to or greater than the implant length.

4. The method of claim 3, wherein the implant is placed in contact with each of the modified first surface region and the modified second surface region and with the implant bridging the separation between the first bone and the second bone.

5. The method of claim 1, wherein the implant is a staple, wherein the first bone is a metatarsal, the second bone is a cuneiform, and the separation between the first bone and the second bone is a joint space between the metatarsal and the cuneiform, and wherein positioning the implant in contact at least with the modified surface region comprises placing a first leg of the staple through the modified first surface region at the metatarsal and placing a second leg of the staple through the modified second surface region at the cuneiform.

6. The method of claim 1, wherein using the contour guide to modify the surface region of at least one of the first bone and the second bone to form the modified surface region at one or both of the first bone and the second bone comprises positioning a bone surface modification instrument at the contour guide and in contact with the surface region of at least one of the first bone and the second bone.

7. The method of claim 6, wherein the bone surface modification instrument, placed at the contour guide and in contact with the surface region of at least one of the first bone and the second bone, is configured to break up bone at the surface region of at least one of the first bone and the second bone.

8. The method of claim 6, wherein the bone surface modification instrument, positioned at the contour guide and in contact with the surface region of at least one of the first bone and the second bone, comprises at least one of a burr and a saw.

9. The method of claim 1, wherein the contour guide comprises a contour guide body having a top side and a bottom side, wherein the bottom side includes a guide slot that defines a guide slot cross-sectional area that is greater than a cross-sectional area of the implant, and wherein positioning the contour guide comprises positioning the bottom side of the contour guide at the first bone and the second bone and across the separation between the first bone and the second bone.

10. The method of claim 9, wherein positioning the bottom side of the contour guide at the first bone and the second bone and across the separation between the first bone and the second bone comprises positioning the guide slot over the first bone and the second bone and across the separation between the first bone and the second bone.

11. The method of claim 10, wherein the contour guide body comprises a guide aperture, and wherein using the contour guide to modify the surface region of at least one of the first bone and the second bone to form the modified surface region at one or both of the first bone and the second bone comprises placing a bone surface modification instrument at least partially in the guide aperture, at least partially in the guide slot, and in contact with the surface region of at least one of the first bone and the second bone.

12. The method of claim 11, wherein the guide aperture is aligned with the guide slot, and, when the contour guide is positioned at the first bone and the second bone and across the separation between the first bone and the second bone, the bone surface modification instrument is first inserted through the guide aperture, then inserted through the guide slot, and then placed in contact with the surface region of at least one of the first bone and the second bone to modify the surface region of at least one of the first bone and the second bone.

13. The method of claim 1, further comprising:

positioning an implant guide sleeve at the first bone and the second bone and across the separation between the first bone and the second bone, wherein the contour guide is positioned at the first bone and the second bone and across the separation between the first bone and the second bone using the implant guide sleeve.

14. The method of claim 13, further comprising:

prior to positioning the contour guide at the first bone and the second bone and across the separation between the first bone and the second bone using the implant guide sleeve, fixating the implant guide sleeve at the first bone and the second bone.

15. The method of claim 13, wherein using the contour guide to modify the surface region of at least one of the first bone and the second bone to form the modified surface region at one or both of the first bone and the second bone comprises using the contour guide to modify the surface region while the contour guide is positioned at least partially within the implant guide sleeve.

16. The method of claim 13, wherein, after positioning the contour guide using the implant guide sleeve and after using the contour guide to modify the surface region of at least one of the first bone and the second bone to form the modified surface region at one or both of the first bone and the second bone, advancing an inserter, operatively connected to the implant, relative to the implant guide sleeve to place the implant in contact at least with the modified surface region.

* * * * *